US008409826B2

(12) United States Patent
Ervasti et al.

(10) Patent No.: US 8,409,826 B2
(45) **Date of Patent: *Apr. 2, 2013**

(54) TAT-UTROPHIN AS A PROTEIN THERAPY FOR DYSTROPHINOPATHIES

(75) Inventors: James M. Ervasti, Shoreview, MN (US); Kevin J. Sonnemann, Minneapolis, MN (US)

(73) Assignee: Wisconsin Alumni Research Foundation, Madison, WI (US)

(*) Notice: Subject to any disclaimer, the term of this patent is extended or adjusted under 35 U.S.C. 154(b) by 102 days.

This patent is subject to a terminal disclaimer.

(21) Appl. No.: 12/940,166

(22) Filed: Nov. 5, 2010

(65) Prior Publication Data

US 2011/0065653 A1 Mar. 17, 2011

Related U.S. Application Data

(63) Continuation of application No. 11/998,798, filed on Nov. 30, 2007, now Pat. No. 7,863,017.

(60) Provisional application No. 60/868,119, filed on Dec. 1, 2006.

(51) Int. Cl.
*C07K 19/00* (2006.01)
*C12N 15/62* (2006.01)

(52) U.S. Cl. ...... 435/69.7; 514/16.5; 530/350; 536/23.4

(58) Field of Classification Search ........................ None
See application file for complete search history.

(56) References Cited

U.S. PATENT DOCUMENTS

| | | | |
|---|---|---|---|
| 5,011,912 | A | 4/1991 | Hopp et al. |
| 2002/0192710 | A1 | 12/2002 | Kaufman |
| 2005/0069985 | A1 | 3/2005 | Kaufman |
| 2005/0158281 | A1 | 7/2005 | Chamberlain et al. |
| 2006/0073586 | A1 | 4/2006 | Xiao |

OTHER PUBLICATIONS

Schwarze et al., In Vivo Protein Transduction: Delivery of a Biologically Active Protein into the Mouse, Sep. 3, 1999, Science 285:1569-1572.*

Rybakova et al., Utropin Binds Laterally along Actin Filaments and Can Couple Costameric Actin with Sarcolemma When Overexpressed in Dystrophin-deficient Muscle, May 2002, Molecular Biology of the Cell 13:1512-1521.*

Sonnemann et al., Functional Substitution by TAT-Utrophin in Dystrophin-Deficient Mice, May 2009, PLoS Medicine 6(5):e1000083, pp. 1-10.*

Lindsay, Mark A., Peptide-mediated cell delivery: application in protein target validation, 2002, Current Opinion in Pharmacology 2:587-594.*

Deconinick et al., Expression of truncated utrophin leads to major functional improvements in dystrophin-deficient muscles of mice, Nov. 1997, Nature Medicine 3(11):1216-1221.*

* cited by examiner

*Primary Examiner* — John Ulm

(74) *Attorney, Agent, or Firm* — Joseph T. Leone, Esq.; DeWitt Ross & Stevens S.C.

(57) ABSTRACT

Disclosed is a fusion protein including a full-length TAT-utrophin or an anti-dystrophinopathic fragment thereof, a method of treating dystrophinopathies (including Duchenne muscular dystrophy) using the fusion protein, a pharmaceutical composition for treating dystrophinopathies in mammals comprising the fusion protein, and nucleic acid constructs for expressing the fusion protein.

39 Claims, 12 Drawing Sheets

| $K_d$ (μM) | $B_{max}$ | Protect? | Protein |
|---|---|---|---|
| 0.2 | 1:14 | Yes | rUTR |
| 0.6 | 1:12 | Yes | UTRN-R10 |
| 1.4 | 1:10 | Yes | UTRN-R9 |
| 1.5 | 1:5 | Partial | UTRN-R6 |
| 2 | 1:3 | No | UTRN-R3 |
| 16 | 1:1 | No | UTR261 |
| No Binding Activity | | | UTRR1-R10 |

FIG. 2

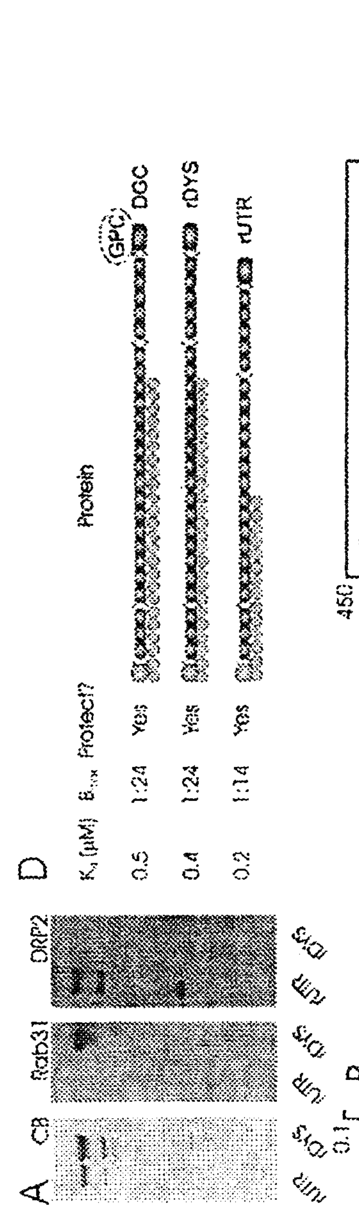
FIG. 3A
FIG. 3B
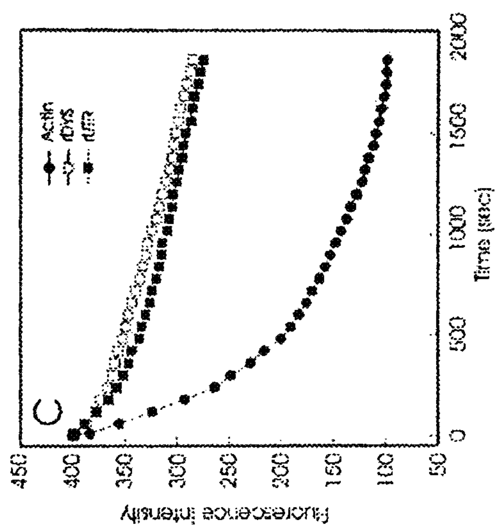
FIG. 3D
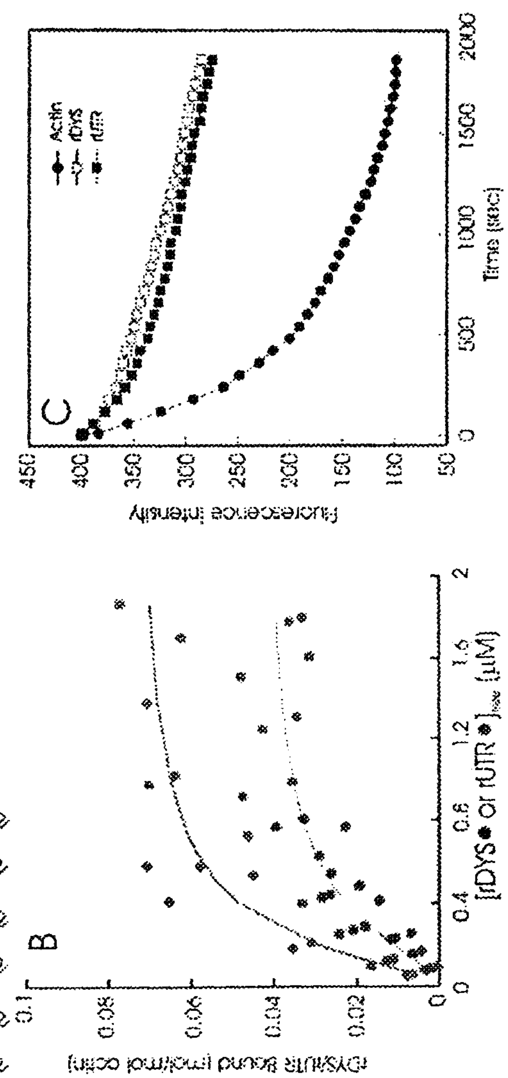
FIG. 3C

| Line/Protein | % Total Protein | % $Dys_{WT}$ |
|---|---|---|
| WT/Dystrophin | 0.02 | 100 |
| WT/Utrophin | 0.0006 | 3 |
| *mdx*/Utrophin | 0.0013 | 7 |
| Fiona/Utrophin | 0.014 | 70 |

FIG. 6A
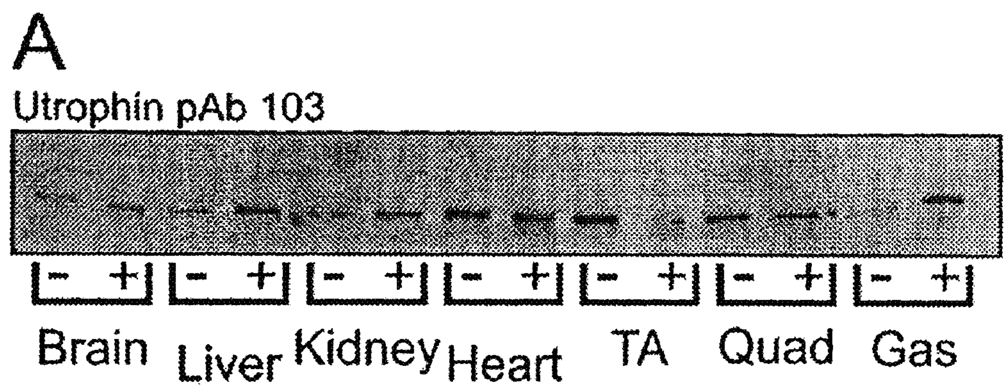
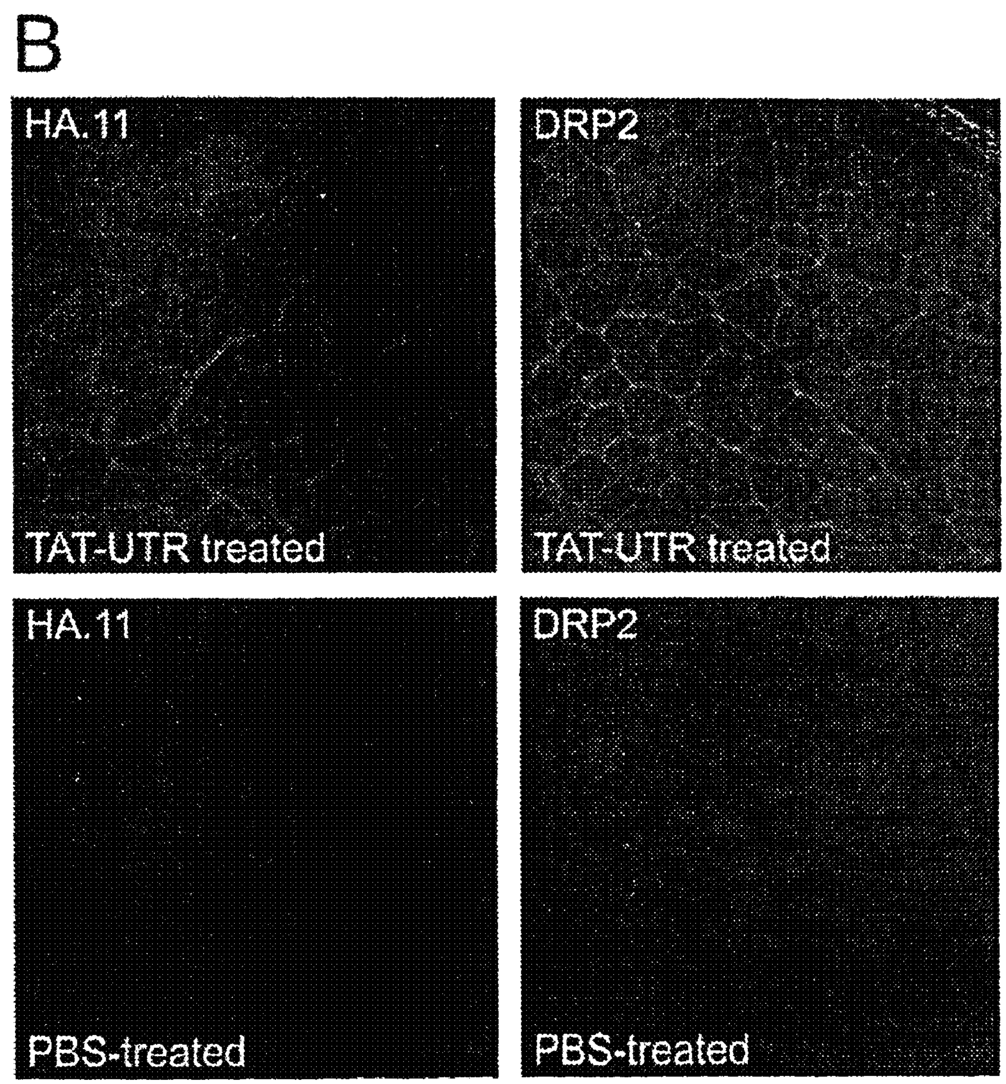
FIG. 6B

FIG. 7A
TA
TAT-UTR treated
FIG. 7D
TA
PBS-treated
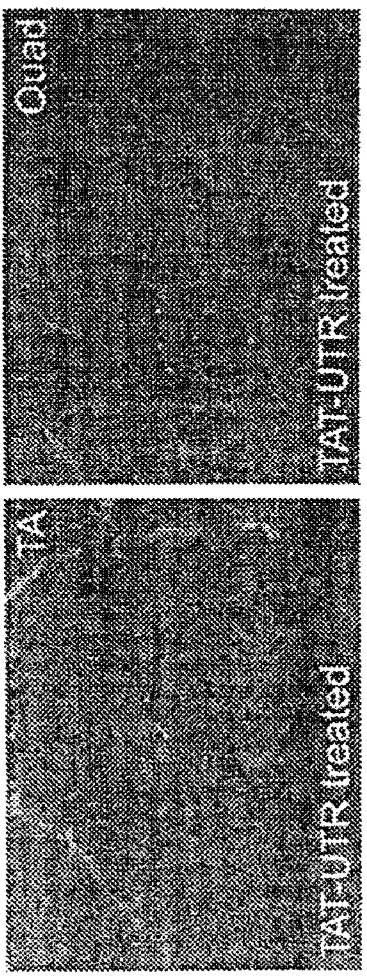
FIG. 7B
FIG. 7C
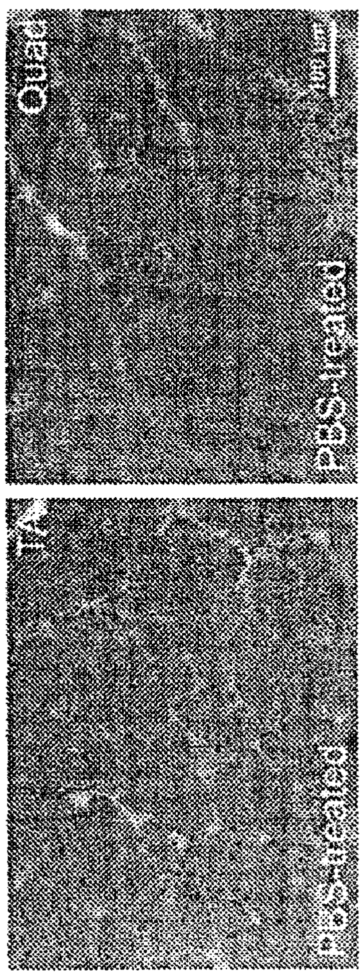
FIG. 7E
FIG. 7F

TAT-UTROPHIN AS A PROTEIN THERAPY FOR DYSTROPHINOPATHIES

CROSS-REFERENCE TO RELATED APPLICATIONS

This is a divisional of application Ser. No. 11/998,798, filed Nov. 30, 2007, now U.S. Pat. No. 7,863,017, issued Jan. 4, 2011 which claims priority to provisional application Ser. No. 60/868,119, filed Dec. 1, 2006, which is incorporated herein by reference.

FEDERAL FUNDING STATEMENT

This invention was made with government support under AR042423 awarded by the National Institutes of Health. The government has certain rights in the invention.

FIELD OF THE INVENTION

The invention is directed to a fusion protein comprising a full-length TAT-utrophin or an anti-dystrophinopathic fragment thereof, a method of treating dystrophinopathies (including Duchenne muscular dystrophy) using the fusion protein and a pharmaceutical composition for treating dystrophinopathies in mammals comprising the fusion protein.

BACKGROUND

Duchenne muscular dystrophy (DMD) is the most prevalent and severe form of human muscular dystrophy. DMD occurs with an incidence of 1 in 4000 male births. Onset of DMD is typically between 3 and 6 years of age with skeletal muscle weakness preferentially affecting the large proximal muscle groups. The disease is invariably progressive, leading to loss of ambulation by 11 to 13 years, and death typically in the 20's. Significant laboratory findings include grossly elevated serum CK-MM levels. Skeletal muscle biopsy samples reveal a dystrophic pattern of muscle degeneration and regeneration with fiber-size variation, increased central nuclei, and progressive interstitial fibrosis.

Becker muscular dystrophy (BMD) was long considered to be a potentially allelic disorder because of its clinical similarities to DMD and a common pattern of X-linked inheritance. The shared genetic basis for DMD and BMD was confirmed after the identification of the protein dystrophin; both DMD and BMD patients were shown to have dystrophin gene mutations. Typically, patients with DMD lack any detectable dystrophin expression in their skeletal muscles, and this is correlated with deletion mutations that disrupt the translational reading frame or point mutations that create stop codons. In contrast, muscle from patients with BMD contains mutated dystrophins having an altered size and/or reduced abundance secondary to deletion mutations that maintain the reading frame.

While clinical descriptions of DMD date back to the 1850's, over 100 years passed before evidence suggested that the muscle cell plasma membrane, or sarcolemma, is compromised in DMD muscle. The molecular basis for DMD and its associated sarcolemmal instability became more clear with landmark studies published in the mid-to-late 1980's which identified the gene encoding dystrophin as being defective in DMD (O'Brien and Kunkel, 2001). The DMD locus spans over 2.5 million bases distinguishing it as the largest gene in the human genome. The array of transcripts expressed from the DMD gene is complex due to the presence of multiple promoters and alternative splicing. The largest transcripts encode dystrophin, a four-domain protein with a predicted molecular weight of 427,000. Dystrophin is the predominant DMD transcript expressed in striated muscle. DMD gene mutations, deletions, or duplications most frequently result in a loss of dystrophin expression in muscle of patients afflicted with DMD. Based on its localization to the cytoplasmic face of the sarcolemma, and its sequence similarity with domains/motifs common to proteins of the actin-based cytoskeleton, dystrophin was hypothesized early on to play a mechanical role in anchoring the sarcolemma to the underlying cytoskeleton. It has also been hypothesized that dystrophin plays a role in protecting the sarcolemma against stress imposed during muscle contraction or stretch.

Biochemical studies aimed at confirming the hypothesized structure and function of dystrophin revealed its tight association with a multi-subunit complex, the so-named dystrophin-glycoprotein complex. See FIG. 1, which is a schematic representation showing the sarcolemma and the interaction of dystrophin with the other elements of the dystrophin-glycoprotein complex. Through its cysteine-rich and C-terminal domains, dystrophin in striated muscle interacts with the integral membrane dystroglycan sub-complex and the sarcoglycan/sarcospan sub-complex, as well as the subsarcolemmal dystrobrevins and syntrophins (Cohn and Campbell, 2000; Blake et al., 2002). The N-terminal domain and a portion of middle rod domain of dystrophin act in concert to effect an extensive lateral association with actin filaments in vitro (Rybakova et al., 1996) and in vivo (Rybakova et al., 2000; Warner et al., 2002; Rybakova and Ervasti, 1997; Amann et al., 1998; Amann et al., 1999).

Utrophin is a widely expressed autosomal gene product with high sequence similarity to dystrophin (Tinsley et al., 1992). Utrophin is distributed throughout the sarcolemma in fetal and regenerating muscle, but is down-regulated in normal adult muscle and is restricted to the myotendinous and neuromuscular junctions (Blake et al., 1996). Because utrophin and dystrophin bind the same complement of proteins (Matsumura et al., 1992; Kramarcy et al., 1994; Winder et al., 1995), it was hypothesized that utrophin may be capable of compensating for dystrophin deficiency. Indeed, continued utrophin expression in adult mdx mice partially attenuates the phenotype associated with dystrophin deficiency. In short, mice lacking both dystrophin and utrophin exhibit a more severe phenotype similar to that seen in human DMD patients (Deconinck et al., 1997a; Grady et al., 1997). Moreover, transgenic overexpression of full-length utrophin completely rescued the dystrophic phenotype in mdx mice (Tinsley et al., 1998).

Methods to express and purify full-length utrophin using a baculovirus system has been demonstrated (Rybakova et al., 2002 and 2006). It has also been shown that purified recombinant utrophin is a soluble, rod-shaped monomer with the expected molecular weight of 400,000 Da. Recombinant utrophin-bound actin filaments display an affinity ($K_d$=0.2 μM) similar to that measured for purified dystrophin-glycoprotein complex (Rybakova et al., 2002). Recombinant utrophin-bound F-actin displays a stoichiometry of 1 utrophin per 14 actin monomers, which implies a more extensive lateral association with actin filaments than anticipated from studies with isolated fragments, but a less extensive lateral association than the 1 per 24 stoichiometry measured for purified recombinant dystrophin (Rybakova et al., 2006) Like the dystrophin-glycoprotein complex, recombinant utrophin protected actin filaments from forced depolymerization in a concentration-dependent manner that saturated at molar ratios equal to or greater than 1 utrophin per 14 actin monomers.

Also different from purified dystrophin-glycoprotein complex, the binding of recombinant utrophin to actin filaments was completely insensitive to increasing ionic strength up to 0.8 M. These results (Rybakova et al., 2002) (Rybakova et al., 2006) indicate that dystrophin and utrophin both bind laterally alongside actin filaments through contributions by the spectrin-like repeats of the rod domain, but that the rod domain epitopes involved differ between the two proteins. Utrophin appears to bind laterally along actin filaments through a contribution of the first 10 acidic spectrin-like repeats (Rybakova et al., 2002) rather than a cluster of basic repeats as employed by dystrophin (Rybakova et al., 1996; Amann et al., 1998); (Rybakova et al., 2006).

Most viruses, including the human immunodeficiency viruses (HIV), encode proteins for regulating genome transcription. In HIV, the tat gene plays a role in driving the transcription of the HIV genetic code. The tat gene encodes a small nuclear protein of from 86 to 101 amino acids, depending upon the viral strain. Both the tat gene and its encoded protein, TAT, are known. The protein itself is designated TAT, for "transactivator protein." The typical HIV-1 laboratory strains HXB2 and NL4-3 express an 86 amino acid-long TAT protein, while other HIV strains express a 101 amino acid-long TAT protein. See, for example, Kuppuswamy et al., 1989.

Despite all that is now known, and despite continuing efforts by many laboratories around the world (Gregorevic and Chamberlain, 2003), there is presently no cure or effective treatment to alleviate the devastating progression of DMD.

SUMMARY OF THE INVENTION

The primary object of the present invention is a method of treating dystrophinopathies in mammals, including humans. The method comprises administering an anti-dystrophinopathic-effective amount of a chimeric protein (i.e., a fusion protein) encoding TAT-utrophin. The chimeric protein is administered in an amount effective to transduce skeletal muscle cells and thereby to correct the pathologies associated with dystrophin deficiency. The chimeric protein may comprise a full-length TAT protein (e.g., 86 amino acids long or 101 amino acids long) or a fragment thereof, such as the HIV-1 TAT protein transduction sequence (see SEQ. ID. NO: 5). Similarly, the chimeric protein may comprise a full-length utrophin protein or an anti-dystrophinopathic-effective fragment thereof. (For purposes of brevity, both full-length and fragmented versions of the chimeric protein will be referred to herein as the "TAT-utrophin chimeric (or fusion) protein.") Utrophin fragments can be evaluated for their anti-dystrophinopathic effects by transgenically over-expressing the putative anti-dystrophinopathic fragment in mdx mice in the same fashion as Tinsley et al., 1998 and observing whether the dystrophic phenotype in the mdx mice is ameliorated or eliminated. Alternatively, the TAT-utrophin chimeras can be tested on mdx mice as described herein below for their anti-dystrophinopathic efficacy.

The invention is also directed to a baculovirus construct that drives the expression of the TAT-utrophin chimeric protein, the chimeric protein encoding TAT-utrophin itself, as well as a pharmaceutical composition for treating dystrophinopathies that comprises an anti-dystrophinopathic amount of the TAT-utrophin chimeric protein in combination with a pharmaceutically suitable carrier.

Thus, one version of the invention is directed to a fusion protein comprising a first protein region which is effective to transduce the fusion protein into mammalian muscle cells. The first protein region preferably comprises an HIV TAT protein or a transduction-effective fragment thereof. The first protein region is operationally linked to a second protein region comprising a full-length utrophin protein or an anti-dystrophinopathic fragment thereof. Also included within the invention are pharmaceutically suitable salts of the fusion proteins.

Another version of the invention is directed to a nucleic acid construct (vector) that drives the expression of the above-noted fusion protein when the construct is transformed into a suitable host or disposed in a suitable cell-free expression system. Many cell-free expression systems are commercially available. For example, Promega (Madison, Wis.) markets a suitable cell-free expression system under the registered trademark "TNT." Promega's "TNT"®-brand systems are single-tube, coupled transcription/translation reactions for eukaryotic cell-free protein expression. To use these systems, 0.2 to 2.0 μg of circular plasmid DNA containing a T7, T3 or SP6 promoter, or a PCR-generated fragment containing a T7 promoter, is added to an aliquot of the "TNT"®-brand Quick Master Mix and incubated in a 50 μl reaction volume for 60 minutes at 30° C. Other cell-free systems are offered commercially by Qiagen (Valencia, Calif.), Invitrogen (Carlsbad, Calif.), and others.

The transformed host itself is also encompassed within the scope of the present invention.

Another version of the invention is directed to a pharmaceutical composition for treating dystrophinopathies in mammals, including humans. The pharmaceutical composition comprises a fusion protein as noted previously, or a pharmaceutically suitable salt thereof, in an anti-dystrophinopathic amount, in combination with a pharmaceutically suitable carrier.

Yet another version of the invention is directed to a method of treating dystrophinopathies, including DMD, in mammals. The method comprises administering to a mammalian subject in need thereof an anti-dystrophinopathic amount of an isolated fusion protein or a pharmaceutically suitable salt thereof, wherein the fusion protein comprises a first region which is effective to transduce the fusion protein into mammalian muscle cells. The first region is operationally linked to a second region comprising a full-length utrophin protein or an anti-dystrophinopathic fragment thereof.

As described herein, the present inventors have expressed full-length utrophin in a baculovirus system and have shown that the expressed protein can be purified as a highly soluble monomer. The monomer has actin-binding activities similar to those measured for recombinant dystrophin and purified dystrophin glycoprotein complex. The invention also encompasses a baculovirus expression construct (i.e. a "bacmid") that encodes full-length mouse utrophin fused with an amino-terminal peptide corresponding to the protein transduction domain of the HIV TAT protein. TAT-utrophin expresses to high levels in insect cells, is fully soluble, and can be rapidly purified by affinity chromatography.

Transduction of TAT-utrophin into the skeletal muscle of dystrophin-deficient mdx mice corrects the dystrophic phenotype displayed by the mdx mice.

BRIEF DESCRIPTION OF THE DRAWINGS

FIG. 2 is a graph depicting the relative lengths and actin-binding properties ($K_d$ and $B_{max}$) of serially-deleted constructs of utrophin.

FIGS. 3A, 3B, 3C, and 3D compare in various terms the actin-binding properties of recombinant dystrophin versus the actin-binding properties of utrophin. FIG. 3A shows parallel gels containing (moving from left to right) a Coomassie blue-stained gel loaded with recombinant utrophin (rUTR) and recombinant dystrophin (rDYS), western blots stained with rabbit 31 antibodies (Rab31) specific for dystrophin, and DRP2 antibodies specific against utrophin. FIG. 3B is a graph depicting F-actin co-sedimentation data for rDYS (lower trace) and rUTR (upper trace); the X-axis plots concentration in μM, the Y-axis plots bound rDYS and rUTR (mol/mol actin). FIG. 3C is a graph depicting the effect of dystrophin/utrophin on depolymerization of actin filaments containing PRODAN-labeled monomers (-●-=actin, -□=rDYS, -■-=rUTR). FIG. 3D is a graph depicting the relative lengths and actin-binding properties ($K_d$ and $B_{max}$) of the serially-deleted constructs.

FIGS. 6A and 6B depict uptake and membrane localization of TAT-utrophin in mdx muscle. FIG. 6A is a western blot that shows increased utrophin immuno-reactivity in several tissues of an mdx mouse after 6 intraperitoneal injections of TAT-UTR (+) compared to PBS-injected controls (−). FIG. 6B depicts the results of immunofluorescence analysis, which shows increased sarcolemmal HA-tag and DRP2 immunoreactivity in the TAT-UTR-treated animal (upper-left and upper-right panels, respectively) as compared to the sarcolemmal HA-tag and DRP2 immunoreactivity in PBS-injected controls (lower-left and lower-right panels, respectively).

FIGS. 7A, 7B, 7C, 7D, 7E, and 7F are a series of photographs showing greatly reduced histopathology in TAT-utrophin-treated mdx muscle versus controls. FIGS. 7A, 7B, and 7C depict TAT-utrophin-treated mdx muscle (TA and quadriceps), while FIGS. 7D, 7E, and 7F depict PBS-treated mdx muscle (TA and quadriceps). Haematoxylin and eosin stained sections revealed decreased numbers of centrally nucleated fibers and less fibrosis in TAT-UTR treated compared to PBS-injected mdx muscle.

DETAILED DESCRIPTION OF THE INVENTION

Definitions and Abbreviations

Figure 1:
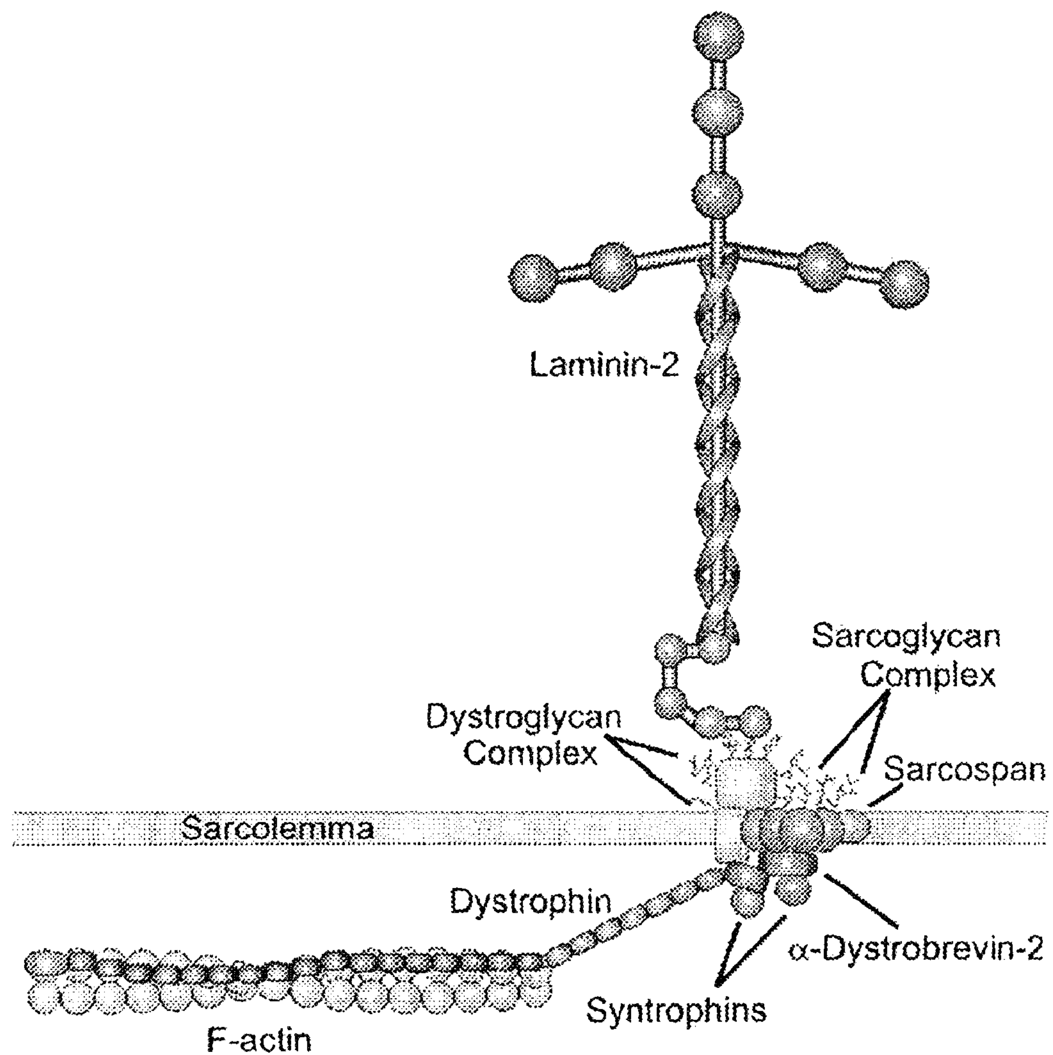
FIG. 1 is a schematic diagram of the dystrophin-glycoprotein complex.

The following abbreviations and definitions are used throughout the specification and claims. Any terms not explicitly defined herein are to be given their accepted meanings in the fields of molecular biology, physiology, and/or biochemistry.

Affinity tag: Any moiety (typically a small oligopeptide) that can be affixed to a protein (by any means) which allows the resulting fused entity to be isolated by affinity chromatography.

Anti-dystrophinopathic fragment: a fragment of a full-length utrophin protein that functions to ameliorate dystrophinopathic symptoms when administered as part of the fusion protein described herein. Explicitly included within this definition are the utrophin fragments shown in SEQ. ID. NOS: 10-25 in the attached Sequence List. (The "delta" nomenclature used in the Sequence List reflects the number of deleted repeats. Thus, the construct "murine TAT-UTR delta 4-21" encodes a murine TAT-utrophin fusion protein deleted for repeats 4-21.) It is preferred that the fragment be no more than 75% of the mass of the full-length utrophin protein, more preferred that the fragment be no more than 50% of the mass of the full-length utrophin protein, and still more preferred that the fragment be no more than 25% of the mass of the full-length utrophin protein.

Bacmid: baculovirus shuttle vector.

BMD: Becker muscular dystrophy.

DMD: Duchenne muscular dystrophy.

Dystrophinopathy: All pathological conditions in mammals, including humans, due in full or in part to mutations in the gene(s) encoding the protein dystrophin (both now known or discovered in the future). Explicitly included within the definition of "dystrophinopathy" are BMD, DMD, EDMD, SBMA, XLDCM, elevated serum creatine kinase, and the like.

EDL: extensor digitorum longus muscle.

EDMD: Emery-Dreifuss muscular dystrophy.

"FLAG"-brand polypeptide: Generally, any polypeptide having the sequence DYKDDDDK (SEQ. ID. NO: 1), or a fragment thereof, such as the tetrapeptide DYKD (SEQ. ID. NO: 28), which can be used for isolating fusion proteins via affinity chromatography. The terms "FLAG" and "ANTI-FLAG" are registered trademarks of Sigma-Aldrich Biotechnology LP (St. Louis, Mo.). "FLAG"-brand polypeptides are available commercially from Sigma-Aldrich. See also Chubet & Brizzard (1996) "Vectors for expression and secretion of FLAG epitope-tagged proteins in mammalian cells," *Biotechniques* 20(1):136-141.

HIV-TAT or TAT: Human immunodeficiency virus transactivator protein. "Tat" is short for "transactivator," a regulatory gene that accelerates the production of more HIV virus. "TAT" designates the protein, while "tat" designates the corresponding gene that encodes the TAT protein. In its native milieu, the TAT protein binds to the start of a new HIV RNA strand. Once bound, TAT encourages the transcription of the remainder of the HIV genetic code. TAT from HIV is a protein containing from 86 to 101 amino acids, depending upon the strain of HIV. The 86 amino acid-long sequence of HIV-1 TAT is shown in SEQ. ID. NO: 2. The entire genomic sequence of the HIV-1 virus, including the tat gene (at nts 5377-5591 and 7925-7970), is shown in SEQ. ID. NO: 3. See Gaynor, R. B. (1995) Regulation of HIV-1 gene expression by the transactivator protein Tat. *Curr Top Microbiol Immunol* 193, 51-77. See also GenBank Accession No. AF033819 for a fully annotated version of the HIV-1 genomic sequence.

LGMD: Limb-Girdle muscular dystrophy.

mdx Mice: A strain of mice arising from a spontaneous mutation (mdx) in inbred C57BL mice. The mutation is X chromosome-linked and produces viable homozygous animals that lack the muscle protein dystrophin. Mdx mice have high serum levels of muscle enzymes, and possess histological lesions similar to human muscular dystrophy. The histological features, linkage, and map position of mdx make these mice a widely utilized animal model for Duchenne muscular dystrophy. Mdx mice can be purchased from several commercial suppliers, including The Jackson Laboratory, Bar Harbor, Me. (sold under the registered trademark "JAX").

Operationally linked: when referring to two or more regions of a protein or a nucleotide sequence, "operationally linked" means the two regions are physically linked either directly or indirectly via intervening amino acid residues, nucleotide bases, or any other type of linking moiety.

PBS: phosphate-buffered saline.

PCR: polymerase chain reaction.

Pharmaceutically-suitable salt: any acid or base addition salt whose counter-ions are non-toxic to the patient in pharmaceutical doses of the salts so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like.

SBMA: Spinal bulbar muscular atrophy (also known as Kennedy's disease).

TA: tibialis anterior muscle.

Transduction: in general, the transfer of DNA from one cell to another; typically transduction is mediated via a bacteriophage, but any means of transferring the DNA from its original source to its ultimate destination are included within the term "transduction" as used herein.

UTR or UTRN: utrophin. The nucleotide sequence for the human utrophin gene and the corresponding amino acid sequence for the encoded human utrophin protein are shown in SEQ ID NOS: 6 and 7, respectively; the nucleotide sequence for the murine utrophin gene and the corresponding amino acid sequence for the murine utrophin protein are shown in SEQ. ID. NOS: 8 and 9, respectively.

WT: wild-type.

XLDCM: X-linked dilated cardiomyopathy.

DETAILED DESCRIPTION OF THE INVENTION

A first version of the invention is directed to a TAT-utrophin fusion protein (TAT-UTR), and use of the TAT-UTR fusion protein to treat dystrophinopathies in mammals, including humans. To demonstrate the efficacy of the TAT-UTR to treat dystrophinopathies in mammals, the mdx mouse is used as a model to demonstrate that TAT-UTR is imported into striated muscle cells and that the TAT-UTR fusion protein eliminates or significantly reduces the dystrophic phenotype in mdx mice.

Thus, in this first version of the invention, purified TAT-utrophin is injected into dystrophin-deficient mdx mice in an anti-dystrophic-effective amount. The mdx mouse model serves to demonstrate efficacy in all mammals, including humans. Measurements are then taken to assess the extent to which the TAT-utrophin is transduced into striated muscle cells in vivo. The localization of the TAT-utrophin is then assessed to determine how much of the TAT-utrophin is localized to the sarcolemma. (As shown in FIG. 1, natural dystrophin exerts its biological effect in close conjunction with the sarcolemma.) Measurements are also taken to determine whether the TAT-UTR fusion protein becomes stably associated with other dystrophin-associated proteins. The progress of mdx mice treated with the TAT-UTR is then followed to measure the improvement of several well-established parameters of the dystrophic phenotype, such as specific force and force drop in the muscles of the treated mice versus the control mice.

A second version of the invention is directed to mini- and micro-TAT-UTR constructs and methods of using these constructs to treat dystrophinopathies in mammals, including humans. Thus, the invention also encompasses truncated mini- and micro-TAT-utrophin constructs and the use of these truncated versions of the protein to treat dystrophinopathies. Reducing the physical size of the fusion protein results in improved protein transduction in vivo. Two representative truncated constructs are described herein. These truncated fusion proteins are designed to retain full activity for all known binding partners of utrophin, but with a 40 to 50% reduction in the mass of the protein. A third construct is designed to mimic the structure of the most extensively truncated, fully-functional dystrophin micro-gene. Using TAT-UTR as a protein-based therapy for treating dystrophinopathies is a relatively low-cost, low-risk, but high-return approach to treating these currently intractable and fatal conditions. At present, there simply is no effective treatment available to treat prevalent dystrophinopathies such as DMD.

The present invention includes a series of utrophin constructs encoding the amino-terminal, actin-binding domain alone (UTRN), or the amino-terminal domain plus 4, 7, 10, or 11 spectrin-like repeats. FIG. 2 depicts the relative lengths of these constructs and their binding characteristics. As shown in FIG. 2, the constructs are designated herein as UTRN-R3, UTRN-R6, UTRN-R9, and UTRN-R10, respectively. Interestingly, the UTRN-R10 protein bound to actin filaments with essentially the same properties as full-length recombinant utrophin (rUTR), which suggests UTRN-R10 encodes the complete actin-binding region of utrophin (see FIG. 2). The UTRN-R9, UTRN-R6, and UTRN-R3 proteins each bound to actin filaments with progressively lower affinity and stoichiometry as compared to full-length utrophin and UTRN-R10. (See FIG. 2.) These results demonstrate that the first ten (10) spectrin-like repeats of utrophin dramatically enhance the F-actin binding affinity and lateral association of the amino-terminal domain and provide a molecular basis for the greater effectiveness of full-length utrophin in rescuing dystrophin-deficient muscle as compared to a utrophin mini-gene deleted for spectrin-like repeats 4-19.

The present inventors have also expressed and characterized full-length mouse dystrophin. Recombinant dystrophin binds to actin filaments with a $K_d$ of 0.4 μM and $B_{max}$ of 1 dystrophin molecule per 24 actin monomers (see FIG. 3D, second construct), which is remarkably close to the actin-binding properties of purified dystrophin-glycoprotein complex (Rybakova et al., 1996). In direct comparisons (see FIGS. 3A, 3B, and 3C), dystrophin and utrophin differed only in their extent of lateral association with actin filaments (1-to-24 for dystrophin and 1-to-14 for utrophin), and in the effect of increasing ionic strength on actin filament binding. These results strongly suggest that dystrophin and utrophin are both actin-binding proteins, but that the molecular epitopes important for filament binding differ between the two proteins.

While transgenic utrophin overexpression rescued all known phenotypes associated with dystrophin-deficiency in mdx mice (Tinsley et al., 1998), there remains a widespread perception that utrophin levels must greatly exceed the amount of dystrophin expressed in normal muscle in order to cause full rescue from the dystrophinopathic phenotype exhibited by mdx mice. This perception is based, at least in part, on an early quantitative estimate (Hoffman et al., 1987) of dystrophin abundance in normal muscle (0.002% of total muscle protein) and the present inventors' own measurements of utrophin expression (Rybakova et al., 2002) in normal (0.0006%) and mdx muscle (0.0013%), as well as in the Fiona line of transgenic mdx mice that overexpress utrophin to levels (0.014%) that fully corrected the mdx phenotype. (See Tinsley et al., 1998). From these measurements, it can reasonably be concluded that up to 7-fold greater levels of utrophin (0.014%/0.002%) may be necessary to compensate for dystrophin deficiency.

However, the early measurements of dystrophin levels in normal muscle used a relatively small recombinant protein fragment (Hoffman et al., 1987). While state-of-the-art at that time, the much smaller protein fragment used as the standard likely transferred to nitrocellulose more efficiently than the full-length dystrophin protein. Thus, it is possible that the previous measurements (Hoffman et al., 1987) may have significantly underestimated the abundance of dystrophin in normal muscle. Therefore, the abundance of dystrophin in normal skeletal muscle has now been measured by quantitative western blotting using full-length recombinant mouse dystrophin as the standard and iodinated secondary antibody as previously described for utrophin (Rybakova et al., 2002). The measurements (see the table shown in FIG. 4) suggest that the abundance of dystrophin in normal muscle is 10-times greater (0.021±0.003%, n=7)(Rybakova et al., 2006) than previously reported (Hoffman et al., 1987). The new measurements more closely agree with the measured abundance of dystrophin (Ohlendieck et al., 1991) in highly purified sarcolemma vesicles (2% of sarcolemmal protein) and with quantitative estimates that sarcolemmal proteins comprise 1% of total muscle protein based on the density of sodium channels in total homogenates (0.09 μmol/mg total protein) and in purified sarcolemmal vesicles (8 μmol/mg sarcolemmal protein) from rat skeletal muscle (Barchi and Weigele, 1979).

Most importantly, however, these data indicate that utrophin can fully rescue the mdx phenotype (Tinsley et al., 1998) when expressed to levels approaching that of dystrophin in normal muscle (0.014%/0.02%=70%).

The present invention is thus a method of using recombinant utrophin as a protein-based therapy for treating dystrophinopathies in general and DMD in particular. The present method uses TAT-utrophin chimeric (i.e., fusion) proteins. The TAT portion of the chimeric protein serves to mobilize the protein (i.e., transduce the protein) into muscle cells. The UTR portion of the chimeric protein serves to ameliorate or to eliminate the dystrophic condition.

One distinct benefit of the invention is that utrophin itself is not toxic. Therefore, the TAT-UTR fusion proteins can be administered in relatively high doses, thereby making it easier to transduce therapeutically effective amounts of the TAT-UTR fusion protein into muscle cells. Ubiquitous transgenic over-expression of utrophin itself caused no toxicity in a broad range of tissues (Fisher et al., 2001). Thus, in the present invention, an 11 kb full-length mammalian utrophin cDNA (mouse) (Guo et al., 1996) was cloned in-frame into the bacterial expression vector pTAT (Nagahara et al., 1998), which was kindly provided by Dr. Steven Dowdy (University of California, San Diego). A Kozak consensus sequence and a"FLAG"-brand type epitope were engineered in-frame 5' to TAT-utrophin by PCR.

Figure 10:
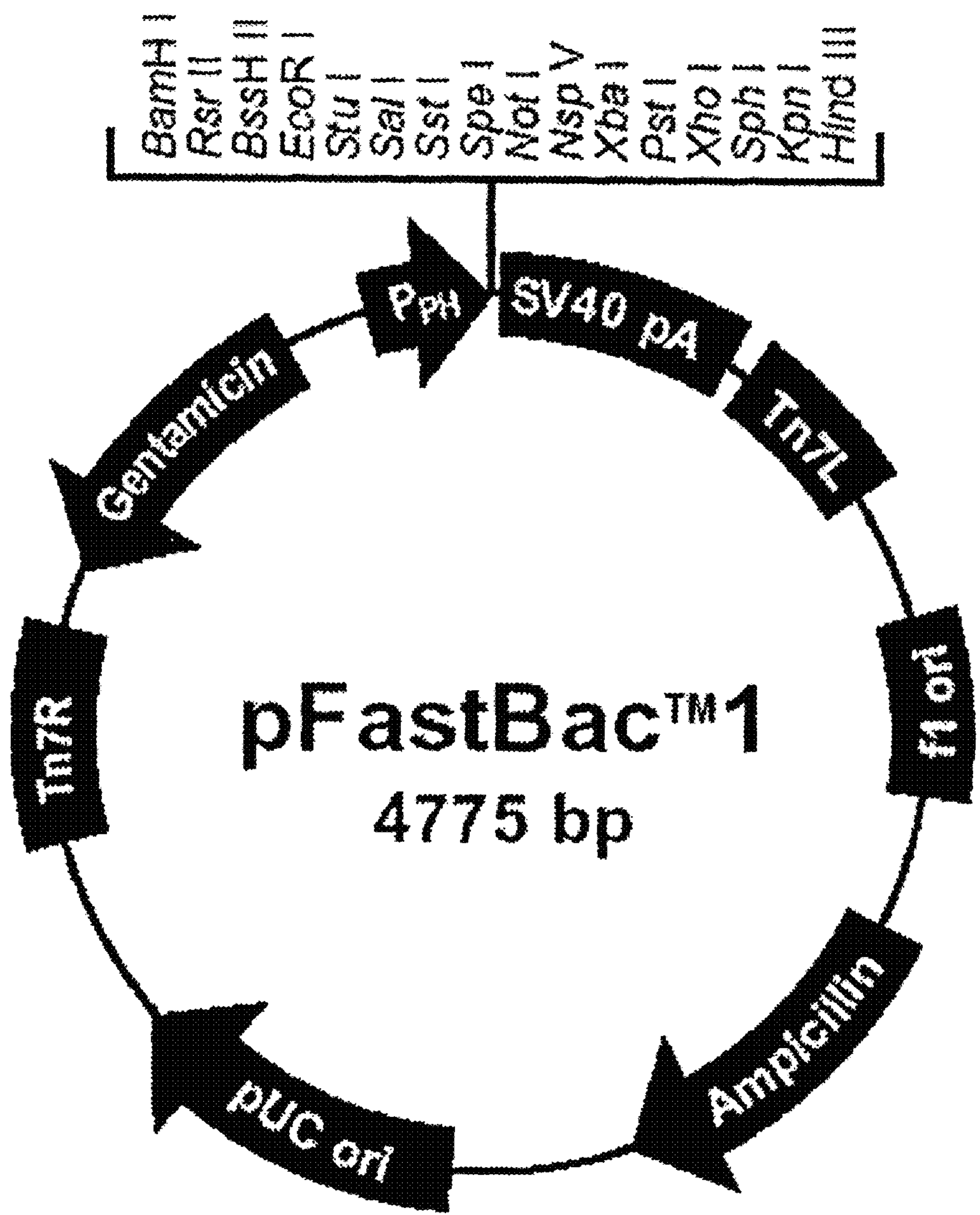
FIG. 10 is a map of the pFastBac1-brand plasmid, available commercially from Invitrogen.

The FLAG-TAT-utrophin construct was inserted into the pFastBac1 donor plasmid (purchased commercially from Invitrogen, Carlsbad, Calif.). A map of the pFastBac1 donor plasmid is shown in FIG. 10 and the complete sequence of pFastBac1 is presented in SEQ. ID. NO: 4. Subsequent transformation into DH10Bac cells (purchased commercially from Invitrogen, catalog no. 18290-015) allowed for site-specific transposition into bMON14272 bacmid DNA. (The bMON14272 bacmid, along with the helper plasmid pMON7124, are included with the DH10Bac cells sold by Invitrogen. See Invitrogen's catalog no. 10359-016, and the product literature for Invitrogen's "BAC-TO-BAC"®-brand baculovirus expression system.)

Figures 4, 5:
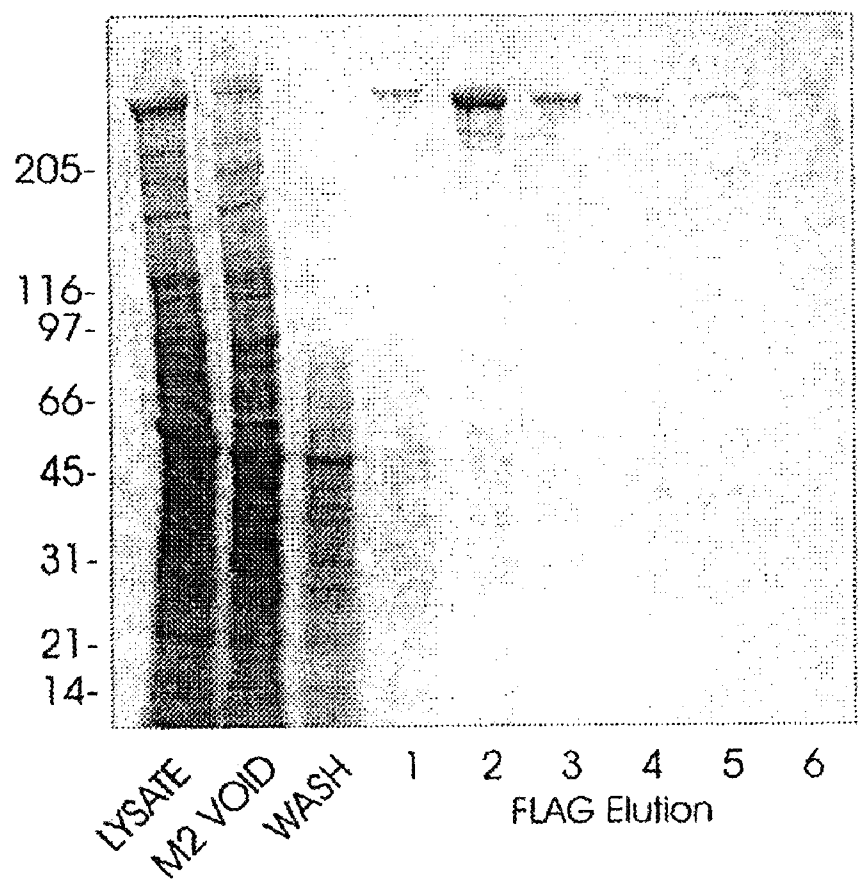
FIG. 4 is a graph depicting the quantitation of dystrophin and utrophin levels in skeletal muscle. The abundance of dystrophin and utrophin was measured in wild-type, mdx, and "Fiona" transgenic mdx mice overexpressing full-length utrophin by quantitative western blot analysis using recombinant dystrophin and utrophin as standards. Values are expressed as percent of total muscle protein and percent of dystrophin abundance in wild-type muscle.
FIG. 5 is a gel showing the expression and purification of TAT-utrophin in the baculovirus system. See the examples for lane assignments.

Colonies containing recombinant bacmid DNA were identified by blue/white screening and high titer viral stocks were used to infect Sf21 insect cells (*Spodoptera frugiperda*) for protein expression. (Sf21 cells are available commercially from a number of international suppliers, including Orbigen Inc., San Diego Calif., and Gentaur, Brussels, Belgium.) Infected Sf21 cells were harvested 72 h post-infection and TAT-utrophin was purified from cell lysates using "ANTI-FLAG"-brand M2 affinity resin (obtained commercially from Sigma-Aldrich, St. Louis, Mo.). The gel depicted in FIG. 5 shows that FLAG-TAT-utrophin is expressed as a fully soluble protein and can be easily purified by "ANTI-FLAG" M2 affinity chromatography. Thus, sufficient TAT-utrophin can easily be prepared to perform a host of experiments. Moving from left-to-right, the lanes of the gel in FIG. 5 depict the cell lysate prior to chromatography, the M2 column void volume, and the M2 column wash. The lanes numbered 1-6 then depict the elution of the M2 column to obtain the resulting fusion protein.

To assess whether TAT-utrophin is measurably transduced into skeletal muscle, a 2.5 week-old mdx mouse received six intraperitoneal injections of TAT-utrophin (20 mg/kg in sterile PBS) administered biweekly. As a control, a littermate mdx mouse was sham-injected with sterile PBS in parallel. At age six weeks, both mice were euthanized, perfused with PBS, and muscle tissue was excised for western blot, immunofluorescence and histological analyses. Western blot analysis of lysates from several tissues showed increased utrophin immunoreactivity in the TAT-utrophin-treated mdx mouse compared to the PBS-injected animal. See FIG. 6A, which is a gel depicting the utrophin immunoreactivity of the treated mouse versus the untreated mouse in several different tissue types. Importantly, immunofluorescence analysis of muscle cryosections revealed both increased HA-tag and DRP2 immunoreactivity localized to the sarcolemma of muscle from the animal treated with TAT-utrophin. See FIG. 6B, where the two upper panels depict immunoreactivity in the treated mouse and the two lower panels depict immunoreactivity in the untreated mouse.

Most strikingly, light microscopic analysis of haematoxylin and eosin-stained muscle cryosections showed dramatically decreased fibrosis and numbers of centrally nucleated myofibers in the TAT-utrophin treated animal compared to PBS-injected control. Compare FIGS. 7A, 7B, and 7C (which are photos of tibialis anterior ("TA") and quadriceps ("QUAD") muscle fibers from treated mice) to FIGS. 7D, 7E, and 7F (which are corresponding photos from untreated mice). In the quadriceps, the percentage of centrally nucleated fibers was 48% in the PBS-injected control, but only 24% in the TAT-utrophin-treated animal. The combined data of FIGS. 6A, 6B, 7A, 7B, 7C, 7D, 7E, and 7F show that TAT-utrophin effectively transduced skeletal muscle cells in vivo, correctly localized to the sarcolemma, and improved the histopathology of dystrophin-deficient mdx muscle.

Figure 8B:
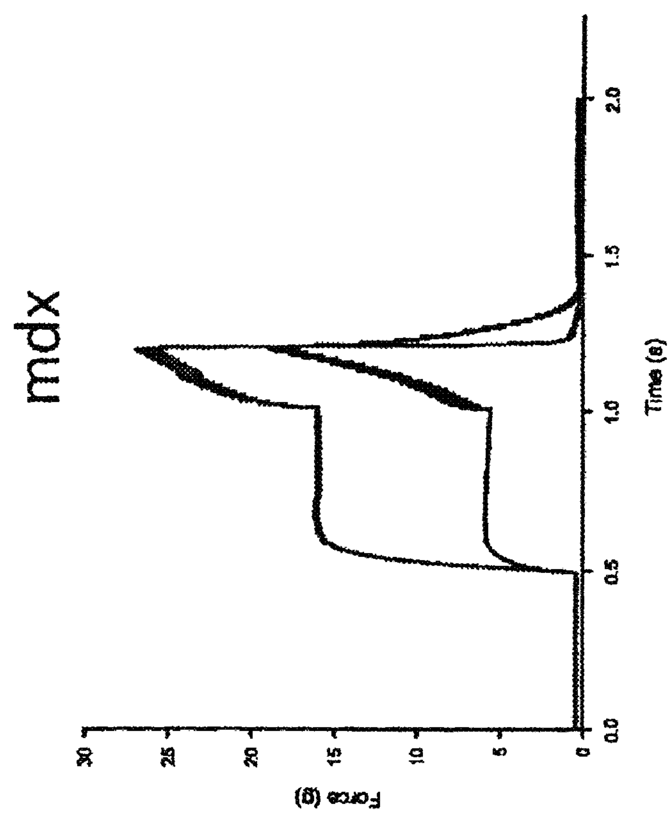
FIGS. 8A and 8B are graphs depicting the increased susceptibility of mdx muscles to eccentric contraction. Shown are tracings of maximal force versus time obtained during the first (upper trace) and fifth (lower trace) eccentric contraction imposed on isolated EDL muscle from wild-type (WT) and dystrophin-deficient mdx mice. Note the greater force drop in mdx muscle versus WT muscle as previously reported by Petrof et al. (1993) and Moens et al. (1993).
Figure 8A:
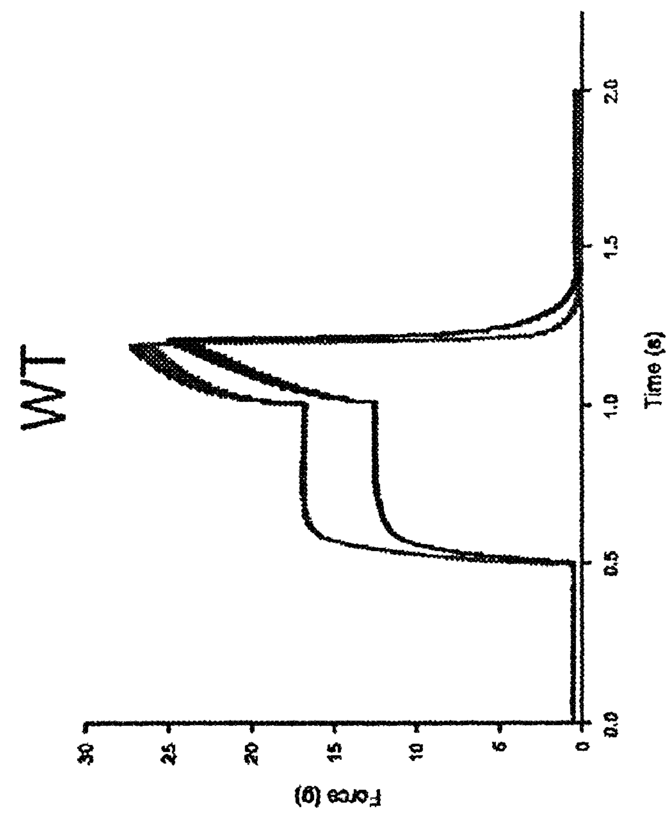

Of course, recovery of muscle function is the ultimate criterion for evaluating the efficacy of any therapy for dystrophinopathies. Several studies have demonstrated that specific force production by mdx muscle is significantly decreased. It has also been shown that mdx muscle is hypersensitive to lengthening and eccentric contraction (Petrof et al., 1993; Moens et al., 1993). Therefore, these parameters were measured in sham- and TAT-utrophin treated mdx mice. (Kind thanks are extended to Dr. Richard L. Moss for his aid in conducting these tests.) FIGS. 8A and 8B provide data demonstrating that the eccentric contraction protocol described in Petrof et al. (1993) and Moens et al. (1993) can be performed and that these tests performed by the present inventors reproduced the key findings of Petrof et al. (1993) and Moens et al. (1993).

Regarding the key utility of the present invention, the Examples presented below clearly demonstrate that dystrophinopathic mammals treated according to the present invention show a significantly increased specific force produced by their muscles as compared to untreated dystrophinopathic mammals, as well as a significantly decreased force drop. See Example 3 and FIGS. 11 and 12. Thus, the utility of the compounds, compositions, and methods of the present invention is to ameliorate the disabling effects of dystrophinopathic conditions in mammals, including DMD in humans.

As indicated above, the invention includes pharmaceutical compositions comprising the fusion protein(s) described herein and/or a pharmaceutically acceptable salt thereof together with a pharmaceutically acceptable carrier. The compositions may also include other therapeutically active substances in addition to the fusion protein and/or salt thereof. The pharmaceutical compositions of the invention comprise an amount of the fusion protein and/or a pharmaceutically suitable salt thereof that is effective to ameliorate dystrophinopathic symptoms in a mammal suffering from a dystrophinopathy. In a pharmaceutical composition of the invention, the carrier must be pharmaceutically acceptable in the sense of being compatible with other ingredients in the particular composition and not deleterious to the recipient thereof. The compositions include those suitable for oral, topical, rectal or parenteral (including subcutaneous, intramuscular, intraperitoneal, intradermal and intravenous) administration. Parenteral administration, either via the intramuscular or the intraperitoneal routes, is preferred.

In a particular version of the invention, the pharmaceutical compositions comprise the active ingredient (the fusion protein or a salt thereof) presented in a unit dosage form.

The term "unit dosage" or "unit dose" is denoted to mean a predetermined amount of the active ingredient sufficient to be effective for treating dystrophinopathy. Preferred unit dosage formulations are those containing a daily dose, daily subdose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form.

Compositions of the present invention suitable for oral administration may be presented as discrete unit dosages, e.g., as capsules, cachets, tablets, boluses, lozenges and the like, each containing a predetermined amount of the active ingredient; as a powder or granules; or in liquid form, e.g., as a collyrium, suspension, solution, syrup, elixir, emulsion, dispersion and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered active compound with any suitable carrier.

Compositions suitable for parenteral administration conveniently comprise a sterile injectable preparation of the active ingredient in, for example, a solution which is preferably isotonic with the blood of the recipient. Useful formulations also comprise concentrated solutions or solids containing the active ingredient which upon dilution with an appropriate solvent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredient formulated into pharmaceutically-acceptable topical vehicles by conventional methodologies. Common formulations include drops, collyriums, aerosol sprays, lotions, gels, ointments, plasters, shampoos, transferosomes, liposomes and the like.

Compositions suitable for inhalation administration, wherein the carrier is a solid, include a micronized powder or liquid formulation having a particle size in the range of from about 5 μm or less to about 500 μm, for rapid inhalation through the nasal or oral passage from a conventional inhalation squeeze or spray container. Suitable liquid nasal compositions include conventional nasal sprays, nasal drops and the like, of aqueous solutions of the active ingredient and optional adjuvants.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants), and the like.

The amount of active ingredient required to be effective for any specific dystrphinopathy in any specific patient will, of course, vary with the individual mammal being treated and is ultimately at the discretion of the medical or veterinary practitioner. The factors to be considered include the species and sex of the mammal, the dystrophinopathic condition being treated, the route of administration, the nature of the formulation, the mammal's body weight, surface area, age and general condition, and the particular compound to be administered.

In general, the pharmaceutical compositions of this invention contain from about 0.5 to about 500 mg and, preferably, from about 5 to about 350 mg of the active ingredient, preferably in a unit dosage form, for each of the indicated activities. However, a suitable effective dose is in the range of about 0.1 to about 200 mg/kg body weight per day, preferably in the range of about 1 to about 100 mg/kg per day, calculated as the non-salt form of the fusion protein. The total daily dose may be given as a single dose, multiple doses, e.g., two to six times per day, or by intravenous or parenteral infusion for a selected duration. Dosages above or below the range cited above are within the scope of the present invention and may be administered to the individual patient if desired and necessary. In topical formulations, the subject compounds are preferably utilized at concentrations of from about 0.1% to about 5.0% by weight.

EXAMPLES

The following Examples are presented solely to provide a more complete description of the invention disclosed and claimed herein. The Examples do not limit the scope of the invention claimed herein in any fashion.

Example 1

Expression, Purification of TAT-Utrophin; General Protocols 1.a. Expression and Purification of TAT-Utrophin. High titer stocks of recombinant baculovirus encoding the "FLAG"-tagged TAT-utrophin chimera were used to infect Sf21 insect cells for protein expression by a shaker culture procedure described in the manufacturer's instructions. Infected Sf21 cells were harvested 72 h post-infection and resuspended in 10 ml of 50 mM Tris-HCl, pH 7.4, 150 mM NaCl, 1% Triton X-100, and a cocktail of protease inhibitors. The soluble lysate was circulated over a 2 ml "ANTI-FLAG" M2 agarose column (Sigma-Aldrich). The column was washed extensively with 10 mM Tris-HCl, pH 7.4, 150 mM NaCl and bound protein eluted with the same buffer containing 100 μg/ml "FLAG"-brand peptide (Sigma-Aldrich). Purified protein was concentrated in a Centricon 100 column (Amicon) and quantified with the Bio-Rad DC Protein Assay Kit using BSA as standard. The typical yield of pure utrophin was 700 μg when only five 177 $cm^2$ plates of cell monolayer were used as a starting material. The protocols can be easily scaled up as needed.

Quality control analysis. The data indicate that TAT-utrophin is abundantly expressed in a highly soluble form that can be readily purified by "ANTI-FLAG" affinity chromatography (see FIG. 5). It is critical to note that including the TAT sequence within the fusion protein has no adverse effect on utrophin structure/function. The purified TAT-utrophin is to be analyzed by gel permeation chromatography (Rybakova and Ervasti, 1997), velocity sedimentation analysis (Ervasti et al., 1991) and electron microscopy after rotary shadowing (Rybakova et al., 2002). These analyses yield quantitative measures for the native molecular weight, dimensions, shape, oligomeric/aggregative state as well as an assessment of proper folding.

The F-actin binding properties of TAT-utrophin are measured using the established high-speed co-sedimentation assay (see FIG. 3B) and binding data is analyzed by nonlinear regression analysis. These experiments will yield both the apparent $K_d$ and $B_{max}$ of recombinant protein binding to F-actin. See FIG. 3D. The ability of different proteins to protect actin filaments from depolymerization is measured by monitoring the time-dependent decay in fluorescence of preformed filaments seeded with PRODAN-labeled (i.e., 6-propionyl-2-(N,N-dimethyl)aminonaphthalene-labeled) monomers at Cys374 (Marriott et al., 1988; Miyata et al., 1997) as shown in FIG. 3C. All data is compared to those measured for recombinant utrophin performed in parallel.

More specifically, an 11 kb full-length murine utrophin cDNA was subcloned in-frame into the bacterial expression vector pTAT to generate PTAT-Utr. To prepare for eventual expression and purification of TAT-Utrophin in Sf21 insect cells using a baculovirus expression system, a Kozak consensus sequence and FLAG-epitope were engineered in-frame at the extreme 5' end of TAT-Utr using PCR primers KJS36 (5' gcggccgcacaccatggactacaaggacgacgatgacaagggctacggccgca agaaac-3') (SEQ. ID. NO: 26) (FLAG-epitope is underlined) and KJS32 (5'-ggagatgcacagcaacagtttcaggacttagg-3') (SEQ. ID. NO: 27). This FLAG-TAT-utrophin construct was inserted into the bacmid donor plasmid pFastBac1 (Invitrogen, Carlsbad, Calif.) and subsequently transformed into DH10BAC (Invitrogen) bacterial cells to allow for site-specific transposition into bacmid DNA. Recombinant bacmid DNA was purified and used to transfect Sf21 cell monolayers in order to generate recombinant baculovirus. Recombinant virus infection of Sf21 monolayers and recombinant protein purification using anti-FLAG M2 affinity resin (Sigma, St. Louis, Mo.) was performed as per the manufacturer's instructions.

Elution fractions were pooled, dialyzed against phosphate buffered saline (PBS) overnight, and concentrated using a Centricon 100 (Millipore, Concord, Mass.). The purified protein was sterilized for injection by passage through a 0.22 μm filter and injected into the intraperitoneal cavity of mdx mice at a concentration of 0.5 to 1.0 mg/ml. The pure protein was stable for up to 4 days when kept on wet ice at 4° C. (assessed by a lack of degradation on Coomassie blue stained SDS-polyacrylamide gels), so a single protein preparation was utilized for up to 2 injections when possible. Otherwise, protein was prepared fresh for each injection.

1.b. Treatment Time Course. Pairs of female C57B1/10ScSn-Dmdmdx/J (The Jackson Laboratory, Bar Harbor, Me.) littermates were treated in parallel, one of which received a dose of 20 μg TAT-utrophin/g body weight while the control mouse received equal volume injections of sterile PBS. A total of 6 biweekly injections were administered over three weeks, beginning at 18 days and culminating at 35 days of age. Three days after the final injection, serum and tissue were collected for creatine kinase, western blot, immunofluorescence, histological, and physiological analyses. Animals were housed and treated in accordance with the standards set by the University of Wisconsin Institutional Animal and Care and Use Committee.

1.c. Protein extracts and Western Blotting. Tissues were dissected from freshly killed mice and snap frozen in liquid nitrogen. Frozen tissue was pulverized with a liquid nitrogen-cooled mortar and pestle and solubilized in 1% SDS, 5 mM EGTA, and a cocktail of protease inhibitors. Samples were incubated for 2 minutes at 100° C. and centrifuged 2 min at 12000×g. The supernatant protein concentration was determined with the Bio-Rad DC protein assay kit using bovine serum albumin as standard. Equal amounts of protein was separated by SDS-PAGE and transferred to nitrocellulose. Western blot analysis of utrophin levels was performed with rabbit polyclonal antibody 103 raised against the carboxyl-terminus of utrophin (generously provided by Dr. Stanley Froehner, University of Washington) diluted 1:250 in BLOTTO (i.e., bovine lacto transfer technique optimizer, a blocking reagent made from nonfat dry milk and PBS) (5% milk in PBS, pH 7.5) and anti-FLAG monoclonal antibody M2 (Sigma) diluted 1:1000 in BLOTTO. (BLOTTO blocking reagents are also commercially available from, for example, Thermo-Fisher Scientific, Waltham, Mass., catalog no. PI-37530.)

1.d. Histological and Morphometric Analysis. Individual muscles were dissected from freshly killed mice, coated with "O.C.T." matrix solution ("TissueTek"®-brand, Sakura Finetek, Torrance, Calif.; O.C.T. refers to "optimum cutting temperature," a specimen matrix formulation comprising water-soluble glycols and resins for cryostat sectioning at temperatures of −10° C. and below), and rapidly frozen in liquid nitrogen-cooled isopentane. Ten (10) μm thick cryosections were cut on a Leica CM3050 cryostat, allowed to dry, and stained with hematoxylin and eosin-phloxine. Sections cut from the mid-belly of both the tibialis anterior and quadriceps were selected for histological assessment. Images were collected on a Zeiss Axiovert 25 microscope and compiled into montages of entire sections in CorelDraw10 and exported to Scion Image (Scion Corporation, Frederick, Md.) for morphometric analyses. The percentage of centrally nucleated fibers and fiber diameters were determined from one muscle of each mouse, with every fiber scored for CNF analysis and ~700 fiber diameters measured per muscle section. A Student's t-test was used to compare average CNF values and average fiber diameter. To determine statistical significance of fiber diameter variability, a student's t-test was performed on the standard deviations of individual muscle sections.

1.e. Immunofluorescence. 10 μm thick cryosections were fixed in 4% paraformaldehyde for 10 minutes, washed 3×10 minutes in PBS, and blocked in 5% goat serum for 30 minutes. Primary antibodies were applied in 5% goat serum overnight at 4° C. and washed off 3×10 minutes in PBS. "ALEXA"®-brand 488- or 568-conjugated secondary antibodies (Invitrogen) were incubated for 30 min before a final 3×10 minute wash cycle. Coverslips were applied with a drop of Anti-Fade Reagent (Molecular Probes) and confocal images obtained using a Bio-Rad MRC1000 scan head mounted transversely to an inverted Nikon Diaphot 200 microscope at the Keck Center for Biological Imaging. Primary monoclonal antibodies used were anti-HA tag HA.11 (BABCO, Berkeley, Calif.) 1:1000; anti-utrophin DRP2 (Novacastra, Newcastle upon Tyne, UK) 1:10; anti-β-dystroglycan b-DG (Novacastra) 1:1000; anti-α-sarcoglycan (NCL-a-SARC; α-SG), (Novacastra) 1:1000; and anti-γ-sarcoglycan g-SARC (Novacastra) 1:1000.

1.f. Contractile Properties. All mechanical properties were adapted from Petrof et al. After rapid PBS perfusion, the extensor digitorum longus (EDL) muscles were quickly dissected tendon to tendon and immersed in an $O_2$-saturated Ringer's solution (135 mM NaCl, 4 mM KCl, 1 mM $MgCl_2$, 10 mM HEPES, 10 mM glucose, and 1.8 mM $CaCl_2$, pH 7.4) at 25° C. Suture silk (4-0) was used to attach one tendon to a rigid support and the other to a dual lever force transducer (Aurora Scientific, Ontario, Canada) and the entire apparatus was immersed in oxygenated Ringer's solution and allowed to equilibrate for 5 minutes. Muscles were stimulated through two platinum plate electrodes on either side of the muscle. A range of twitch stimulations were performed to determine $L_o$, the muscle length at which maximal twitch force was produced. After 5 minutes of recovery, the EDL was maximally activated to determine maximal tetanic tension. Data were normalized against cross-sectional area of each individual muscle.

Protection against mechanical injury was assessed by subjecting the muscle to a series of five eccentric contractions (ECC). Each ECC consisted of maximally activating the muscle for 700 ms, with a stretch of 0.5 $L_o$/s over the final 200 ms to result in a total stretch of 0.1 $L_o$. Five minutes of recovery time was allowed between each ECC. Force drop was calculated as (ECC1-ECC5)/ECC1. Data were compared using ANOVA followed by a Tukey post hoc test.

1.g. Serum CK Analysis. Retro-orbital bleeds were performed on anesthetized mice using heparinized capillary tubes. Approximately 100 μl of blood was obtained per mouse, centrifuged at 5000 rpm and the serum layer removed and stored at −80° C. for analysis. Creatine kinase levels were determined using Vitros CK DT slides (Ortho-Clinical Diagnostics, Raritan, N.J.) and analyzed using a Kodak Ektachem DT60 Analyzer as per the manufacturer's instructions. Data were collected in Units/ml and compared using a Student's T-test.

Example 2

Effect of TAT-Utrophin on the Dystrophic Phenotype of mdx Mice

In this Example, purified TAT-utrophin is injected into dystrophin-deficient mdx mice. The mice are then examined to assess the extent to which the TAT-utrophin is transduced into striated muscle cells in vivo. The extent of uptake is measured, and the amount of TAT-utrophin localized to the sarcolemma is determined. Optionally, it may also be determined whether the TAT-utrophin becomes stably associated with other dystrophin-associated proteins. The quantitative improvement of several well-established parameters of the dystrophic phenotype is then measured in mdx mice treated with TAT-utrophin and compared to untreated controls and placebo groups.

Administration of TAT-utrophin—Purified TAT-utrophin is dialyzed against phosphate-buffered saline and sterilized by passage through a Millex-GP 0.22 μm filter. Assuming 100% protein transduction specifically into skeletal muscle, a minimal dose of 11 μg TAT-utrophin per gram body weight is believed to compensate for dystrophin deficiency. Of course, it is likely that TAT-utrophin will distribute to all tissues and transduction efficiency will almost certainly be less than complete. Therefore, TAT-utrophin is preferably administered via intraperitoneal injection at several different concentrations ranging from 1-5 mg/ml and total injection volumes of 0.1-0.5 ml.

Measurement of TAT-Utrophin Uptake and Cellular Location—TAT-utrophin uptake into skeletal muscle and cellular localization is assessed by two methods. In the first method, mice are deeply anesthetized with avertin, the chest wall is opened, and the animals are infused for 20 minutes with phosphate-buffered saline through the left ventricle with an outflow path from the right atrium. Skeletal muscles are then dissected and used in the preparation of KCl-washed skeletal muscle membranes (Ohlendieck et al., 1991), or immediately snap-frozen in liquid nitrogen to prepare SDS total protein lysates (Rybakova et al., 2002). Both preparations are analyzed for TAT-utrophin content by quantitative western blot analysis using "ANTI-FLAG"-brand M2 antibody (Sigma-Aldrich) detected with $^{125}$I-goat anti-mouse IgG and the signals quantitated by phosphor autoradiography. Analysis of total protein lysates and KCl-washed membranes provides a measure of the fraction of TAT-utrophin stably associated with the sarcolemma. The absolute utrophin content in SDS muscle lysates of TAT-utrophin-treated mice is also quantitatively compared to the utrophin content of sham-treated mdx mice and transgenic mdx mice expressing full-length utrophin (Fiona) to levels that rescue all known phenotypes of mdx mice. These comparisons provide a quantitative assessment of the TAT-utrophin uptake relative to a fully-rescued transgenic animal model.

In the second method, anesthetized animals are infused for 2 minutes with PBS followed by a 20 minute infusion of 2% paraformaldehyde in PBS. Various skeletal muscles are dissected, post-fixed for 5 minutes in 2% paraformaldehyde, and frozen in liquid nitrogen-cooled isopentane. From 8 μm cryosections, both the uptake and cellular location of TAT-utrophin is assessed using confocal immunofluorescence microscopy.

The KCl-washed membranes, SDS lysates and cryosections prepared from TAT-utrophin-treated mdx mice are also used to detect alterations in the abundance and sarcolemmal localization of other proteins within the dystrophin-glycoprotein complex including α- and β-dystroglycan, α-, β-, γ- and δ-sarcoglycans, syntrophin and α-dystrobrevins. Relative protein abundance can be assessed by quantitative western blot analysis of total muscle SDS extracts (Rybakova et al., 2002), while cellular localization and organization can be assessed by immunofluorescence analysis of both longitudinal and transverse cryosections and mechanically peeled sarcolemma (Rybakova et al., 2000).

Assessment of costamere structure and function—To assess whether TAT-utrophin treatment can restore mechanical coupling between the sarcolemma and costameric γ-actin, confocal immunofluorescence microscopy analysis is performed on mechanically peeled sarcolemma (Rybakova et al., 2000) from sham and TAT-utrophin-treated mdx mice. Paraformaldehyde-fixed sarcolemma are blocked for 2 h at 4° C. with 5% serum in PBS and incubated with the appropriate primary antibodies overnight at 4° C. The specimens are washed with PBS, incubated with fluorescent secondary antibody for 30 min at 37° C., rinsed and sealed under coverslips in an anti-fade solution.

Assessment of Dystrophic Phenotype—Skeletal and cardiac muscle of dystrophin-deficient mdx mice exhibits several histologic and physiologic defects in common with patients suffering from Duchenne muscular dystrophy. Most notable (and easily measured) are a dramatic elevation in centrally nucleated fibers of irregular size resulting from muscle fiber necrosis/regeneration and elevated serum creatine kinase levels due to sarcolemmal instability.

For histologic analysis, 8 μm cryosections of skeletal muscle from control, sham-injected, and TAT-utrophin-injected mdx mice are stained with haematoxylin and eosin and the percentage of central nuclei and mean fiber diameter measured. Histological analyses are also performed on several different muscles to compare the effects of TAT-utrophin on different fiber types, and muscles experiencing different work loads and activities. Measurement of these parameters in C57BL/10 control and sham-injected mdx mice provides a baseline and elevated values for normal and dystrophic muscle, respectively. While the number of centrally-nucleated fibers is already quite high (~40%) in 4 week-old mdx mice (Warner et al., 2002), this parameter doubles yet again by 10-12 weeks of age (Warner et al., 2002). Therefore, it is possible to measure a decrease in the percentage of centrally nucleated fibers in mdx mice treated for 2 months with TAT-utrophin compared to sham-treated mice.

To assess for sarcolemmal damage, quantitative colorimetric analysis of serum creatine kinase levels is performed using CK DT slides (Ortho-Clinical Diagnostics) measured with a Kodak Ektachem DT 60 Analyzer. A minimum of 5 animals in each treatment regime are measured at several time points post-injection. Evans blue infiltration is also assessed, which has been shown to accumulate significantly in dystrophin deficient mdx cardiac and skeletal muscle (Straub et al., 1997). Evans blue dye in sterile PBS is injected into the tail veins of control and knockout littermates and the animals sacrificed 3-6 h after dye administration. After skinning, the animals are visually inspected for macroscopic dye uptake by a blue coloration of limb muscles. 100% of mdx mice and 0% of control mice exhibit indication of membrane damage by this technique (Straub et al., 1997). In addition, 8 μm cryosections are examined by immunofluorescence microscopy to quantitate the fraction of muscle cells infiltrated by Evans blue (Straub et al., 1997).

Assessment of contractile function—Several studies have demonstrated that specific force production by mdx muscle is significantly decreased and hypersensitive to lengthening, or eccentric contraction (Petrof et al., 1993; Moens et al., 1993). Thus, the measure isometric twitch and tetanic tension in intact muscles from sham- and TAT-utrophin treated mdx mice are measured. The EDL muscle is dissected tendon to tendon and allowed to equilibrate in oxygenated mammalian Ringers' solution (Eddinger et al., 1986), and then tied into a dual mode force transducer (Aurora Scientific). The muscle length ($L_o$) at which maximal twitch tension is obtained is determined with a single pulse at a stimulation frequency of 2500 Hz at increasing muscle lengths. After a 10 minute wait, the muscle undergoes a series of 5 eccentric contractions (ECC) with the maximal tetanic tension measured for each round. The ECC protocol involves stimulation at 150 Hz at $L_o$ for 500 msec followed by lengthening the muscle by 0.5 $L_o$/sec for 200 msec before relaxing at a rate of 0.5 $L_o$/sec for 200 msec. This protocol results in a stretch equal to 10% $L_o$. There is a 5 minute wait in between each ECC to allow the muscle to recover. All measurements are recorded and analyzed using Dynamic Muscle Control and Analysis Software (Aurora Scientific).

Example 3

Generation of Mini- and Micro-TAT-Utrophin Constructs

In parallel with the experiments described in Example 1, the invention also encompasses fusion proteins wherein the utrophin portion of the fusion protein has been truncated (to lower the molecular weight of the fusion protein), without deleteriously impacting the anti-dystrophinopathic activity of the fusion protein. Thus, the invention encompasses truncated, but fully functional mini- and micro-TAT-utrophin constructs. It is hoped that reducing the size of the chimera leads to improved protein uptake.

Figures 9A, 9B:
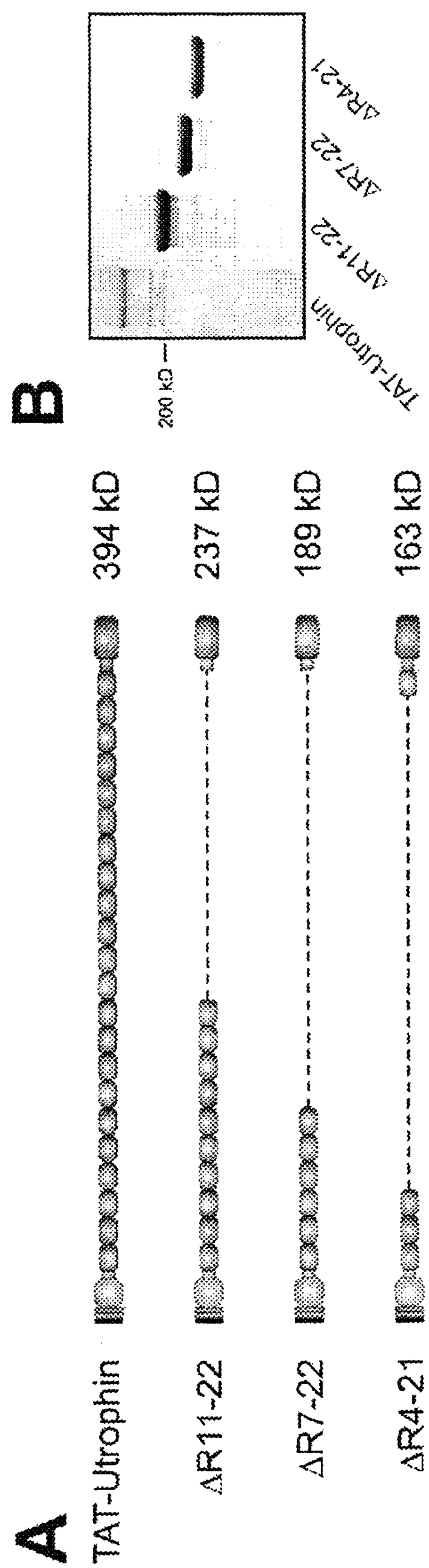
FIG. 9A is a schematic representation of mini- and micro-TAT-utrophin constructs according to the present invention.
FIG. 9B is a Coomassie Blue-stained protein gel of the truncated TAT-utrophin constructs depicted schematically in FIG. 9A.

Bacmid construction—Mini- and micro-TAT-utrophin constructs are generated with the "BAC-TO-BAC"-brand expression system (Invitrogen), which has been used to express full-length mouse utrophin (Rybakova et al., 2002), dystrophin (see FIG. 3A), and numerous truncation constructs (see FIG. 2). Briefly, all expression constructs are PCR-amplified from the TAT-utrophin construct using PfuUltra high-fidelity DNA polymerase (Stratagene) to incorporate an amino-terminal "FLAG"-brand type purification tag (DYKDDDDK) (SEQ. ID. NO: 1) followed by the HIV TAT protein transduction sequence (YGRKKRRQRRR) (SEQ. ID. NO: 5). The HIV TAT protein transduction sequence is preferred. However, any sequence that functions to transduce the fusion protein into mammalian muscle cells may be used in its place. The mini- and micro-constructs planned or actually made are shown schematically in FIG. 9. Preferably, the constructs all contain intact cysteine-rich and carboxy-terminal domains to ensure optimal β-dystroglycan binding activity (Ishikawa-Sakurai et al., 2004).

Based on actin-binding studies of serially-truncated utrophin constructs performed by the present inventors (data not shown), it is expected that TAT-UTRΔR11-22 should have near-optimal actin filament binding activity, but with a 40% reduction in molecular weight (237,000) compared to full-length utrophin (394,000). TAT-UTRΔR7-22, which is less than half the molecular weight of full-length utrophin (189,000) will also be evaluated, but at the expense of diminished actin-binding activity. TAT-UTRΔR4-21 will also be generated and tested. This construct is expected to bind actin with the lowest affinity. It is an attractive compound for incorporation into a pharmaceutical composition because based on its small size (42% of full-length utrophin), and in light of the success of the analogous dystrophin micro-gene to rescue the mdx phenotype (Harper et al., 2002).

pFASTBAC1 donor plasmids carrying each new TAT construct is transformed into DH10BAC for site-specific transposition into bMON14272 bacmid DNA. Colonies containing recombinant bacmid DNA are identified by blue-white screening and high titer viral stocks produced for infection of Sf21 insect cells for protein expression. Protein purification, quality control and transduction efficacy are performed as described earlier.

Example 4

Dose-Dependent Amelioration of Dystrophin-Deficient Phenotype

To determine whether the ability of TAT-utrophin to ameliorate the dystrophin-deficient phenotype is dose-dependent, the protective effects of increased dosages of TAT-utrophin were assessed on the dystrophin-deficient mdx mouse. An initial dosage of 20 mg protein/g mouse body weight was arbitrarily designated as a dosage of "1×." A study was then performed in which littermate mdx mice were injected with 1× (20 μg protein/g body weight), 2× (40 μg protein/g body weight), and 5× (100 μg protein/g body weight) levels of TAT-utrophin. The timeline of treatment was consistent with the original 1× studies (see above) in which 2.5 week-old mdx mice received six intraperitoneal injections at the indicated dosage. The doses were administered bi-weekly. As controls, littermate mdx mice received sterile PBS injections in parallel. At six weeks of age, treated and control mice were euthanized and assessed for several functional and histological parameters of dystrophin deficiency.

Figure 11:
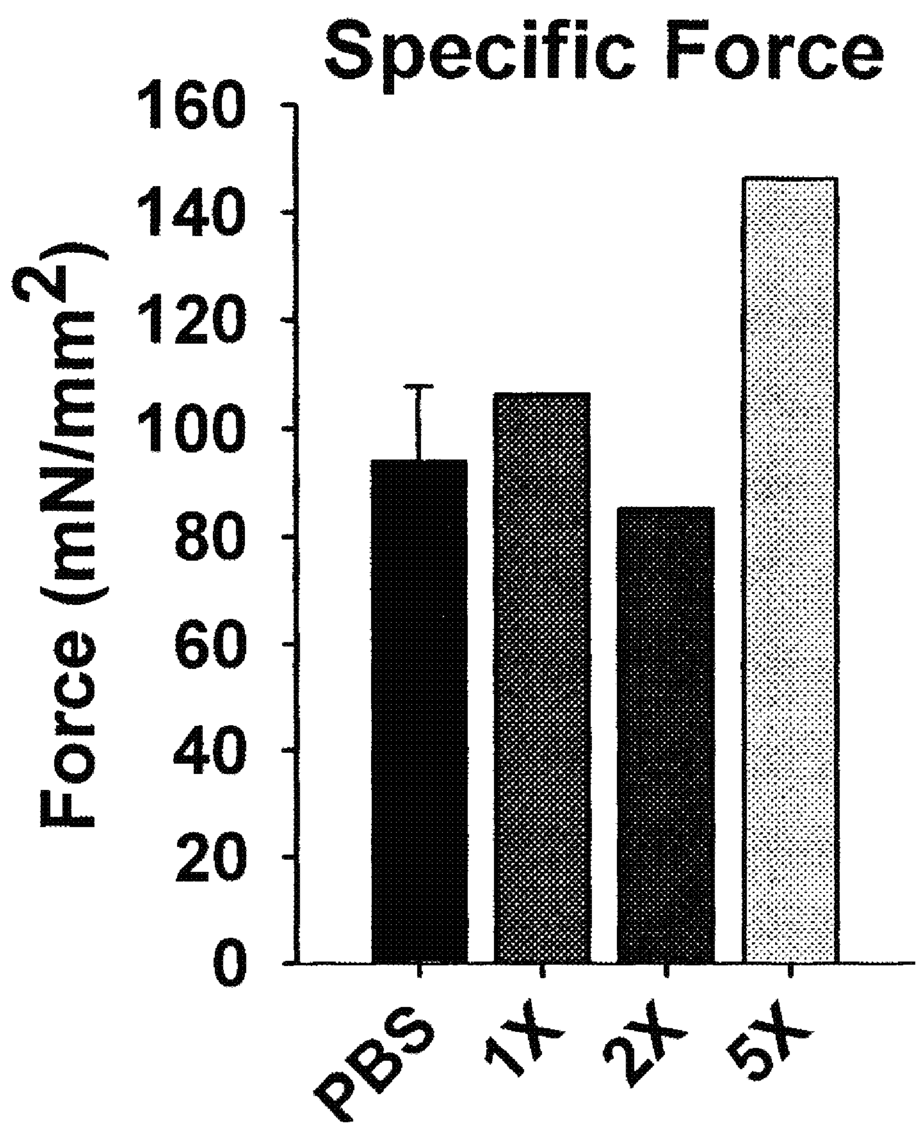
FIG. 11 is a histogram depicting the dose-dependent ability of TAT-utrophin to increase the specific force of muscle tissue in mdx mice treated with the TAT-utrophin.

Of note, the 5×-treated mdx mouse demonstrated an approximately 45% increase in specific force generation over PBS-injected mice (see FIG. 11, which depicts the results for PBS-treated versus TAT-utrophin-treated mice). Specific force is an index of maximal force generated by a muscle normalized against the cross-sectional area of the muscle; mdx muscle typically generates approximately 25-30% less specific force than wild-type mice (Petrof et al., 1993).

Figure 12:
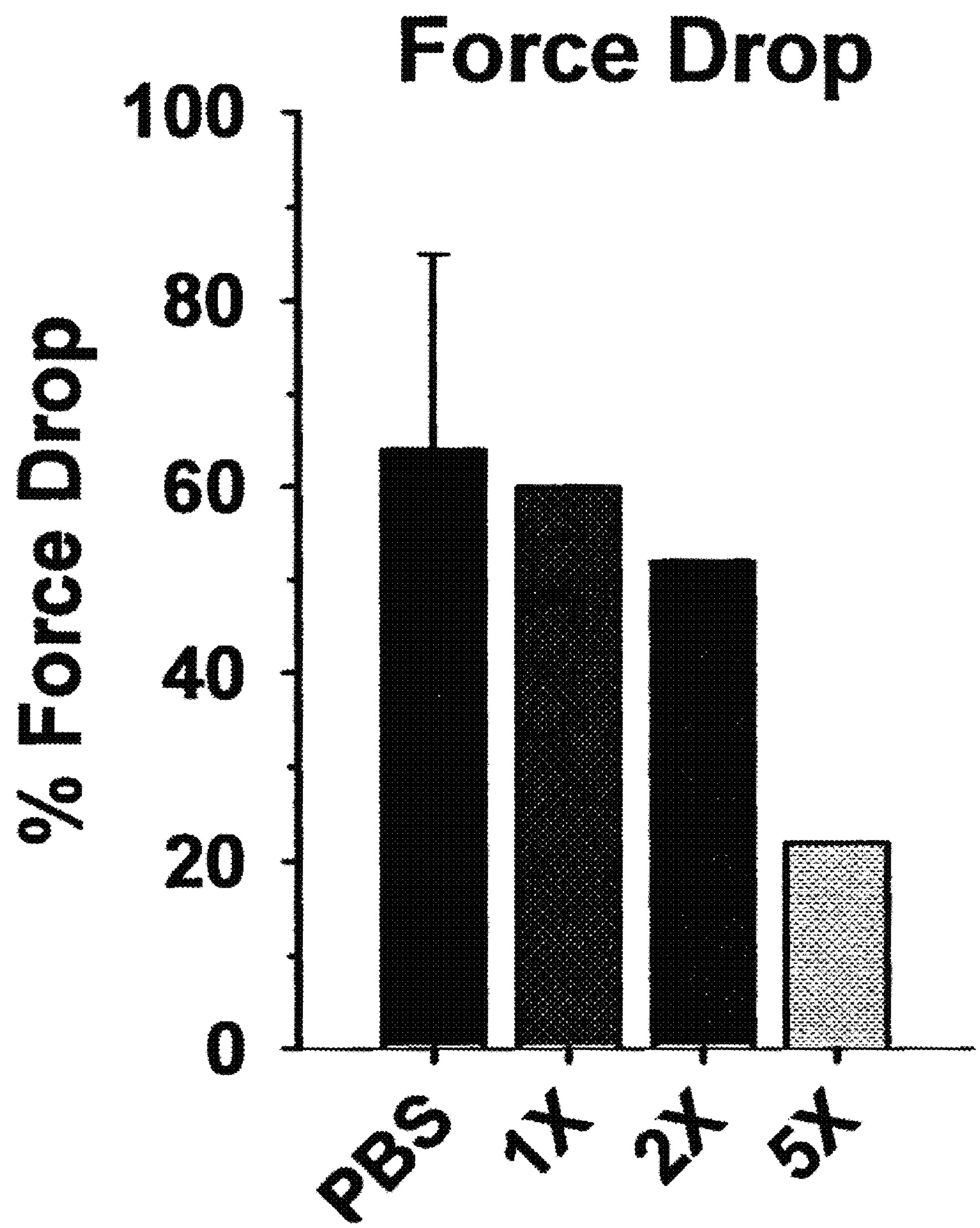
FIG. 12 is a histogram depicting the dose-dependent ability of TAT-utrophin to decrease contraction-induced injury of muscle tissue in mdx mice treated with the TAT-utrophin.

Additionally, the treated mdx mice exhibited a dose-dependent improvement in protection against contraction-induced injury (see FIG. 12, which depicts the results for PBS-treated versus TAT-utrophin-treated mice). Contraction-induced injury is a parameter quantified by the drop in maximal force generation after five (5) consecutive damaging eccentric contractions. Wild-type force drop values are typically 15-25%, while the corresponding mdx values range from 60-80% (Petrof et al., 1993). As shown in FIG. 12, the 5×-treated mdx mice had a force drop value in the range of 20%, which is well within the range for non-mdx, wild-type mice. In contrast, the PBS-treated mdx mice had a force drop value typical of mdx mice, an approximately 65% drop.

Example 5

Reduction of Serum Creatine Kinase in TAT-Utrophin-Treated Mice

Figures 13A, 13B:
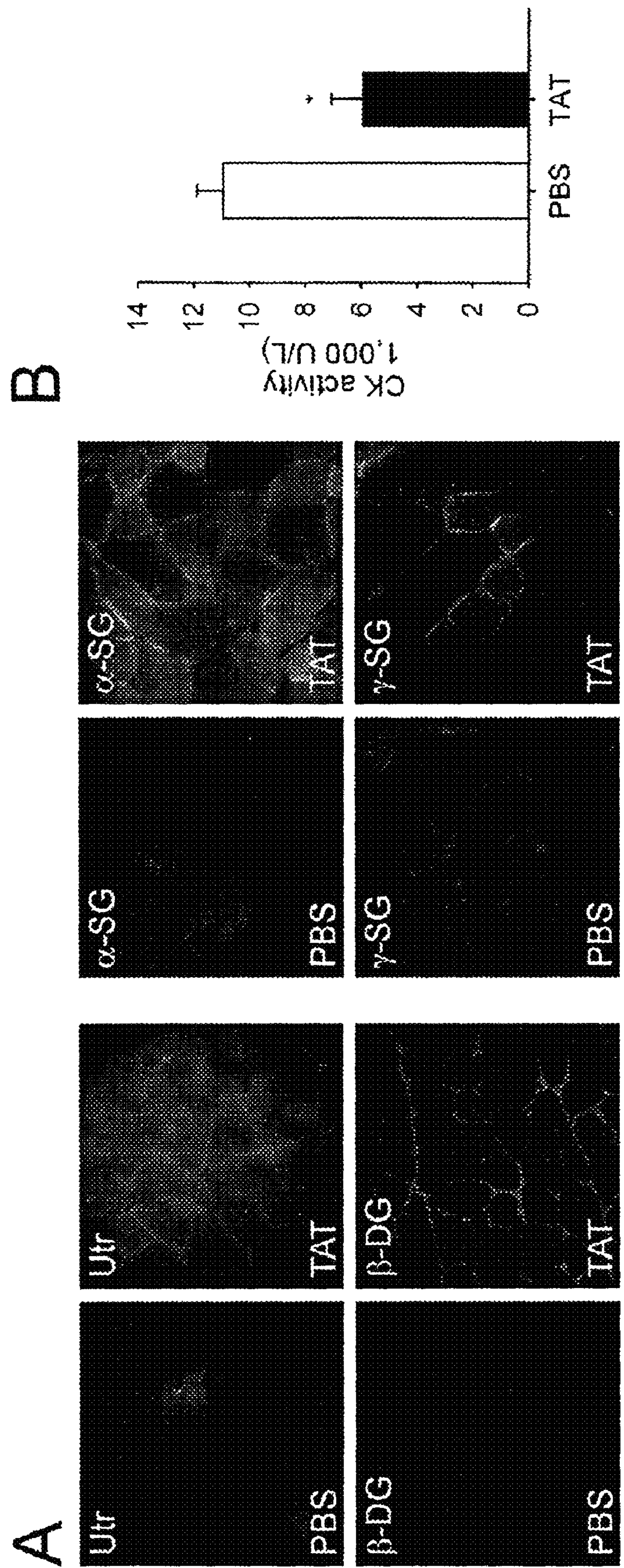
FIG. 13A depicts the results of immunofluorescence analysis on 10 μm thick cryosections from PBS- or TAT-utrophin-injected quadriceps from mdx mice. Primary antibodies to utrophin (NCL-DRP2; Utr), β-dystroglycan (NCL-b-DG; 13-DG), α-sarcoglycan (NCL-a-SARC; α-SG), and γ-sarcoglycan (NCL-g-SARC; γ-SG) demonstrated peripherally localized dystrophin complex members in the TAT-utrophin-treated mice.
FIG. 13B is a histogram depicting serum activity levels of the muscle enzyme creatine kinase from PBS- or TAT-utrophin-injected quadriceps from mdx mice. Creatine kinase levels were reduced 50% in 38 day-old TAT-utrophin-treated mice as compared to PBS-injected controls. (*) denotes $p<0.05$.

To assess whether the protective effects of TAT-utrophin were mitigated through restoration of dystrophin complex members to the sarcolemma, immunofluorescence analyses were carried out on cryosections from TAT-utrophin and PBS-injected quadriceps. While no signal was observed on cryosections from PBS-treated muscle stained for the transmembrane glycoproteins β-dystroglycan, α-sarcoglycan, and γ-sarcoglycan, each antibody probe revealed intense staining along the periphery of muscle cells from TAT-utrophin-treated mice (FIG. 13A). Sarcolemmal integrity was also assessed by measuring serum levels of the muscle-specific enzyme creatine kinase (CK), which are typically elevated ~20 fold in mdx mice. TAT-utrophin-treated mice demonstrated a 50% reduction in serum CK activity compared to PBS-injected controls. See FIG. 13B. These results strongly indicate that TAT-utrophin not only restored dystrophin complex members to the sarcolemma but also partially protected against membrane instability.

The significance of these Examples is that they show that the TAT-utrophin constructs function to ameliorate dystrophinopathy in a dose-dependent fashion. The Examples also show the now best-known combination of transduction efficiency, size, and pharmacological activity to rescue phenotypically dystrophic mammals.

REFERENCES

Amann, K. J., Guo, W. X. A., and Ervasti, J. M. (1999). Utrophin lacks the rod domain actin binding activity of dystrophin. *J. Biol. Chem.* 274:35375-35380.

Amann, K. J., Renley, B. A., and Ervasti, J. M. (1998). A cluster of basic repeats in the dystrophin rod domain binds F-actin through an electrostatic interaction. *J. Biol. Chem.* 273:28419-28423.

Barchi, R. L. & Weigele, J. B. (1979). Characteristics of saxitoxin binding to the sodium channel of sarcolemma isolated from rat skeletal muscle. *J. Physiol.* 295:383-396.

Blake, D. J., Tinsley, J. M., and Davies, K. E. (1996). Utrophin: A structural and functional comparison to dystrophin. *Brain Pathol.* 6:37-47.

Blake, D. J., Weir, A., Newey, S. E., and Davies, K. E. (2002). Function and genetics of dystrophin and dystrophin-related proteins in muscle. *Physiol Rev.* 82:291-329.

Cohn, R. D. & Campbell, K. P. (2000). Molecular basis of muscular dystrophies. *Muscle Nerve* 23:1456-1471.

Deconinck, A. E., Rafael, J. A., Skinner, J. A., Brown, S. C., Potter, A. C., Metzinger, L., Watt, D. J., Dickson, J. G., Tinsley, J. M., and Davies, K. E. (1997a). Utrophin-dystrophin-deficient mice as a model for Duchenne muscular dystrophy. *Cell* 90:717-727.

Deconinck, N., Tinsley, J., De Backer, F., Fisher, R., Kahn, D., Phelps, S., Davies, K., and Gillis, J. M. (1997b). Expression of truncated utrophin leads to major functional improvements in dystrophin-deficient muscles of mice. *Nature Med.* 3:1216-1221.

Eddinger, T. J., Cassens, R. G., and Moss, R. L. (1986). Mechanical and histochemical characterization of skeletal muscles from senescent rats. *Am. J. Physiol.* 251:C421-C430.

Ervasti, J. M., Kahl, S. D., and Campbell, K. P. (1991). Purification of dystrophin from skeletal muscle. *J. Biol. Chem.* 266:9161-9165.

Fisher, R., Tinsley, J. M., Phelps, S. R., Squire, S. E., Townsend, E. R., Martin, J. E., and Davies, K. E. (2001). Non-toxic ubiquitous over-expression of utrophin in the mdx mouse. *Neuromuscul. Disord.* 11:713-721.

Grady, R. M., Teng, H. B., Nichol, M. C., Cunningham, J. C., Wilkinson, R. S., and Sanes, J. R. (1997). Skeletal and cardiac myopathies in mice lacking utrophin and dystrophin: A model for Duchenne muscular dystrophy. *Cell* 90:729-738.

Gregorevic, P. and Chamberlain, J. S. (2003). Gene therapy for muscular dystrophy—a review of promising progress. *Expert. Opin. Biol. Ther.* 3:803-814.

Guo, W. X. A., Nichol, M., and Merlie, J. P. (1996). Cloning and expression of full length mouse utrophin: The differential association of utrophin and dystrophin with AChR clusters. *FEBS Lett.* 398:259-264.

Harper, S. Q., Hauser, M. A., DelloRusso, C., Duan, D., Crawford, R. W., Phelps, S. F., Harper, H. A., Robinson, A. S., Engelhardt, J. F., Brooks, S. V., and Chamberlain, J. S. (2002). Modular flexibility of dystrophin: implications for gene therapy of Duchenne muscular dystrophy. *Nat. Med.* 8:253-261.

Hoffman, E. P., Brown, R. H., and Kunkel, L. M. (1987). Dystrophin: the protein product of the Duchenne muscular dystrophy locus. *Cell* 51:919-928.

Ishikawa-Sakurai, M., Yoshida, M., Imamura, M., Davies, K. E., and Ozawa, E. (2004). ZZ domain is essentially required for the physiological binding of dystrophin and utrophin to beta-dystroglycan. *Hum. Mol. Genet.* 13:693-702.

Joliot, A. and Prochiantz, A. (2004). Transduction peptides: from technology to physiology. *Nat. Cell Biol.* 6:189-196.

Khurana, T. S. and Davies, K. E. (2003). Pharmacological strategies for muscular dystrophy. *Nat. Rev. Drug Discov.* 2:379-390.

Krag, T. O., Bogdanovich, S., Jensen, C. J., Fischer, M. D., Hansen-Schwartz, J., Javazon, E. H., Flake, A. W., Edvinsson, L., and Khurana, T. S. (2004). Heregulin ameliorates the dystrophic phenotype in mdx mice. *Proc. Natl. Acad. Sci. U.S.A.* 101:13856-13860.

Kramarcy, N. R., Vidal, A., Froehner, S. C., and Sealock, R. (1994). Association of utrophin and multiple dystrophin short forms with the mammalian $M_r$ 58,000 dystrophin-associated protein (syntrophin). *J. Biol. Chem.* 269:2870-2876.

Kuppuswamy, M., Subramanian, T., Srinivasan, A., and Chinnadurai, G. (1989). Multiple functional domains of Tat, the trans-activator of HIV-1, defined by mutational analysis. *Nucleic Acids Research,* 17(9):3551-3561.

Lindsay, M. A. (2002). Peptide-mediated cell delivery: application in protein target validation. *Curr. Opin. Pharmacol.* 2:587-594.

Marriott, G., Zechel, K., and Jovin, T. M. (1988). Spectroscopic and functional characterization of an environmentally sensitive fluorescent actin conjugate. *Biochemistry* 27:6214-6220.

Matsumura, K., Ervasti, J. M., Ohlendieck, K., Kahl, S. D., and Campbell, K. P. (1992). Association of dystrophin-related protein with dystrophin-associated proteins in mdx mouse muscle. *Nature* 360:588-591.

Miyata, H., Kinosita, K., Jr., and Marriott, G. (1997). Cooperative association of actin protomers and crosslinked actin oligomers in filaments at low ionic strength. *J. Biochem.* (Tokyo) 121:527-533.

Moens, P., Baatsen, P. H., and Marechal, G. (1993). Increased susceptibility of EDL muscles from mdx mice to damage induced by contractions with stretch. *J. Muscle Res. Cell Motil.* 14:446-451.

Nagahara, H., Vocero-Akbani, A. M., Snyder, E. L., Ho, A., Latham, D. G., Lissy, N. A., Becker-Hapak, M., Ezhevsky, S. A., and Dowdy, S. F. (1998). Transduction of full-length TAT fusion proteins into mammalian cells: TAT-p27Kip1 induces cell migration. *Nat. Med.* 4:1449-1452.

O'Brien, K. F. and Kunkel, L. M. (2001). Dystrophin and muscular dystrophy: past, present, and future. *Mol. Genet. Metab.* 74:75-88.

Ohlendieck, K., Ervasti, J. M., Snook, J. B., and Campbell, K. P. (1991). Dystrophin-glycoprotein complex is highly enriched in isolated skeletal muscle sarcolemma. *J. Cell Biol.* 112:135-148.

Petrof, B. J., Shrager, J. B., Stedman, H. H., Kelly, A. M., and Sweeney, H. L. (1993). Dystrophin protects the sarcolemma from stresses developed during muscle contraction. *Proc. Natl. Acad. Sci. U.S.A.* 90:3710-3714.

Rybakova, I. N., Amann, K. J., and Ervasti, J. M. (1996). A new model for the interaction of dystrophin with F-actin. *J. Cell Biol.* 135:661-672.

Rybakova, I. N. and Ervasti, J. M. (1997). Dystrophin-glycoprotein complex is monomeric and stabilizes actin filaments in vitro through a lateral association. *J. Biol. Chem.* 272:28771-28778.

Rybakova, I. N., Patel, J. R., Davies, K. E., Yurchenco, P. D., and Ervasti, J. M. (2002). Utrophin binds laterally along actin filaments and can couple costameric actin with the sarcolemma when overexpressed in dystrophin-deficient muscle. *Mol. Biol. Cell* 13:1512-1521.

Rybakova, I. N., Patel, J R., and Ervasti, J. M. (2000). The dystrophin complex forms a mechanically strong link between the sarcolemma and costameric actin. *J. Cell Biol.* 150:1209-1214.

Rybakova, I. N., Humston J. L., Sonnemann, K. J., Ervasti, J. M. (2006) Dystrophin and utrophin bind actin through distinct modes of contact. *J Biol. Chem.* 281 (15): 9996-10001.

Schwarze, S. R., Ho, A., Vocero-Akbani, A., and Dowdy, S. F. (1999). In vivo protein transduction: delivery of a biologically active protein into the mouse. *Science* 285:1569-1572.

Schwarze, S. R., Hruska, K. A., and Dowdy, S. F. (2000). Protein transduction: unrestricted delivery into all cells? *Trends Cell Biol.* 10:290-295.

Snyder, E. L. and Dowdy, S. F. (2004). Cell penetrating peptides in drug delivery. *Pharm. Res.* 21:389-393.

Straub, V., Rafael, J. A., Chamberlain, J. S., and Campbell, K. P. (1997). Animal models for muscular dystrophy show different patterns of sarcolemmal disruption. *J. Cell Biol.* 139:375-385.

Tinsley, J., Deconinck, N., Fisher, R., Kahn, D., Phelps, S., Gillis, J. M., and Davies, K. (1998). Expression of full-length utrophin prevents muscular dystrophy in mdx mice. *Nature Med.* 4:1441-1444.

Tinsley, J. M., Blake, D. J., Roche, A., Byth, B. C., Knight, A. E., Kendrick-Jones, J., Suthers, G. K., Love, D. R., Edwards, Y. H., and Davies, K. E. (1992). Primary structure of dystrophin-related protein. *Nature* 360:591-593.

Tinsley, J. M., Potter, A. C., Phelps, S. R., Fisher, R., Trickett, J. I., and Davies, K. E. (1996). Amelioration of the dystrophic phenotype of mdx mice using a truncated utrophin transgene. *Nature* 384:349-353.

Wang, B., Li, J., and Xiao, X. (2000). Adeno-associated virus vector carrying human mindystrophin genes effectively ameliorates muscular dystrophy in mdx mouse model. Proc. Natl. Acad. Sci. U.S.A. 97:13714-13719.

Warner, L. E., DelloRusso, C., Crawford, R. W., Rybakova, I. N., Patel, J. R., Ervasti, J. M., and Chamberlain, J. S. (2002). Expression of Dp260 in muscle tethers the actin cytoskeleton to the dystrophin-glycoprotein complex. *Hum. Mol. Genet.* 11:1095-1105.

Winder, S. J., Hemmings, L., Maciver, S. K., Bolton, S. J., Tinsley, J. M., Davies, K. E., Critchley, D. R., and Kendrick-Jones, J. (1995). Utrophin actin binding domain: analysis of actin binding and cellular targeting. *J. Cell Sci.* 108(1):63-71.

What is claimed is:

1. An isolated fusion protein comprising:

a first protein region which is effective to transduce the fusion protein into mammalian muscle cells, operationally linked to;

a second protein region comprising a full-length utrophin protein or an anti-dystrophinopathic fragment thereof.

2. The isolated fusion protein of claim 1, further comprising an affinity tag operationally linked to the fusion protein.

3. The isolated fusion protein of claim 2, wherein the affinity tag comprises an amino acid sequence DYKDDDDK (SEQ. ID. NO: 1) or a fragment thereof.

4. The isolated fusion protein of claim 2, wherein the affinity tag comprises an amino acid sequence DYKD (SEQ. ID. NO: 28).

5. The isolated fusion protein of claim 1, wherein the second protein region is an anti-dystrophinopathic utrophin fragment comprising an amino-terminal actin-binding domain of the utrophin protein, or the amino-terminal actin-binding domain plus 4, 7, 10, or 11 spectrin-like repeats.

6. The isolated fusion protein of claim 1, wherein the second protein region is an amino acid sequence selected from the group consisting of SEQ. ID. NOS: 7 and 9.

7. The isolated fusion protein of claim 1, which is an amino acid sequence selected from the group consisting of SEQ. ID. NOS: 11, 13, 15, 17, 19, 21, 23, and 25.

8. The isolated fusion protein of claim 1, wherein the second protein region is an anti-dystrophinopathic utrophin fragment comprising an amino-terminal actin-binding domain of the utrophin protein, or the amino-terminal actin-binding domain plus 4, 7, 10, or 11 spectrin-like repeats.

9. The isolated fusion protein of claim 1, wherein the second protein region is an amino acid sequence selected from the group consisting of SEQ. ID. NOS: 7 and 9.

10. The isolated fusion protein of claim 1, wherein the first protein region is an amino acid sequence as shown in SEQ. ID. NO: 2.

11. The isolated fusion protein of claim 10, wherein the second protein region is an anti-dystrophinopathic utrophin fragment comprising an amino-terminal actin-binding domain of the utrophin protein, or the amino-terminal actin-binding domain plus 4, 7, 10, or 11 spectrin-like repeats.

12. The isolated fusion protein of claim 10, wherein the second protein region is an amino acid sequence selected from the group consisting of SEQ. ID. NOS: 7 and 9.

13. The isolated fusion protein of claim 1, wherein the first protein region is an amino acid sequence as shown in SEQ. ID. NO: 5: YGRKKRRQRRR.

14. The isolated fusion protein of claim 13, wherein the second protein region is an anti-dystrophinopathic utrophin fragment comprising an amino-terminal actin-binding domain of the utrophin protein, or the amino-terminal actin-binding domain plus 4, 7, 10, or 11 spectrin-like repeats.

15. The isolated fusion protein of claim 13, wherein the second protein region is an amino acid sequence selected from the group consisting of SEQ. ID. NOS: 7 and 9.

16. The isolated fusion protein of claim 1, wherein the second protein region is an anti-dystrophinopathic utrophin fragment comprising no more than 75% of the mass of the full-length utrophin protein.

17. The isolated fusion protein of claim 1, wherein the second protein region is an anti-dystrophinopathic utrophin fragment comprising no more than 50% of the mass of the full-length utrophin protein.

18. The isolated fusion protein of claim 1, wherein the second protein region is an anti-dystrophinopathic utrophin fragment comprising no more than 25% of the mass of the full-length utrophin protein.

19. Pharmaceutically suitable salts of the isolated fusion protein recited in claim 1.

20. A pharmaceutical composition for treating dystrophinopathies in mammals, including humans, comprising:

an isolated fusion protein or a pharmaceutically suitable salt thereof as recited in claim 1, in combination with a pharmaceutically suitable carrier.

21. A method of treating dystrophinopathies in mammals, the method comprising administering to a mammalian subject in need thereof an anti-dystrophinopathic amount of an isolated fusion protein or a pharmaceutically suitable salt thereof as recited in claim 1.

22. An isolated nucleic acid expression construct encoding a fusion protein, the nucleic acid expression construct comprising:

a first nucleic acid region that encodes a first protein region of the fusion protein, wherein the first protein region is effective to transduce the fusion protein into mammalian muscle cells, operationally linked to;

a second nucleic acid region that encodes a second protein region of the fusion protein, wherein the second protein region comprises a full-length utrophin protein or an anti-dystrophinopathic fragment thereof;

wherein the expression construct drives expression of the fusion protein when transformed into a suitable host cell or disposed into a suitable cell-free expression system.

23. The isolated nucleic acid expression construct of claim 22, further comprising a third nucleic acid region that encodes an affinity tag that is operationally linked to the fusion protein.

24. The isolated nucleic acid expression construct of claim 22, wherein the third nucleic acid region encodes an amino acid sequence DYKDDDDK (SEQ. ID. NO: 1) or a fragment thereof.

25. The isolated nucleic acid expression construct of claim 22, wherein the third nucleic acid region encodes an amino acid sequence DYKD (SEQ. ID. NO: 28).

26. The isolated nucleic acid expression construct of claim 22, wherein the second nucleic acid region encodes an anti-dystrophinopathic utrophin fragment comprising an amino-terminal actin-binding domain of the utrophin protein, or the amino-terminal actin-binding domain plus 4, 7, 10, or 11 spectrin-like repeats.

27. The isolated nucleic acid expression construct of claim 22, wherein the second nucleic acid region encodes an amino acid sequence selected from the group consisting of SEQ. ID. NOS: 7 and 9.

28. The isolated nucleic acid expression construct of claim 22, which is a nucleic acid sequence selected from the group consisting of SEQ. ID. NOS: 10, 12, 14, 16, 18, 20, 22, and 24.

29. The isolated nucleic acid expression construct of claim 22, wherein the second nucleic acid region encodes an anti-dystrophinopathic utrophin fragment comprising an amino-terminal actin-binding domain of the utrophin protein, or the amino-terminal actin-binding domain plus 4, 7, 10, or 11 spectrin-like repeats.

30. The isolated nucleic acid expression construct of claim 22, wherein the second nucleic acid region encodes an amino acid sequence selected from the group consisting of SEQ. ID. NOS: 7 and 9.

31. The isolated nucleic acid expression construct of claim 22, wherein the first nucleic acid region encodes an amino acid sequence as shown in SEQ. ID. NO: 2.

32. The isolated nucleic acid expression construct of claim 31, wherein the second nucleic acid region encodes an anti-dystrophinopathic utrophin fragment comprising an amino-terminal actin-binding domain of the utrophin protein, or the amino-terminal actin-binding domain plus 4, 7, 10, or 11 spectrin-like repeats.

33. The isolated nucleic acid expression construct of claim 31, wherein the second nucleic acid region encodes an amino acid sequence selected from the group consisting of SEQ. ID. NOS: 7 and 9.

34. The isolated nucleic acid expression construct of claim 22, wherein the first nucleic acid region encodes an amino acid sequence as shown in SEQ. ID. NO: 5: YGRKKRRQRRR.

35. The isolated nucleic acid expression construct of claim 34, wherein the second nucleic acid region encodes an anti-dystrophinopathic utrophin fragment comprising an amino-terminal actin-binding domain of the utrophin protein, or the amino-terminal actin-binding domain plus 4, 7, 10, or 11 spectrin-like repeats.

36. The isolated nucleic acid expression construct of claim 34, wherein the second nucleic acid region encodes an amino acid sequence selected from the group consisting of SEQ. ID. NOS: 7 and 9.

37. The isolated nucleic acid expression construct of claim 22, wherein the second nucleic acid region encodes an anti-dystrophinopathic utrophin fragment comprising no more than 75% of the mass of the full-length utrophin protein.

38. The isolated nucleic acid expression construct of claim 22, wherein the second nucleic acid region encodes an anti-dystrophinopathic utrophin fragment comprising no more than 50% of the mass of the full-length utrophin protein.

39. The isolated nucleic acid expression construct of claim 22, wherein the second nucleic acid region encodes an anti-dystrophinopathic utrophin fragment comprising no more than 25% of the mass of the full-length utrophin protein.

* * * * *

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Synthetic "FLAG"-type polypeptide binding tag

<400> SEQUENCE: 1

Asp Tyr Lys Asp Asp Asp Asp Lys
1               5


<210> SEQ ID NO 2
<211> LENGTH: 86
<212> TYPE: PRT
<213> ORGANISM: Human immunodeficiency virus type 1
<220> FEATURE:
<221> NAME/KEY: MISC_FEATURE
<222> LOCATION: (47)..(57)
<223> OTHER INFORMATION: Protein Transduction Sequence

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85


<210> SEQ ID NO 3
<211> LENGTH: 9181
<212> TYPE: DNA
<213> ORGANISM: Human immunodeficiency virus type 1
<220> FEATURE:
<221> NAME/KEY: gene
```

```
<222> LOCATION: (5377)..(5591)
<220> FEATURE:
<221> NAME/KEY: gene
<222> LOCATION: (7925)..(7970)

<400> SEQUENCE: 3

ggtctctctg gttagaccag atctgagcct gggagctctc tggctaacta gggaacccac     60

tgcttaagcc tcaataaagc ttgccttgag tgcttcaagt agtgtgtgcc cgtctgttgt    120

gtgactctgg taactagaga tccctcagac ccttttagtc agtgtggaaa atctctagca    180

gtggcgcccg aacagggacc tgaaagcgaa agggaaacca gaggagctct ctcgacgcag    240

gactcggctt gctgaagcgc gcacggcaag aggcgagggg cggcgactgg tgagtacgcc    300

aaaaattttg actagcggag gctagaagga gagagatggg tgcgagagcg tcagtattaa    360

gcgggggaga attagatcga tgggaaaaaa ttcggttaag gccaggggga aagaaaaaat    420

ataaattaaa acatatagta tgggcaagca gggagctaga acgattcgca gttaatcctg    480

gcctgttaga aacatcagaa ggctgtagac aaatactggg acagctacaa ccatcccttc    540

agacaggatc agaagaactt agatcattat ataatacagt agcaaccctc tattgtgtgc    600

atcaaaggat agagataaaa gacaccaagg aagctttaga caagatagag gaagagcaaa    660

acaaaagtaa gaaaaaagca cagcaagcag cagctgacac aggacacagc aatcaggtca    720

gccaaaatta ccctatagtg cagaacatcc aggggcaaat ggtacatcag gccatatcac    780

ctagaacttt aaatgcatgg gtaaaagtag tagaagagaa ggctttcagc ccagaagtga    840

tacccatgtt ttcagcatta tcagaaggag ccaccccaca agatttaaac accatgctaa    900

acacagtggg gggacatcaa gcagccatgc aaatgttaaa agagaccatc aatgaggaag    960

ctgcagaatg ggatagagtg catccagtgc atgcagggcc tattgcacca ggccagatga   1020

gagaaccaag gggaagtgac atagcaggaa ctactagtac ccttcaggaa caaataggat   1080

ggatgacaaa taatccacct atcccagtag gagaaattta taaaagatgg ataatcctgg   1140

gattaaataa aatagtaaga atgtatagcc ctaccagcat tctggacata agacaaggac   1200

caaaggaacc ctttagagac tatgtagacc ggttctataa aactctaaga gccgagcaag   1260

cttcacagga ggtaaaaaat tggatgacag aaaccttgtt ggtccaaaat gcgaacccag   1320

attgtaagac tattttaaaa gcattgggac cagcggctac actagaagaa atgatgacag   1380

catgtcaggg agtaggagga cccggccata aggcaagagt tttggctgaa gcaatgagcc   1440

aagtaacaaa ttcagctacc ataatgatgc agagaggcaa ttttaggaac caaagaaaga   1500

ttgttaagtg tttcaattgt ggcaaagaag ggcacacagc cagaaattgc agggccccta   1560

ggaaaaaggg ctgttggaaa tgtggaaagg aaggacacca aatgaaagat tgtactgaga   1620

gacaggctaa tttttaggg aagatctggc cttcctacaa gggaaggcca gggaattttc    1680

ttcagagcag accagagcca acagccccac cagaagagag cttcaggtct ggggtagaga   1740

caacaactcc ccctcagaag caggagccga tagacaagga actgtatcct ttaacttccc   1800

tcaggtcact ctttggcaac gacccctcgt cacaataaag ataggggggc aactaaagga   1860

agctctatta gatacaggag cagatgatac agtattagaa gaaatgagtt tgccaggaag   1920

atggaaacca aaaatgatag ggggaattgg aggttttatc aaagtaagac agtatgatca   1980

gatactcata gaaatctgtg gacataaagc tataggtaca gtattagtag gacctacacc   2040

tgtcaacata attggaagaa atctgttgac tcagattggt tgcactttaa attttcccat   2100

tagccctatt gagactgtac cagtaaaatt aaagccagga atggatggcc caaaagttaa   2160

acaatggcca ttgacagaag aaaaaataaa agcattagta gaaatttgta cagagatgga   2220
```

-continued

```
aaaggaaggg aaaatttcaa aaattgggcc tgaaaatcca tacaatactc cagtatttgc 2280
cataaagaaa aaagacagta ctaaatggag aaaattagta gatttcagag aacttaataa 2340
gagaactcaa gacttctggg aagttcaatt aggaatacca catcccgcag ggttaaaaaa 2400
gaaaaaatca gtaacagtac tggatgtggg tgatgcatat ttttcagttc ccttagatga 2460
agacttcagg aagtatactg catttaccat acctagtata aacaatgaga caccagggat 2520
tagatatcag tacaatgtgc ttccacaggg atggaaagga tcaccagcaa tattccaaag 2580
tagcatgaca aaaatcttag agccttttag aaaacaaaat ccagacatag ttatctatca 2640
atacatggat gatttgtatg taggatctga cttagaaata gggcagcata gaacaaaaat 2700
agaggagctg agacaacatc tgttgaggtg gggacttacc acaccagaca aaaaacatca 2760
gaaagaacct ccattccttt ggatgggtta tgaactccat cctgataaat ggacagtaca 2820
gcctatagtg ctgccagaaa aagacagctg gactgtcaat gacatacaga agttagtggg 2880
gaaattgaat tgggcaagtc agatttaccc agggattaaa gtaaggcaat tatgtaaact 2940
ccttagagga accaaagcac taacagaagt aataccacta acagaagaag cagagctaga 3000
actggcagaa aacagagaga ttctaaaaga accagtacat ggagtgtatt atgacccatc 3060
aaaagactta atagcagaaa tacagaagca ggggcaaggc caatggacat atcaaattta 3120
tcaagagcca tttaaaaatc tgaaaacagg aaaatatgca agaatgaggg gtgcccacac 3180
taatgatgta aaacaattaa cagaggcagt gcaaaaaata accacagaaa gcatagtaat 3240
atggggaaag actcctaaat ttaaactgcc catacaaaag gaaacatggg aaacatggtg 3300
gacagagtat tggcaagcca cctggattcc tgagtgggag tttgttaata cccctccctt 3360
agtgaaatta tggtaccagt tagagaaaga acccatagta ggagcagaaa ccttctatgt 3420
agatggggca gctaacaggg agactaaatt aggaaaagca ggatatgtta ctaatagagg 3480
aagacaaaaa gttgtcaccc taactgacac aacaaatcag aagactgagt tacaagcaat 3540
ttatctagct ttgcaggatt cggggattaga agtaaacata gtaacagact cacaatatgc 3600
attaggaatc attcaagcac aaccagatca aagtgaatca gagttagtca atcaaataat 3660
agagcagtta ataaaaaagg aaaaggtcta tctggcatgg gtaccagcac acaaaggaat 3720
tggaggaaat gaacaagtag ataaattagt cagtgctgga atcaggaaag tactattttt 3780
agatggaata gataaggccc aagatgaaca tgagaaatat cacagtaatt ggagagcaat 3840
ggctagtgat tttaacctgc cacctgtagt agcaaaagaa atagtagcca gctgtgataa 3900
atgtcagcta aaaggagaag ccatgcatgg acaagtagac tgtagtccag gaatatggca 3960
actagattgt acacatttag aaggaaaagt tatcctggta gcagttcatg tagccagtgg 4020
atatatagaa gcagaagtta ttccagcaga aacagggcag gaaacagcat attttctttt 4080
aaaattagca ggaagatggc cagtaaaaac aatacatact gacaatggca gcaatttcac 4140
cggtgctacg gttagggccg cctgttggtg ggcgggaatc aagcaggaat ttggaattcc 4200
ctacaatccc caaagtcaag gagtagtaga atctatgaat aaagaattaa agaaaattat 4260
aggacaggta agagatcagg ctgaacatct taagacagca gtacaaatgg cagtattcat 4320
ccacaatttt aaaagaaaag gggggattgg ggggtacagt gcaggggaaa gaatagtaga 4380
cataatagca acagacatac aaactaaaga attacaaaaa caaattacaa aaattcaaaa 4440
ttttcgggtt tattacaggg acagcagaaa tccactttgg aaaggaccag caaagctcct 4500
ctggaaaggt gaaggggcag tagtaataca agataatagt gacataaaag tagtgccaag 4560
aagaaaagca aagatcatta gggattatgg aaaacagatg gcaggtgatg attgtgtggc 4620
```

```
aagtagacag gatgaggatt agaacatgga aaagtttagt aaaacaccat atgtatgttt   4680
cagggaaagc taggggatgg ttttatagac atcactatga aagccctcat ccaagaataa   4740
gttcagaagt acacatccca ctaggggatg ctagattggt aataacaaca tattggggtc   4800
tgcatacagg agaaagagac tggcatttgg gtcagggagt ctccatagaa tggaggaaaa   4860
agagatatag cacacaagta gaccctgaac tagcagacca actaattcat ctgtattact   4920
ttgactgttt ttcagactct gctataagaa aggccttatt aggacacata gttagcccta   4980
ggtgtgaata tcaagcagga cataacaagg taggatctct acaatacttg gcactagcag   5040
cattaataac accaaaaaag ataaagccac ctttgcctag tgttacgaaa ctgacagagg   5100
atagatggaa caagccccag aagaccaagg gccacagagg gagccacaca atgaatggac   5160
actagagctt ttagaggagc ttaagaatga agctgttaga cattttccta ggatttggct   5220
ccatggctta gggcaacata tctatgaaac ttatggggat acttgggcag gagtggaagc   5280
cataataaga attctgcaac aactgctgtt tatccatttt cagaattggg tgtcgacata   5340
gcagaatagg cgttactcga cagaggagag caagaaatgg agccagtaga tcctagacta   5400
gagccctgga agcatccagg aagtcagcct aaaactgctt gtaccaattg ctattgtaaa   5460
aagtgttgct ttcattgcca agtttgtttc ataacaaaag ccttaggcat ctcctatggc   5520
aggaagaagc ggagacagcg acgaagagct catcagaaca gtcagactca tcaagcttct   5580
ctatcaaagc agtaagtagt acatgtaatg caacctatac caatagtagc aatagtagca   5640
ttagtagtag caataataat agcaatagtt gtgtggtcca tagtaatcat agaatatagg   5700
aaaatattaa gacaaagaaa aatagacagg ttaattgata gactaataga aagagcagaa   5760
gacagtggca atgagagtga aggagaaata tcagcacttg tggagatggg ggtggagatg   5820
gggcaccatg ctccttggga tgttgatgat ctgtagtgct acagaaaaat tgtgggtcac   5880
agtctattat ggggtacctg tgtggaagga agcaaccacc actctatttt gtgcatcaga   5940
tgctaaagca tatgatacag aggtacataa tgtttgggcc acacatgcct gtgtacccac   6000
agaccccaac ccacaagaag tagtattggt aaatgtgaca gaaaatttta acatgtggaa   6060
aaatgacatg gtagaacaga tgcatgagga tataatcagt ttatgggatc aaagcctaaa   6120
gccatgtgta aaattaaccc cactctgtgt tagtttaaag tgcactgatt tgaagaatga   6180
tactaatacc aatagtagta gcgggagaat gataatggag aaaggagaga taaaaaactg   6240
ctctttcaat atcagcacaa gcataagagg taaggtgcag aaagaatatg catttttta    6300
taaacttgat ataataccaa tagataatga tactaccagc tataagttga caagttgtaa   6360
cacctcagtc attacacagg cctgtccaaa ggtatccttt gagccaattc ccatacatta   6420
ttgtgccccg gctggttttg cgattctaaa atgtaataat aagacgttca atggaacagg   6480
accatgtaca aatgtcagca cagtacaatg tacacatgga attaggccag tagtatcaac   6540
tcaactgctg ttaaatggca gtctagcaga agaagaggta gtaattagat ctgtcaattt   6600
cacggacaat gctaaaacca taatagtaca gctgaacaca tctgtagaaa ttaattgtac   6660
aagacccaac aacaatacaa gaaaaagaat ccgtatccag agaggaccag ggagagcatt   6720
tgttacaata ggaaaaatag gaaatatgag acaagcacat tgtaacatta gtagagcaaa   6780
atggaataac actttaaaac agatagctag caaattaaga gaacaatttg gaaataataa   6840
aacaataatc tttaagcaat cctcaggagg ggacccagaa attgtaacgc acagttttaa   6900
ttgtggaggg gaatttttct actgtaattc aacacaactg tttaatagta cttggtttaa   6960
tagtacttgg agtactgaag ggtcaaataa cactgaagga agtgacacaa tcaccctccc   7020
```

```
atgcagaata aaacaaatta taaacatgtg gcagaaagta ggaaaagcaa tgtatgcccc   7080
tcccatcagt ggacaaatta gatgttcatc aaatattaca gggctgctat taacaagaga   7140
tggtggtaat agcaacaatg agtccgagat cttcagacct ggaggaggag atatgaggga   7200
caattggaga agtgaattat ataaatataa agtagtaaaa attgaaccat taggagtagc   7260
acccaccaag gcaaagagaa gagtggtgca gagagaaaaa agagcagtgg gaataggagc   7320
tttgttcctt gggttcttgg gagcagcagg aagcactatg ggcgcagcct caatgacgct   7380
gacggtacag gccagacaat tattgtctgg tatagtgcag cagcagaaca atttgctgag   7440
ggctattgag gcgcaacagc atctgttgca actcacagtc tggggcatca agcagctcca   7500
ggcaagaatc ctggctgtgg aaagatacct aaaggatcaa cagctcctgg ggatttgggg   7560
ttgctctgga aaactcattt gcaccactgc tgtgccttgg aatgctagtt ggagtaataa   7620
atctctggaa cagatttgga atcacacgac ctggatggag tgggacagag aaattaacaa   7680
ttacacaagc ttaatacact ccttaattga agaatcgcaa aaccagcaag aaaagaatga   7740
acaagaatta ttggaattag ataaatgggc aagtttgtgg aattggttta acataacaaa   7800
ttggctgtgg tatataaaat tattcataat gatagtagga ggcttggtag gtttaagaat   7860
agtttttgct gtactttcta tagtgaatag agttaggcag ggatattcac cattatcgtt   7920
tcagacccac ctcccaaccc cgaggggacc cgacaggccc gaaggaatag aagaagaagg   7980
tggagagaga gacagagaca gatccattcg attagtgaac ggatccttgg cacttatctg   8040
ggacgatctg cggagcctgt gcctcttcag ctaccaccgc ttgagagact tactcttgat   8100
tgtaacgagg attgtggaac ttctgggacg cagggggtgg gaagccctca aatattggtg   8160
gaatctccta cagtattgga gtcaggaact aaagaatagt gctgttagct tgctcaatgc   8220
cacagccata gcagtagctg aggggacaga tagggttata gaagtagtac aaggagcttg   8280
tagagctatt cgccacatac ctagaagaat aagacagggc ttggaaagga ttttgctata   8340
agatgggtgg caagtggtca aaaagtagtg tgattggatg gcctactgta agggaaagaa   8400
tgagacgagc tgagccagca gcagataggg tgggagcagc atctcgagac ctggaaaaac   8460
atggagcaat cacaagtagc aatacagcag ctaccaatgc tgcttgtgcc tggctagaag   8520
cacaagagga ggaggaggtg ggttttccag tcacacctca ggtaccttta agaccaatga   8580
cttacaaggc agctgtagat cttagccact ttttaaaaga aaaggggga ctggaagggc   8640
taattcactc ccaaagaaga caagatatcc ttgatctgtg gatctaccac acacaaggct   8700
acttccctga ttagcagaac tacacaccag ggccaggggt cagatatcca ctgacctttg   8760
gatggtgcta caagctagta ccagttgagc cagataagat agaagaggcc aataaaggag   8820
agaacaccag cttgttacac cctgtgagcc tgcatgggat ggatgacccg gagagagaag   8880
tgttagagtg gaggtttgac agccgcctag catttcatca cgtggcccga gagctgcatc   8940
cggagtactt caagaactgc tgacatcgag cttgctacaa gggactttcc gctggggact   9000
ttccagggag gcgtggcctg ggcgggactg gggagtggcg agccctcaga tcctgcatat   9060
aagcagctgc tttttgcctg tactgggtct ctctggttag accagatctg agcctgggag   9120
ctctctggct aactagggaa cccactgctt aagcctcaat aaagcttgcc ttgagtgctt   9180
c                                                                   9181
```

<210> SEQ ID NO 4
<211> LENGTH: 4776
<212> TYPE: DNA
<213> ORGANISM: Artificial Sequence
<220> FEATURE:
<223> OTHER INFORMATION: Plasmid pFastBac 1

<400> SEQUENCE: 4

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440

cattggtaac tgtcagacca agtttactca tatatacttt agattgattt aaaacttcat   1500

ttttaattta aaaggatcta ggtgaagatc ctttttgata atctcatgac caaaatccct   1560

taacgtgagt tttcgttcca ctgagcgtca gaccccgtag aaaagatcaa aggatcttct   1620

tgagatcctt tttttctgcg cgtaatctgc tgcttgcaaa caaaaaaacc accgctacca   1680

gcggtggttt gtttgccgga tcaagagcta ccaactcttt ttccgaaggt aactggcttc   1740

agcagagcgc agataccaaa tactgtcctt ctagtgtagc cgtagttagg ccaccacttc   1800

aagaactctg tagcaccgcc tacatacctc gctctgctaa tcctgttacc agtggctgct   1860

gccagtggcg ataagtcgtg tcttaccggg ttggactcaa gacgatagtt accggataag   1920

gcgcagcggt cgggctgaac ggggggttcg tgcacacagc ccagcttgga gcgaacgacc   1980

tacaccgaac tgagatacct acagcgtgag cattgagaaa gcgccacgct tcccgaaggg   2040

agaaaggcgg acaggtatcc ggtaagcggc agggtcggaa caggagagcg cacgagggag   2100

cttccagggg gaaacgcctg gtatctttat agtcctgtcg ggtttcgcca cctctgactt   2160

gagcgtcgat ttttgtgatg ctcgtcaggg gggcggagcc tatggaaaaa cgccagcaac   2220

gcggcctttt tacggttcct ggccttttgc tggccttttg ctcacatgtt ctttcctgcg   2280
```

```
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcccgg tccgaagcgc gcggaattca aaggcctacg tcgacgagct   4080
cactagtcgc ggccgctttc gaatctagag cctgcagtct cgaggcatgc ggtaccaagc   4140
ttgtcgagaa gtactagagg atcataatca gccataccac atttgtagag gttttacttg   4200
ctttaaaaaa cctcccacac ctccccctga acctgaaaca taaaatgaat gcaattgttg   4260
ttgttaactt gtttattgca gcttataatg gttacaaata aagcaatagc atcacaaatt   4320
tcacaaataa agcatttttt tcactgcatt ctagttgtgg tttgtccaaa ctcatcaatg   4380
tatcttatca tgtctggatc tgatcactgc ttgagcctag gagatccgaa ccagataagt   4440
gaaatctagt tccaaactat tttgtcattt ttaattttcg tattagctta cgacgctaca   4500
cccagttccc atctattttg tcactcttcc ctaaataatc cttaaaaact ccatttccac   4560
ccctcccagt tcccaactat tttgtccgcc cacagcgggg catttttctt cctgttatgt   4620
ttttaatcaa acatcctgcc aactccatgt gacaaaccgt catcttcggc tacttttttct   4680
```

ctgtcacaga atgaaaattt ttctgtcatc tcttcgttat taatgtttgt aattgactga 4740
atatcaacgc ttatttgcag cctgaatggc gaatgg 4776

<210> SEQ ID NO 5
<211> LENGTH: 11
<212> TYPE: PRT
<213> ORGANISM: Human immunodeficiency virus type 1

<400> SEQUENCE: 5

Tyr Gly Arg Lys Lys Arg Arg Gln Arg Arg Arg
1 5 10

<210> SEQ ID NO 6
<211> LENGTH: 12436
<212> TYPE: DNA
<213> ORGANISM: Homo sapiens

<400> SEQUENCE: 6
gtattgatgt caagctgaac catcgtagga agttgaaagc cttagaaaga ggacttggta 60
aagtttttgg attatcttga aactctggca agatggccaa gtatggagaa catgaagcca 120
gtcctgacaa tgggcagaac gaattcagtg atatcattaa gtccagatct gatgaacaca 180
atgacgtaca gaagaaaacc tttaccaaat ggataaatgc tcgattttca aagagtggga 240
aaccacccat caatgatatg ttcacagacc tcaaagatgg aaggaagcta ttggatcttc 300
tagaaggcct cacaggaaca tcactgccaa aggaacgtgg ttccacaagg gtacatgcct 360
taaataacgt caacagagtg ctgcaggttt tacatcagaa caatgtggaa ttagtgaata 420
tagggggaac tgacattgtg gatggaaatc acaaactgac tttggggtta ctttggagca 480
tcattttgca ctggcaggtg aaagatgtca tgaaggatgt catgtcggac ctgcagcaga 540
cgaacagtga gaagatcctg ctcagctggg tgcgtcagac caccaggccc tacagccaag 600
tcaacgtcct caacttcacc accagctgga cagatggact cgcctttaat gctgtcctcc 660
accgacataa acctgatctc ttcagctggg ataaagttgt caaaatgtca ccaattgaga 720
gacttgaaca tgccttcagc aaggctcaaa cttatttggg aattgaaaag ctgttagatc 780
ctgaagatgt tgccgttcag cttcctgaca agaaatccat aattatgtat ttaacatctt 840
tgtttgaggt gctacctcag caagtcacca tagacgccat ccgtgaggta gagacactcc 900
caaggaaata taaaaaagaa tgtgaagaag aggcaattaa tatacagagt acagcgcctg 960
aggaggagca tgagagtccc cgagctgaaa ctcccagcac tgtcactgag gttgacatgg 1020
atctggacag ctatcagatt gcgttggagg aagtgctgac ctggttgctt tctgctgagg 1080
acactttcca ggagcaggat gatatttctg atgatgttga agaagtcaaa gaccagtttg 1140
caacccatga agcttttatg atggaactga ctgcacacca gagcagtgtg ggcagcgtcc 1200
tgcaggcagg caaccaactg ataacacaag gaactctgtc agacgaagaa gaatttgaga 1260
ttcaggaaca gatgaccctg ctgaatgcta gatgggaggc tcttagggtg gagagtatgg 1320
acagacagtc ccggctgcac gatgtgctga tggaactgca gaagaagcaa ctgcagcagc 1380
tctccgcctg gttaacactc acagaggagc gcattcagaa gatggaaact tgcccccctgg 1440 atgatgatgt aaaatctcta caaaagctgc tagaagaaca taaaagtttg caaagtgatc 1500
ttgaggctga acaggtgaaa gtaaattcac taactcacat ggtggtcatt gttgatgaaa 1560
acagtggtga gagtgctaca gctatcctag aagaccagtt acagaaactt ggtgagcgct 1620
ggacagcagt atgccgttgg actgaagaac gctggaatag gttacaagaa atcaatatat 1680

```
tgtggcagga attattggaa gaacagtgct tgttgaaagc ttggttaacc gaaaaagaag   1740
aggctttaaa taaagtccag acaagcaact tcaaagacca aaaggaacta agtgtcagtg   1800
ttcgacgtct ggctattttg aaggaagaca tggaaatgaa gcgtcaaaca ttggatcagc   1860
tgagtgagat tggccaggat gtgggacaat tacttgataa ttccaaggca tctaagaaga   1920
tcaacagtga ctcagaggaa ctgactcaaa gatgggattc tttggttcag agactagaag   1980
attcctccaa ccaggtgact caggctgtag caaagctggg gatgtctcag attcctcaga   2040
aggacctttt ggagactgtt cgtgtaagag aacaagcaat tacaaaaaaa tctaagcagg   2100
aactgcctcc tcctcctccc ccaaagaaga gacagatcca tgtggatatt gaagctaaga   2160
aaaagtttga tgctataagt gcagagctgt tgaactggat tttgaaatgg aaaactgcca   2220
ttcagaccac agagataaaa gagtatatga agatgcaaga cacttccgaa atgaaaaaga   2280
agttgaaggc attagaaaaa gaacagagag aaagaatccc cagagcagat gaattaaacc   2340
aaactggaca aatccttgtg gagcaaatgg gaaaagaagg ccttcctact gaagaaataa   2400
aaaatgttct ggagaaggtt tcatcagaat ggaagaatgt atctcaacat ttggaagatc   2460
tagaaagaaa gattcagcta caggaagata taaatgctta tttcaagcag cttgatgagc   2520
ttgaaaaggt catcaagaca aaggaggagt gggtaaaaca cacttccatt tctgaatctt   2580
cccggcagtc cttgccaagc ttgaaggatt cctgtcagcg ggaattgaca aatcttcttg   2640
gccttcaccc caaaattgaa atggctcgtg caagctgctc ggccctgatg tctcagcctt   2700
ctgccccaga ttttgtccag cggggcttcg atagctttct gggccgctac caagctgtac   2760
aagaggctgt agaggatcgt caacaacatc tagagaatga actgaagggc caacctggac   2820
atgcatatct ggaaacattg aaaacactga aagatgtgct aaatgattca gaaaataagg   2880
cccaggtgtc tctgaatgtc cttaatgatc ttgccaaggt ggagaaggcc ctgcaagaaa   2940
aaaagaccct tgatgaaatc cttgagaatc agaaacctgc attacataaa cttgcagaag   3000
aaacaaaggc tctggagaaa aatgttcatc ctgatgtaga aaaattatat aagcaagaat   3060
ttgatgatgt gcaaggaaag tggaacaagc taaaggtctt ggtttccaaa gatctacatt   3120
tgcttgagga aattgctctc acactcagag cttttgaggc cgattcaaca gtcattgaga   3180
agtggatgga tggcgtgaaa gacttcttaa tgaaacagca ggctgcccaa ggagacgacg   3240
caggtctaca gaggcagtta gaccagtgct ctgcatttgt taatgaaata gaaacaattg   3300
aatcatctct gaaaaacatg aaggaaatag agactaatct tcgaagtggt ccagttgctg   3360
gaataaaaac ttgggtgcag acaagactag gtgactacca aactcaactg gagaaactta   3420
gcaaggagat cgctactcaa aaaagtaggt tgtctgaaag tcaagaaaaa gctgcgaacc   3480
tgaagaaaga cttggcagag atgcaggaat ggatgaccca ggccgaggaa gaatatttgg   3540
agcgggattt tgagtacaag tcaccagaag agcttgagag tgctgtggaa gagatgaaga   3600
gggcaaaaga ggatgtgttg cagaaggagg tgagagtgaa gattctcaag gacaacatca   3660
agttattagc tgccaaggtg ccctctggtg gccaggagtt gacgtctgag ctgaatgttg   3720
tgctggagaa ttaccaactt ctttgtaata gaattcgagg aaagtgccac acgctagagg   3780
aggtctggtc ttgttggatt gaactgcttc actatttgga tcttgaaact acctggttaa   3840
acactttgga agagcggatg aagagcacag aggtcctgcc tgagaagacg gatgctgtca   3900
acgaagccct ggagtctctg gaatctgttc tgcgccaccc ggcagataat cgcacccaga   3960
ttcgagagct tggccagact ctgattgatg gggggatcct ggatgatata atcagtgaga   4020
aactggaggc tttcaacagc cgatatgaag atctaagtca cctggcagag agcaagcaga   4080
```

-continued

```
tttctttgga aaagcaactc caggtgctgc gggaaactga ccagatgctt caagtcttgc   4140
aagagagctt gggggagctg gacaaacagc tcaccacata cctgactgac aggatagatg   4200
ctttccaagt tccacaggaa gctcagaaaa tccaagcaga gatctcagcc catgagctaa   4260
ccctagagga gttgagaaga aatatgcgtt ctcagcccct gacctcccca gagagtagga   4320
ctgccagagg aggaagtcag atggatgtgc tacagaggaa actccgagag gtgtccacaa   4380
agttccagct tttccagaag ccagctaact tcgagcagcg catgctggac tgcaagcgtg   4440
tgctggatgg cgtgaaagca gaacttcacg ttctggatgt gaaggacgta gaccctgacg   4500
tcatacagac gcacctggac aagtgtatga aactgtataa aactttgagt gaagtcaaac   4560
ttgaagtgga aactgtgatt aaaacaggaa gacatattgt ccagaaacag caaacggaca   4620
acccaaaagg gatggatgag cagctgactt ccctgaaggt tctttacaat gacctgggcg   4680
cacaggtgac agaaggaaaa caggatctgg aaagagcatc acagttggcc cggaaaatga   4740
agaaagaggc tgcttctctc tctgaatggc tttctgctac tgaaactgaa ttggtacaga   4800
agtccacttc agaaggtctg cttggtgact tggatacaga aatttcctgg gctaaaaatg   4860
ttctgaagga tctggaaaag agaaaagctg atttaaatac catcacagag agtagtgctg   4920
ccctgcaaaa cttgattgag ggcagtgagc ctattttaga agagaggctc tgcgtcctta   4980
acgctgggtg gagccgagtt cgtacctgga ctgaagattg gtgcaatacc ttgatgaacc   5040
atcagaacca gctagaaata tttgatggga acgtggctca cataagtacc tggctttatc   5100
aagctgaagc tctattggat gaaattgaaa agaaaccaac aagtaaacag gaagaaattg   5160
tgaagcgttt agtatctgag ctggatgatg ccaacctcca ggttgaaaat gtccgcgatc   5220
aagcccttat tttgatgaat gcccgtggaa gctcaagcag ggagcttgta gaaccaaagt   5280
tagctgagct gaataggaac tttgaaaagg tgtctcaaca tatcaaaagt gccaaattgc   5340
taattgctca ggaaccatta taccaatgtt tggtcaccac tgaaacattt gaaactggtg   5400
tgcctttctc tgacttggaa aaattagaaa atgacataga aaatatgtta aaatttgtgg   5460
aaaaacactt ggaatccagt gatgaagatg aaaagatgga tgaggagagt gcccagattg   5520
aggaagttct acaaagagga gaagaaatgt tacatcaacc tatggaagat aataaaaaag   5580
aaaagatccg tttgcaatta ttacttttgc atactagata caacaaaatt aaggcaatcc   5640
ctattcaaca gaggaaaatg ggtcaacttg cttctggaat tagatcatca cttcttccta   5700
cagattatct ggttgaaatt aacaaaattt tactttgcat ggatgatgtt gaattatcgc   5760
ttaatgttcc agagctcaac actgctattt acgaagactt ctcttttcag gaagactctc   5820
tgaagaatat caaagaccaa ctggacaaac ttggagagca gattgcagtc attcatgaaa   5880
aacagccaga tgtcatcctt gaagcctctg gacctgaagc cattcagatc agagatacac   5940
ttactcagct gaatgcaaaa tgggacagaa ttaatagaat gtacagtgat cggaaaggtt   6000
gttttgacag ggcaatggaa gaatggagac agttccattg tgaccttaat gacctcacac   6060
agtggataac agaggctgaa gaattactgg ttgatacctg tgctccaggt ggcagcctgg   6120
acttagagaa agccaggata catcagcagg aacttgaggt gggcatcagc agccaccagc   6180
ccagttttgc agcactaaac cgaactgggg atgggattgt gcagaaactc tcccaggcag   6240
atggaagctt cttgaaagaa aaactggcag gtttaaacca acgctgggat gcaattgttg   6300
cagaagtgaa ggataggcag ccaaggctaa aaggagaaag taagcaggtg atgaagtaca   6360
ggcatcagct agatgagatt atctgttggt taacaaaggc tgagcatgct atgcaaaaga   6420
gatcaaccac cgaattggga gaaaacctgc aagaattaag agacttaact caagaaatgg   6480
```

```
aagtacatgc tgaaaaactc aaatggctga atagaactga attggagatg ctttcagata   6540

aaagtctgag tttacctgaa agggataaaa tttcagaaag cttaaggact gtaaatatga   6600

catggaataa gatttgcaga gaggtgccta ccaccctgaa ggaatgcatc caggagccca   6660

gttctgtttc acagacaagg attgctgctc atcctaatgt ccaaaaggtg gtgctagtat   6720

catctgcgtc agatattcct gttcagtctc atcgtacttc ggaaatttca attcctgctg   6780

atcttgataa aactataaca gaactagccg actggctggt attaatcgac cagatgctga   6840

agtccaacat tgtcactgtt ggggatgtag aagagatcaa taagaccgtt tcccgaatga   6900

aaattacaaa ggctgactta gaacagcgcc atcctcagct ggattatgtt tttacattgg   6960

cacagaattt gaaaaataaa gcttccagtt cagatatgag aacagcaatt acagaaaaat   7020

tggaaagggt caagaaccag tgggatggca cccagcatgg cgttgagcta agacagcagc   7080

agcttgagga catgattatt gacagtcttc agtgggatga ccatagggag gagactgaag   7140

aactgatgag aaaatatgag gctcgactct atattcttca gcaagcccga cgggatccac   7200

tcaccaaaca aatttctgat aaccaaatac tgcttcaaga actgggtcct ggagatggta   7260

tcgtcatggc gttcgataac gtcctgcaga aactcctgga ggaatatggg agtgatgaca   7320

caaggaatgt gaaagaaacc acagagtact taaaaacatc atggatcaat ctcaaacaaa   7380

gtattgctga cagacagaac gccttggagg ctgagtggag gacggtgcag gcctctcgca   7440

gagatctgga aaacttcctg aagtggatcc aagaagcaga gaccacagtg aatgtgcttg   7500

tggatgcctc tcatcgggag aatgctcttc aggatagtat cttggccagg gaactcaaac   7560

agcagatgca ggacatccag gcagaaattg atgcccacaa tgacatattt aaaagcattg   7620

acggaaacag gcagaagatg gtaaaagctt tgggaaattc tgaagaggct actatgcttc   7680

aacatcgact ggatgatatg aaccaaagat ggaatgactt aaaagcaaaa tctgctagca   7740

tcagggccca tttggaggcc agcgctgaga agtggaacag gttgctgatg tccttagaag   7800

aactgatcaa atggctgaat atgaaagatg aagagcttaa gaaacaaatg cctattggag   7860

gagatgttcc agccttacag ctccagtatg accattgtaa ggccctgaga cgggagttaa   7920

aggagaaaga atattctgtc ctgaatgctg tcgaccaggc ccgagttttc ttggctgatc   7980

agccaattga ggcccctgaa gagccaagaa gaaacctaca atcaaaaaca gaattaactc   8040

ctgaggagag agcccaaaag attgccaaag ccatgcgcaa acagtcttct gaagtcaaag   8100

aaaaatggga aagtctaaat gctgtaacta gcaattggca aaagcaagtg gacaaggcat   8160

tggagaaact cagagacctg cagggagcta tggatgacct ggacgctgac atgaaggagg   8220

cagagtccgt gcggaatggc tggaagcccg tgggagactt actcattgac tcgctgcagg   8280

atcacattga aaaaatcatg gcatttagag aagaaattgc accaatcaac tttaaagtta   8340

aaacggtgaa tgatttatcc agtcagctgt ctccacttga cctgcatccc tctctaaaga   8400

tgtctcgcca gctagatgac cttaatatgc gatggaaact tttacaggtt tctgtggatg   8460

atcgccttaa acagcttcag gaagcccaca gagattttgg accatcctct cagcattttc   8520

tctctacgtc agtccagctg ccgtggcaaa gatccatttc acataataaa gtgccctatt   8580

acatcaacca tcaaacacag accacctgtt gggaccatcc taaaatgacc gaactctttc   8640

aatcccttgc tgacctgaat aatgtacgtt tttctgccta ccgtacagca atcaaaatcc   8700

gaagactaca aaaagcacta tgtttggatc tcttagagtt gagtacaaca aatgaaattt   8760

tcaaacagca caagttgaac caaaatgacc agctcctcag tgttccagat gtcatcaact   8820

gtctgacaac aacttatgat ggacttgagc aaatgcataa ggacctggtc aacgttccac   8880
```

-continued

```
tctgtgttga tatgtgtctc aattggttgc tcaatgtcta tgacacgggt cgaactggaa   8940
aaattagagt gcagagtctg aagattggat taatgtctct ctccaaaggt ctcttggaag   9000
aaaaatacag atatctcttt aaggaagttg cagggccaac agaaatgtgt gaccagaggc   9060
agctgggcct gttacttcat gatgccatcc agatccccg gcagctaggt gaagtagcag    9120
cttttggagg cagtaatatt gagcctagtg ttcgcagctg cttccaacag aataacaata   9180
aaccagaaat aagtgtgaaa gagtttatag attggatgca tttggaacca cagtccatgg   9240
tttggctccc agttttacat cgagtggcag cagcggagac tgcaaaacat caggccaaat   9300
gcaacatctg taaagaatgt ccaattgtcg ggttcaggta tagaagcctt aagcatttta   9360
actatgatgt ctgccagagt tgtttctttt cgggtcgaac agcaaaaggt cacaaattac   9420
attacccaat ggtggaatat tgtataccta caacatctgg ggaagatgta cgagacttca   9480
caaaggtact taagaacaag ttcaggtcga agaagtactt tgccaaacac cctcgacttg   9540
gttacctgcc tgtccagaca gttcttgaag gtgacaactt agagactcct atcacactca   9600
tcagtatgtg gccagagcac tatgacccct cacaatctcc tcaactgttt catgatgaca   9660
cccattcaag aatagaacaa tatgccacac gactggccca gatggaaagg actaatgggt   9720
cttttctcac tgatagcagc tccaccacag gaagtgtgga agacgagcac gccctcatcc   9780
agcagtattg ccaaacactc ggaggagagt ccccagtgag ccagccgcag agcccagctc   9840
agatcctgaa gtcagtagag agggaagaac gtggagaact ggagaggatc attgctgacc   9900
tggaggaaga acaaagaaat ctacaggtgg agtatgagca gctgaaggac cagcacctcc   9960
gaagggggct ccctgtcggt tcaccgccag agtcgattat atctccccat cacacgtctg  10020
aggattcaga acttatagca gaagcaaaac tcctcaggca gcacaaaggt cggctggagg  10080
ctaggatgca gattttagaa gatcacaata aacagctgga gtctcagctc caccgcctcc  10140
gacagctgct ggagcagcct gaatctgatt cccgaatcaa tggtgtttcc ccatgggctt  10200
ctcctcagca ttctgcactg agctactcgc ttgatccaga tgcctccggc ccacagttcc  10260
accaggcagc gggagaggac ctgctggccc caccgcacga caccagcacg gatctcacgg  10320
aggtcatgga gcagattcac agcacgtttc catcttgctg cccaaatgtt cccagcaggc  10380
cacaggcaat gtgaagtatt catccggcca accaatgttt cctgacgtac agtgttgccc  10440
ttttcagcaa atgccaattc caagttccat taaatcagaa gctccatggc tccttggccc  10500
acgatgttga gtgctgactg tgtgttctac tgaaagagta aaacactgac tatccaaaga  10560
gaaatggata ttttgttttt ataataacca tatattattg ttttcttctt ccctttctat  10620
gcaagtgtaa attaatgaac agagaggtat ttggaaatgg taatacattt gtcacggatt  10680
tgtataatgt atacagcatt gggaaagtgg gtgggggctt tctaatatga taccgtcttt  10740
ttaataacta tgacaaagct tacataagaa ttagaagacc actttacatt tttacattcc  10800
ttctgctgtt catattaacc ttgcacaatt acttcatttt ttctttgact cttttaccac  10860
aatgttttgg ttatttataa tttatcagcc atatgtttat cagccatata accaactaga  10920
tcccaaatag atccatgtat ttgtttccgt gatttggcca cattaataaa ttcataaatt  10980
tcaatcaaat atcttatata tacacacata tggtttaagc tacagccctg tgtatgccgt  11040
ttaactttat ttgacgttgc ccacttactt ctttgctgac cacttggata accgtaataa  11100
aaatcctata agcctaaatg gcatttcttt tgggatattt ttcctgcatt ttattccctt  11160
tttatataag taggaattaa ttatttattt tatgtcttaa tctatttgat aaagaagact  11220
acattataat aatctcaaag atcatattac caaaggttgc ccacttgagc atattttcat  11280
```

```
tttgacacag aaacaaaatt tagtacaacc tttcctagtt cccatgtctt gattttcatc  11340

attacatgca cagcagacct ttacctattg tgataccaga acacatcatt gtctttggtt  11400

cccttcaaag agaattttat tgttgttttg tattttcaag tccttaatag ttcttgaaac  11460

tcctagttgt tttcttgttg aaagcagaca cacatttagt gcacggctta ttttaccttt  11520

cgggtgaaag atcagatgtt tttataccct tcacttgatc aatatatttg gaaagaatgt  11580

ttatcaaaag tctatgtcac tgcttctaca gaagaatgaa attaatgctt aggtgatggt  11640

acctccacct acatcttttt gagtgcattc aattatgtat tttggtttag cttctgattt  11700

aacatttaat tgattcagtt taaacatgtt acttaattag caaatgtaga ggaaccaaaa  11760

aaaggtgaaa ataatatgtt ttgattcaaa cctaaagaca taaaaacata aagacatttt  11820

aactttgggt tctctttagc tgggatctgg ccagaaggag gcttaaagtt agaaattgct  11880

attattttag aataggttgg gtgggttggg gggcaagggt gtctatttgc agcagagata  11940

ttttgaaaag aagaaaattg ttttatataa aaaggaaagc catgaccacc tttctacctc  12000

agatccatct tcatccattg cattggaaac tgctttatgc tgctgcagtc tgcaaagtct  12060

agagctttta tcaggccatg tcatacccaa gaaagcacct atttaaagaa aaaacaattc  12120

cctgagctct caactccaag ttgtagattt ggtgtcttcc ttgttcttac tttaaaaagt  12180

catgtgttaa ttttttttct gcctgtattt gtatgcaaaa tgtcctctat ctgctattaa  12240

agaaaagcta cgtaaaacac tacattgtaa ccttctaagt aataataaat aaaaagaaat  12300

atattgcagt aacaatggga agtaagtatg tagttctttt gaaatatgtg gtaaagaact  12360

aatcacagac tatcatctaa tctggttaca tattgtattt ttcatcctga ataaaagtaa  12420

ttttaacaca aaaaaa                                                   12436
```

```
<210> SEQ ID NO 7
<211> LENGTH: 3433
<212> TYPE: PRT
<213> ORGANISM: Homo sapiens

<400> SEQUENCE: 7

Met Ala Lys Tyr Gly Glu His Glu Ala Ser Pro Asp Asn Gly Gln Asn
1               5                   10                  15

Glu Phe Ser Asp Ile Ile Lys Ser Arg Ser Asp Glu His Asn Asp Val
            20                  25                  30

Gln Lys Lys Thr Phe Thr Lys Trp Ile Asn Ala Arg Phe Ser Lys Ser
        35                  40                  45

Gly Lys Pro Pro Ile Asn Asp Met Phe Thr Asp Leu Lys Asp Gly Arg
    50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Asn Val Glu Leu Val Asn Ile Gly Gly
            100                 105                 110

Thr Asp Ile Val Asp Gly Asn His Lys Leu Thr Leu Gly Leu Leu Trp
        115                 120                 125

Ser Ile Ile Leu His Trp Gln Val Lys Asp Val Met Lys Asp Val Met
    130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175
```

```
Thr Ser Trp Thr Asp Gly Leu Ala Phe Asn Ala Val Leu His Arg His
            180                 185                 190

Lys Pro Asp Leu Phe Ser Trp Asp Lys Val Val Lys Met Ser Pro Ile
        195                 200                 205

Glu Arg Leu Glu His Ala Phe Ser Lys Ala Gln Thr Tyr Leu Gly Ile
    210                 215                 220

Glu Lys Leu Leu Asp Pro Glu Asp Val Ala Val Gln Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Glu Thr Leu Pro Arg Lys
            260                 265                 270

Tyr Lys Lys Glu Cys Glu Glu Glu Ala Ile Asn Ile Gln Ser Thr Ala
        275                 280                 285

Pro Glu Glu Glu His Glu Ser Pro Arg Ala Glu Thr Pro Ser Thr Val
    290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Asp Gln Phe Ala Thr His
            340                 345                 350

Glu Ala Phe Met Met Glu Leu Thr Ala His Gln Ser Ser Val Gly Ser
        355                 360                 365

Val Leu Gln Ala Gly Asn Gln Leu Ile Thr Gln Gly Thr Leu Ser Asp
    370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Asp Arg Gln Ser Arg Leu His
                405                 410                 415

Asp Val Leu Met Glu Leu Gln Lys Lys Gln Leu Gln Gln Leu Ser Ala
            420                 425                 430

Trp Leu Thr Leu Thr Glu Glu Arg Ile Gln Lys Met Glu Thr Cys Pro
        435                 440                 445

Leu Asp Asp Asp Val Lys Ser Leu Gln Lys Leu Leu Glu Glu His Lys
    450                 455                 460

Ser Leu Gln Ser Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Ile Leu Glu Asp Gln Leu Gln Lys Leu Gly Glu Arg Trp Thr Ala
            500                 505                 510

Val Cys Arg Trp Thr Glu Glu Arg Trp Asn Arg Leu Gln Glu Ile Asn
        515                 520                 525

Ile Leu Trp Gln Glu Leu Leu Glu Glu Gln Cys Leu Leu Lys Ala Trp
    530                 535                 540

Leu Thr Glu Lys Glu Glu Ala Leu Asn Lys Val Gln Thr Ser Asn Phe
545                 550                 555                 560

Lys Asp Gln Lys Glu Leu Ser Val Ser Val Arg Arg Leu Ala Ile Leu
                565                 570                 575

Lys Glu Asp Met Glu Met Lys Arg Gln Thr Leu Asp Gln Leu Ser Glu
            580                 585                 590

Ile Gly Gln Asp Val Gly Gln Leu Leu Asp Asn Ser Lys Ala Ser Lys
```

```
        595                 600                 605

Lys Ile Asn Ser Asp Ser Glu Glu Leu Thr Gln Arg Trp Asp Ser Leu
    610                 615                 620

Val Gln Arg Leu Glu Asp Ser Ser Asn Gln Val Thr Gln Ala Val Ala
625                 630                 635                 640

Lys Leu Gly Met Ser Gln Ile Pro Gln Lys Asp Leu Leu Glu Thr Val
                645                 650                 655

Arg Val Arg Glu Gln Ala Ile Thr Lys Lys Ser Lys Gln Glu Leu Pro
            660                 665                 670

Pro Pro Pro Pro Pro Lys Lys Arg Gln Ile His Val Asp Ile Glu Ala
        675                 680                 685

Lys Lys Lys Phe Asp Ala Ile Ser Ala Glu Leu Leu Asn Trp Ile Leu
    690                 695                 700

Lys Trp Lys Thr Ala Ile Gln Thr Thr Glu Ile Lys Glu Tyr Met Lys
705                 710                 715                 720

Met Gln Asp Thr Ser Glu Met Lys Lys Lys Leu Lys Ala Leu Glu Lys
                725                 730                 735

Glu Gln Arg Glu Arg Ile Pro Arg Ala Asp Glu Leu Asn Gln Thr Gly
            740                 745                 750

Gln Ile Leu Val Glu Gln Met Gly Lys Glu Gly Leu Pro Thr Glu Glu
        755                 760                 765

Ile Lys Asn Val Leu Glu Lys Val Ser Ser Glu Trp Lys Asn Val Ser
    770                 775                 780

Gln His Leu Glu Asp Leu Glu Arg Lys Ile Gln Leu Gln Glu Asp Ile
785                 790                 795                 800

Asn Ala Tyr Phe Lys Gln Leu Asp Glu Leu Glu Lys Val Ile Lys Thr
                805                 810                 815

Lys Glu Glu Trp Val Lys His Thr Ser Ile Ser Glu Ser Ser Arg Gln
            820                 825                 830

Ser Leu Pro Ser Leu Lys Asp Ser Cys Gln Arg Glu Leu Thr Asn Leu
        835                 840                 845

Leu Gly Leu His Pro Lys Ile Glu Met Ala Arg Ala Ser Cys Ser Ala
    850                 855                 860

Leu Met Ser Gln Pro Ser Ala Pro Asp Phe Val Gln Arg Gly Phe Asp
865                 870                 875                 880

Ser Phe Leu Gly Arg Tyr Gln Ala Val Gln Glu Ala Val Glu Asp Arg
                885                 890                 895

Gln Gln His Leu Glu Asn Glu Leu Lys Gly Gln Pro Gly His Ala Tyr
            900                 905                 910

Leu Glu Thr Leu Lys Thr Leu Lys Asp Val Leu Asn Asp Ser Glu Asn
        915                 920                 925

Lys Ala Gln Val Ser Leu Asn Val Leu Asn Asp Leu Ala Lys Val Glu
    930                 935                 940

Lys Ala Leu Gln Glu Lys Lys Thr Leu Asp Glu Ile Leu Glu Asn Gln
945                 950                 955                 960

Lys Pro Ala Leu His Lys Leu Ala Glu Glu Thr Lys Ala Leu Glu Lys
                965                 970                 975

Asn Val His Pro Asp Val Glu Lys Leu Tyr Lys Gln Glu Phe Asp Asp
            980                 985                 990

Val Gln Gly Lys Trp Asn Lys Leu  Lys Val Leu Val Ser  Lys Asp Leu
        995                 1000                1005

His Leu  Leu Glu Glu Ile Ala  Leu Thr Leu Arg Ala  Phe Glu Ala
    1010                 1015                 1020
```

```
Asp Ser  Thr Val Ile Glu Lys  Trp Met Asp Gly Val  Lys Asp Phe
    1025                 1030                 1035

Leu Met  Lys Gln Gln Ala Ala  Gln Gly Asp Asp Ala  Gly Leu Gln
    1040                 1045                 1050

Arg Gln  Leu Asp Gln Cys Ser  Ala Phe Val Asn Glu  Ile Glu Thr
    1055                 1060                 1065

Ile Glu  Ser Ser Leu Lys Asn  Met Lys Glu Ile Glu  Thr Asn Leu
    1070                 1075                 1080

Arg Ser  Gly Pro Val Ala Gly  Ile Lys Thr Trp Val  Gln Thr Arg
    1085                 1090                 1095

Leu Gly  Asp Tyr Gln Thr Gln  Leu Glu Lys Leu Ser  Lys Glu Ile
    1100                 1105                 1110

Ala Thr  Gln Lys Ser Arg Leu  Ser Glu Ser Gln Glu  Lys Ala Ala
    1115                 1120                 1125

Asn Leu  Lys Lys Asp Leu Ala  Glu Met Gln Glu Trp  Met Thr Gln
    1130                 1135                 1140

Ala Glu  Glu Glu Tyr Leu Glu  Arg Asp Phe Glu Tyr  Lys Ser Pro
    1145                 1150                 1155

Glu Glu  Leu Glu Ser Ala Val  Glu Glu Met Lys Arg  Ala Lys Glu
    1160                 1165                 1170

Asp Val  Leu Gln Lys Glu Val  Arg Val Lys Ile Leu  Lys Asp Asn
    1175                 1180                 1185

Ile Lys  Leu Leu Ala Ala Lys  Val Pro Ser Gly Gly  Gln Glu Leu
    1190                 1195                 1200

Thr Ser  Glu Leu Asn Val Val  Leu Glu Asn Tyr Gln  Leu Leu Cys
    1205                 1210                 1215

Asn Arg  Ile Arg Gly Lys Cys  His Thr Leu Glu Glu  Val Trp Ser
    1220                 1225                 1230

Cys Trp  Ile Glu Leu Leu His  Tyr Leu Asp Leu Glu  Thr Thr Trp
    1235                 1240                 1245

Leu Asn  Thr Leu Glu Glu Arg  Met Lys Ser Thr Glu  Val Leu Pro
    1250                 1255                 1260

Glu Lys  Thr Asp Ala Val Asn  Glu Ala Leu Glu Ser  Leu Glu Ser
    1265                 1270                 1275

Val Leu  Arg His Pro Ala Asp  Asn Arg Thr Gln Ile  Arg Glu Leu
    1280                 1285                 1290

Gly Gln  Thr Leu Ile Asp Gly  Gly Ile Leu Asp Asp  Ile Ile Ser
    1295                 1300                 1305

Glu Lys  Leu Glu Ala Phe Asn  Ser Arg Tyr Glu Asp  Leu Ser His
    1310                 1315                 1320

Leu Ala  Glu Ser Lys Gln Ile  Ser Leu Glu Lys Gln  Leu Gln Val
    1325                 1330                 1335

Leu Arg  Glu Thr Asp Gln Met  Leu Gln Val Leu Gln  Glu Ser Leu
    1340                 1345                 1350

Gly Glu  Leu Asp Lys Gln Leu  Thr Thr Tyr Leu Thr  Asp Arg Ile
    1355                 1360                 1365

Asp Ala  Phe Gln Val Pro Gln  Glu Ala Gln Lys Ile  Gln Ala Glu
    1370                 1375                 1380

Ile Ser  Ala His Glu Leu Thr  Leu Glu Glu Leu Arg  Arg Asn Met
    1385                 1390                 1395

Arg Ser  Gln Pro Leu Thr Ser  Pro Glu Ser Arg Thr  Ala Arg Gly
    1400                 1405                 1410

Gly Ser  Gln Met Asp Val Leu  Gln Arg Lys Leu Arg  Glu Val Ser
    1415                 1420                 1425
```

```
Thr Lys  Phe Gln Leu Phe Gln  Lys Pro Ala Asn Phe  Glu Gln Arg
    1430                 1435                 1440

Met Leu  Asp Cys Lys Arg Val  Leu Asp Gly Val Lys  Ala Glu Leu
    1445                 1450                 1455

His Val  Leu Asp Val Lys Asp  Val Asp Pro Asp Val  Ile Gln Thr
    1460                 1465                 1470

His Leu  Asp Lys Cys Met Lys  Leu Tyr Lys Thr Leu  Ser Glu Val
    1475                 1480                 1485

Lys Leu  Glu Val Glu Thr Val  Ile Lys Thr Gly Arg  His Ile Val
    1490                 1495                 1500

Gln Lys  Gln Gln Thr Asp Asn  Pro Lys Gly Met Asp  Glu Gln Leu
    1505                 1510                 1515

Thr Ser  Leu Lys Val Leu Tyr  Asn Asp Leu Gly Ala  Gln Val Thr
    1520                 1525                 1530

Glu Gly  Lys Gln Asp Leu Glu  Arg Ala Ser Gln Leu  Ala Arg Lys
    1535                 1540                 1545

Met Lys  Lys Glu Ala Ala Ser  Leu Ser Glu Trp Leu  Ser Ala Thr
    1550                 1555                 1560

Glu Thr  Glu Leu Val Gln Lys  Ser Thr Ser Glu Gly  Leu Leu Gly
    1565                 1570                 1575

Asp Leu  Asp Thr Glu Ile Ser  Trp Ala Lys Asn Val  Leu Lys Asp
    1580                 1585                 1590

Leu Glu  Lys Arg Lys Ala Asp  Leu Asn Thr Ile Thr  Glu Ser Ser
    1595                 1600                 1605

Ala Ala  Leu Gln Asn Leu Ile  Glu Gly Ser Glu Pro  Ile Leu Glu
    1610                 1615                 1620

Glu Arg  Leu Cys Val Leu Asn  Ala Gly Trp Ser Arg  Val Arg Thr
    1625                 1630                 1635

Trp Thr  Glu Asp Trp Cys Asn  Thr Leu Met Asn His  Gln Asn Gln
    1640                 1645                 1650

Leu Glu  Ile Phe Asp Gly Asn  Val Ala His Ile Ser  Thr Trp Leu
    1655                 1660                 1665

Tyr Gln  Ala Glu Ala Leu Leu  Asp Glu Ile Glu Lys  Lys Pro Thr
    1670                 1675                 1680

Ser Lys  Gln Glu Glu Ile Val  Lys Arg Leu Val Ser  Glu Leu Asp
    1685                 1690                 1695

Asp Ala  Asn Leu Gln Val Glu  Asn Val Arg Asp Gln  Ala Leu Ile
    1700                 1705                 1710

Leu Met  Asn Ala Arg Gly Ser  Ser Ser Arg Glu Leu  Val Glu Pro
    1715                 1720                 1725

Lys Leu  Ala Glu Leu Asn Arg  Asn Phe Glu Lys Val  Ser Gln His
    1730                 1735                 1740

Ile Lys  Ser Ala Lys Leu Leu  Ile Ala Gln Glu Pro  Leu Tyr Gln
    1745                 1750                 1755

Cys Leu  Val Thr Thr Glu Thr  Phe Glu Thr Gly Val  Pro Phe Ser
    1760                 1765                 1770

Asp Leu  Glu Lys Leu Glu Asn  Asp Ile Glu Asn Met  Leu Lys Phe
    1775                 1780                 1785

Val Glu  Lys His Leu Glu Ser  Ser Asp Glu Asp Glu  Lys Met Asp
    1790                 1795                 1800

Glu Glu  Ser Ala Gln Ile Glu  Glu Val Leu Gln Arg  Gly Glu Glu
    1805                 1810                 1815

Met Leu  His Gln Pro Met Glu  Asp Asn Lys Lys Glu  Lys Ile Arg
```

```
    1820                1825                1830

Leu Gln  Leu Leu Leu Leu His  Thr Arg Tyr Asn Lys  Ile Lys Ala
    1835                1840                1845

Ile Pro  Ile Gln Gln Arg Lys  Met Gly Gln Leu Ala  Ser Gly Ile
    1850                1855                1860

Arg Ser  Ser Leu Leu Pro Thr  Asp Tyr Leu Val Glu  Ile Asn Lys
    1865                1870                1875

Ile Leu  Leu Cys Met Asp Asp  Val Glu Leu Ser Leu  Asn Val Pro
    1880                1885                1890

Glu Leu  Asn Thr Ala Ile Tyr  Glu Asp Phe Ser Phe  Gln Glu Asp
    1895                1900                1905

Ser Leu  Lys Asn Ile Lys Asp  Gln Leu Asp Lys Leu  Gly Glu Gln
    1910                1915                1920

Ile Ala  Val Ile His Glu Lys  Gln Pro Asp Val Ile  Leu Glu Ala
    1925                1930                1935

Ser Gly  Pro Glu Ala Ile Gln  Ile Arg Asp Thr Leu  Thr Gln Leu
    1940                1945                1950

Asn Ala  Lys Trp Asp Arg Ile  Asn Arg Met Tyr Ser  Asp Arg Lys
    1955                1960                1965

Gly Cys  Phe Asp Arg Ala Met  Glu Glu Trp Arg Gln  Phe His Cys
    1970                1975                1980

Asp Leu  Asn Asp Leu Thr Gln  Trp Ile Thr Glu Ala  Glu Glu Leu
    1985                1990                1995

Leu Val  Asp Thr Cys Ala Pro  Gly Gly Ser Leu Asp  Leu Glu Lys
    2000                2005                2010

Ala Arg  Ile His Gln Gln Glu  Leu Glu Val Gly Ile  Ser Ser His
    2015                2020                2025

Gln Pro  Ser Phe Ala Ala Leu  Asn Arg Thr Gly Asp  Gly Ile Val
    2030                2035                2040

Gln Lys  Leu Ser Gln Ala Asp  Gly Ser Phe Leu Lys  Glu Lys Leu
    2045                2050                2055

Ala Gly  Leu Asn Gln Arg Trp  Asp Ala Ile Val Ala  Glu Val Lys
    2060                2065                2070

Asp Arg  Gln Pro Arg Leu Lys  Gly Glu Ser Lys Gln  Val Met Lys
    2075                2080                2085

Tyr Arg  His Gln Leu Asp Glu  Ile Ile Cys Trp Leu  Thr Lys Ala
    2090                2095                2100

Glu His  Ala Met Gln Lys Arg  Ser Thr Thr Glu Leu  Gly Glu Asn
    2105                2110                2115

Leu Gln  Glu Leu Arg Asp Leu  Thr Gln Glu Met Glu  Val His Ala
    2120                2125                2130

Glu Lys  Leu Lys Trp Leu Asn  Arg Thr Glu Leu Glu  Met Leu Ser
    2135                2140                2145

Asp Lys  Ser Leu Ser Leu Pro  Glu Arg Asp Lys Ile  Ser Glu Ser
    2150                2155                2160

Leu Arg  Thr Val Asn Met Thr  Trp Asn Lys Ile Cys  Arg Glu Val
    2165                2170                2175

Pro Thr  Thr Leu Lys Glu Cys  Ile Gln Glu Pro Ser  Ser Val Ser
    2180                2185                2190

Gln Thr  Arg Ile Ala Ala His  Pro Asn Val Gln Lys  Val Val Leu
    2195                2200                2205

Val Ser  Ser Ala Ser Asp Ile  Pro Val Gln Ser His  Arg Thr Ser
    2210                2215                2220
```

```
Glu Ile  Ser Ile Pro Ala Asp  Leu Asp Lys Thr Ile  Thr Glu Leu
    2225                 2230                 2235

Ala Asp  Trp Leu Val Leu Ile  Asp Gln Met Leu Lys  Ser Asn Ile
    2240                 2245                 2250

Val Thr  Val Gly Asp Val Glu  Glu Ile Asn Lys Thr  Val Ser Arg
    2255                 2260                 2265

Met Lys  Ile Thr Lys Ala Asp  Leu Glu Gln Arg His  Pro Gln Leu
    2270                 2275                 2280

Asp Tyr  Val Phe Thr Leu Ala  Gln Asn Leu Lys Asn  Lys Ala Ser
    2285                 2290                 2295

Ser Ser  Asp Met Arg Thr Ala  Ile Thr Glu Lys Leu  Glu Arg Val
    2300                 2305                 2310

Lys Asn  Gln Trp Asp Gly Thr  Gln His Gly Val Glu  Leu Arg Gln
    2315                 2320                 2325

Gln Gln  Leu Glu Asp Met Ile  Ile Asp Ser Leu Gln  Trp Asp Asp
    2330                 2335                 2340

His Arg  Glu Glu Thr Glu Glu  Leu Met Arg Lys Tyr  Glu Ala Arg
    2345                 2350                 2355

Leu Tyr  Ile Leu Gln Gln Ala  Arg Arg Asp Pro Leu  Thr Lys Gln
    2360                 2365                 2370

Ile Ser  Asp Asn Gln Ile Leu  Leu Gln Glu Leu Gly  Pro Gly Asp
    2375                 2380                 2385

Gly Ile  Val Met Ala Phe Asp  Asn Val Leu Gln Lys  Leu Leu Glu
    2390                 2395                 2400

Glu Tyr  Gly Ser Asp Asp Thr  Arg Asn Val Lys Glu  Thr Thr Glu
    2405                 2410                 2415

Tyr Leu  Lys Thr Ser Trp Ile  Asn Leu Lys Gln Ser  Ile Ala Asp
    2420                 2425                 2430

Arg Gln  Asn Ala Leu Glu Ala  Glu Trp Arg Thr Val  Gln Ala Ser
    2435                 2440                 2445

Arg Arg  Asp Leu Glu Asn Phe  Leu Lys Trp Ile Gln  Glu Ala Glu
    2450                 2455                 2460

Thr Thr  Val Asn Val Leu Val  Asp Ala Ser His Arg  Glu Asn Ala
    2465                 2470                 2475

Leu Gln  Asp Ser Ile Leu Ala  Arg Glu Leu Lys Gln  Gln Met Gln
    2480                 2485                 2490

Asp Ile  Gln Ala Glu Ile Asp  Ala His Asn Asp Ile  Phe Lys Ser
    2495                 2500                 2505

Ile Asp  Gly Asn Arg Gln Lys  Met Val Lys Ala Leu  Gly Asn Ser
    2510                 2515                 2520

Glu Glu  Ala Thr Met Leu Gln  His Arg Leu Asp Asp  Met Asn Gln
    2525                 2530                 2535

Arg Trp  Asn Asp Leu Lys Ala  Lys Ser Ala Ser Ile  Arg Ala His
    2540                 2545                 2550

Leu Glu  Ala Ser Ala Glu Lys  Trp Asn Arg Leu Leu  Met Ser Leu
    2555                 2560                 2565

Glu Glu  Leu Ile Lys Trp Leu  Asn Met Lys Asp Glu  Glu Leu Lys
    2570                 2575                 2580

Lys Gln  Met Pro Ile Gly Gly  Asp Val Pro Ala Leu  Gln Leu Gln
    2585                 2590                 2595

Tyr Asp  His Cys Lys Ala Leu  Arg Arg Glu Leu Lys  Glu Lys Glu
    2600                 2605                 2610

Tyr Ser  Val Leu Asn Ala Val  Asp Gln Ala Arg Val  Phe Leu Ala
    2615                 2620                 2625
```

```
Asp Gln  Pro Ile Glu Ala Pro  Glu Glu Pro Arg Arg  Asn Leu Gln
    2630                 2635                 2640

Ser Lys  Thr Glu Leu Thr Pro  Glu Glu Arg Ala Gln  Lys Ile Ala
    2645                 2650                 2655

Lys Ala  Met Arg Lys Gln Ser  Ser Glu Val Lys Glu  Lys Trp Glu
    2660                 2665                 2670

Ser Leu  Asn Ala Val Thr Ser  Asn Trp Gln Lys Gln  Val Asp Lys
    2675                 2680                 2685

Ala Leu  Glu Lys Leu Arg Asp  Leu Gln Gly Ala Met  Asp Asp Leu
    2690                 2695                 2700

Asp Ala  Asp Met Lys Glu Ala  Glu Ser Val Arg Asn  Gly Trp Lys
    2705                 2710                 2715

Pro Val  Gly Asp Leu Leu Ile  Asp Ser Leu Gln Asp  His Ile Glu
    2720                 2725                 2730

Lys Ile  Met Ala Phe Arg Glu  Glu Ile Ala Pro Ile  Asn Phe Lys
    2735                 2740                 2745

Val Lys  Thr Val Asn Asp Leu  Ser Ser Gln Leu Ser  Pro Leu Asp
    2750                 2755                 2760

Leu His  Pro Ser Leu Lys Met  Ser Arg Gln Leu Asp  Asp Leu Asn
    2765                 2770                 2775

Met Arg  Trp Lys Leu Leu Gln  Val Ser Val Asp Asp  Arg Leu Lys
    2780                 2785                 2790

Gln Leu  Gln Glu Ala His Arg  Asp Phe Gly Pro Ser  Ser Gln His
    2795                 2800                 2805

Phe Leu  Ser Thr Ser Val Gln  Leu Pro Trp Gln Arg  Ser Ile Ser
    2810                 2815                 2820

His Asn  Lys Val Pro Tyr Tyr  Ile Asn His Gln Thr  Gln Thr Thr
    2825                 2830                 2835

Cys Trp  Asp His Pro Lys Met  Thr Glu Leu Phe Gln  Ser Leu Ala
    2840                 2845                 2850

Asp Leu  Asn Asn Val Arg Phe  Ser Ala Tyr Arg Thr  Ala Ile Lys
    2855                 2860                 2865

Ile Arg  Arg Leu Gln Lys Ala  Leu Cys Leu Asp Leu  Leu Glu Leu
    2870                 2875                 2880

Ser Thr  Thr Asn Glu Ile Phe  Lys Gln His Lys Leu  Asn Gln Asn
    2885                 2890                 2895

Asp Gln  Leu Leu Ser Val Pro  Asp Val Ile Asn Cys  Leu Thr Thr
    2900                 2905                 2910

Thr Tyr  Asp Gly Leu Glu Gln  Met His Lys Asp Leu  Val Asn Val
    2915                 2920                 2925

Pro Leu  Cys Val Asp Met Cys  Leu Asn Trp Leu Leu  Asn Val Tyr
    2930                 2935                 2940

Asp Thr  Gly Arg Thr Gly Lys  Ile Arg Val Gln Ser  Leu Lys Ile
    2945                 2950                 2955

Gly Leu  Met Ser Leu Ser Lys  Gly Leu Leu Glu Glu  Lys Tyr Arg
    2960                 2965                 2970

Tyr Leu  Phe Lys Glu Val Ala  Gly Pro Thr Glu Met  Cys Asp Gln
    2975                 2980                 2985

Arg Gln  Leu Gly Leu Leu Leu  His Asp Ala Ile Gln  Ile Pro Arg
    2990                 2995                 3000

Gln Leu  Gly Glu Val Ala Ala  Phe Gly Gly Ser Asn  Ile Glu Pro
    3005                 3010                 3015

Ser Val  Arg Ser Cys Phe Gln  Gln Asn Asn Asn Lys  Pro Glu Ile
```

```
    3020                3025                3030

Ser Val  Lys Glu Phe Ile Asp  Trp Met His Leu Glu  Pro Gln Ser
    3035                3040                3045

Met Val  Trp Leu Pro Val Leu  His Arg Val Ala Ala  Ala Glu Thr
    3050                3055                3060

Ala Lys  His Gln Ala Lys Cys  Asn Ile Cys Lys Glu  Cys Pro Ile
    3065                3070                3075

Val Gly  Phe Arg Tyr Arg Ser  Leu Lys His Phe Asn  Tyr Asp Val
    3080                3085                3090

Cys Gln  Ser Cys Phe Phe Ser  Gly Arg Thr Ala Lys  Gly His Lys
    3095                3100                3105

Leu His  Tyr Pro Met Val Glu  Tyr Cys Ile Pro Thr  Thr Ser Gly
    3110                3115                3120

Glu Asp  Val Arg Asp Phe Thr  Lys Val Leu Lys Asn  Lys Phe Arg
    3125                3130                3135

Ser Lys  Lys Tyr Phe Ala Lys  His Pro Arg Leu Gly  Tyr Leu Pro
    3140                3145                3150

Val Gln  Thr Val Leu Glu Gly  Asp Asn Leu Glu Thr  Pro Ile Thr
    3155                3160                3165

Leu Ile  Ser Met Trp Pro Glu  His Tyr Asp Pro Ser  Gln Ser Pro
    3170                3175                3180

Gln Leu  Phe His Asp Asp Thr  His Ser Arg Ile Glu  Gln Tyr Ala
    3185                3190                3195

Thr Arg  Leu Ala Gln Met Glu  Arg Thr Asn Gly Ser  Phe Leu Thr
    3200                3205                3210

Asp Ser  Ser Ser Thr Thr Gly  Ser Val Glu Asp Glu  His Ala Leu
    3215                3220                3225

Ile Gln  Gln Tyr Cys Gln Thr  Leu Gly Gly Glu Ser  Pro Val Ser
    3230                3235                3240

Gln Pro  Gln Ser Pro Ala Gln  Ile Leu Lys Ser Val  Glu Arg Glu
    3245                3250                3255

Glu Arg  Gly Glu Leu Glu Arg  Ile Ile Ala Asp Leu  Glu Glu Glu
    3260                3265                3270

Gln Arg  Asn Leu Gln Val Glu  Tyr Glu Gln Leu Lys  Asp Gln His
    3275                3280                3285

Leu Arg  Arg Gly Leu Pro Val  Gly Ser Pro Pro Glu  Ser Ile Ile
    3290                3295                3300

Ser Pro  His His Thr Ser Glu  Asp Ser Glu Leu Ile  Ala Glu Ala
    3305                3310                3315

Lys Leu  Leu Arg Gln His Lys  Gly Arg Leu Glu Ala  Arg Met Gln
    3320                3325                3330

Ile Leu  Glu Asp His Asn Lys  Gln Leu Glu Ser Gln  Leu His Arg
    3335                3340                3345

Leu Arg  Gln Leu Leu Glu Gln  Pro Glu Ser Asp Ser  Arg Ile Asn
    3350                3355                3360

Gly Val  Ser Pro Trp Ala Ser  Pro Gln His Ser Ala  Leu Ser Tyr
    3365                3370                3375

Ser Leu  Asp Pro Asp Ala Ser  Gly Pro Gln Phe His  Gln Ala Ala
    3380                3385                3390

Gly Glu  Asp Leu Leu Ala Pro  Pro His Asp Thr Ser  Thr Asp Leu
    3395                3400                3405

Thr Glu  Val Met Glu Gln Ile  His Ser Thr Phe Pro  Ser Cys Cys
    3410                3415                3420
```

-continued

Pro Asn Val Pro Ser Arg Pro Gln Ala Met
3425 3430

<210> SEQ ID NO 8
<211> LENGTH: 12382
<212> TYPE: DNA
<213> ORGANISM: Mus musculus

<400> SEQUENCE: 8
gtattcatgc tagcctggac catttttcag atttagcctt cagaagagga tctgggaaag 60
cctttggatt atactgaaac tcattcaaga tggccaagta tggggacctt gaagccaggc 120
ctgatgatgg gcagaacgaa ttcagtgaca tcattaagtc cagatctgat gaacacaatg 180
atgtacagaa gaaaaccttt accaaatgga taaacgctcg attttccaag agtgggaaac 240
cacccatcag tgatatgttc tcagacctca aagatgggag aaagctcttg gatcttctcg 300
aaggcctcac aggaacatca ttgccaaagg aacgtggttc cacaagggtg catgccttaa 360
acaatgtcaa ccgagtgcta caggttttac atcagaacaa tgtggacttg gtgaatattg 420
gaggcacgga cattgtggat ggaaatccca agctgacttt agggttactc tggagcatca 480
ttctgcactg gcaggtgaag gatgtcatga aagatatcat gtcagacctg cagcagacaa 540
acagcgagaa gatcctgctg agctgggtgc ggcagaccac caggccctac agtcaagtca 600
acgtcctcaa cttcaccacc agctggaccg atggactcgc gttcaacgcc gtgctccacc 660
ggcacaaacc agatctcttc agctgggaca gagtggtcaa aatgtcccca attgagagac 720
ttgaacatgc ttttagcaag gcccacactt atttgggaat tgaaaagctt ctagatcctg 780
aagatgttgc tgtgcatctc cctgacaaga aatccataat tatgtattta acgtctctgt 840
ttgaggtgct tcctcagcaa gtcacgatag atgccatccg agaggtggag actctcccaa 900
ggaagtataa gaaagaatgt gaagaggaag aaattcatat ccagagtgca gtgctggcag 960
aggaaggcca gagtccccga gctgagaccc ctagcaccgt cactgaagtg gacatggatt 1020
tggacagcta ccagatagcg ctagaggaag tgctgacgtg gctgctgtcc gcggaggaca 1080
cgttccagga gcaagatgac atttctgatg atgtcgaaga agtcaaagag cagtttgcta 1140
cccatgaaac ttttatgatg gagctgacag cacaccagag cagcgtgggg agcgtcctgc 1200
aggctggcaa ccagctgatg acacaaggga ctctgtcaga ggaggaggag tttgagatcc 1260
aggaacagat gaccttgctg aatgcaaggt gggaggcgct ccgggtggag agcatggaga 1320
ggcagtcccg gctgcacgac gctctgatgg agctgcagaa gaaacagctg cagcagctct 1380
caagctggct ggccctcaca gaagagcgca ttcagaagat ggagagcctc ccgctgggtg 1440
atgacctgcc ctccctgcag aagctgcttc aagaacataa aagtttgcaa aatgaccttg 1500
aagctgaaca ggtgaaggta aattccttaa ctcacatggt ggtgattgtg gatgaaaaca 1560
gtggggagag tgccacagct cttctggaag atcagttaca gaaactgggt gagcgctgga 1620
cagctgtatg ccgctggact gaagaacgtt ggaacaggtt gcaagaaatc agtattctgt 1680
ggcaggaatt attggaagag cagtgtctgt tggaggcttg gctcaccgaa aaggaagagg 1740
ctttgaataa agttcaaacc agcaacttta aagaccagaa ggaactaagt gtcagtgtcc 1800
ggcgtctggc tatattgaag gaagacatgg aaatgaagag gcagactctg gatcaactga 1860
gtgagattgg ccaggatgtg ggccaattac tcagtaatcc caaggcatct aagaagatga 1920
acagtgactc tgaggagcta acacagagat gggattctct ggttcagaga ctcgaagact 1980
cttctaacca ggtgactcag gcggtagcga agctcggcat gtcccagatt ccacagaagg 2040
acctattgga gaccgttcat gtgagagaac aagggatggt gaagaagccc aagcaggaac 2100

```
tgcctcctcc tcccccacca aagaagagac agattcacgt ggacgtggag gccaagaaaa   2160
agtttgatgc tataagtaca gagctgctga actggatttt gaaatcaaag actgccattc   2220
agaacacaga gatgaaagaa tataagaagt cgcaggagac ctcaggaatg aaaaagaaat   2280
tgaagggatt agagaaagaa cagaaggaaa atctgccccg actggacgaa ctgaatcaaa   2340
ccggacaaac cctccgggag caaatgggaa aagaaggcct ttccactgaa gaagtaaacg   2400
atgttctgga aagggtttcg ttggagtgga agatgatatc tcagcagcta gaagatctgg   2460
gaaggaagat ccagctgcag gaagatataa atgcttattt taagcagctt gatgccattg   2520
aggagaccat caaggagaag gaagagtggc tgaggggcac acccatttct gaatcgcccc   2580
ggcagccctt gccaggctta aaggattctt gccagaggga actgacagat ctccttggcc   2640
ttcaccccag aattgagacg ctgtgtgcaa gctgttcagc cctgaagtct cagccctgtg   2700
tcccaggttt tgtccagcag ggttttgacg accttcgaca tcattaccag gctgtgcgga   2760
aggctttaga ggaataccaa caacaactag aaaatgagct gaagagccag cctggacccg   2820
cgtatttgga cacactgaat accctgaaaa aaatgctaag cgagtcagaa aaggcggccc   2880
aggcctctct gaatgccctg aacgatccca tagcggtgga gcaggccctg caggagaaaa   2940
aggcccttga tgaaaccctt gagaatcaga aacatacgtt acataagctt tcagaagaaa   3000
cgaagacttt ggagaaaaat atgcttcctg atgtggggaa aatgtataaa caagaatttg   3060
atgatgtcca aggcagatgg aataaagtaa agaccaaggt ttccagagac ttacacttgc   3120
tcgaggaaat cacccccaga ctccgagatt ttgaggctga ttcagaagtc attgagaagt   3180
gggtgagtgg catcaaagac ttcctcatga aagaacaggc tgctcaagga gacgctgctg   3240
cgctgcagag ccagcttgac caatgtgcta cgtttgctaa tgaaatcgaa accatcgagt   3300
catctctgaa gaacatgagg gaagtagaga ctagccttca gaggtgtcca gtcactggag   3360
tcaagacatg ggtacaggca agactagtgg attaccaatc ccaactggag aaattcagca   3420
aagagattgc tattcaaaaa agcaggctgt cagatagtca agaaaaagcc ctgaacttga   3480
aaaaggattt ggctgagatg caggagtgga tggcacaggc tgaagaggac tacctggaga   3540
gggacttcga gtacaaatct ccagaagaac tcgagagtgc ggtggaggaa atgaagaggg   3600
caaaagagga ggtgctgcag aaggaggtga gggtgaaaat tctgaaggac agcatcaagc   3660
tggtggctgc caaggtgccc tctggtggcc aggagttgac gtcggaattc aacgaggtgc   3720
tggagagcta ccagcttctg tgcaatagaa ttcgagggaa gtgccacaca ctggaggagg   3780
tctggtcttg ctgggtggag ctgcttcact atctggacct ggagaccacg tggttgaaca   3840
ccttggagga gcgcgtgagg agcacggagg ccctgcctga gagggcagaa gctgttcatg   3900
aagctctgga gtctcttgag tctgttttgc gccatccggc ggataatcgc acccagattc   3960
gggaacttgg gcagactctg attgatggtg gaatcctgga tgacataatc agcgagaagc   4020
tggaggcttt taacagccgc tacgaagagc tgagtcactt ggcggagagc aaacagattt   4080
ctttggagaa gcaactccag gtcctccgcg aaactgacca catgcttcag gtgctgaagg   4140
agagcctggg ggagctggac aaacagctta ccacatacct gacggacagg atcgatgcct   4200
tccaactgcc acaggaagct cagaagatcc aagccgaaat ctcagcccat gagctcaccc   4260
tggaggagct gaggaagaat gtgcgctccc agccccccgac gtcccctgag ggcagggcca   4320
ccagaggagg aagtcagatg gacatgctac agaggaaact tcgagaggtc tccaccaaat   4380
tccagctttt ccagaagccc gcaaatttcg agcagcggat gctggactgc aagcgtgtgt   4440
tggagggagt gaaggccgag cttcatgtcc tcgatgtgag ggatgtggac cctgacgtca   4500
```

```
ttcaggccca cttggacaag tgcatgaaac tatataaaac gttgagtgaa gtcaaacttg   4560
aagttgagac tgtcatcaaa acagggaggc acattgtcca gaagcagcag acggacaacc   4620
cgaaaagcat ggacgaacag cttacatctc tgaaagtcct ctacaatgac ctgggcgcac   4680
aggtgacaga agggaagcaa gacctggaaa gagcctcaca gctgtccagg aagatgaaga   4740
aggaggctgc cgtcctctct gaatggctct ctgccacaga ggcagaacta gtgcagaaat   4800
ccacatcaga aggcgtgatt ggtgacctgg acacagaaat ctcctgggct aaaagtattc   4860
tcaaggatct ggaaaagagg aaagttgact taaatggcat tacagagagc agtgccgccc   4920
ttcagcactt ggtcttgggc agtgagtctg ttctggaaga gaacctctgt gtgctcaatg   4980
ctggatggag ccgagtgcgg acgtggaccg aagactggtg caacaccttg ctgaaccatc   5040
aaaaccagct ggagctattt gatggacacg tcgctcacat cagtacctgg ctctatcaag   5100
ccgaagctct gctggatgag atcgaaaaga aaccagcgag taaacaggaa gaaattgtga   5160
agcgtttact gtctgaattg gatgatgcca gcctccaggt tgagaatgtt cgggaacaag   5220
ccatcatctt ggtgaatgct cgtggaagcg ccagcaggga actcgtggaa ccaaaattag   5280
ccgagctgag caggaacttt gaaaaggtgt cccagcacat aaagagcgcc cgaatgctga   5340
ttggtcagga cccttcatcc taccaaggct tggaccctgc tggaactgtt caagctgctg   5400
agtctttctc tgacttggaa aacttagaac aagacataga aacatgttg aaagttgtgg   5460
aaaagcactt ggaccccaat aacgatgaga agatggatga ggagcaagcc cagattgagg   5520
aagttctaca aagaggggag catttgttac atgaacctat ggaggacagt aagaaagaaa   5580
agatccgctt gcagttgtta cttttgcata ctcgttacaa caaaattaag acaatcccta   5640
tccagcagag aaaaacaatt ccagtttctt ctggaattac atcatcagcc ctccctgcag   5700
attatttggt tgaaattaat aaaattttac tcactctgga tgacattgaa ttatcactta   5760
atatgccgga gctaaacacc actgtctaca aagacttctc tttccaggaa gactctctga   5820
agagtatcaa aggtcaactg gacagacttg gagagcagat tgcagttgtt cacgagaagc   5880
agccggatgt catcgtggaa gcctctggcc ctgaggccat tcagatcagg gacatgctcg   5940
ctcagctgaa tgcaaaatgg gaccgagtga atagagtgta cagtgatcgg agagggtcct   6000
ttgccagggc tgtggaggaa tggaggcagt tccaccatga ccttgatgac cttacacagt   6060
ggctatctga agctgaagac ctgctggtag acacttgtgc tccagatggt agcctggacc   6120
tggagaaagc cagggcacag cagctggaac tggaagaggg cctcagcagc caccagccca   6180
gcctgatcaa ggttaaccga aagggggagg accttgttca gagactccgc ccctcggagg   6240
caagcttcct gaaggagaag ctggcaggtt tcaaccagcg ctggagcact cttgtagctg   6300
aggtggaggc tttgcagccc aggctaaaag gagaaagtca gcaggtgttg gggtataaga   6360
gacggctaga tgaggtcacc tgctggttaa cgaaagtgga gagtgctgtg cagaagagat   6420
caacccctga cccggaagaa agcccacagg aattaacaga tttagcccaa gagacggaag   6480
ttcaagctga aaacattaag tggctgaaca gagcagaact ggaaatgctt tcagacaaaa   6540
atctgagttt gcgtgaaaga gagaaacttt cggaaagttt aaggaatgta aacacaacat   6600
ggaccaaggt atgcagagaa gtgcctagcc tcctgaagac acgcacccaa gacccctgct   6660
ctgccccaca gatgaggatg gctgctcatc ccaacgtcca aaaggtggtg ctagtatcat   6720
ctgcatcaga tgctcctctg cgtggcggcc tggaaatctc ggttcctgct gatttggata   6780
aaaccatcac agaactggct gactggctgg tattgatcga ccaaatgctg aagtccaaca   6840
ttgtcactgt gggggacgtg aaagagatca ataagacagt ttcccggatg aaaatcacaa   6900
```

```
aggctgattt agaacaacgc catcctcagc ttgattgtgt atttaccttg gcccaaaatt   6960
tgaaaaacaa agcttccagt tcagatgtga ggacagcaat cacagaaaaa ttggaaaagc   7020
tgaagaccca gtgggagagt actcagcatg gtgtggagct gcggcggcag cagctggagg   7080
acatggttgt ggacagcctg cagtgggacg accacaggga agagactgaa gagctcatga   7140
gaaaatacga ggctcgcttc tacatgctgc agcaggcccg ccgggaccca cttagcaaac   7200
aagtttctga taatcaacta ttgcttcaag agctggggtc tggcgatggt gtcatcatgg   7260
cgtttgataa tgtcctgcag aaacttctgg aagaatacag tggcgatgac acaaggaatg   7320
tggaagaaac cacggagtac ttgaaaacat catgggtcaa tctcaaacaa agcatcgctg   7380
atagacagag tgccttggag gctgagctac agacagtgca gacttctcgt agagacctgg   7440
agaactttgt caagtggctt caggaagcag aaaccacagc aaatgtgctg gccgatgcct   7500
ctcagcggga gaatgctctt caggacagtg tcctggcccg gcagctccga cagcagatgc   7560
tggacatcca ggcagaaatt gatgcccaca atgacatatt taaaagcatc gatggaaacc   7620
ggcagaagat ggtgaaagct ctggggaatt ctgaggaagc aacaatgctt cagcatcgac   7680
tggatgacat gaaccaaaga tggaatgatt tgaaggcaaa atctgctagc atcagggccc   7740
atttggaggc cagtgctgag aaatggaacc ggttgctggc atcgctggaa gagctgatca   7800
aatggctcaa tatgaaagat gaggagctta agaagcagat gcccattgga ggggacgtcc   7860
ctgccttaca gctccagtat gaccactgca aggtgctgag acgtgagcta aaggagaaag   7920
agtattctgt gctgaacgcc gtagatcaag ctcgagtttt tctggctgat cagccaatag   7980
aggcccccga agaaccaaga agaaacccac aatcaaagac agagttgact cctgaggaga   8040
gagcccagaa gatcgccaaa gccatgcgca agcagtcttc tgaagtccga gagaagtggg   8100
aaaatctaaa tgctgtcact agcaactggc aaaagcaagt agggaaggcg ttagagaaac   8160
tccgagacct gcagggagct atggacgacc tggacgcaga catgaaggag gtggaggctg   8220
tgcggaatgg ctggaagccc gtgggagacc tgcttataga ctccctgcag gatcacatcg   8280
agaaaaccct ggcgtttaga gaagaaattg caccaatcaa cttaaaagta aaaacaatga   8340
atgacctgtc cagtcagctg tctccacttg acttgcatcc atctctaaag atgtctcgcc   8400
agctggatga ccttaatatg cgatggaaac ttctacaggt ttccgtggac gatcgcctta   8460
agcagctcca ggaagcccac agagattttg ggccatcttc tcaacacttt ctgtccactt   8520
cagtccagct gccgtggcag agatccattt cacataataa agtgccctat tacatcaacc   8580
atcaaacaca gacaacctgt tgggatcatc ctaaaatgac tgagctcttc caatcccttg   8640
ctgatctgaa taatgtacgt ttctctgcct accgcacagc aatcaaaatt cgaaggctgc   8700
aaaaagcatt atgtctggat ctcttagagc tgaatacgac gaatgaagtt ttcaagcagc   8760
acaaactgaa ccaaaatgat cagctcctga gtgtcccaga cgtcatcaac tgtctgacca   8820
ccacttacga tgggcttgag cagctgcaca aggacttggt caatgttcca ctctgcgtcg   8880
atatgtgtct caactggctg ctcaacgtat acgacacggg ccggactgga aaaattcggg   8940
tacagagtct gaagattgga ttgatgtctc tctccaaagg cctcttagaa gagaaataca   9000
gatgtctctt taaggaggtg gcagggccaa cagagatgtg tgaccagcgg cagcttggcc   9060
tgctacttca cgatgccatc cagatcccta ggcagctggg ggaagtagca gcctttgggg   9120
gcagtaacat tgagcccagt gtccgcagct gcttccagca gaataacaac aagccagaaa   9180
tcagtgtgaa ggagtttata gactggatgc atttggaacc ccagtccatg gtgtggttgc   9240
cggttctgca tcgggtcgca gctgctgaga ctgcaaaaca tcaggccaaa tgcaacatct   9300
```

```
gcaaagaatg cccgattgtt gggttcagat acaggagcct aaagcatttt aattatgatg   9360
tctgccagag ttgcttcttt tctggaagaa cagcaaaggg ccacaagtta cattacccga   9420
tggtagaata ctgcataccg acaacatctg ggaagatgt gagagatttc actaaggtgc    9480
tgaagaacaa gttcaggtcc aagaaatatt ttgccaaaca tcctcggctt ggctacctgc   9540
ctgtccagac cgtgctggaa ggggacaact tagaaactcc tatcacgctc atcagtatgt   9600
ggccagagca ctatgacccc tcccagtccc ctcagctgtt tcatgatgac acccactcaa   9660
gaatagagca atacgctaca cgactggccc agatggaaag gacaaacggg tccttcctaa   9720
ctgatagcag ctctacaaca ggaagcgtgg aggatgagca tgccctcatc cagcagtact   9780
gccagaccct gggcggggag tcacctgtga gtcagccgca gagtccagct cagatcctga   9840
agtccgtgga gagggaagag cgtggggaac tggagcggat cattgctgac ttggaggaag   9900
agcaaagaaa tctgcaggtg gagtatgagc agctgaagga gcagcaccta agaaggggtc   9960
tccctgtggg ctcccctcca gactccatcg tatctcctca ccacacatct gaggactcag  10020
aacttatagc agaagctaaa ctcctgcggc agcacaaagg gcggctggag gcgaggatgc  10080
aaattttgga agatcacaat aaacagctgg agtctcagct gcaccgcctc agacagctcc  10140
tggagcagcc tgactctgac tcccgcatca atggtgtctc cccctgggct tccccacagc  10200
attctgcatt gagctactca cttgacactg acccaggccc acagttccac caggcagcat  10260
ctgaggacct gctggcccca cctcacgaca ctagcacgga cctcacggac gtgatggagc  10320
agatcaacag cacgtttccc tcttgcagct caaatgtccc cagcaggcca caggcaatgt  10380
gagcatctat ccagccagcc aacatttccc gaccttcagt attgccctct tctgcaaatg  10440
ccaatcccaa gacccattca accccaaagc tccgtggctc cacgacacaa gctgttgagt  10500
gcttactggg tgttctactg agggaaccaa acactgacta tccaaagaga aaaggatatt  10560
ttggttttct aataacgtat attattgttt tcttctcccc tttctatgca actgtaaatt  10620
aatgaacaga gaagtatttg gaggtggtaa agcatttgtc actgatttgt ataatatata  10680
cagccatggg aaagtgggtg ggggctttct aatatgaaac tgtcttttta ataaccaaga  10740
gaaaaaattg cataagaatt agaccacttt acattattac attccttctg ctgttcacat  10800
taaccttgta caataacttc acttattatt tgactgtttt accattatgt tttggttatt  10860
tataaattta tcagccatac aaacaaatag attctatgta tttgtttcta taatctggcc  10920
aaattcctaa gttcatatat ttgaatcaaa tattttacat atgtggagta ggcaggcatt  10980
ctgaagatac tatttaactt tagttgacgt cacacacacc atcctttagt aaccactgga  11040
tgactacact aaaaatcctg tggactttaa cggcaagctg ctggggtatt tttcctcctg  11100
tttttattcc ttttttgtaa gtagatcttg acgtctttat ttatttcatc ttgcaatctc  11160
tataataaag aagactgtat tgtaatagtc tcaaaaaatt attttaccaa gggttaccat  11220
ttaagcatat tttcattttg attcagaaac caaagttggt acaacctctc ctagtacttg  11280
caaccttggt tttcatgaga aaacacacgg caggctttgc ccattgtgag gagagcacac  11340
atcatgctct tcagtttcct ttgaatagac ttttattgtt gtttttgtat ttttcgagtc  11400
ctgtgtaagt tttgaaagct ctggttgttt cctttgtgaa agcaggcaga tacttattgg  11460
ctgtctcatt tgaagctttg gagcagatag tcagatgtct catgacccct cacttggcca  11520
gcagcacatc cgagaaggat gtcactcaca agcctacacc acggcttctc tagaatgaaa  11580
tcagtgctcg gatgattgta tccctgcctc tacttctgag tgtgttcaac taggtattgg  11640
cttcttttc ttttcttt cttttttttt taatttaaca cttaattgcc gattttagag  11700
```

aaaccaaaaa taaaggtgaa ggtaatatgt tttgattcaa acatatatgc ttttaaaaca 11760
tcaggacatg ctaactttgg gttctctttc actgggatct ggccagaagg aggctgaaag 11820
ttagaaattg ctattctttt aggatcggtt gggtgggttg gggggcaagg gtgtctattt 11880
gcagcataga tattttgaga cgaagaaaat tgttttatat aaggggagag ccatgatcac 11940
ctttctacct cagaaccacc ttcctccatt gtgttggaca tagctttata tgccgcagtg 12000
tgcaaaacct agggctgtag tcaggccttt ccatacccag gaagcacctg tgtaaagaag 12060
atcaacagaa actcccggaa ctcagaaccc caagttgtag atttggtgtc gtccttgttc 12120
ttgctttgag gagtcatgta ttcttttatt tcctgcctgt atttgtatgc aaaatgatct 12180
ctatctgcta ttacagaaaa agctacacaa aacactacat tgtaaccttc tgagtaataa 12240
ataagaggaa atatattaca gtaaccatga tgagaaataa gtgtattgtt cttttgaaat 12300
atgtggttaa tcgcagactg tcatctaatc tgttacatac cgtatttttc atcctgaata 12360
aaagtaattt taacacaaaa tg 12382

<210> SEQ ID NO 9
<211> LENGTH: 3430
<212> TYPE: PRT
<213> ORGANISM: Mus musculus

<400> SEQUENCE: 9

Met Ala Lys Tyr Gly Asp Leu Glu Ala Arg Pro Asp Asp Gly Gln Asn
1 5 10 15

Glu Phe Ser Asp Ile Ile Lys Ser Arg Ser Asp Glu His Asn Asp Val
20 25 30

Gln Lys Lys Thr Phe Thr Lys Trp Ile Asn Ala Arg Phe Ser Lys Ser
35 40 45

Gly Lys Pro Pro Ile Ser Asp Met Phe Ser Asp Leu Lys Asp Gly Arg
50 55 60

Lys Leu Leu Asp Leu Leu Glu Gly Leu Thr Gly Thr Ser Leu Pro Lys
65 70 75 80

Glu Arg Gly Ser Thr Arg Val His Ala Leu Asn Asn Val Asn Arg Val
85 90 95

Leu Gln Val Leu His Gln Asn Asn Val Asp Leu Val Asn Ile Gly Gly
100 105 110

Thr Asp Ile Val Asp Gly Asn Pro Lys Leu Thr Leu Gly Leu Leu Trp
115 120 125

Ser Ile Ile Leu His Trp Gln Val Lys Asp Val Met Lys Asp Ile Met
130 135 140

Ser Asp Leu Gln Gln Thr Asn Ser Glu Lys Ile Leu Leu Ser Trp Val
145 150 155 160

Arg Gln Thr Thr Arg Pro Tyr Ser Gln Val Asn Val Leu Asn Phe Thr
165 170 175

Thr Ser Trp Thr Asp Gly Leu Ala Phe Asn Ala Val Leu His Arg His
180 185 190

Lys Pro Asp Leu Phe Ser Trp Asp Arg Val Val Lys Met Ser Pro Ile
195 200 205

Glu Arg Leu Glu His Ala Phe Ser Lys Ala His Thr Tyr Leu Gly Ile
210 215 220

Glu Lys Leu Leu Asp Pro Glu Asp Val Ala Val His Leu Pro Asp Lys
225 230 235 240

Lys Ser Ile Ile Met Tyr Leu Thr Ser Leu Phe Glu Val Leu Pro Gln
245 250 255

-continued

```
Gln Val Thr Ile Asp Ala Ile Arg Glu Val Glu Thr Leu Pro Arg Lys
            260                 265                 270

Tyr Lys Lys Glu Cys Glu Glu Glu Glu Ile His Ile Gln Ser Ala Val
        275                 280                 285

Leu Ala Glu Glu Gly Gln Ser Pro Arg Ala Glu Thr Pro Ser Thr Val
    290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Glu Gln Phe Ala Thr His
            340                 345                 350

Glu Thr Phe Met Met Glu Leu Thr Ala His Gln Ser Ser Val Gly Ser
        355                 360                 365

Val Leu Gln Ala Gly Asn Gln Leu Met Thr Gln Gly Thr Leu Ser Glu
    370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Glu Arg Gln Ser Arg Leu His
                405                 410                 415

Asp Ala Leu Met Glu Leu Gln Lys Lys Gln Leu Gln Gln Leu Ser Ser
            420                 425                 430

Trp Leu Ala Leu Thr Glu Glu Arg Ile Gln Lys Met Glu Ser Leu Pro
        435                 440                 445

Leu Gly Asp Asp Leu Pro Ser Leu Gln Lys Leu Leu Gln Glu His Lys
    450                 455                 460

Ser Leu Gln Asn Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Leu Leu Glu Asp Gln Leu Gln Lys Leu Gly Glu Arg Trp Thr Ala
            500                 505                 510

Val Cys Arg Trp Thr Glu Glu Arg Trp Asn Arg Leu Gln Glu Ile Ser
        515                 520                 525

Ile Leu Trp Gln Glu Leu Leu Glu Glu Gln Cys Leu Leu Glu Ala Trp
    530                 535                 540

Leu Thr Glu Lys Glu Glu Ala Leu Asn Lys Val Gln Thr Ser Asn Phe
545                 550                 555                 560

Lys Asp Gln Lys Glu Leu Ser Val Ser Val Arg Arg Leu Ala Ile Leu
                565                 570                 575

Lys Glu Asp Met Glu Met Lys Arg Gln Thr Leu Asp Gln Leu Ser Glu
            580                 585                 590

Ile Gly Gln Asp Val Gly Gln Leu Leu Ser Asn Pro Lys Ala Ser Lys
        595                 600                 605

Lys Met Asn Ser Asp Ser Glu Glu Leu Thr Gln Arg Trp Asp Ser Leu
    610                 615                 620

Val Gln Arg Leu Glu Asp Ser Ser Asn Gln Val Thr Gln Ala Val Ala
625                 630                 635                 640

Lys Leu Gly Met Ser Gln Ile Pro Gln Lys Asp Leu Leu Glu Thr Val
                645                 650                 655

His Val Arg Glu Gln Gly Met Val Lys Lys Pro Lys Gln Glu Leu Pro
            660                 665                 670

Pro Pro Pro Pro Pro Lys Lys Arg Gln Ile His Val Asp Val Glu Ala
```

```
        675                 680                 685

Lys Lys Lys Phe Asp Ala Ile Ser Thr Glu Leu Leu Asn Trp Ile Leu
    690                 695                 700

Lys Ser Lys Thr Ala Ile Gln Asn Thr Glu Met Lys Glu Tyr Lys Lys
705                 710                 715                 720

Ser Gln Glu Thr Ser Gly Met Lys Lys Lys Leu Lys Gly Leu Glu Lys
                725                 730                 735

Glu Gln Lys Glu Asn Leu Pro Arg Leu Asp Glu Leu Asn Gln Thr Gly
            740                 745                 750

Gln Thr Leu Arg Glu Gln Met Gly Lys Glu Gly Leu Ser Thr Glu Glu
        755                 760                 765

Val Asn Asp Val Leu Glu Arg Val Ser Leu Glu Trp Lys Met Ile Ser
    770                 775                 780

Gln Gln Leu Glu Asp Leu Gly Arg Lys Ile Gln Leu Gln Glu Asp Ile
785                 790                 795                 800

Asn Ala Tyr Phe Lys Gln Leu Asp Ala Ile Glu Glu Thr Ile Lys Glu
                805                 810                 815

Lys Glu Glu Trp Leu Arg Gly Thr Pro Ile Ser Glu Ser Pro Arg Gln
            820                 825                 830

Pro Leu Pro Gly Leu Lys Asp Ser Cys Gln Arg Glu Leu Thr Asp Leu
        835                 840                 845

Leu Gly Leu His Pro Arg Ile Glu Thr Leu Cys Ala Ser Cys Ser Ala
    850                 855                 860

Leu Lys Ser Gln Pro Cys Val Pro Gly Phe Val Gln Gln Gly Phe Asp
865                 870                 875                 880

Asp Leu Arg His His Tyr Gln Ala Val Arg Lys Ala Leu Glu Glu Tyr
                885                 890                 895

Gln Gln Gln Leu Glu Asn Glu Leu Lys Ser Gln Pro Gly Pro Ala Tyr
            900                 905                 910

Leu Asp Thr Leu Asn Thr Leu Lys Lys Met Leu Ser Glu Ser Glu Lys
        915                 920                 925

Ala Ala Gln Ala Ser Leu Asn Ala Leu Asn Asp Pro Ile Ala Val Glu
    930                 935                 940

Gln Ala Leu Gln Glu Lys Lys Ala Leu Asp Glu Thr Leu Glu Asn Gln
945                 950                 955                 960

Lys His Thr Leu His Lys Leu Ser Glu Glu Thr Lys Thr Leu Glu Lys
                965                 970                 975

Asn Met Leu Pro Asp Val Gly Lys Met Tyr Lys Gln Glu Phe Asp Asp
            980                 985                 990

Val Gln Gly Arg Trp Asn Lys Val  Lys Thr Lys Val Ser  Arg Asp Leu
        995                 1000                1005

His Leu  Leu Glu Glu Ile Thr  Pro Arg Leu Arg Asp  Phe Glu Ala
    1010                1015                1020

Asp Ser  Glu Val Ile Glu Lys  Trp Val Ser Gly Ile  Lys Asp Phe
    1025                1030                1035

Leu Met  Lys Glu Gln Ala Ala  Gln Gly Asp Ala Ala  Ala Leu Gln
    1040                1045                1050

Ser Gln  Leu Asp Gln Cys Ala  Thr Phe Ala Asn Glu  Ile Glu Thr
    1055                1060                1065

Ile Glu  Ser Ser Leu Lys Asn  Met Arg Glu Val Glu  Thr Ser Leu
    1070                1075                1080

Gln Arg  Cys Pro Val Thr Gly  Val Lys Thr Trp Val  Gln Ala Arg
    1085                1090                1095
```

-continued

```
Leu Val  Asp Tyr Gln Ser Gln  Leu Glu Lys Phe Ser  Lys Glu Ile
    1100                 1105                 1110

Ala Ile  Gln Lys Ser Arg Leu  Ser Asp Ser Gln Glu  Lys Ala Leu
    1115                 1120                 1125

Asn Leu  Lys Lys Asp Leu Ala  Glu Met Gln Glu Trp  Met Ala Gln
    1130                 1135                 1140

Ala Glu  Glu Asp Tyr Leu Glu  Arg Asp Phe Glu Tyr  Lys Ser Pro
    1145                 1150                 1155

Glu Glu  Leu Glu Ser Ala Val  Glu Glu Met Lys Arg  Ala Lys Glu
    1160                 1165                 1170

Glu Val  Leu Gln Lys Glu Val  Arg Val Lys Ile Leu  Lys Asp Ser
    1175                 1180                 1185

Ile Lys  Leu Val Ala Ala Lys  Val Pro Ser Gly Gly  Gln Glu Leu
    1190                 1195                 1200

Thr Ser  Glu Phe Asn Glu Val  Leu Glu Ser Tyr Gln  Leu Leu Cys
    1205                 1210                 1215

Asn Arg  Ile Arg Gly Lys Cys  His Thr Leu Glu Glu  Val Trp Ser
    1220                 1225                 1230

Cys Trp  Val Glu Leu Leu His  Tyr Leu Asp Leu Glu  Thr Thr Trp
    1235                 1240                 1245

Leu Asn  Thr Leu Glu Glu Arg  Val Arg Ser Thr Glu  Ala Leu Pro
    1250                 1255                 1260

Glu Arg  Ala Glu Ala Val His  Glu Ala Leu Glu Ser  Leu Glu Ser
    1265                 1270                 1275

Val Leu  Arg His Pro Ala Asp  Asn Arg Thr Gln Ile  Arg Glu Leu
    1280                 1285                 1290

Gly Gln  Thr Leu Ile Asp Gly  Gly Ile Leu Asp Asp  Ile Ile Ser
    1295                 1300                 1305

Glu Lys  Leu Glu Ala Phe Asn  Ser Arg Tyr Glu Glu  Leu Ser His
    1310                 1315                 1320

Leu Ala  Glu Ser Lys Gln Ile  Ser Leu Glu Lys Gln  Leu Gln Val
    1325                 1330                 1335

Leu Arg  Glu Thr Asp His Met  Leu Gln Val Leu Lys  Glu Ser Leu
    1340                 1345                 1350

Gly Glu  Leu Asp Lys Gln Leu  Thr Thr Tyr Leu Thr  Asp Arg Ile
    1355                 1360                 1365

Asp Ala  Phe Gln Leu Pro Gln  Glu Ala Gln Lys Ile  Gln Ala Glu
    1370                 1375                 1380

Ile Ser  Ala His Glu Leu Thr  Leu Glu Glu Leu Arg  Lys Asn Val
    1385                 1390                 1395

Arg Ser  Gln Pro Pro Thr Ser  Pro Glu Gly Arg Ala  Thr Arg Gly
    1400                 1405                 1410

Gly Ser  Gln Met Asp Met Leu  Gln Arg Lys Leu Arg  Glu Val Ser
    1415                 1420                 1425

Thr Lys  Phe Gln Leu Phe Gln  Lys Pro Ala Asn Phe  Glu Gln Arg
    1430                 1435                 1440

Met Leu  Asp Cys Lys Arg Val  Leu Glu Gly Val Lys  Ala Glu Leu
    1445                 1450                 1455

His Val  Leu Asp Val Arg Asp  Val Asp Pro Asp Val  Ile Gln Ala
    1460                 1465                 1470

His Leu  Asp Lys Cys Met Lys  Leu Tyr Lys Thr Leu  Ser Glu Val
    1475                 1480                 1485

Lys Leu  Glu Val Glu Thr Val  Ile Lys Thr Gly Arg  His Ile Val
    1490                 1495                 1500
```

```
Gln Lys  Gln Gln Thr Asp Asn  Pro Lys Ser Met Asp  Glu Gln Leu
    1505                 1510                 1515

Thr Ser  Leu Lys Val Leu Tyr  Asn Asp Leu Gly Ala  Gln Val Thr
    1520                 1525                 1530

Glu Gly  Lys Gln Asp Leu Glu  Arg Ala Ser Gln Leu  Ser Arg Lys
    1535                 1540                 1545

Met Lys  Lys Glu Ala Ala Val  Leu Ser Glu Trp Leu  Ser Ala Thr
    1550                 1555                 1560

Glu Ala  Glu Leu Val Gln Lys  Ser Thr Ser Glu Gly  Val Ile Gly
    1565                 1570                 1575

Asp Leu  Asp Thr Glu Ile Ser  Trp Ala Lys Ser Ile  Leu Lys Asp
    1580                 1585                 1590

Leu Glu  Lys Arg Lys Val Asp  Leu Asn Gly Ile Thr  Glu Ser Ser
    1595                 1600                 1605

Ala Ala  Leu Gln His Leu Val  Leu Gly Ser Glu Ser  Val Leu Glu
    1610                 1615                 1620

Glu Asn  Leu Cys Val Leu Asn  Ala Gly Trp Ser Arg  Val Arg Thr
    1625                 1630                 1635

Trp Thr  Glu Asp Trp Cys Asn  Thr Leu Leu Asn His  Gln Asn Gln
    1640                 1645                 1650

Leu Glu  Leu Phe Asp Gly His  Val Ala His Ile Ser  Thr Trp Leu
    1655                 1660                 1665

Tyr Gln  Ala Glu Ala Leu Leu  Asp Glu Ile Glu Lys  Lys Pro Ala
    1670                 1675                 1680

Ser Lys  Gln Glu Glu Ile Val  Lys Arg Leu Leu Ser  Glu Leu Asp
    1685                 1690                 1695

Asp Ala  Ser Leu Gln Val Glu  Asn Val Arg Glu Gln  Ala Ile Ile
    1700                 1705                 1710

Leu Val  Asn Ala Arg Gly Ser  Ala Ser Arg Glu Leu  Val Glu Pro
    1715                 1720                 1725

Lys Leu  Ala Glu Leu Ser Arg  Asn Phe Glu Lys Val  Ser Gln His
    1730                 1735                 1740

Ile Lys  Ser Ala Arg Met Leu  Ile Gly Gln Asp Pro  Ser Ser Tyr
    1745                 1750                 1755

Gln Gly  Leu Asp Pro Ala Gly  Thr Val Gln Ala Ala  Glu Ser Phe
    1760                 1765                 1770

Ser Asp  Leu Glu Asn Leu Glu  Gln Asp Ile Glu Asn  Met Leu Lys
    1775                 1780                 1785

Val Val  Glu Lys His Leu Asp  Pro Asn Asn Asp Glu  Lys Met Asp
    1790                 1795                 1800

Glu Glu  Gln Ala Gln Ile Glu  Glu Val Leu Gln Arg  Gly Glu His
    1805                 1810                 1815

Leu Leu  His Glu Pro Met Glu  Asp Ser Lys Lys Glu  Lys Ile Arg
    1820                 1825                 1830

Leu Gln  Leu Leu Leu Leu His  Thr Arg Tyr Asn Lys  Ile Lys Thr
    1835                 1840                 1845

Ile Pro  Ile Gln Gln Arg Lys  Thr Ile Pro Val Ser  Ser Gly Ile
    1850                 1855                 1860

Thr Ser  Ser Ala Leu Pro Ala  Asp Tyr Leu Val Glu  Ile Asn Lys
    1865                 1870                 1875

Ile Leu  Leu Thr Leu Asp Asp  Ile Glu Leu Ser Leu  Asn Met Pro
    1880                 1885                 1890

Glu Leu  Asn Thr Thr Val Tyr  Lys Asp Phe Ser Phe  Gln Glu Asp
```

```
    1895                1900                1905

Ser Leu  Lys Ser Ile Lys Gly  Gln Leu Asp Arg Leu  Gly Glu Gln
    1910                1915                1920

Ile Ala  Val Val His Glu Lys  Gln Pro Asp Val Ile  Val Glu Ala
    1925                1930                1935

Ser Gly  Pro Glu Ala Ile Gln  Ile Arg Asp Met Leu  Ala Gln Leu
    1940                1945                1950

Asn Ala  Lys Trp Asp Arg Val  Asn Arg Val Tyr Ser  Asp Arg Arg
    1955                1960                1965

Gly Ser  Phe Ala Arg Ala Val  Glu Glu Trp Arg Gln  Phe His His
    1970                1975                1980

Asp Leu  Asp Asp Leu Thr Gln  Trp Leu Ser Glu Ala  Glu Asp Leu
    1985                1990                1995

Leu Val  Asp Thr Cys Ala Pro  Asp Gly Ser Leu Asp  Leu Glu Lys
    2000                2005                2010

Ala Arg  Ala Gln Gln Leu Glu  Leu Glu Glu Gly Leu  Ser Ser His
    2015                2020                2025

Gln Pro  Ser Leu Ile Lys Val  Asn Arg Lys Gly Glu  Asp Leu Val
    2030                2035                2040

Gln Arg  Leu Arg Pro Ser Glu  Ala Ser Phe Leu Lys  Glu Lys Leu
    2045                2050                2055

Ala Gly  Phe Asn Gln Arg Trp  Ser Thr Leu Val Ala  Glu Val Glu
    2060                2065                2070

Ala Leu  Gln Pro Arg Leu Lys  Gly Glu Ser Gln Gln  Val Leu Gly
    2075                2080                2085

Tyr Lys  Arg Arg Leu Asp Glu  Val Thr Cys Trp Leu  Thr Lys Val
    2090                2095                2100

Glu Ser  Ala Val Gln Lys Arg  Ser Thr Pro Asp Pro  Glu Glu Ser
    2105                2110                2115

Pro Gln  Glu Leu Thr Asp Leu  Ala Gln Glu Thr Glu  Val Gln Ala
    2120                2125                2130

Glu Asn  Ile Lys Trp Leu Asn  Arg Ala Glu Leu Glu  Met Leu Ser
    2135                2140                2145

Asp Lys  Asn Leu Ser Leu Arg  Glu Arg Glu Lys Leu  Ser Glu Ser
    2150                2155                2160

Leu Arg  Asn Val Asn Thr Thr  Trp Thr Lys Val Cys  Arg Glu Val
    2165                2170                2175

Pro Ser  Leu Leu Lys Thr Arg  Thr Gln Asp Pro Cys  Ser Ala Pro
    2180                2185                2190

Gln Met  Arg Met Ala Ala His  Pro Asn Val Gln Lys  Val Val Leu
    2195                2200                2205

Val Ser  Ser Ala Ser Asp Ala  Pro Leu Arg Gly Gly  Leu Glu Ile
    2210                2215                2220

Ser Val  Pro Ala Asp Leu Asp  Lys Thr Ile Thr Glu  Leu Ala Asp
    2225                2230                2235

Trp Leu  Val Leu Ile Asp Gln  Met Leu Lys Ser Asn  Ile Val Thr
    2240                2245                2250

Val Gly  Asp Val Lys Glu Ile  Asn Lys Thr Val Ser  Arg Met Lys
    2255                2260                2265

Ile Thr  Lys Ala Asp Leu Glu  Gln Arg His Pro Gln  Leu Asp Cys
    2270                2275                2280

Val Phe  Thr Leu Ala Gln Asn  Leu Lys Asn Lys Ala  Ser Ser Ser
    2285                2290                2295
```

-continued

```
Asp Val  Arg Thr Ala Ile Thr  Glu Lys Leu Glu Lys  Leu Lys Thr
    2300                 2305                 2310

Gln Trp  Glu Ser Thr Gln His  Gly Val Glu Leu Arg  Arg Gln Gln
    2315                 2320                 2325

Leu Glu  Asp Met Val Val Asp  Ser Leu Gln Trp Asp  Asp His Arg
    2330                 2335                 2340

Glu Glu  Thr Glu Glu Leu Met  Arg Lys Tyr Glu Ala  Arg Phe Tyr
    2345                 2350                 2355

Met Leu  Gln Gln Ala Arg Arg  Asp Pro Leu Ser Lys  Gln Val Ser
    2360                 2365                 2370

Asp Asn  Gln Leu Leu Leu Gln  Glu Leu Gly Ser Gly  Asp Gly Val
    2375                 2380                 2385

Ile Met  Ala Phe Asp Asn Val  Leu Gln Lys Leu Leu  Glu Glu Tyr
    2390                 2395                 2400

Ser Gly  Asp Asp Thr Arg Asn  Val Glu Glu Thr Thr  Glu Tyr Leu
    2405                 2410                 2415

Lys Thr  Ser Trp Val Asn Leu  Lys Gln Ser Ile Ala  Asp Arg Gln
    2420                 2425                 2430

Ser Ala  Leu Glu Ala Glu Leu  Gln Thr Val Gln Thr  Ser Arg Arg
    2435                 2440                 2445

Asp Leu  Glu Asn Phe Val Lys  Trp Leu Gln Glu Ala  Glu Thr Thr
    2450                 2455                 2460

Ala Asn  Val Leu Ala Asp Ala  Ser Gln Arg Glu Asn  Ala Leu Gln
    2465                 2470                 2475

Asp Ser  Val Leu Ala Arg Gln  Leu Arg Gln Gln Met  Leu Asp Ile
    2480                 2485                 2490

Gln Ala  Glu Ile Asp Ala His  Asn Asp Ile Phe Lys  Ser Ile Asp
    2495                 2500                 2505

Gly Asn  Arg Gln Lys Met Val  Lys Ala Leu Gly Asn  Ser Glu Glu
    2510                 2515                 2520

Ala Thr  Met Leu Gln His Arg  Leu Asp Asp Met Asn  Gln Arg Trp
    2525                 2530                 2535

Asn Asp  Leu Lys Ala Lys Ser  Ala Ser Ile Arg Ala  His Leu Glu
    2540                 2545                 2550

Ala Ser  Ala Glu Lys Trp Asn  Arg Leu Leu Ala Ser  Leu Glu Glu
    2555                 2560                 2565

Leu Ile  Lys Trp Leu Asn Met  Lys Asp Glu Glu Leu  Lys Lys Gln
    2570                 2575                 2580

Met Pro  Ile Gly Gly Asp Val  Pro Ala Leu Gln Leu  Gln Tyr Asp
    2585                 2590                 2595

His Cys  Lys Val Leu Arg Arg  Glu Leu Lys Glu Lys  Glu Tyr Ser
    2600                 2605                 2610

Val Leu  Asn Ala Val Asp Gln  Ala Arg Val Phe Leu  Ala Asp Gln
    2615                 2620                 2625

Pro Ile  Glu Ala Pro Glu Glu  Pro Arg Arg Asn Pro  Gln Ser Lys
    2630                 2635                 2640

Thr Glu  Leu Thr Pro Glu Glu  Arg Ala Gln Lys Ile  Ala Lys Ala
    2645                 2650                 2655

Met Arg  Lys Gln Ser Ser Glu  Val Arg Glu Lys Trp  Glu Asn Leu
    2660                 2665                 2670

Asn Ala  Val Thr Ser Asn Trp  Gln Lys Gln Val Gly  Lys Ala Leu
    2675                 2680                 2685

Glu Lys  Leu Arg Asp Leu Gln  Gly Ala Met Asp Asp  Leu Asp Ala
    2690                 2695                 2700
```

```
Asp Met  Lys Glu Val Glu Ala  Val Arg Asn Gly Trp  Lys Pro Val
    2705                 2710                 2715

Gly Asp  Leu Leu Ile Asp Ser  Leu Gln Asp His Ile  Glu Lys Thr
    2720                 2725                 2730

Leu Ala  Phe Arg Glu Glu Ile  Ala Pro Ile Asn Leu  Lys Val Lys
    2735                 2740                 2745

Thr Met  Asn Asp Leu Ser Ser  Gln Leu Ser Pro Leu  Asp Leu His
    2750                 2755                 2760

Pro Ser  Leu Lys Met Ser Arg  Gln Leu Asp Asp Leu  Asn Met Arg
    2765                 2770                 2775

Trp Lys  Leu Leu Gln Val Ser  Val Asp Asp Arg Leu  Lys Gln Leu
    2780                 2785                 2790

Gln Glu  Ala His Arg Asp Phe  Gly Pro Ser Ser Gln  His Phe Leu
    2795                 2800                 2805

Ser Thr  Ser Val Gln Leu Pro  Trp Gln Arg Ser Ile  Ser His Asn
    2810                 2815                 2820

Lys Val  Pro Tyr Tyr Ile Asn  His Gln Thr Gln Thr  Thr Cys Trp
    2825                 2830                 2835

Asp His  Pro Lys Met Thr Glu  Leu Phe Gln Ser Leu  Ala Asp Leu
    2840                 2845                 2850

Asn Asn  Val Arg Phe Ser Ala  Tyr Arg Thr Ala Ile  Lys Ile Arg
    2855                 2860                 2865

Arg Leu  Gln Lys Ala Leu Cys  Leu Asp Leu Leu Glu  Leu Asn Thr
    2870                 2875                 2880

Thr Asn  Glu Val Phe Lys Gln  His Lys Leu Asn Gln  Asn Asp Gln
    2885                 2890                 2895

Leu Leu  Ser Val Pro Asp Val  Ile Asn Cys Leu Thr  Thr Thr Tyr
    2900                 2905                 2910

Asp Gly  Leu Glu Gln Leu His  Lys Asp Leu Val Asn  Val Pro Leu
    2915                 2920                 2925

Cys Val  Asp Met Cys Leu Asn  Trp Leu Leu Asn Val  Tyr Asp Thr
    2930                 2935                 2940

Gly Arg  Thr Gly Lys Ile Arg  Val Gln Ser Leu Lys  Ile Gly Leu
    2945                 2950                 2955

Met Ser  Leu Ser Lys Gly Leu  Leu Glu Glu Lys Tyr  Arg Cys Leu
    2960                 2965                 2970

Phe Lys  Glu Val Ala Gly Pro  Thr Glu Met Cys Asp  Gln Arg Gln
    2975                 2980                 2985

Leu Gly  Leu Leu Leu His Asp  Ala Ile Gln Ile Pro  Arg Gln Leu
    2990                 2995                 3000

Gly Glu  Val Ala Ala Phe Gly  Gly Ser Asn Ile Glu  Pro Ser Val
    3005                 3010                 3015

Arg Ser  Cys Phe Gln Gln Asn  Asn Asn Lys Pro Glu  Ile Ser Val
    3020                 3025                 3030

Lys Glu  Phe Ile Asp Trp Met  His Leu Glu Pro Gln  Ser Met Val
    3035                 3040                 3045

Trp Leu  Pro Val Leu His Arg  Val Ala Ala Ala Glu  Thr Ala Lys
    3050                 3055                 3060

His Gln  Ala Lys Cys Asn Ile  Cys Lys Glu Cys Pro  Ile Val Gly
    3065                 3070                 3075

Phe Arg  Tyr Arg Ser Leu Lys  His Phe Asn Tyr Asp  Val Cys Gln
    3080                 3085                 3090

Ser Cys  Phe Phe Ser Gly Arg  Thr Ala Lys Gly His  Lys Leu His
```

```
    3095                3100                3105

Tyr Pro  Met Val Glu Tyr Cys  Ile Pro Thr Thr Ser  Gly Glu Asp
    3110                3115                3120

Val Arg  Asp Phe Thr Lys Val  Leu Lys Asn Lys Phe  Arg Ser Lys
    3125                3130                3135

Lys Tyr  Phe Ala Lys His Pro  Arg Leu Gly Tyr Leu  Pro Val Gln
    3140                3145                3150

Thr Val  Leu Glu Gly Asp Asn  Leu Glu Thr Pro Ile  Thr Leu Ile
    3155                3160                3165

Ser Met  Trp Pro Glu His Tyr  Asp Pro Ser Gln Ser  Pro Gln Leu
    3170                3175                3180

Phe His  Asp Asp Thr His Ser  Arg Ile Glu Gln Tyr  Ala Thr Arg
    3185                3190                3195

Leu Ala  Gln Met Glu Arg Thr  Asn Gly Ser Phe Leu  Thr Asp Ser
    3200                3205                3210

Ser Ser  Thr Thr Gly Ser Val  Glu Asp Glu His Ala  Leu Ile Gln
    3215                3220                3225

Gln Tyr  Cys Gln Thr Leu Gly  Gly Glu Ser Pro Val  Ser Gln Pro
    3230                3235                3240

Gln Ser  Pro Ala Gln Ile Leu  Lys Ser Val Glu Arg  Glu Glu Arg
    3245                3250                3255

Gly Glu  Leu Glu Arg Ile Ile  Ala Asp Leu Glu Glu  Glu Gln Arg
    3260                3265                3270

Asn Leu  Gln Val Glu Tyr Glu  Gln Leu Lys Glu Gln  His Leu Arg
    3275                3280                3285

Arg Gly  Leu Pro Val Gly Ser  Pro Pro Asp Ser Ile  Val Ser Pro
    3290                3295                3300

His His  Thr Ser Glu Asp Ser  Glu Leu Ile Ala Glu  Ala Lys Leu
    3305                3310                3315

Leu Arg  Gln His Lys Gly Arg  Leu Glu Ala Arg Met  Gln Ile Leu
    3320                3325                3330

Glu Asp  His Asn Lys Gln Leu  Glu Ser Gln Leu His  Arg Leu Arg
    3335                3340                3345

Gln Leu  Leu Glu Gln Pro Asp  Ser Asp Ser Arg Ile  Asn Gly Val
    3350                3355                3360

Ser Pro  Trp Ala Ser Pro Gln  His Ser Ala Leu Ser  Tyr Ser Leu
    3365                3370                3375

Asp Thr  Asp Pro Gly Pro Gln  Phe His Gln Ala Ala  Ser Glu Asp
    3380                3385                3390

Leu Leu  Ala Pro Pro His Asp  Thr Ser Thr Asp Leu  Thr Asp Val
    3395                3400                3405

Met Glu  Gln Ile Asn Ser Thr  Phe Pro Ser Cys Ser  Ser Asn Val
    3410                3415                3420

Pro Ser  Arg Pro Gln Ala Met
    3425                3430


<210> SEQ ID NO 10
<211> LENGTH: 4083
<212> TYPE: DNA
<213> ORGANISM: Homo sapiens
<220> FEATURE:
<221> NAME/KEY: CDS
<222> LOCATION: (1)..(4083)
<220> FEATURE:
<221> NAME/KEY: misc_feature
<222> LOCATION: (1)..(117)
<223> OTHER INFORMATION: TAT and epitope tag coding region
```

<400> SEQUENCE: 10

```
atg gac tac aag gac gac gat gac aag ggc tac ggc cgc aag aaa cgc      48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac      96
Arg Gln Arg Arg Arg Gly Gly Ser Thr Met Ser Gly Tyr Pro Tyr Asp
            20                  25                  30

gtc cca gac tat gct ggc tcc atg gcc aag tat gga gaa cat gaa gcc     144
Val Pro Asp Tyr Ala Gly Ser Met Ala Lys Tyr Gly Glu His Glu Ala
        35                  40                  45

agt cct gac aat ggg cag aac gaa ttc agt gat atc att aag tcc aga     192
Ser Pro Asp Asn Gly Gln Asn Glu Phe Ser Asp Ile Ile Lys Ser Arg
    50                  55                  60

tct gat gaa cac aat gac gta cag aag aaa acc ttt acc aaa tgg ata     240
Ser Asp Glu His Asn Asp Val Gln Lys Lys Thr Phe Thr Lys Trp Ile
65                  70                  75                  80

aat gct cga ttt tca aag agt ggg aaa cca ccc atc aat gat atg ttc     288
Asn Ala Arg Phe Ser Lys Ser Gly Lys Pro Pro Ile Asn Asp Met Phe
                85                  90                  95

aca gac ctc aaa gat gga agg aag cta ttg gat ctt cta gaa ggc ctc     336
Thr Asp Leu Lys Asp Gly Arg Lys Leu Leu Asp Leu Leu Glu Gly Leu
            100                 105                 110

aca gga aca tca ctg cca aag gaa cgt ggt tcc aca agg gta cat gcc     384
Thr Gly Thr Ser Leu Pro Lys Glu Arg Gly Ser Thr Arg Val His Ala
        115                 120                 125

tta aat aac gtc aac aga gtg ctg cag gtt tta cat cag aac aat gtg     432
Leu Asn Asn Val Asn Arg Val Leu Gln Val Leu His Gln Asn Asn Val
    130                 135                 140

gaa tta gtg aat ata ggg gga act gac att gtg gat gga aat cac aaa     480
Glu Leu Val Asn Ile Gly Gly Thr Asp Ile Val Asp Gly Asn His Lys
145                 150                 155                 160

ctg act ttg ggg tta ctt tgg agc atc att ttg cac tgg cag gtg aaa     528
Leu Thr Leu Gly Leu Leu Trp Ser Ile Ile Leu His Trp Gln Val Lys
                165                 170                 175

gat gtc atg aag gat gtc atg tcg gac ctg cag cag acg aac agt gag     576
Asp Val Met Lys Asp Val Met Ser Asp Leu Gln Gln Thr Asn Ser Glu
            180                 185                 190

aag atc ctg ctc agc tgg gtg cgt cag acc acc agg ccc tac agc caa     624
Lys Ile Leu Leu Ser Trp Val Arg Gln Thr Thr Arg Pro Tyr Ser Gln
        195                 200                 205

gtc aac gtc ctc aac ttc acc acc agc tgg aca gat gga ctc gcc ttt     672
Val Asn Val Leu Asn Phe Thr Thr Ser Trp Thr Asp Gly Leu Ala Phe
    210                 215                 220

aat gct gtc ctc cac cga cat aaa cct gat ctc ttc agc tgg gat aaa     720
Asn Ala Val Leu His Arg His Lys Pro Asp Leu Phe Ser Trp Asp Lys
225                 230                 235                 240

gtt gtc aaa atg tca cca att gag aga ctt gaa cat gcc ttc agc aag     768
Val Val Lys Met Ser Pro Ile Glu Arg Leu Glu His Ala Phe Ser Lys
                245                 250                 255

gct caa act tat ttg gga att gaa aag ctg tta gat cct gaa gat gtt     816
Ala Gln Thr Tyr Leu Gly Ile Glu Lys Leu Leu Asp Pro Glu Asp Val
            260                 265                 270

gcc gtt cag ctt cct gac aag aaa tcc ata att atg tat tta aca tct     864
Ala Val Gln Leu Pro Asp Lys Lys Ser Ile Ile Met Tyr Leu Thr Ser
        275                 280                 285

ttg ttt gag gtg cta cct cag caa gtc acc ata gac gcc atc cgt gag     912
Leu Phe Glu Val Leu Pro Gln Gln Val Thr Ile Asp Ala Ile Arg Glu
    290                 295                 300

gta gag aca ctc cca agg aaa tat aaa aaa gaa tgt gaa gaa gag gca     960
```

```
Val Glu Thr Leu Pro Arg Lys Tyr Lys Lys Glu Cys Glu Glu Glu Ala
305                 310                 315                 320

att aat ata cag agt aca gcg cct gag gag gag cat gag agt ccc cga      1008
Ile Asn Ile Gln Ser Thr Ala Pro Glu Glu Glu His Glu Ser Pro Arg
                325                 330                 335

gct gaa act ccc agc act gtc act gag gtt gac atg gat ctg gac agc      1056
Ala Glu Thr Pro Ser Thr Val Thr Glu Val Asp Met Asp Leu Asp Ser
            340                 345                 350

tat cag att gcg ttg gag gaa gtg ctg acc tgg ttg ctt tct gct gag      1104
Tyr Gln Ile Ala Leu Glu Glu Val Leu Thr Trp Leu Leu Ser Ala Glu
        355                 360                 365

gac act ttc cag gag cag gat gat att tct gat gat gtt gaa gaa gtc      1152
Asp Thr Phe Gln Glu Gln Asp Asp Ile Ser Asp Asp Val Glu Glu Val
    370                 375                 380

aaa gac cag ttt gca acc cat gaa gct ttt atg atg gaa ctg act gca      1200
Lys Asp Gln Phe Ala Thr His Glu Ala Phe Met Met Glu Leu Thr Ala
385                 390                 395                 400

cac cag agc agt gtg ggc agc gtc ctg cag gca ggc aac caa ctg ata      1248
His Gln Ser Ser Val Gly Ser Val Leu Gln Ala Gly Asn Gln Leu Ile
                405                 410                 415

aca caa gga act ctg tca gac gaa gaa gaa ttt gag att cag gaa cag      1296
Thr Gln Gly Thr Leu Ser Asp Glu Glu Glu Phe Glu Ile Gln Glu Gln
            420                 425                 430

atg acc ctg ctg aat gct aga tgg gag gct ctt agg gtg gag agt atg      1344
Met Thr Leu Leu Asn Ala Arg Trp Glu Ala Leu Arg Val Glu Ser Met
        435                 440                 445

gac aga cag tcc cgg ctg cac gat gtg ctg atg gaa ctg cag aag aag      1392
Asp Arg Gln Ser Arg Leu His Asp Val Leu Met Glu Leu Gln Lys Lys
    450                 455                 460

caa ctg cag cag ctc tcc gcc tgg tta aca ctc aca gag gag cgc att      1440
Gln Leu Gln Gln Leu Ser Ala Trp Leu Thr Leu Thr Glu Glu Arg Ile
465                 470                 475                 480

cag aag atg gaa act tgc ccc ctg gat gat gat gta aaa tct cta caa      1488
Gln Lys Met Glu Thr Cys Pro Leu Asp Asp Asp Val Lys Ser Leu Gln
                485                 490                 495

aag ctg cta gaa gaa cat aaa agt ttg caa agt gat ctt gag gct gaa      1536
Lys Leu Leu Glu Glu His Lys Ser Leu Gln Ser Asp Leu Glu Ala Glu
            500                 505                 510

cag gtg aaa gta aat tca cta act cac atg gtg gtc att gtt gat gaa      1584
Gln Val Lys Val Asn Ser Leu Thr His Met Val Val Ile Val Asp Glu
        515                 520                 525

aac agt ggt gag agt gct aca gct atc cta gaa gac cag tta cag aaa      1632
Asn Ser Gly Glu Ser Ala Thr Ala Ile Leu Glu Asp Gln Leu Gln Lys
    530                 535                 540

ctt ggt gag cgc tgg aca gca gta tgc cgt tgg act gaa gaa cgc tgg      1680
Leu Gly Glu Arg Trp Thr Ala Val Cys Arg Trp Thr Glu Glu Arg Trp
545                 550                 555                 560

aat agg tta caa gaa atc aat ata ttg tgg cag gaa tta ttg gaa gaa      1728
Asn Arg Leu Gln Glu Ile Asn Ile Leu Trp Gln Glu Leu Leu Glu Glu
                565                 570                 575

cag tgc ttg ttg aaa gct tgg tta acc gaa aaa gaa gag gct tta aat      1776
Gln Cys Leu Leu Lys Ala Trp Leu Thr Glu Lys Glu Glu Ala Leu Asn
            580                 585                 590

aaa gtc cag aca agc aac ttc aaa gac caa aag gaa cta agt gtc agt      1824
Lys Val Gln Thr Ser Asn Phe Lys Asp Gln Lys Glu Leu Ser Val Ser
        595                 600                 605

gtt cga cgt ctg gct att ttg aag gaa gac atg gaa atg aag cgt caa      1872
Val Arg Arg Leu Ala Ile Leu Lys Glu Asp Met Glu Met Lys Arg Gln
    610                 615                 620

aca ttg gat cag ctg agt gag att ggc cag gat gtg gga caa tta ctt      1920
```

```
Thr Leu Asp Gln Leu Ser Glu Ile Gly Gln Asp Val Gly Gln Leu Leu
625                 630                 635                 640

gat aat tcc aag gca tct aag aag atc aac agt gac tca gag gaa ctg      1968
Asp Asn Ser Lys Ala Ser Lys Lys Ile Asn Ser Asp Ser Glu Glu Leu
                645                 650                 655

act caa aga tgg gat tct ttg gtt cag aga cta gaa gat tcc tcc aac      2016
Thr Gln Arg Trp Asp Ser Leu Val Gln Arg Leu Glu Asp Ser Ser Asn
            660                 665                 670

cag gtg act cag gct gta gca aag ctg ggg atg tct cag att cct cag      2064
Gln Val Thr Gln Ala Val Ala Lys Leu Gly Met Ser Gln Ile Pro Gln
        675                 680                 685

aag gac ctt ttg gag act gtt cgt gta aga gaa caa gca att aca aaa      2112
Lys Asp Leu Leu Glu Thr Val Arg Val Arg Glu Gln Ala Ile Thr Lys
    690                 695                 700

aaa tct aag cag gaa ctg cct cct cct cct ccc cca aag aag aga cag      2160
Lys Ser Lys Gln Glu Leu Pro Pro Pro Pro Pro Pro Lys Lys Arg Gln
705                 710                 715                 720

atc cat gtg gat gcc cac aga gat ttt gga cca tcc tct cag cat ttt      2208
Ile His Val Asp Ala His Arg Asp Phe Gly Pro Ser Ser Gln His Phe
                725                 730                 735

ctc tct acg tca gtc cag ctg ccg tgg caa aga tcc att tca cat aat      2256
Leu Ser Thr Ser Val Gln Leu Pro Trp Gln Arg Ser Ile Ser His Asn
            740                 745                 750

aaa gtg ccc tat tac atc aac cat caa aca cag acc acc tgt tgg gac      2304
Lys Val Pro Tyr Tyr Ile Asn His Gln Thr Gln Thr Thr Cys Trp Asp
        755                 760                 765

cat cct aaa atg acc gaa ctc ttt caa tcc ctt gct gac ctg aat aat      2352
His Pro Lys Met Thr Glu Leu Phe Gln Ser Leu Ala Asp Leu Asn Asn
    770                 775                 780

gta cgt ttt tct gcc tac cgt aca gca atc aaa atc cga aga cta caa      2400
Val Arg Phe Ser Ala Tyr Arg Thr Ala Ile Lys Ile Arg Arg Leu Gln
785                 790                 795                 800

aaa gca cta tgt ttg gat ctc tta gag ttg agt aca aca aat gaa att      2448
Lys Ala Leu Cys Leu Asp Leu Leu Glu Leu Ser Thr Thr Asn Glu Ile
                805                 810                 815

ttc aaa cag cac aag ttg aac caa aat gac cag ctc ctc agt gtt cca      2496
Phe Lys Gln His Lys Leu Asn Gln Asn Asp Gln Leu Leu Ser Val Pro
            820                 825                 830

gat gtc atc aac tgt ctg aca aca act tat gat gga ctt gag caa atg      2544
Asp Val Ile Asn Cys Leu Thr Thr Thr Tyr Asp Gly Leu Glu Gln Met
        835                 840                 845

cat aag gac ctg gtc aac gtt cca ctc tgt gtt gat atg tgt ctc aat      2592
His Lys Asp Leu Val Asn Val Pro Leu Cys Val Asp Met Cys Leu Asn
    850                 855                 860

tgg ttg ctc aat gtc tat gac acg ggt cga act gga aaa att aga gtg      2640
Trp Leu Leu Asn Val Tyr Asp Thr Gly Arg Thr Gly Lys Ile Arg Val
865                 870                 875                 880

cag agt ctg aag att gga tta atg tct ctc tcc aaa ggt ctc ttg gaa      2688
Gln Ser Leu Lys Ile Gly Leu Met Ser Leu Ser Lys Gly Leu Leu Glu
                885                 890                 895

gaa aaa tac aga tat ctc ttt aag gaa gtt gca ggg cca aca gaa atg      2736
Glu Lys Tyr Arg Tyr Leu Phe Lys Glu Val Ala Gly Pro Thr Glu Met
            900                 905                 910

tgt gac cag agg cag ctg ggc ctg tta ctt cat gat gcc atc cag atc      2784
Cys Asp Gln Arg Gln Leu Gly Leu Leu Leu His Asp Ala Ile Gln Ile
        915                 920                 925

ccc cgg cag cta ggt gaa gta gca gct ttt gga ggc agt aat att gag      2832
Pro Arg Gln Leu Gly Glu Val Ala Ala Phe Gly Gly Ser Asn Ile Glu
    930                 935                 940

cct agt gtt cgc agc tgc ttc caa cag aat aac aat aaa cca gaa ata      2880
```

```
Pro Ser Val Arg Ser Cys Phe Gln Gln Asn Asn Asn Lys Pro Glu Ile
945                 950                 955                 960

agt gtg aaa gag ttt ata gat tgg atg cat ttg gaa cca cag tcc atg     2928
Ser Val Lys Glu Phe Ile Asp Trp Met His Leu Glu Pro Gln Ser Met
                965                 970                 975

gtt tgg ctc cca gtt tta cat cga gtg gca gca gcg gag act gca aaa     2976
Val Trp Leu Pro Val Leu His Arg Val Ala Ala Ala Glu Thr Ala Lys
            980                 985                 990

cat cag gcc aaa tgc aac atc tgt  aaa gaa tgt cca att  gtc ggg ttc   3024
His Gln Ala Lys Cys Asn Ile Cys  Lys Glu Cys Pro Ile  Val Gly Phe
        995                 1000                1005

agg tat  aga agc ctt aag cat  ttt aac tat gat gtc  tgc cag agt     3069
Arg Tyr  Arg Ser Leu Lys His  Phe Asn Tyr Asp Val  Cys Gln Ser
    1010                1015                1020

tgt ttc  ttt tcg ggt cga aca  gca aaa ggt cac aaa  tta cat tac     3114
Cys Phe  Phe Ser Gly Arg Thr  Ala Lys Gly His Lys  Leu His Tyr
    1025                1030                1035

cca atg  gtg gaa tat tgt ata  cct aca aca tct ggg  gaa gat gta     3159
Pro Met  Val Glu Tyr Cys Ile  Pro Thr Thr Ser Gly  Glu Asp Val
    1040                1045                1050

cga gac  ttc aca aag gta ctt  aag aac aag ttc agg  tcg aag aag     3204
Arg Asp  Phe Thr Lys Val Leu  Lys Asn Lys Phe Arg  Ser Lys Lys
    1055                1060                1065

tac ttt  gcc aaa cac cct cga  ctt ggt tac ctg cct  gtc cag aca     3249
Tyr Phe  Ala Lys His Pro Arg  Leu Gly Tyr Leu Pro  Val Gln Thr
    1070                1075                1080

gtt ctt  gaa ggt gac aac tta  gag act cct atc aca  ctc atc agt     3294
Val Leu  Glu Gly Asp Asn Leu  Glu Thr Pro Ile Thr  Leu Ile Ser
    1085                1090                1095

atg tgg  cca gag cac tat gac  ccc tca caa tct cct  caa ctg ttt     3339
Met Trp  Pro Glu His Tyr Asp  Pro Ser Gln Ser Pro  Gln Leu Phe
    1100                1105                1110

cat gat  gac acc cat tca aga  ata gaa caa tat gcc  aca cga ctg     3384
His Asp  Asp Thr His Ser Arg  Ile Glu Gln Tyr Ala  Thr Arg Leu
    1115                1120                1125

gcc cag  atg gaa agg act aat  ggg tct ttt ctc act  gat agc agc     3429
Ala Gln  Met Glu Arg Thr Asn  Gly Ser Phe Leu Thr  Asp Ser Ser
    1130                1135                1140

tcc acc  aca gga agt gtg gaa  gac gag cac gcc ctc  atc cag cag     3474
Ser Thr  Thr Gly Ser Val Glu  Asp Glu His Ala Leu  Ile Gln Gln
    1145                1150                1155

tat tgc  caa aca ctc gga gga  gag tcc cca gtg agc  cag ccg cag     3519
Tyr Cys  Gln Thr Leu Gly Gly  Glu Ser Pro Val Ser  Gln Pro Gln
    1160                1165                1170

agc cca  gct cag atc ctg aag  tca gta gag agg gaa  gaa cgt gga     3564
Ser Pro  Ala Gln Ile Leu Lys  Ser Val Glu Arg Glu  Glu Arg Gly
    1175                1180                1185

gaa ctg  gag agg atc att gct  gac ctg gag gaa gaa  caa aga aat     3609
Glu Leu  Glu Arg Ile Ile Ala  Asp Leu Glu Glu Glu  Gln Arg Asn
    1190                1195                1200

cta cag  gtg gag tat gag cag  ctg aag gac cag cac  ctc cga agg     3654
Leu Gln  Val Glu Tyr Glu Gln  Leu Lys Asp Gln His  Leu Arg Arg
    1205                1210                1215

ggg ctc  cct gtc ggt tca ccg  cca gag tcg att ata  tct ccc cat     3699
Gly Leu  Pro Val Gly Ser Pro  Pro Glu Ser Ile Ile  Ser Pro His
    1220                1225                1230

cac acg  tct gag gat tca gaa  ctt ata gca gaa gca  aaa ctc ctc     3744
His Thr  Ser Glu Asp Ser Glu  Leu Ile Ala Glu Ala  Lys Leu Leu
    1235                1240                1245

agg cag  cac aaa ggt cgg ctg  gag gct agg atg cag  att tta gaa     3789
```

```
Arg Gln  His Lys Gly Arg Leu  Glu Ala Arg Met Gln  Ile Leu Glu
    1250                 1255                 1260

gat cac  aat aaa cag ctg gag  tct cag ctc cac cgc  ctc cga cag      3834
Asp His  Asn Lys Gln Leu Glu  Ser Gln Leu His Arg  Leu Arg Gln
    1265                 1270                 1275

ctg ctg  gag cag cct gaa tct  gat tcc cga atc aat  ggt gtt tcc      3879
Leu Leu  Glu Gln Pro Glu Ser  Asp Ser Arg Ile Asn  Gly Val Ser
    1280                 1285                 1290

cca tgg  gct tct cct cag cat  tct gca ctg agc tac  tcg ctt gat      3924
Pro Trp  Ala Ser Pro Gln His  Ser Ala Leu Ser Tyr  Ser Leu Asp
    1295                 1300                 1305

cca gat  gcc tcc ggc cca cag  ttc cac cag gca gcg  gga gag gac      3969
Pro Asp  Ala Ser Gly Pro Gln  Phe His Gln Ala Ala  Gly Glu Asp
    1310                 1315                 1320

ctg ctg  gcc cca ccg cac gac  acc agc acg gat ctc  acg gag gtc      4014
Leu Leu  Ala Pro Pro His Asp  Thr Ser Thr Asp Leu  Thr Glu Val
    1325                 1330                 1335

atg gag  cag att cac agc acg  ttt cca tct tgc tgc  cca aat gtt      4059
Met Glu  Gln Ile His Ser Thr  Phe Pro Ser Cys Cys  Pro Asn Val
    1340                 1345                 1350

ccc agc  agg cca cag gca atg  tga                                  4083
Pro Ser  Arg Pro Gln Ala Met
    1355                 1360


<210> SEQ ID NO 11
<211> LENGTH: 1360
<212> TYPE: PRT
<213> ORGANISM: Homo sapiens

<400> SEQUENCE: 11

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Glu His Glu Ala
        35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220
```

```
Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270

Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Ala
305                 310                 315                 320

Ile Asn Ile Gln Ser Thr Ala Pro Glu Glu Glu His Glu Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln Asp Asp Ile Ser Asp Asp Val Glu Glu Val
    370                 375                 380

Lys Asp Gln Phe Ala Thr His Glu Ala Phe Met Met Glu Leu Thr Ala
385                 390                 395                 400

His Gln Ser Ser Val Gly Ser Val Leu Gln Ala Gly Asn Gln Leu Ile
                405                 410                 415

Thr Gln Gly Thr Leu Ser Asp Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Asp Arg Gln Ser Arg Leu His Asp Val Leu Met Glu Leu Gln Lys Lys
    450                 455                 460

Gln Leu Gln Gln Leu Ser Ala Trp Leu Thr Leu Thr Glu Glu Arg Ile
465                 470                 475                 480

Gln Lys Met Glu Thr Cys Pro Leu Asp Asp Asp Val Lys Ser Leu Gln
                485                 490                 495

Lys Leu Leu Glu Glu His Lys Ser Leu Gln Ser Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Ile Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Asn Ile Leu Trp Gln Glu Leu Leu Glu Glu
                565                 570                 575

Gln Cys Leu Leu Lys Ala Trp Leu Thr Glu Lys Glu Glu Ala Leu Asn
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Asp Asn Ser Lys Ala Ser Lys Lys Ile Asn Ser Asp Ser Glu Glu Leu
```

```
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val Arg Val Arg Glu Gln Ala Ile Thr Lys
    690                 695                 700

Lys Ser Lys Gln Glu Leu Pro Pro Pro Pro Pro Pro Lys Lys Arg Gln
705                 710                 715                 720

Ile His Val Asp Ala His Arg Asp Phe Gly Pro Ser Ser Gln His Phe
                725                 730                 735

Leu Ser Thr Ser Val Gln Leu Pro Trp Gln Arg Ser Ile Ser His Asn
            740                 745                 750

Lys Val Pro Tyr Tyr Ile Asn His Gln Thr Gln Thr Thr Cys Trp Asp
        755                 760                 765

His Pro Lys Met Thr Glu Leu Phe Gln Ser Leu Ala Asp Leu Asn Asn
    770                 775                 780

Val Arg Phe Ser Ala Tyr Arg Thr Ala Ile Lys Ile Arg Arg Leu Gln
785                 790                 795                 800

Lys Ala Leu Cys Leu Asp Leu Leu Glu Leu Ser Thr Thr Asn Glu Ile
                805                 810                 815

Phe Lys Gln His Lys Leu Asn Gln Asn Asp Gln Leu Leu Ser Val Pro
            820                 825                 830

Asp Val Ile Asn Cys Leu Thr Thr Thr Tyr Asp Gly Leu Glu Gln Met
        835                 840                 845

His Lys Asp Leu Val Asn Val Pro Leu Cys Val Asp Met Cys Leu Asn
    850                 855                 860

Trp Leu Leu Asn Val Tyr Asp Thr Gly Arg Thr Gly Lys Ile Arg Val
865                 870                 875                 880

Gln Ser Leu Lys Ile Gly Leu Met Ser Leu Ser Lys Gly Leu Leu Glu
                885                 890                 895

Glu Lys Tyr Arg Tyr Leu Phe Lys Glu Val Ala Gly Pro Thr Glu Met
            900                 905                 910

Cys Asp Gln Arg Gln Leu Gly Leu Leu Leu His Asp Ala Ile Gln Ile
        915                 920                 925

Pro Arg Gln Leu Gly Glu Val Ala Ala Phe Gly Gly Ser Asn Ile Glu
    930                 935                 940

Pro Ser Val Arg Ser Cys Phe Gln Gln Asn Asn Asn Lys Pro Glu Ile
945                 950                 955                 960

Ser Val Lys Glu Phe Ile Asp Trp Met His Leu Glu Pro Gln Ser Met
                965                 970                 975

Val Trp Leu Pro Val Leu His Arg Val Ala Ala Ala Glu Thr Ala Lys
            980                 985                 990

His Gln Ala Lys Cys Asn Ile Cys  Lys Glu Cys Pro Ile  Val Gly Phe
        995                 1000                1005

Arg Tyr  Arg Ser Leu Lys His  Phe Asn Tyr Asp Val  Cys Gln Ser
    1010                1015                1020

Cys Phe  Phe Ser Gly Arg Thr  Ala Lys Gly His Lys  Leu His Tyr
    1025                1030                1035

Pro Met  Val Glu Tyr Cys Ile  Pro Thr Thr Ser Gly  Glu Asp Val
    1040                1045                1050

Arg Asp  Phe Thr Lys Val Leu  Lys Asn Lys Phe Arg  Ser Lys Lys
    1055                1060                1065
```

```
Tyr Phe  Ala Lys His Pro Arg  Leu Gly Tyr Leu Pro  Val Gln Thr
    1070                 1075                 1080

Val Leu  Glu Gly Asp Asn Leu  Glu Thr Pro Ile Thr  Leu Ile Ser
    1085                 1090                 1095

Met Trp  Pro Glu His Tyr Asp  Pro Ser Gln Ser Pro  Gln Leu Phe
    1100                 1105                 1110

His Asp  Asp Thr His Ser Arg  Ile Glu Gln Tyr Ala  Thr Arg Leu
    1115                 1120                 1125

Ala Gln  Met Glu Arg Thr Asn  Gly Ser Phe Leu Thr  Asp Ser Ser
    1130                 1135                 1140

Ser Thr  Thr Gly Ser Val Glu  Asp Glu His Ala Leu  Ile Gln Gln
    1145                 1150                 1155

Tyr Cys  Gln Thr Leu Gly Gly  Glu Ser Pro Val Ser  Gln Pro Gln
    1160                 1165                 1170

Ser Pro  Ala Gln Ile Leu Lys  Ser Val Glu Arg Glu  Glu Arg Gly
    1175                 1180                 1185

Glu Leu  Glu Arg Ile Ile Ala  Asp Leu Glu Glu Glu  Gln Arg Asn
    1190                 1195                 1200

Leu Gln  Val Glu Tyr Glu Gln  Leu Lys Asp Gln His  Leu Arg Arg
    1205                 1210                 1215

Gly Leu  Pro Val Gly Ser Pro  Pro Glu Ser Ile Ile  Ser Pro His
    1220                 1225                 1230

His Thr  Ser Glu Asp Ser Glu  Leu Ile Ala Glu Ala  Lys Leu Leu
    1235                 1240                 1245

Arg Gln  His Lys Gly Arg Leu  Glu Ala Arg Met Gln  Ile Leu Glu
    1250                 1255                 1260

Asp His  Asn Lys Gln Leu Glu  Ser Gln Leu His Arg  Leu Arg Gln
    1265                 1270                 1275

Leu Leu  Glu Gln Pro Glu Ser  Asp Ser Arg Ile Asn  Gly Val Ser
    1280                 1285                 1290

Pro Trp  Ala Ser Pro Gln His  Ser Ala Leu Ser Tyr  Ser Leu Asp
    1295                 1300                 1305

Pro Asp  Ala Ser Gly Pro Gln  Phe His Gln Ala Ala  Gly Glu Asp
    1310                 1315                 1320

Leu Leu  Ala Pro Pro His Asp  Thr Ser Thr Asp Leu  Thr Glu Val
    1325                 1330                 1335

Met Glu  Gln Ile His Ser Thr  Phe Pro Ser Cys Cys  Pro Asn Val
    1340                 1345                 1350

Pro Ser  Arg Pro Gln Ala Met
    1355                 1360


<210> SEQ ID NO 12
<211> LENGTH: 5070
<212> TYPE: DNA
<213> ORGANISM: Homo sapiens
<220> FEATURE:
<221> NAME/KEY: CDS
<222> LOCATION: (1)..(5070)
<220> FEATURE:
<221> NAME/KEY: misc_feature
<222> LOCATION: (1)..(117)
<223> OTHER INFORMATION: TAT and epitope tag coding sequence

<400> SEQUENCE: 12

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
```

```
Arg Gln Arg Arg Arg Gly Gly Ser Thr Met Ser Gly Tyr Pro Tyr Asp
            20                  25                  30

gtc cca gac tat gct ggc tcc atg gcc aag tat gga gaa cat gaa gcc      144
Val Pro Asp Tyr Ala Gly Ser Met Ala Lys Tyr Gly Glu His Glu Ala
        35                  40                  45

agt cct gac aat ggg cag aac gaa ttc agt gat atc att aag tcc aga      192
Ser Pro Asp Asn Gly Gln Asn Glu Phe Ser Asp Ile Ile Lys Ser Arg
    50                  55                  60

tct gat gaa cac aat gac gta cag aag aaa acc ttt acc aaa tgg ata      240
Ser Asp Glu His Asn Asp Val Gln Lys Lys Thr Phe Thr Lys Trp Ile
65                  70                  75                  80

aat gct cga ttt tca aag agt ggg aaa cca ccc atc aat gat atg ttc      288
Asn Ala Arg Phe Ser Lys Ser Gly Lys Pro Pro Ile Asn Asp Met Phe
                85                  90                  95

aca gac ctc aaa gat gga agg aag cta ttg gat ctt cta gaa ggc ctc      336
Thr Asp Leu Lys Asp Gly Arg Lys Leu Leu Asp Leu Leu Glu Gly Leu
            100                 105                 110

aca gga aca tca ctg cca aag gaa cgt ggt tcc aca agg gta cat gcc      384
Thr Gly Thr Ser Leu Pro Lys Glu Arg Gly Ser Thr Arg Val His Ala
        115                 120                 125

tta aat aac gtc aac aga gtg ctg cag gtt tta cat cag aac aat gtg      432
Leu Asn Asn Val Asn Arg Val Leu Gln Val Leu His Gln Asn Asn Val
    130                 135                 140

gaa tta gtg aat ata ggg gga act gac att gtg gat gga aat cac aaa      480
Glu Leu Val Asn Ile Gly Gly Thr Asp Ile Val Asp Gly Asn His Lys
145                 150                 155                 160

ctg act ttg ggg tta ctt tgg agc atc att ttg cac tgg cag gtg aaa      528
Leu Thr Leu Gly Leu Leu Trp Ser Ile Ile Leu His Trp Gln Val Lys
                165                 170                 175

gat gtc atg aag gat gtc atg tcg gac ctg cag cag acg aac agt gag      576
Asp Val Met Lys Asp Val Met Ser Asp Leu Gln Gln Thr Asn Ser Glu
            180                 185                 190

aag atc ctg ctc agc tgg gtg cgt cag acc acc agg ccc tac agc caa      624
Lys Ile Leu Leu Ser Trp Val Arg Gln Thr Thr Arg Pro Tyr Ser Gln
        195                 200                 205

gtc aac gtc ctc aac ttc acc acc agc tgg aca gat gga ctc gcc ttt      672
Val Asn Val Leu Asn Phe Thr Thr Ser Trp Thr Asp Gly Leu Ala Phe
    210                 215                 220

aat gct gtc ctc cac cga cat aaa cct gat ctc ttc agc tgg gat aaa      720
Asn Ala Val Leu His Arg His Lys Pro Asp Leu Phe Ser Trp Asp Lys
225                 230                 235                 240

gtt gtc aaa atg tca cca att gag aga ctt gaa cat gcc ttc agc aag      768
Val Val Lys Met Ser Pro Ile Glu Arg Leu Glu His Ala Phe Ser Lys
                245                 250                 255

gct caa act tat ttg gga att gaa aag ctg tta gat cct gaa gat gtt      816
Ala Gln Thr Tyr Leu Gly Ile Glu Lys Leu Leu Asp Pro Glu Asp Val
            260                 265                 270

gcc gtt cag ctt cct gac aag aaa tcc ata att atg tat tta aca tct      864
Ala Val Gln Leu Pro Asp Lys Lys Ser Ile Ile Met Tyr Leu Thr Ser
        275                 280                 285

ttg ttt gag gtg cta cct cag caa gtc acc ata gac gcc atc cgt gag      912
Leu Phe Glu Val Leu Pro Gln Gln Val Thr Ile Asp Ala Ile Arg Glu
    290                 295                 300

gta gag aca ctc cca agg aaa tat aaa aaa gaa tgt gaa gaa gag gca      960
Val Glu Thr Leu Pro Arg Lys Tyr Lys Lys Glu Cys Glu Glu Glu Ala
305                 310                 315                 320

att aat ata cag agt aca gcg cct gag gag gag cat gag agt ccc cga     1008
Ile Asn Ile Gln Ser Thr Ala Pro Glu Glu Glu His Glu Ser Pro Arg
                325                 330                 335

gct gaa act ccc agc act gtc act gag gtt gac atg gat ctg gac agc     1056
```

```
Ala Glu Thr Pro Ser Thr Val Thr Glu Val Asp Met Asp Leu Asp Ser
            340                 345                 350

tat cag att gcg ttg gag gaa gtg ctg acc tgg ttg ctt tct gct gag     1104
Tyr Gln Ile Ala Leu Glu Glu Val Leu Thr Trp Leu Leu Ser Ala Glu
        355                 360                 365

gac act ttc cag gag cag gat gat att tct gat gat gtt gaa gaa gtc     1152
Asp Thr Phe Gln Glu Gln Asp Asp Ile Ser Asp Asp Val Glu Glu Val
    370                 375                 380

aaa gac cag ttt gca acc cat gaa gct ttt atg atg gaa ctg act gca     1200
Lys Asp Gln Phe Ala Thr His Glu Ala Phe Met Met Glu Leu Thr Ala
385                 390                 395                 400

cac cag agc agt gtg ggc agc gtc ctg cag gca ggc aac caa ctg ata     1248
His Gln Ser Ser Val Gly Ser Val Leu Gln Ala Gly Asn Gln Leu Ile
                405                 410                 415

aca caa gga act ctg tca gac gaa gaa gaa ttt gag att cag gaa cag     1296
Thr Gln Gly Thr Leu Ser Asp Glu Glu Glu Phe Glu Ile Gln Glu Gln
            420                 425                 430

atg acc ctg ctg aat gct aga tgg gag gct ctt agg gtg gag agt atg     1344
Met Thr Leu Leu Asn Ala Arg Trp Glu Ala Leu Arg Val Glu Ser Met
        435                 440                 445

gac aga cag tcc cgg ctg cac gat gtg ctg atg gaa ctg cag aag aag     1392
Asp Arg Gln Ser Arg Leu His Asp Val Leu Met Glu Leu Gln Lys Lys
    450                 455                 460

caa ctg cag cag ctc tcc gcc tgg tta aca ctc aca gag gag cgc att     1440
Gln Leu Gln Gln Leu Ser Ala Trp Leu Thr Leu Thr Glu Glu Arg Ile
465                 470                 475                 480

cag aag atg gaa act tgc ccc ctg gat gat gat gta aaa tct cta caa     1488
Gln Lys Met Glu Thr Cys Pro Leu Asp Asp Asp Val Lys Ser Leu Gln
                485                 490                 495

aag ctg cta gaa gaa cat aaa agt ttg caa agt gat ctt gag gct gaa     1536
Lys Leu Leu Glu Glu His Lys Ser Leu Gln Ser Asp Leu Glu Ala Glu
            500                 505                 510

cag gtg aaa gta aat tca cta act cac atg gtg gtc att gtt gat gaa     1584
Gln Val Lys Val Asn Ser Leu Thr His Met Val Val Ile Val Asp Glu
        515                 520                 525

aac agt ggt gag agt gct aca gct atc cta gaa gac cag tta cag aaa     1632
Asn Ser Gly Glu Ser Ala Thr Ala Ile Leu Glu Asp Gln Leu Gln Lys
    530                 535                 540

ctt ggt gag cgc tgg aca gca gta tgc cgt tgg act gaa gaa cgc tgg     1680
Leu Gly Glu Arg Trp Thr Ala Val Cys Arg Trp Thr Glu Glu Arg Trp
545                 550                 555                 560

aat agg tta caa gaa atc aat ata ttg tgg cag gaa tta ttg gaa gaa     1728
Asn Arg Leu Gln Glu Ile Asn Ile Leu Trp Gln Glu Leu Leu Glu Glu
                565                 570                 575

cag tgc ttg ttg aaa gct tgg tta acc gaa aaa gaa gag gct tta aat     1776
Gln Cys Leu Leu Lys Ala Trp Leu Thr Glu Lys Glu Glu Ala Leu Asn
            580                 585                 590

aaa gtc cag aca agc aac ttc aaa gac caa aag gaa cta agt gtc agt     1824
Lys Val Gln Thr Ser Asn Phe Lys Asp Gln Lys Glu Leu Ser Val Ser
        595                 600                 605

gtt cga cgt ctg gct att ttg aag gaa gac atg gaa atg aag cgt caa     1872
Val Arg Arg Leu Ala Ile Leu Lys Glu Asp Met Glu Met Lys Arg Gln
    610                 615                 620

aca ttg gat cag ctg agt gag att ggc cag gat gtg gga caa tta ctt     1920
Thr Leu Asp Gln Leu Ser Glu Ile Gly Gln Asp Val Gly Gln Leu Leu
625                 630                 635                 640

gat aat tcc aag gca tct aag aag atc aac agt gac tca gag gaa ctg     1968
Asp Asn Ser Lys Ala Ser Lys Lys Ile Asn Ser Asp Ser Glu Glu Leu
                645                 650                 655

act caa aga tgg gat tct ttg gtt cag aga cta gaa gat tcc tcc aac     2016
```

```
Thr Gln Arg Trp Asp Ser Leu Val Gln Arg Leu Glu Asp Ser Ser Asn
            660                 665                 670

cag gtg act cag gct gta gca aag ctg ggg atg tct cag att cct cag      2064
Gln Val Thr Gln Ala Val Ala Lys Leu Gly Met Ser Gln Ile Pro Gln
        675                 680                 685

aag gac ctt ttg gag act gtt cgt gta aga gaa caa gca att aca aaa      2112
Lys Asp Leu Leu Glu Thr Val Arg Val Arg Glu Gln Ala Ile Thr Lys
    690                 695                 700

aaa tct aag cag gaa ctg cct cct cct cct ccc cca aag aag aga cag      2160
Lys Ser Lys Gln Glu Leu Pro Pro Pro Pro Pro Pro Lys Lys Arg Gln
705                 710                 715                 720

atc cat gtg gat att gaa gct aag aaa aag ttt gat gct ata agt gca      2208
Ile His Val Asp Ile Glu Ala Lys Lys Lys Phe Asp Ala Ile Ser Ala
                725                 730                 735

gag ctg ttg aac tgg att ttg aaa tgg aaa act gcc att cag acc aca      2256
Glu Leu Leu Asn Trp Ile Leu Lys Trp Lys Thr Ala Ile Gln Thr Thr
            740                 745                 750

gag ata aaa gag tat atg aag atg caa gac act tcc gaa atg aaa aag      2304
Glu Ile Lys Glu Tyr Met Lys Met Gln Asp Thr Ser Glu Met Lys Lys
        755                 760                 765

aag ttg aag gca tta gaa aaa gaa cag aga gaa aga atc ccc aga gca      2352
Lys Leu Lys Ala Leu Glu Lys Glu Gln Arg Glu Arg Ile Pro Arg Ala
    770                 775                 780

gat gaa tta aac caa act gga caa atc ctt gtg gag caa atg gga aaa      2400
Asp Glu Leu Asn Gln Thr Gly Gln Ile Leu Val Glu Gln Met Gly Lys
785                 790                 795                 800

gaa ggc ctt cct act gaa gaa ata aaa aat gtt ctg gag aag gtt tca      2448
Glu Gly Leu Pro Thr Glu Glu Ile Lys Asn Val Leu Glu Lys Val Ser
                805                 810                 815

tca gaa tgg aag aat gta tct caa cat ttg gaa gat cta gaa aga aag      2496
Ser Glu Trp Lys Asn Val Ser Gln His Leu Glu Asp Leu Glu Arg Lys
            820                 825                 830

att cag cta cag gaa gat ata aat gct tat ttc aag cag ctt gat gag      2544
Ile Gln Leu Gln Glu Asp Ile Asn Ala Tyr Phe Lys Gln Leu Asp Glu
        835                 840                 845

ctt gaa aag gtc atc aag aca aag gag gag tgg gta aaa cac act tcc      2592
Leu Glu Lys Val Ile Lys Thr Lys Glu Glu Trp Val Lys His Thr Ser
    850                 855                 860

att tct gaa tct tcc cgg cag tcc ttg cca agc ttg aag gat tcc tgt      2640
Ile Ser Glu Ser Ser Arg Gln Ser Leu Pro Ser Leu Lys Asp Ser Cys
865                 870                 875                 880

cag cgg gaa ttg aca aat ctt ctt ggc ctt cac ccc aaa att gaa atg      2688
Gln Arg Glu Leu Thr Asn Leu Leu Gly Leu His Pro Lys Ile Glu Met
                885                 890                 895

gct cgt gca agc tgc tcg gcc ctg atg tct cag cct tct gcc cca gat      2736
Ala Arg Ala Ser Cys Ser Ala Leu Met Ser Gln Pro Ser Ala Pro Asp
            900                 905                 910

ttt gtc cag cgg ggc ttc gat agc ttt ctg ggc cgc tac caa gct gta      2784
Phe Val Gln Arg Gly Phe Asp Ser Phe Leu Gly Arg Tyr Gln Ala Val
        915                 920                 925

caa gag gct gta gag gat cgt caa caa cat cta gag aat gaa ctg aag      2832
Gln Glu Ala Val Glu Asp Arg Gln Gln His Leu Glu Asn Glu Leu Lys
    930                 935                 940

ggc caa cct gga cat gca tat ctg gaa aca ttg aaa aca ctg aaa gat      2880
Gly Gln Pro Gly His Ala Tyr Leu Glu Thr Leu Lys Thr Leu Lys Asp
945                 950                 955                 960

gtg cta aat gat tca gaa aat aag gcc cag gtg tct ctg aat gtc ctt      2928
Val Leu Asn Asp Ser Glu Asn Lys Ala Gln Val Ser Leu Asn Val Leu
                965                 970                 975

aat gat ctt gcc aag gtg gag aag gcc ctg caa gaa aaa aag acc ctt      2976
```

```
Asn Asp Leu Ala Lys Val Glu Lys Ala Leu Gln Glu Lys Lys Thr Leu
            980                 985                 990

gat gaa atc ctt gag aat cag aaa  cct gca tta cat aaa  ctt gca gaa    3024
Asp Glu Ile Leu Glu Asn Gln Lys  Pro Ala Leu His Lys  Leu Ala Glu
        995                 1000                 1005

gaa aca  aag gct ctg gag aaa  aat gtt cat cct gat  gta gaa aaa      3069
Glu Thr  Lys Ala Leu Glu Lys  Asn Val His Pro Asp  Val Glu Lys
    1010                 1015                 1020

tta tat  aag caa gaa ttt gat  gat gtg caa gga aag  tgg aac aag      3114
Leu Tyr  Lys Gln Glu Phe Asp  Asp Val Gln Gly Lys  Trp Asn Lys
    1025                 1030                 1035

cta aag  gtc ttg gtt tcc aaa  gat cta cat ttg ctt  gag gaa att      3159
Leu Lys  Val Leu Val Ser Lys  Asp Leu His Leu Leu  Glu Glu Ile
    1040                 1045                 1050

gcc cac  aga gat ttt gga cca  tcc tct cag cat ttt  ctc tct acg      3204
Ala His  Arg Asp Phe Gly Pro  Ser Ser Gln His Phe  Leu Ser Thr
    1055                 1060                 1065

tca gtc  cag ctg ccg tgg caa  aga tcc att tca cat  aat aaa gtg      3249
Ser Val  Gln Leu Pro Trp Gln  Arg Ser Ile Ser His  Asn Lys Val
    1070                 1075                 1080

ccc tat  tac atc aac cat caa  aca cag acc acc tgt  tgg gac cat      3294
Pro Tyr  Tyr Ile Asn His Gln  Thr Gln Thr Thr Cys  Trp Asp His
    1085                 1090                 1095

cct aaa  atg acc gaa ctc ttt  caa tcc ctt gct gac  ctg aat aat      3339
Pro Lys  Met Thr Glu Leu Phe  Gln Ser Leu Ala Asp  Leu Asn Asn
    1100                 1105                 1110

gta cgt  ttt tct gcc tac cgt  aca gca atc aaa atc  cga aga cta      3384
Val Arg  Phe Ser Ala Tyr Arg  Thr Ala Ile Lys Ile  Arg Arg Leu
    1115                 1120                 1125

caa aaa  gca cta tgt ttg gat  ctc tta gag ttg agt  aca aca aat      3429
Gln Lys  Ala Leu Cys Leu Asp  Leu Leu Glu Leu Ser  Thr Thr Asn
    1130                 1135                 1140

gaa att  ttc aaa cag cac aag  ttg aac caa aat gac  cag ctc ctc      3474
Glu Ile  Phe Lys Gln His Lys  Leu Asn Gln Asn Asp  Gln Leu Leu
    1145                 1150                 1155

agt gtt  cca gat gtc atc aac  tgt ctg aca aca act  tat gat gga      3519
Ser Val  Pro Asp Val Ile Asn  Cys Leu Thr Thr Thr  Tyr Asp Gly
    1160                 1165                 1170

ctt gag  caa atg cat aag gac  ctg gtc aac gtt cca  ctc tgt gtt      3564
Leu Glu  Gln Met His Lys Asp  Leu Val Asn Val Pro  Leu Cys Val
    1175                 1180                 1185

gat atg  tgt ctc aat tgg ttg  ctc aat gtc tat gac  acg ggt cga      3609
Asp Met  Cys Leu Asn Trp Leu  Leu Asn Val Tyr Asp  Thr Gly Arg
    1190                 1195                 1200

act gga  aaa att aga gtg cag  agt ctg aag att gga  tta atg tct      3654
Thr Gly  Lys Ile Arg Val Gln  Ser Leu Lys Ile Gly  Leu Met Ser
    1205                 1210                 1215

ctc tcc  aaa ggt ctc ttg gaa  gaa aaa tac aga tat  ctc ttt aag      3699
Leu Ser  Lys Gly Leu Leu Glu  Glu Lys Tyr Arg Tyr  Leu Phe Lys
    1220                 1225                 1230

gaa gtt  gca ggg cca aca gaa  atg tgt gac cag agg  cag ctg ggc      3744
Glu Val  Ala Gly Pro Thr Glu  Met Cys Asp Gln Arg  Gln Leu Gly
    1235                 1240                 1245

ctg tta  ctt cat gat gcc atc  cag atc ccc cgg cag  cta ggt gaa      3789
Leu Leu  Leu His Asp Ala Ile  Gln Ile Pro Arg Gln  Leu Gly Glu
    1250                 1255                 1260

gta gca  gct ttt gga ggc agt  aat att gag cct agt  gtt cgc agc      3834
Val Ala  Ala Phe Gly Gly Ser  Asn Ile Glu Pro Ser  Val Arg Ser
    1265                 1270                 1275

tgc ttc  caa cag aat aac aat  aaa cca gaa ata agt  gtg aaa gag      3879
```

```
Cys Phe Gln Gln Asn Asn Asn Lys Pro Glu Ile Ser Val Lys Glu
    1280                1285                1290

ttt ata gat tgg atg cat ttg gaa cca cag tcc atg gtt tgg ctc      3924
Phe Ile Asp Trp Met His Leu Glu Pro Gln Ser Met Val Trp Leu
    1295                1300                1305

cca gtt tta cat cga gtg gca gca gcg gag act gca aaa cat cag      3969
Pro Val Leu His Arg Val Ala Ala Ala Glu Thr Ala Lys His Gln
    1310                1315                1320

gcc aaa tgc aac atc tgt aaa gaa tgt cca att gtc ggg ttc agg      4014
Ala Lys Cys Asn Ile Cys Lys Glu Cys Pro Ile Val Gly Phe Arg
    1325                1330                1335

tat aga agc ctt aag cat ttt aac tat gat gtc tgc cag agt tgt      4059
Tyr Arg Ser Leu Lys His Phe Asn Tyr Asp Val Cys Gln Ser Cys
    1340                1345                1350

ttc ttt tcg ggt cga aca gca aaa ggt cac aaa tta cat tac cca      4104
Phe Phe Ser Gly Arg Thr Ala Lys Gly His Lys Leu His Tyr Pro
    1355                1360                1365

atg gtg gaa tat tgt ata cct aca aca tct ggg gaa gat gta cga      4149
Met Val Glu Tyr Cys Ile Pro Thr Thr Ser Gly Glu Asp Val Arg
    1370                1375                1380

gac ttc aca aag gta ctt aag aac aag ttc agg tcg aag aag tac      4194
Asp Phe Thr Lys Val Leu Lys Asn Lys Phe Arg Ser Lys Lys Tyr
    1385                1390                1395

ttt gcc aaa cac cct cga ctt ggt tac ctg cct gtc cag aca gtt      4239
Phe Ala Lys His Pro Arg Leu Gly Tyr Leu Pro Val Gln Thr Val
    1400                1405                1410

ctt gaa ggt gac aac tta gag act cct atc aca ctc atc agt atg      4284
Leu Glu Gly Asp Asn Leu Glu Thr Pro Ile Thr Leu Ile Ser Met
    1415                1420                1425

tgg cca gag cac tat gac ccc tca caa tct cct caa ctg ttt cat      4329
Trp Pro Glu His Tyr Asp Pro Ser Gln Ser Pro Gln Leu Phe His
    1430                1435                1440

gat gac acc cat tca aga ata gaa caa tat gcc aca cga ctg gcc      4374
Asp Asp Thr His Ser Arg Ile Glu Gln Tyr Ala Thr Arg Leu Ala
    1445                1450                1455

cag atg gaa agg act aat ggg tct ttt ctc act gat agc agc tcc      4419
Gln Met Glu Arg Thr Asn Gly Ser Phe Leu Thr Asp Ser Ser Ser
    1460                1465                1470

acc aca gga agt gtg gaa gac gag cac gcc ctc atc cag cag tat      4464
Thr Thr Gly Ser Val Glu Asp Glu His Ala Leu Ile Gln Gln Tyr
    1475                1480                1485

tgc caa aca ctc gga gga gag tcc cca gtg agc cag ccg cag agc      4509
Cys Gln Thr Leu Gly Gly Glu Ser Pro Val Ser Gln Pro Gln Ser
    1490                1495                1500

cca gct cag atc ctg aag tca gta gag agg gaa gaa cgt gga gaa      4554
Pro Ala Gln Ile Leu Lys Ser Val Glu Arg Glu Glu Arg Gly Glu
    1505                1510                1515

ctg gag agg atc att gct gac ctg gag gaa gaa caa aga aat cta      4599
Leu Glu Arg Ile Ile Ala Asp Leu Glu Glu Glu Gln Arg Asn Leu
    1520                1525                1530

cag gtg gag tat gag cag ctg aag gac cag cac ctc cga agg ggg      4644
Gln Val Glu Tyr Glu Gln Leu Lys Asp Gln His Leu Arg Arg Gly
    1535                1540                1545

ctc cct gtc ggt tca ccg cca gag tcg att ata tct ccc cat cac      4689
Leu Pro Val Gly Ser Pro Pro Glu Ser Ile Ile Ser Pro His His
    1550                1555                1560

acg tct gag gat tca gaa ctt ata gca gaa gca aaa ctc ctc agg      4734
Thr Ser Glu Asp Ser Glu Leu Ile Ala Glu Ala Lys Leu Leu Arg
    1565                1570                1575

cag cac aaa ggt cgg ctg gag gct agg atg cag att tta gaa gat      4779
```

```
Gln His  Lys Gly Arg Leu Glu  Ala Arg Met Gln Ile  Leu Glu Asp
    1580                 1585                 1590

cac aat  aaa cag ctg gag tct  cag ctc cac cgc ctc  cga cag ctg      4824
His Asn  Lys Gln Leu Glu Ser  Gln Leu His Arg Leu  Arg Gln Leu
    1595                 1600                 1605

ctg gag  cag cct gaa tct gat  tcc cga atc aat ggt  gtt tcc cca      4869
Leu Glu  Gln Pro Glu Ser Asp  Ser Arg Ile Asn Gly  Val Ser Pro
    1610                 1615                 1620

tgg gct  tct cct cag cat tct  gca ctg agc tac tcg  ctt gat cca      4914
Trp Ala  Ser Pro Gln His Ser  Ala Leu Ser Tyr Ser  Leu Asp Pro
    1625                 1630                 1635

gat gcc  tcc ggc cca cag ttc  cac cag gca gcg gga  gag gac ctg      4959
Asp Ala  Ser Gly Pro Gln Phe  His Gln Ala Ala Gly  Glu Asp Leu
    1640                 1645                 1650

ctg gcc  cca ccg cac gac acc  agc acg gat ctc acg  gag gtc atg      5004
Leu Ala  Pro Pro His Asp Thr  Ser Thr Asp Leu Thr  Glu Val Met
    1655                 1660                 1665

gag cag  att cac agc acg ttt  cca tct tgc tgc cca  aat gtt ccc      5049
Glu Gln  Ile His Ser Thr Phe  Pro Ser Cys Cys Pro  Asn Val Pro
    1670                 1675                 1680

agc agg  cca cag gca atg tga                                        5070
Ser Arg  Pro Gln Ala Met
    1685


<210> SEQ ID NO 13
<211> LENGTH: 1689
<212> TYPE: PRT
<213> ORGANISM: Homo sapiens

<400> SEQUENCE: 13

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Glu His Glu Ala
        35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220
```

```
Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270

Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Ala
305                 310                 315                 320

Ile Asn Ile Gln Ser Thr Ala Pro Glu Glu Glu His Glu Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln Asp Asp Ile Ser Asp Asp Val Glu Glu Val
    370                 375                 380

Lys Asp Gln Phe Ala Thr His Glu Ala Phe Met Met Glu Leu Thr Ala
385                 390                 395                 400

His Gln Ser Ser Val Gly Ser Val Leu Gln Ala Gly Asn Gln Leu Ile
                405                 410                 415

Thr Gln Gly Thr Leu Ser Asp Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Asp Arg Gln Ser Arg Leu His Asp Val Leu Met Glu Leu Gln Lys Lys
    450                 455                 460

Gln Leu Gln Gln Leu Ser Ala Trp Leu Thr Leu Thr Glu Glu Arg Ile
465                 470                 475                 480

Gln Lys Met Glu Thr Cys Pro Leu Asp Asp Asp Val Lys Ser Leu Gln
                485                 490                 495

Lys Leu Leu Glu Glu His Lys Ser Leu Gln Ser Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Ile Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Asn Ile Leu Trp Gln Glu Leu Leu Glu Glu
                565                 570                 575

Gln Cys Leu Leu Lys Ala Trp Leu Thr Glu Lys Glu Glu Ala Leu Asn
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Asp Asn Ser Lys Ala Ser Lys Lys Ile Asn Ser Asp Ser Glu Glu Leu
```

```
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val Arg Val Arg Glu Gln Ala Ile Thr Lys
    690                 695                 700

Lys Ser Lys Gln Glu Leu Pro Pro Pro Pro Pro Pro Lys Lys Arg Gln
705                 710                 715                 720

Ile His Val Asp Ile Glu Ala Lys Lys Lys Phe Asp Ala Ile Ser Ala
                725                 730                 735

Glu Leu Leu Asn Trp Ile Leu Lys Trp Lys Thr Ala Ile Gln Thr Thr
            740                 745                 750

Glu Ile Lys Glu Tyr Met Lys Met Gln Asp Thr Ser Glu Met Lys Lys
        755                 760                 765

Lys Leu Lys Ala Leu Glu Lys Glu Gln Arg Glu Arg Ile Pro Arg Ala
    770                 775                 780

Asp Glu Leu Asn Gln Thr Gly Gln Ile Leu Val Glu Gln Met Gly Lys
785                 790                 795                 800

Glu Gly Leu Pro Thr Glu Glu Ile Lys Asn Val Leu Glu Lys Val Ser
                805                 810                 815

Ser Glu Trp Lys Asn Val Ser Gln His Leu Glu Asp Leu Glu Arg Lys
            820                 825                 830

Ile Gln Leu Gln Glu Asp Ile Asn Ala Tyr Phe Lys Gln Leu Asp Glu
        835                 840                 845

Leu Glu Lys Val Ile Lys Thr Lys Glu Glu Trp Val Lys His Thr Ser
    850                 855                 860

Ile Ser Glu Ser Ser Arg Gln Ser Leu Pro Ser Leu Lys Asp Ser Cys
865                 870                 875                 880

Gln Arg Glu Leu Thr Asn Leu Leu Gly Leu His Pro Lys Ile Glu Met
                885                 890                 895

Ala Arg Ala Ser Cys Ser Ala Leu Met Ser Gln Pro Ser Ala Pro Asp
            900                 905                 910

Phe Val Gln Arg Gly Phe Asp Ser Phe Leu Gly Arg Tyr Gln Ala Val
        915                 920                 925

Gln Glu Ala Val Glu Asp Arg Gln Gln His Leu Glu Asn Glu Leu Lys
    930                 935                 940

Gly Gln Pro Gly His Ala Tyr Leu Glu Thr Leu Lys Thr Leu Lys Asp
945                 950                 955                 960

Val Leu Asn Asp Ser Glu Asn Lys Ala Gln Val Ser Leu Asn Val Leu
                965                 970                 975

Asn Asp Leu Ala Lys Val Glu Lys Ala Leu Gln Glu Lys Lys Thr Leu
            980                 985                 990

Asp Glu Ile Leu Glu Asn Gln Lys  Pro Ala Leu His Lys  Leu Ala Glu
        995                 1000                1005

Glu Thr  Lys Ala Leu Glu Lys  Asn Val His Pro Asp  Val Glu Lys
    1010                1015                1020

Leu Tyr  Lys Gln Glu Phe Asp  Asp Val Gln Gly Lys  Trp Asn Lys
    1025                1030                1035

Leu Lys  Val Leu Val Ser Lys  Asp Leu His Leu Leu  Glu Glu Ile
    1040                1045                1050

Ala His  Arg Asp Phe Gly Pro  Ser Ser Gln His Phe  Leu Ser Thr
    1055                1060                1065
```

```
Ser Val  Gln Leu Pro Trp Gln  Arg Ser Ile Ser His  Asn Lys Val
    1070                 1075                 1080

Pro Tyr  Tyr Ile Asn His Gln  Thr Gln Thr Thr Cys  Trp Asp His
    1085                 1090                 1095

Pro Lys  Met Thr Glu Leu Phe  Gln Ser Leu Ala Asp  Leu Asn Asn
    1100                 1105                 1110

Val Arg  Phe Ser Ala Tyr Arg  Thr Ala Ile Lys Ile  Arg Arg Leu
    1115                 1120                 1125

Gln Lys  Ala Leu Cys Leu Asp  Leu Leu Glu Leu Ser  Thr Thr Asn
    1130                 1135                 1140

Glu Ile  Phe Lys Gln His Lys  Leu Asn Gln Asn Asp  Gln Leu Leu
    1145                 1150                 1155

Ser Val  Pro Asp Val Ile Asn  Cys Leu Thr Thr Thr  Tyr Asp Gly
    1160                 1165                 1170

Leu Glu  Gln Met His Lys Asp  Leu Val Asn Val Pro  Leu Cys Val
    1175                 1180                 1185

Asp Met  Cys Leu Asn Trp Leu  Leu Asn Val Tyr Asp  Thr Gly Arg
    1190                 1195                 1200

Thr Gly  Lys Ile Arg Val Gln  Ser Leu Lys Ile Gly  Leu Met Ser
    1205                 1210                 1215

Leu Ser  Lys Gly Leu Leu Glu  Glu Lys Tyr Arg Tyr  Leu Phe Lys
    1220                 1225                 1230

Glu Val  Ala Gly Pro Thr Glu  Met Cys Asp Gln Arg  Gln Leu Gly
    1235                 1240                 1245

Leu Leu  Leu His Asp Ala Ile  Gln Ile Pro Arg Gln  Leu Gly Glu
    1250                 1255                 1260

Val Ala  Ala Phe Gly Gly Ser  Asn Ile Glu Pro Ser  Val Arg Ser
    1265                 1270                 1275

Cys Phe  Gln Gln Asn Asn Asn  Lys Pro Glu Ile Ser  Val Lys Glu
    1280                 1285                 1290

Phe Ile  Asp Trp Met His Leu  Glu Pro Gln Ser Met  Val Trp Leu
    1295                 1300                 1305

Pro Val  Leu His Arg Val Ala  Ala Ala Glu Thr Ala  Lys His Gln
    1310                 1315                 1320

Ala Lys  Cys Asn Ile Cys Lys  Glu Cys Pro Ile Val  Gly Phe Arg
    1325                 1330                 1335

Tyr Arg  Ser Leu Lys His Phe  Asn Tyr Asp Val Cys  Gln Ser Cys
    1340                 1345                 1350

Phe Phe  Ser Gly Arg Thr Ala  Lys Gly His Lys Leu  His Tyr Pro
    1355                 1360                 1365

Met Val  Glu Tyr Cys Ile Pro  Thr Thr Ser Gly Glu  Asp Val Arg
    1370                 1375                 1380

Asp Phe  Thr Lys Val Leu Lys  Asn Lys Phe Arg Ser  Lys Lys Tyr
    1385                 1390                 1395

Phe Ala  Lys His Pro Arg Leu  Gly Tyr Leu Pro Val  Gln Thr Val
    1400                 1405                 1410

Leu Glu  Gly Asp Asn Leu Glu  Thr Pro Ile Thr Leu  Ile Ser Met
    1415                 1420                 1425

Trp Pro  Glu His Tyr Asp Pro  Ser Gln Ser Pro Gln  Leu Phe His
    1430                 1435                 1440

Asp Asp  Thr His Ser Arg Ile  Glu Gln Tyr Ala Thr  Arg Leu Ala
    1445                 1450                 1455

Gln Met  Glu Arg Thr Asn Gly  Ser Phe Leu Thr Asp  Ser Ser Ser
    1460                 1465                 1470
```

```
Thr Thr  Gly Ser Val Glu Asp  Glu His Ala Leu Ile  Gln Gln Tyr
    1475                 1480                 1485

Cys Gln  Thr Leu Gly Gly Glu  Ser Pro Val Ser Gln  Pro Gln Ser
    1490                 1495                 1500

Pro Ala  Gln Ile Leu Lys Ser  Val Glu Arg Glu Glu  Arg Gly Glu
    1505                 1510                 1515

Leu Glu  Arg Ile Ile Ala Asp  Leu Glu Glu Glu Gln  Arg Asn Leu
    1520                 1525                 1530

Gln Val  Glu Tyr Glu Gln Leu  Lys Asp Gln His Leu  Arg Arg Gly
    1535                 1540                 1545

Leu Pro  Val Gly Ser Pro Pro  Glu Ser Ile Ile Ser  Pro His His
    1550                 1555                 1560

Thr Ser  Glu Asp Ser Glu Leu  Ile Ala Glu Ala Lys  Leu Leu Arg
    1565                 1570                 1575

Gln His  Lys Gly Arg Leu Glu  Ala Arg Met Gln Ile  Leu Glu Asp
    1580                 1585                 1590

His Asn  Lys Gln Leu Glu Ser  Gln Leu His Arg Leu  Arg Gln Leu
    1595                 1600                 1605

Leu Glu  Gln Pro Glu Ser Asp  Ser Arg Ile Asn Gly  Val Ser Pro
    1610                 1615                 1620

Trp Ala  Ser Pro Gln His Ser  Ala Leu Ser Tyr Ser  Leu Asp Pro
    1625                 1630                 1635

Asp Ala  Ser Gly Pro Gln Phe  His Gln Ala Ala Gly  Glu Asp Leu
    1640                 1645                 1650

Leu Ala  Pro Pro His Asp Thr  Ser Thr Asp Leu Thr  Glu Val Met
    1655                 1660                 1665

Glu Gln  Ile His Ser Thr Phe  Pro Ser Cys Cys Pro  Asn Val Pro
    1670                 1675                 1680

Ser Arg  Pro Gln Ala Met
    1685


<210> SEQ ID NO 14
<211> LENGTH: 6033
<212> TYPE: DNA
<213> ORGANISM: Homo sapiens
<220> FEATURE:
<221> NAME/KEY: CDS
<222> LOCATION: (1)..(6033)
<220> FEATURE:
<221> NAME/KEY: misc_feature
<222> LOCATION: (1)..(117)
<223> OTHER INFORMATION: TAT and epitope tag coding sequence

<400> SEQUENCE: 14

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
Arg Gln Arg Arg Arg Gly Gly Ser Thr Met Ser Gly Tyr Pro Tyr Asp
            20                  25                  30

gtc cca gac tat gct ggc tcc atg gcc aag tat gga gaa cat gaa gcc      144
Val Pro Asp Tyr Ala Gly Ser Met Ala Lys Tyr Gly Glu His Glu Ala
        35                  40                  45

agt cct gac aat ggg cag aac gaa ttc agt gat atc att aag tcc aga      192
Ser Pro Asp Asn Gly Gln Asn Glu Phe Ser Asp Ile Ile Lys Ser Arg
    50                  55                  60

tct gat gaa cac aat gac gta cag aag aaa acc ttt acc aaa tgg ata      240
Ser Asp Glu His Asn Asp Val Gln Lys Lys Thr Phe Thr Lys Trp Ile
65                  70                  75                  80
```

```
aat gct cga ttt tca aag agt ggg aaa cca ccc atc aat gat atg ttc      288
Asn Ala Arg Phe Ser Lys Ser Gly Lys Pro Pro Ile Asn Asp Met Phe
                85                  90                  95

aca gac ctc aaa gat gga agg aag cta ttg gat ctt cta gaa ggc ctc      336
Thr Asp Leu Lys Asp Gly Arg Lys Leu Leu Asp Leu Leu Glu Gly Leu
            100                 105                 110

aca gga aca tca ctg cca aag gaa cgt ggt tcc aca agg gta cat gcc      384
Thr Gly Thr Ser Leu Pro Lys Glu Arg Gly Ser Thr Arg Val His Ala
        115                 120                 125

tta aat aac gtc aac aga gtg ctg cag gtt tta cat cag aac aat gtg      432
Leu Asn Asn Val Asn Arg Val Leu Gln Val Leu His Gln Asn Asn Val
    130                 135                 140

gaa tta gtg aat ata ggg gga act gac att gtg gat gga aat cac aaa      480
Glu Leu Val Asn Ile Gly Gly Thr Asp Ile Val Asp Gly Asn His Lys
145                 150                 155                 160

ctg act ttg ggg tta ctt tgg agc atc att ttg cac tgg cag gtg aaa      528
Leu Thr Leu Gly Leu Leu Trp Ser Ile Ile Leu His Trp Gln Val Lys
                165                 170                 175

gat gtc atg aag gat gtc atg tcg gac ctg cag cag acg aac agt gag      576
Asp Val Met Lys Asp Val Met Ser Asp Leu Gln Gln Thr Asn Ser Glu
            180                 185                 190

aag atc ctg ctc agc tgg gtg cgt cag acc acc agg ccc tac agc caa      624
Lys Ile Leu Leu Ser Trp Val Arg Gln Thr Thr Arg Pro Tyr Ser Gln
        195                 200                 205

gtc aac gtc ctc aac ttc acc acc agc tgg aca gat gga ctc gcc ttt      672
Val Asn Val Leu Asn Phe Thr Thr Ser Trp Thr Asp Gly Leu Ala Phe
    210                 215                 220

aat gct gtc ctc cac cga cat aaa cct gat ctc ttc agc tgg gat aaa      720
Asn Ala Val Leu His Arg His Lys Pro Asp Leu Phe Ser Trp Asp Lys
225                 230                 235                 240

gtt gtc aaa atg tca cca att gag aga ctt gaa cat gcc ttc agc aag      768
Val Val Lys Met Ser Pro Ile Glu Arg Leu Glu His Ala Phe Ser Lys
                245                 250                 255

gct caa act tat ttg gga att gaa aag ctg tta gat cct gaa gat gtt      816
Ala Gln Thr Tyr Leu Gly Ile Glu Lys Leu Leu Asp Pro Glu Asp Val
            260                 265                 270

gcc gtt cag ctt cct gac aag aaa tcc ata att atg tat tta aca tct      864
Ala Val Gln Leu Pro Asp Lys Lys Ser Ile Ile Met Tyr Leu Thr Ser
        275                 280                 285

ttg ttt gag gtg cta cct cag caa gtc acc ata gac gcc atc cgt gag      912
Leu Phe Glu Val Leu Pro Gln Gln Val Thr Ile Asp Ala Ile Arg Glu
    290                 295                 300

gta gag aca ctc cca agg aaa tat aaa aaa gaa tgt gaa gaa gag gca      960
Val Glu Thr Leu Pro Arg Lys Tyr Lys Lys Glu Cys Glu Glu Glu Ala
305                 310                 315                 320

att aat ata cag agt aca gcg cct gag gag gag cat gag agt ccc cga     1008
Ile Asn Ile Gln Ser Thr Ala Pro Glu Glu Glu His Glu Ser Pro Arg
                325                 330                 335

gct gaa act ccc agc act gtc act gag gtt gac atg gat ctg gac agc     1056
Ala Glu Thr Pro Ser Thr Val Thr Glu Val Asp Met Asp Leu Asp Ser
            340                 345                 350

tat cag att gcg ttg gag gaa gtg ctg acc tgg ttg ctt tct gct gag     1104
Tyr Gln Ile Ala Leu Glu Glu Val Leu Thr Trp Leu Leu Ser Ala Glu
        355                 360                 365

gac act ttc cag gag cag gat gat att tct gat gat gtt gaa gaa gtc     1152
Asp Thr Phe Gln Glu Gln Asp Asp Ile Ser Asp Asp Val Glu Glu Val
    370                 375                 380

aaa gac cag ttt gca acc cat gaa gct ttt atg atg gaa ctg act gca     1200
Lys Asp Gln Phe Ala Thr His Glu Ala Phe Met Met Glu Leu Thr Ala
385                 390                 395                 400
```

```
cac cag agc agt gtg ggc agc gtc ctg cag gca ggc aac caa ctg ata      1248
His Gln Ser Ser Val Gly Ser Val Leu Gln Ala Gly Asn Gln Leu Ile
                405                 410                 415

aca caa gga act ctg tca gac gaa gaa gaa ttt gag att cag gaa cag      1296
Thr Gln Gly Thr Leu Ser Asp Glu Glu Glu Phe Glu Ile Gln Glu Gln
            420                 425                 430

atg acc ctg ctg aat gct aga tgg gag gct ctt agg gtg gag agt atg      1344
Met Thr Leu Leu Asn Ala Arg Trp Glu Ala Leu Arg Val Glu Ser Met
        435                 440                 445

gac aga cag tcc cgg ctg cac gat gtg ctg atg gaa ctg cag aag aag      1392
Asp Arg Gln Ser Arg Leu His Asp Val Leu Met Glu Leu Gln Lys Lys
    450                 455                 460

caa ctg cag cag ctc tcc gcc tgg tta aca ctc aca gag gag cgc att      1440
Gln Leu Gln Gln Leu Ser Ala Trp Leu Thr Leu Thr Glu Glu Arg Ile
465                 470                 475                 480

cag aag atg gaa act tgc ccc ctg gat gat gat gta aaa tct cta caa      1488
Gln Lys Met Glu Thr Cys Pro Leu Asp Asp Asp Val Lys Ser Leu Gln
                485                 490                 495

aag ctg cta gaa gaa cat aaa agt ttg caa agt gat ctt gag gct gaa      1536
Lys Leu Leu Glu Glu His Lys Ser Leu Gln Ser Asp Leu Glu Ala Glu
            500                 505                 510

cag gtg aaa gta aat tca cta act cac atg gtg gtc att gtt gat gaa      1584
Gln Val Lys Val Asn Ser Leu Thr His Met Val Val Ile Val Asp Glu
        515                 520                 525

aac agt ggt gag agt gct aca gct atc cta gaa gac cag tta cag aaa      1632
Asn Ser Gly Glu Ser Ala Thr Ala Ile Leu Glu Asp Gln Leu Gln Lys
    530                 535                 540

ctt ggt gag cgc tgg aca gca gta tgc cgt tgg act gaa gaa cgc tgg      1680
Leu Gly Glu Arg Trp Thr Ala Val Cys Arg Trp Thr Glu Glu Arg Trp
545                 550                 555                 560

aat agg tta caa gaa atc aat ata ttg tgg cag gaa tta ttg gaa gaa      1728
Asn Arg Leu Gln Glu Ile Asn Ile Leu Trp Gln Glu Leu Leu Glu Glu
                565                 570                 575

cag tgc ttg ttg aaa gct tgg tta acc gaa aaa gaa gag gct tta aat      1776
Gln Cys Leu Leu Lys Ala Trp Leu Thr Glu Lys Glu Glu Ala Leu Asn
            580                 585                 590

aaa gtc cag aca agc aac ttc aaa gac caa aag gaa cta agt gtc agt      1824
Lys Val Gln Thr Ser Asn Phe Lys Asp Gln Lys Glu Leu Ser Val Ser
        595                 600                 605

gtt cga cgt ctg gct att ttg aag gaa gac atg gaa atg aag cgt caa      1872
Val Arg Arg Leu Ala Ile Leu Lys Glu Asp Met Glu Met Lys Arg Gln
    610                 615                 620

aca ttg gat cag ctg agt gag att ggc cag gat gtg gga caa tta ctt      1920
Thr Leu Asp Gln Leu Ser Glu Ile Gly Gln Asp Val Gly Gln Leu Leu
625                 630                 635                 640

gat aat tcc aag gca tct aag aag atc aac agt gac tca gag gaa ctg      1968
Asp Asn Ser Lys Ala Ser Lys Lys Ile Asn Ser Asp Ser Glu Glu Leu
                645                 650                 655

act caa aga tgg gat tct ttg gtt cag aga cta gaa gat tcc tcc aac      2016
Thr Gln Arg Trp Asp Ser Leu Val Gln Arg Leu Glu Asp Ser Ser Asn
            660                 665                 670

cag gtg act cag gct gta gca aag ctg ggg atg tct cag att cct cag      2064
Gln Val Thr Gln Ala Val Ala Lys Leu Gly Met Ser Gln Ile Pro Gln
        675                 680                 685

aag gac ctt ttg gag act gtt cgt gta aga gaa caa gca att aca aaa      2112
Lys Asp Leu Leu Glu Thr Val Arg Val Arg Glu Gln Ala Ile Thr Lys
    690                 695                 700

aaa tct aag cag gaa ctg cct cct cct cct ccc cca aag aag aga cag      2160
Lys Ser Lys Gln Glu Leu Pro Pro Pro Pro Pro Pro Lys Lys Arg Gln
705                 710                 715                 720
```

```
atc cat gtg gat att gaa gct aag aaa aag ttt gat gct ata agt gca      2208
Ile His Val Asp Ile Glu Ala Lys Lys Lys Phe Asp Ala Ile Ser Ala
                725                 730                 735

gag ctg ttg aac tgg att ttg aaa tgg aaa act gcc att cag acc aca      2256
Glu Leu Leu Asn Trp Ile Leu Lys Trp Lys Thr Ala Ile Gln Thr Thr
            740                 745                 750

gag ata aaa gag tat atg aag atg caa gac act tcc gaa atg aaa aag      2304
Glu Ile Lys Glu Tyr Met Lys Met Gln Asp Thr Ser Glu Met Lys Lys
        755                 760                 765

aag ttg aag gca tta gaa aaa gaa cag aga gaa aga atc ccc aga gca      2352
Lys Leu Lys Ala Leu Glu Lys Glu Gln Arg Glu Arg Ile Pro Arg Ala
    770                 775                 780

gat gaa tta aac caa act gga caa atc ctt gtg gag caa atg gga aaa      2400
Asp Glu Leu Asn Gln Thr Gly Gln Ile Leu Val Glu Gln Met Gly Lys
785                 790                 795                 800

gaa ggc ctt cct act gaa gaa ata aaa aat gtt ctg gag aag gtt tca      2448
Glu Gly Leu Pro Thr Glu Glu Ile Lys Asn Val Leu Glu Lys Val Ser
                805                 810                 815

tca gaa tgg aag aat gta tct caa cat ttg gaa gat cta gaa aga aag      2496
Ser Glu Trp Lys Asn Val Ser Gln His Leu Glu Asp Leu Glu Arg Lys
            820                 825                 830

att cag cta cag gaa gat ata aat gct tat ttc aag cag ctt gat gag      2544
Ile Gln Leu Gln Glu Asp Ile Asn Ala Tyr Phe Lys Gln Leu Asp Glu
        835                 840                 845

ctt gaa aag gtc atc aag aca aag gag gag tgg gta aaa cac act tcc      2592
Leu Glu Lys Val Ile Lys Thr Lys Glu Glu Trp Val Lys His Thr Ser
    850                 855                 860

att tct gaa tct tcc cgg cag tcc ttg cca agc ttg aag gat tcc tgt      2640
Ile Ser Glu Ser Ser Arg Gln Ser Leu Pro Ser Leu Lys Asp Ser Cys
865                 870                 875                 880

cag cgg gaa ttg aca aat ctt ctt ggc ctt cac ccc aaa att gaa atg      2688
Gln Arg Glu Leu Thr Asn Leu Leu Gly Leu His Pro Lys Ile Glu Met
                885                 890                 895

gct cgt gca agc tgc tcg gcc ctg atg tct cag cct tct gcc cca gat      2736
Ala Arg Ala Ser Cys Ser Ala Leu Met Ser Gln Pro Ser Ala Pro Asp
            900                 905                 910

ttt gtc cag cgg ggc ttc gat agc ttt ctg ggc cgc tac caa gct gta      2784
Phe Val Gln Arg Gly Phe Asp Ser Phe Leu Gly Arg Tyr Gln Ala Val
        915                 920                 925

caa gag gct gta gag gat cgt caa caa cat cta gag aat gaa ctg aag      2832
Gln Glu Ala Val Glu Asp Arg Gln Gln His Leu Glu Asn Glu Leu Lys
    930                 935                 940

ggc caa cct gga cat gca tat ctg gaa aca ttg aaa aca ctg aaa gat      2880
Gly Gln Pro Gly His Ala Tyr Leu Glu Thr Leu Lys Thr Leu Lys Asp
945                 950                 955                 960

gtg cta aat gat tca gaa aat aag gcc cag gtg tct ctg aat gtc ctt      2928
Val Leu Asn Asp Ser Glu Asn Lys Ala Gln Val Ser Leu Asn Val Leu
                965                 970                 975

aat gat ctt gcc aag gtg gag aag gcc ctg caa gaa aaa aag acc ctt      2976
Asn Asp Leu Ala Lys Val Glu Lys Ala Leu Gln Glu Lys Lys Thr Leu
            980                 985                 990

gat gaa atc ctt gag aat cag aaa  cct gca tta cat aaa  ctt gca gaa    3024
Asp Glu Ile Leu Glu Asn Gln Lys  Pro Ala Leu His Lys  Leu Ala Glu
        995                 1000                 1005

gaa aca  aag gct ctg gag aaa  aat gtt cat cct gat  gta gaa aaa      3069
Glu Thr  Lys Ala Leu Glu Lys  Asn Val His Pro Asp  Val Glu Lys
    1010                 1015                 1020

tta tat  aag caa gaa ttt gat  gat gtg caa gga aag  tgg aac aag      3114
Leu Tyr  Lys Gln Glu Phe Asp  Asp Val Gln Gly Lys  Trp Asn Lys
    1025                 1030                 1035
```

```
cta aag  gtc ttg gtt tcc aaa  gat cta cat ttg ctt  gag gaa att      3159
Leu Lys  Val Leu Val Ser Lys  Asp Leu His Leu Leu  Glu Glu Ile
    1040                 1045                 1050

gct ctc  aca ctc aga gct ttt  gag gcc gat tca aca  gtc att gag      3204
Ala Leu  Thr Leu Arg Ala Phe  Glu Ala Asp Ser Thr  Val Ile Glu
    1055                 1060                 1065

aag tgg  atg gat ggc gtg aaa  gac ttc tta atg aaa  cag cag gct      3249
Lys Trp  Met Asp Gly Val Lys  Asp Phe Leu Met Lys  Gln Gln Ala
    1070                 1075                 1080

gcc caa  gga gac gac gca ggt  cta cag agg cag tta  gac cag tgc      3294
Ala Gln  Gly Asp Asp Ala Gly  Leu Gln Arg Gln Leu  Asp Gln Cys
    1085                 1090                 1095

tct gca  ttt gtt aat gaa ata  gaa aca att gaa tca  tct ctg aaa      3339
Ser Ala  Phe Val Asn Glu Ile  Glu Thr Ile Glu Ser  Ser Leu Lys
    1100                 1105                 1110

aac atg  aag gaa ata gag act  aat ctt cga agt ggt  cca gtt gct      3384
Asn Met  Lys Glu Ile Glu Thr  Asn Leu Arg Ser Gly  Pro Val Ala
    1115                 1120                 1125

gga ata  aaa act tgg gtg cag  aca aga cta ggt gac  tac caa act      3429
Gly Ile  Lys Thr Trp Val Gln  Thr Arg Leu Gly Asp  Tyr Gln Thr
    1130                 1135                 1140

caa ctg  gag aaa ctt agc aag  gag atc gct act caa  aaa agt agg      3474
Gln Leu  Glu Lys Leu Ser Lys  Glu Ile Ala Thr Gln  Lys Ser Arg
    1145                 1150                 1155

ttg tct  gaa agt caa gaa aaa  gct gcg aac ctg aag  aaa gac ttg      3519
Leu Ser  Glu Ser Gln Glu Lys  Ala Ala Asn Leu Lys  Lys Asp Leu
    1160                 1165                 1170

gca gag  atg cag gaa tgg atg  acc cag gcc gag gaa  gaa tat ttg      3564
Ala Glu  Met Gln Glu Trp Met  Thr Gln Ala Glu Glu  Glu Tyr Leu
    1175                 1180                 1185

gag cgg  gat ttt gag tac aag  tca cca gaa gag ctt  gag agt gct      3609
Glu Arg  Asp Phe Glu Tyr Lys  Ser Pro Glu Glu Leu  Glu Ser Ala
    1190                 1195                 1200

gtg gaa  gag atg aag agg gca  aaa gag gat gtg ttg  cag aag gag      3654
Val Glu  Glu Met Lys Arg Ala  Lys Glu Asp Val Leu  Gln Lys Glu
    1205                 1210                 1215

gtg aga  gtg aag att ctc aag  gac aac atc aag tta  tta gct gcc      3699
Val Arg  Val Lys Ile Leu Lys  Asp Asn Ile Lys Leu  Leu Ala Ala
    1220                 1225                 1230

aag gtg  ccc tct ggt ggc cag  gag ttg acg tct gag  ctg aat gtt      3744
Lys Val  Pro Ser Gly Gly Gln  Glu Leu Thr Ser Glu  Leu Asn Val
    1235                 1240                 1245

gtg ctg  gag aat tac caa ctt  ctt tgt aat aga att  cga gga aag      3789
Val Leu  Glu Asn Tyr Gln Leu  Leu Cys Asn Arg Ile  Arg Gly Lys
    1250                 1255                 1260

tgc cac  acg cta gag gag gtc  tgg tct tgt tgg att  gaa ctg ctt      3834
Cys His  Thr Leu Glu Glu Val  Trp Ser Cys Trp Ile  Glu Leu Leu
    1265                 1270                 1275

cac tat  ttg gat ctt gaa act  acc tgg tta aac act  ttg gaa gag      3879
His Tyr  Leu Asp Leu Glu Thr  Thr Trp Leu Asn Thr  Leu Glu Glu
    1280                 1285                 1290

cgg atg  aag agc aca gag gtc  ctg cct gag aag acg  gat gct gtc      3924
Arg Met  Lys Ser Thr Glu Val  Leu Pro Glu Lys Thr  Asp Ala Val
    1295                 1300                 1305

aac gaa  gcc ctg gag tct ctg  gaa tct gtt ctg cgc  cac ccg gca      3969
Asn Glu  Ala Leu Glu Ser Leu  Glu Ser Val Leu Arg  His Pro Ala
    1310                 1315                 1320

gat aat  cgc acc cag att cga  gag ctt ggc cag act  ctg att gat      4014
Asp Asn  Arg Thr Gln Ile Arg  Glu Leu Gly Gln Thr  Leu Ile Asp
    1325                 1330                 1335
```

```
ggg ggg  atc ctg gat gat ata  atc agt gag aaa ctg  gag gct ttc      4059
Gly Gly  Ile Leu Asp Asp Ile  Ile Ser Glu Lys Leu  Glu Ala Phe
    1340                1345                1350

aac agc  cga tat gaa gat cta  agt cac ctg gca gag  agc aag cag      4104
Asn Ser  Arg Tyr Glu Asp Leu  Ser His Leu Ala Glu  Ser Lys Gln
    1355                1360                1365

att tct  ttg gaa aag caa gcc  cac aga gat ttt gga  cca tcc tct      4149
Ile Ser  Leu Glu Lys Gln Ala  His Arg Asp Phe Gly  Pro Ser Ser
    1370                1375                1380

cag cat  ttt ctc tct acg tca  gtc cag ctg ccg tgg  caa aga tcc      4194
Gln His  Phe Leu Ser Thr Ser  Val Gln Leu Pro Trp  Gln Arg Ser
    1385                1390                1395

att tca  cat aat aaa gtg ccc  tat tac atc aac cat  caa aca cag      4239
Ile Ser  His Asn Lys Val Pro  Tyr Tyr Ile Asn His  Gln Thr Gln
    1400                1405                1410

acc acc  tgt tgg gac cat cct  aaa atg acc gaa ctc  ttt caa tcc      4284
Thr Thr  Cys Trp Asp His Pro  Lys Met Thr Glu Leu  Phe Gln Ser
    1415                1420                1425

ctt gct  gac ctg aat aat gta  cgt ttt tct gcc tac  cgt aca gca      4329
Leu Ala  Asp Leu Asn Asn Val  Arg Phe Ser Ala Tyr  Arg Thr Ala
    1430                1435                1440

atc aaa  atc cga aga cta caa  aaa gca cta tgt ttg  gat ctc tta      4374
Ile Lys  Ile Arg Arg Leu Gln  Lys Ala Leu Cys Leu  Asp Leu Leu
    1445                1450                1455

gag ttg  agt aca aca aat gaa  att ttc aaa cag cac  aag ttg aac      4419
Glu Leu  Ser Thr Thr Asn Glu  Ile Phe Lys Gln His  Lys Leu Asn
    1460                1465                1470

caa aat  gac cag ctc ctc agt  gtt cca gat gtc atc  aac tgt ctg      4464
Gln Asn  Asp Gln Leu Leu Ser  Val Pro Asp Val Ile  Asn Cys Leu
    1475                1480                1485

aca aca  act tat gat gga ctt  gag caa atg cat aag  gac ctg gtc      4509
Thr Thr  Thr Tyr Asp Gly Leu  Glu Gln Met His Lys  Asp Leu Val
    1490                1495                1500

aac gtt  cca ctc tgt gtt gat  atg tgt ctc aat tgg  ttg ctc aat      4554
Asn Val  Pro Leu Cys Val Asp  Met Cys Leu Asn Trp  Leu Leu Asn
    1505                1510                1515

gtc tat  gac acg ggt cga act  gga aaa att aga gtg  cag agt ctg      4599
Val Tyr  Asp Thr Gly Arg Thr  Gly Lys Ile Arg Val  Gln Ser Leu
    1520                1525                1530

aag att  gga tta atg tct ctc  tcc aaa ggt ctc ttg  gaa gaa aaa      4644
Lys Ile  Gly Leu Met Ser Leu  Ser Lys Gly Leu Leu  Glu Glu Lys
    1535                1540                1545

tac aga  tat ctc ttt aag gaa  gtt gca ggg cca aca  gaa atg tgt      4689
Tyr Arg  Tyr Leu Phe Lys Glu  Val Ala Gly Pro Thr  Glu Met Cys
    1550                1555                1560

gac cag  agg cag ctg ggc ctg  tta ctt cat gat gcc  atc cag atc      4734
Asp Gln  Arg Gln Leu Gly Leu  Leu Leu His Asp Ala  Ile Gln Ile
    1565                1570                1575

ccc cgg  cag cta ggt gaa gta  gca gct ttt gga ggc  agt aat att      4779
Pro Arg  Gln Leu Gly Glu Val  Ala Ala Phe Gly Gly  Ser Asn Ile
    1580                1585                1590

gag cct  agt gtt cgc agc tgc  ttc caa cag aat aac  aat aaa cca      4824
Glu Pro  Ser Val Arg Ser Cys  Phe Gln Gln Asn Asn  Asn Lys Pro
    1595                1600                1605

gaa ata  agt gtg aaa gag ttt  ata gat tgg atg cat  ttg gaa cca      4869
Glu Ile  Ser Val Lys Glu Phe  Ile Asp Trp Met His  Leu Glu Pro
    1610                1615                1620

cag tcc  atg gtt tgg ctc cca  gtt tta cat cga gtg  gca gca gcg      4914
Gln Ser  Met Val Trp Leu Pro  Val Leu His Arg Val  Ala Ala Ala
    1625                1630                1635
```

```
gag act gca aaa cat cag gcc aaa tgc aac atc tgt aaa gaa tgt      4959
Glu Thr Ala Lys His Gln Ala Lys Cys Asn Ile Cys Lys Glu Cys
    1640                1645                1650

cca att gtc ggg ttc agg tat aga agc ctt aag cat ttt aac tat      5004
Pro Ile Val Gly Phe Arg Tyr Arg Ser Leu Lys His Phe Asn Tyr
    1655                1660                1665

gat gtc tgc cag agt tgt ttc ttt tcg ggt cga aca gca aaa ggt      5049
Asp Val Cys Gln Ser Cys Phe Phe Ser Gly Arg Thr Ala Lys Gly
    1670                1675                1680

cac aaa tta cat tac cca atg gtg gaa tat tgt ata cct aca aca      5094
His Lys Leu His Tyr Pro Met Val Glu Tyr Cys Ile Pro Thr Thr
    1685                1690                1695

tct ggg gaa gat gta cga gac ttc aca aag gta ctt aag aac aag      5139
Ser Gly Glu Asp Val Arg Asp Phe Thr Lys Val Leu Lys Asn Lys
    1700                1705                1710

ttc agg tcg aag aag tac ttt gcc aaa cac cct cga ctt ggt tac      5184
Phe Arg Ser Lys Lys Tyr Phe Ala Lys His Pro Arg Leu Gly Tyr
    1715                1720                1725

ctg cct gtc cag aca gtt ctt gaa ggt gac aac tta gag act cct      5229
Leu Pro Val Gln Thr Val Leu Glu Gly Asp Asn Leu Glu Thr Pro
    1730                1735                1740

atc aca ctc atc agt atg tgg cca gag cac tat gac ccc tca caa      5274
Ile Thr Leu Ile Ser Met Trp Pro Glu His Tyr Asp Pro Ser Gln
    1745                1750                1755

tct cct caa ctg ttt cat gat gac acc cat tca aga ata gaa caa      5319
Ser Pro Gln Leu Phe His Asp Asp Thr His Ser Arg Ile Glu Gln
    1760                1765                1770

tat gcc aca cga ctg gcc cag atg gaa agg act aat ggg tct ttt      5364
Tyr Ala Thr Arg Leu Ala Gln Met Glu Arg Thr Asn Gly Ser Phe
    1775                1780                1785

ctc act gat agc agc tcc acc aca gga agt gtg gaa gac gag cac      5409
Leu Thr Asp Ser Ser Ser Thr Thr Gly Ser Val Glu Asp Glu His
    1790                1795                1800

gcc ctc atc cag cag tat tgc caa aca ctc gga gga gag tcc cca      5454
Ala Leu Ile Gln Gln Tyr Cys Gln Thr Leu Gly Gly Glu Ser Pro
    1805                1810                1815

gtg agc cag ccg cag agc cca gct cag atc ctg aag tca gta gag      5499
Val Ser Gln Pro Gln Ser Pro Ala Gln Ile Leu Lys Ser Val Glu
    1820                1825                1830

agg gaa gaa cgt gga gaa ctg gag agg atc att gct gac ctg gag      5544
Arg Glu Glu Arg Gly Glu Leu Glu Arg Ile Ile Ala Asp Leu Glu
    1835                1840                1845

gaa gaa caa aga aat cta cag gtg gag tat gag cag ctg aag gac      5589
Glu Glu Gln Arg Asn Leu Gln Val Glu Tyr Glu Gln Leu Lys Asp
    1850                1855                1860

cag cac ctc cga agg ggg ctc cct gtc ggt tca ccg cca gag tcg      5634
Gln His Leu Arg Arg Gly Leu Pro Val Gly Ser Pro Pro Glu Ser
    1865                1870                1875

att ata tct ccc cat cac acg tct gag gat tca gaa ctt ata gca      5679
Ile Ile Ser Pro His His Thr Ser Glu Asp Ser Glu Leu Ile Ala
    1880                1885                1890

gaa gca aaa ctc ctc agg cag cac aaa ggt cgg ctg gag gct agg      5724
Glu Ala Lys Leu Leu Arg Gln His Lys Gly Arg Leu Glu Ala Arg
    1895                1900                1905

atg cag att tta gaa gat cac aat aaa cag ctg gag tct cag ctc      5769
Met Gln Ile Leu Glu Asp His Asn Lys Gln Leu Glu Ser Gln Leu
    1910                1915                1920

cac cgc ctc cga cag ctg ctg gag cag cct gaa tct gat tcc cga      5814
His Arg Leu Arg Gln Leu Leu Glu Gln Pro Glu Ser Asp Ser Arg
    1925                1930                1935
```

```
atc aat  ggt gtt tcc cca tgg  gct tct cct cag cat  tct gca ctg      5859
Ile Asn  Gly Val Ser Pro Trp  Ala Ser Pro Gln His  Ser Ala Leu
    1940                 1945                 1950

agc tac  tcg ctt gat cca gat  gcc tcc ggc cca cag  ttc cac cag      5904
Ser Tyr  Ser Leu Asp Pro Asp  Ala Ser Gly Pro Gln  Phe His Gln
    1955                 1960                 1965

gca gcg  gga gag gac ctg ctg  gcc cca ccg cac gac  acc agc acg      5949
Ala Ala  Gly Glu Asp Leu Leu  Ala Pro Pro His Asp  Thr Ser Thr
    1970                 1975                 1980

gat ctc  acg gag gtc atg gag  cag att cac agc acg  ttt cca tct      5994
Asp Leu  Thr Glu Val Met Glu  Gln Ile His Ser Thr  Phe Pro Ser
    1985                 1990                 1995

tgc tgc  cca aat gtt ccc agc  agg cca cag gca atg  tga              6033
Cys Cys  Pro Asn Val Pro Ser  Arg Pro Gln Ala Met
    2000                 2005                 2010


<210> SEQ ID NO 15
<211> LENGTH: 2010
<212> TYPE: PRT
<213> ORGANISM: Homo sapiens

<400> SEQUENCE: 15

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Glu His Glu Ala
        35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270
```

-continued

```
Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Ala
305                 310                 315                 320

Ile Asn Ile Gln Ser Thr Ala Pro Glu Glu Glu His Glu Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln Asp Asp Ile Ser Asp Asp Val Glu Glu Val
    370                 375                 380

Lys Asp Gln Phe Ala Thr His Glu Ala Phe Met Met Glu Leu Thr Ala
385                 390                 395                 400

His Gln Ser Ser Val Gly Ser Val Leu Gln Ala Gly Asn Gln Leu Ile
                405                 410                 415

Thr Gln Gly Thr Leu Ser Asp Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Asp Arg Gln Ser Arg Leu His Asp Val Leu Met Glu Leu Gln Lys Lys
    450                 455                 460

Gln Leu Gln Gln Leu Ser Ala Trp Leu Thr Leu Thr Glu Glu Arg Ile
465                 470                 475                 480

Gln Lys Met Glu Thr Cys Pro Leu Asp Asp Asp Val Lys Ser Leu Gln
                485                 490                 495

Lys Leu Leu Glu Glu His Lys Ser Leu Gln Ser Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Ile Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Asn Ile Leu Trp Gln Glu Leu Leu Glu Glu
                565                 570                 575

Gln Cys Leu Leu Lys Ala Trp Leu Thr Glu Lys Glu Glu Ala Leu Asn
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Asp Asn Ser Lys Ala Ser Lys Lys Ile Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val Arg Val Arg Glu Gln Ala Ile Thr Lys
    690                 695                 700
```

```
Lys Ser Lys Gln Glu Leu Pro Pro Pro Pro Pro Pro Lys Lys Arg Gln
705                 710                 715                 720

Ile His Val Asp Ile Glu Ala Lys Lys Lys Phe Asp Ala Ile Ser Ala
                725                 730                 735

Glu Leu Leu Asn Trp Ile Leu Lys Trp Lys Thr Ala Ile Gln Thr Thr
            740                 745                 750

Glu Ile Lys Glu Tyr Met Lys Met Gln Asp Thr Ser Glu Met Lys Lys
        755                 760                 765

Lys Leu Lys Ala Leu Glu Lys Glu Gln Arg Glu Arg Ile Pro Arg Ala
    770                 775                 780

Asp Glu Leu Asn Gln Thr Gly Gln Ile Leu Val Glu Gln Met Gly Lys
785                 790                 795                 800

Glu Gly Leu Pro Thr Glu Glu Ile Lys Asn Val Leu Glu Lys Val Ser
                805                 810                 815

Ser Glu Trp Lys Asn Val Ser Gln His Leu Glu Asp Leu Glu Arg Lys
            820                 825                 830

Ile Gln Leu Gln Glu Asp Ile Asn Ala Tyr Phe Lys Gln Leu Asp Glu
        835                 840                 845

Leu Glu Lys Val Ile Lys Thr Lys Glu Glu Trp Val Lys His Thr Ser
    850                 855                 860

Ile Ser Glu Ser Ser Arg Gln Ser Leu Pro Ser Leu Lys Asp Ser Cys
865                 870                 875                 880

Gln Arg Glu Leu Thr Asn Leu Leu Gly Leu His Pro Lys Ile Glu Met
                885                 890                 895

Ala Arg Ala Ser Cys Ser Ala Leu Met Ser Gln Pro Ser Ala Pro Asp
            900                 905                 910

Phe Val Gln Arg Gly Phe Asp Ser Phe Leu Gly Arg Tyr Gln Ala Val
        915                 920                 925

Gln Glu Ala Val Glu Asp Arg Gln Gln His Leu Glu Asn Glu Leu Lys
    930                 935                 940

Gly Gln Pro Gly His Ala Tyr Leu Glu Thr Leu Lys Thr Leu Lys Asp
945                 950                 955                 960

Val Leu Asn Asp Ser Glu Asn Lys Ala Gln Val Ser Leu Asn Val Leu
                965                 970                 975

Asn Asp Leu Ala Lys Val Glu Lys Ala Leu Gln Glu Lys Lys Thr Leu
            980                 985                 990

Asp Glu Ile Leu Glu Asn Gln Lys  Pro Ala Leu His Lys  Leu Ala Glu
        995                 1000                1005

Glu Thr  Lys Ala Leu Glu Lys  Asn Val His Pro Asp  Val Glu Lys
    1010                1015                1020

Leu Tyr  Lys Gln Glu Phe Asp  Asp Val Gln Gly Lys  Trp Asn Lys
    1025                1030                1035

Leu Lys  Val Leu Val Ser Lys  Asp Leu His Leu Leu  Glu Glu Ile
    1040                1045                1050

Ala Leu  Thr Leu Arg Ala Phe  Glu Ala Asp Ser Thr  Val Ile Glu
    1055                1060                1065

Lys Trp  Met Asp Gly Val Lys  Asp Phe Leu Met Lys  Gln Gln Ala
    1070                1075                1080

Ala Gln  Gly Asp Asp Ala Gly  Leu Gln Arg Gln Leu  Asp Gln Cys
    1085                1090                1095

Ser Ala  Phe Val Asn Glu Ile  Glu Thr Ile Glu Ser  Ser Leu Lys
    1100                1105                1110

Asn Met  Lys Glu Ile Glu Thr  Asn Leu Arg Ser Gly  Pro Val Ala
```

-continued

```
    1115                1120                1125

Gly Ile  Lys Thr Trp Val Gln  Thr Arg Leu Gly Asp  Tyr Gln Thr
    1130                1135                1140

Gln Leu  Glu Lys Leu Ser Lys  Glu Ile Ala Thr Gln  Lys Ser Arg
    1145                1150                1155

Leu Ser  Glu Ser Gln Glu Lys  Ala Ala Asn Leu Lys  Lys Asp Leu
    1160                1165                1170

Ala Glu  Met Gln Glu Trp Met  Thr Gln Ala Glu Glu  Glu Tyr Leu
    1175                1180                1185

Glu Arg  Asp Phe Glu Tyr Lys  Ser Pro Glu Glu Leu  Glu Ser Ala
    1190                1195                1200

Val Glu  Glu Met Lys Arg Ala  Lys Glu Asp Val Leu  Gln Lys Glu
    1205                1210                1215

Val Arg  Val Lys Ile Leu Lys  Asp Asn Ile Lys Leu  Leu Ala Ala
    1220                1225                1230

Lys Val  Pro Ser Gly Gly Gln  Glu Leu Thr Ser Glu  Leu Asn Val
    1235                1240                1245

Val Leu  Glu Asn Tyr Gln Leu  Leu Cys Asn Arg Ile  Arg Gly Lys
    1250                1255                1260

Cys His  Thr Leu Glu Glu Val  Trp Ser Cys Trp Ile  Glu Leu Leu
    1265                1270                1275

His Tyr  Leu Asp Leu Glu Thr  Thr Trp Leu Asn Thr  Leu Glu Glu
    1280                1285                1290

Arg Met  Lys Ser Thr Glu Val  Leu Pro Glu Lys Thr  Asp Ala Val
    1295                1300                1305

Asn Glu  Ala Leu Glu Ser Leu  Glu Ser Val Leu Arg  His Pro Ala
    1310                1315                1320

Asp Asn  Arg Thr Gln Ile Arg  Glu Leu Gly Gln Thr  Leu Ile Asp
    1325                1330                1335

Gly Gly  Ile Leu Asp Asp Ile  Ile Ser Glu Lys Leu  Glu Ala Phe
    1340                1345                1350

Asn Ser  Arg Tyr Glu Asp Leu  Ser His Leu Ala Glu  Ser Lys Gln
    1355                1360                1365

Ile Ser  Leu Glu Lys Gln Ala  His Arg Asp Phe Gly  Pro Ser Ser
    1370                1375                1380

Gln His  Phe Leu Ser Thr Ser  Val Gln Leu Pro Trp  Gln Arg Ser
    1385                1390                1395

Ile Ser  His Asn Lys Val Pro  Tyr Tyr Ile Asn His  Gln Thr Gln
    1400                1405                1410

Thr Thr  Cys Trp Asp His Pro  Lys Met Thr Glu Leu  Phe Gln Ser
    1415                1420                1425

Leu Ala  Asp Leu Asn Asn Val  Arg Phe Ser Ala Tyr  Arg Thr Ala
    1430                1435                1440

Ile Lys  Ile Arg Arg Leu Gln  Lys Ala Leu Cys Leu  Asp Leu Leu
    1445                1450                1455

Glu Leu  Ser Thr Thr Asn Glu  Ile Phe Lys Gln His  Lys Leu Asn
    1460                1465                1470

Gln Asn  Asp Gln Leu Leu Ser  Val Pro Asp Val Ile  Asn Cys Leu
    1475                1480                1485

Thr Thr  Thr Tyr Asp Gly Leu  Glu Gln Met His Lys  Asp Leu Val
    1490                1495                1500

Asn Val  Pro Leu Cys Val Asp  Met Cys Leu Asn Trp  Leu Leu Asn
    1505                1510                1515
```

```
Val Tyr Asp Thr Gly Arg Thr Gly Lys Ile Arg Val Gln Ser Leu
    1520                1525                1530

Lys Ile Gly Leu Met Ser Leu Ser Lys Gly Leu Leu Glu Glu Lys
    1535                1540                1545

Tyr Arg Tyr Leu Phe Lys Glu Val Ala Gly Pro Thr Glu Met Cys
    1550                1555                1560

Asp Gln Arg Gln Leu Gly Leu Leu Leu His Asp Ala Ile Gln Ile
    1565                1570                1575

Pro Arg Gln Leu Gly Glu Val Ala Ala Phe Gly Gly Ser Asn Ile
    1580                1585                1590

Glu Pro Ser Val Arg Ser Cys Phe Gln Gln Asn Asn Asn Lys Pro
    1595                1600                1605

Glu Ile Ser Val Lys Glu Phe Ile Asp Trp Met His Leu Glu Pro
    1610                1615                1620

Gln Ser Met Val Trp Leu Pro Val Leu His Arg Val Ala Ala Ala
    1625                1630                1635

Glu Thr Ala Lys His Gln Ala Lys Cys Asn Ile Cys Lys Glu Cys
    1640                1645                1650

Pro Ile Val Gly Phe Arg Tyr Arg Ser Leu Lys His Phe Asn Tyr
    1655                1660                1665

Asp Val Cys Gln Ser Cys Phe Phe Ser Gly Arg Thr Ala Lys Gly
    1670                1675                1680

His Lys Leu His Tyr Pro Met Val Glu Tyr Cys Ile Pro Thr Thr
    1685                1690                1695

Ser Gly Glu Asp Val Arg Asp Phe Thr Lys Val Leu Lys Asn Lys
    1700                1705                1710

Phe Arg Ser Lys Lys Tyr Phe Ala Lys His Pro Arg Leu Gly Tyr
    1715                1720                1725

Leu Pro Val Gln Thr Val Leu Glu Gly Asp Asn Leu Glu Thr Pro
    1730                1735                1740

Ile Thr Leu Ile Ser Met Trp Pro Glu His Tyr Asp Pro Ser Gln
    1745                1750                1755

Ser Pro Gln Leu Phe His Asp Asp Thr His Ser Arg Ile Glu Gln
    1760                1765                1770

Tyr Ala Thr Arg Leu Ala Gln Met Glu Arg Thr Asn Gly Ser Phe
    1775                1780                1785

Leu Thr Asp Ser Ser Ser Thr Thr Gly Ser Val Glu Asp Glu His
    1790                1795                1800

Ala Leu Ile Gln Gln Tyr Cys Gln Thr Leu Gly Gly Glu Ser Pro
    1805                1810                1815

Val Ser Gln Pro Gln Ser Pro Ala Gln Ile Leu Lys Ser Val Glu
    1820                1825                1830

Arg Glu Glu Arg Gly Glu Leu Glu Arg Ile Ile Ala Asp Leu Glu
    1835                1840                1845

Glu Glu Gln Arg Asn Leu Gln Val Glu Tyr Glu Gln Leu Lys Asp
    1850                1855                1860

Gln His Leu Arg Arg Gly Leu Pro Val Gly Ser Pro Pro Glu Ser
    1865                1870                1875

Ile Ile Ser Pro His His Thr Ser Glu Asp Ser Glu Leu Ile Ala
    1880                1885                1890

Glu Ala Lys Leu Leu Arg Gln His Lys Gly Arg Leu Glu Ala Arg
    1895                1900                1905

Met Gln Ile Leu Glu Asp His Asn Lys Gln Leu Glu Ser Gln Leu
    1910                1915                1920
```

```
His Arg  Leu Arg Gln Leu Leu  Glu Gln Pro Glu Ser  Asp Ser Arg
    1925                1930                1935

Ile Asn  Gly Val Ser Pro Trp  Ala Ser Pro Gln His  Ser Ala Leu
    1940                1945                1950

Ser Tyr  Ser Leu Asp Pro Asp  Ala Ser Gly Pro Gln  Phe His Gln
    1955                1960                1965

Ala Ala  Gly Glu Asp Leu Leu  Ala Pro Pro His Asp  Thr Ser Thr
    1970                1975                1980

Asp Leu  Thr Glu Val Met Glu  Gln Ile His Ser Thr  Phe Pro Ser
    1985                1990                1995

Cys Cys  Pro Asn Val Pro Ser  Arg Pro Gln Ala Met
    2000                2005                2010


<210> SEQ ID NO 16
<211> LENGTH: 6327
<212> TYPE: DNA
<213> ORGANISM: Homo sapiens
<220> FEATURE:
<221> NAME/KEY: CDS
<222> LOCATION: (1)..(6327)
<220> FEATURE:
<221> NAME/KEY: misc_feature
<222> LOCATION: (1)..(117)
<223> OTHER INFORMATION: TAT and epitope tag coding sequence

<400> SEQUENCE: 16

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
Arg Gln Arg Arg Arg Gly Gly Ser Thr Met Ser Gly Tyr Pro Tyr Asp
            20                  25                  30

gtc cca gac tat gct ggc tcc atg gcc aag tat gga gaa cat gaa gcc      144
Val Pro Asp Tyr Ala Gly Ser Met Ala Lys Tyr Gly Glu His Glu Ala
        35                  40                  45

agt cct gac aat ggg cag aac gaa ttc agt gat atc att aag tcc aga      192
Ser Pro Asp Asn Gly Gln Asn Glu Phe Ser Asp Ile Ile Lys Ser Arg
    50                  55                  60

tct gat gaa cac aat gac gta cag aag aaa acc ttt acc aaa tgg ata      240
Ser Asp Glu His Asn Asp Val Gln Lys Lys Thr Phe Thr Lys Trp Ile
65                  70                  75                  80

aat gct cga ttt tca aag agt ggg aaa cca ccc atc aat gat atg ttc      288
Asn Ala Arg Phe Ser Lys Ser Gly Lys Pro Pro Ile Asn Asp Met Phe
                85                  90                  95

aca gac ctc aaa gat gga agg aag cta ttg gat ctt cta gaa ggc ctc      336
Thr Asp Leu Lys Asp Gly Arg Lys Leu Leu Asp Leu Leu Glu Gly Leu
            100                 105                 110

aca gga aca tca ctg cca aag gaa cgt ggt tcc aca agg gta cat gcc      384
Thr Gly Thr Ser Leu Pro Lys Glu Arg Gly Ser Thr Arg Val His Ala
        115                 120                 125

tta aat aac gtc aac aga gtg ctg cag gtt tta cat cag aac aat gtg      432
Leu Asn Asn Val Asn Arg Val Leu Gln Val Leu His Gln Asn Asn Val
    130                 135                 140

gaa tta gtg aat ata ggg gga act gac att gtg gat gga aat cac aaa      480
Glu Leu Val Asn Ile Gly Gly Thr Asp Ile Val Asp Gly Asn His Lys
145                 150                 155                 160

ctg act ttg ggg tta ctt tgg agc atc att ttg cac tgg cag gtg aaa      528
Leu Thr Leu Gly Leu Leu Trp Ser Ile Ile Leu His Trp Gln Val Lys
                165                 170                 175

gat gtc atg aag gat gtc atg tcg gac ctg cag cag acg aac agt gag      576
Asp Val Met Lys Asp Val Met Ser Asp Leu Gln Gln Thr Asn Ser Glu
```

```
            180                 185                 190

aag atc ctg ctc agc tgg gtg cgt cag acc acc agg ccc tac agc caa      624
Lys Ile Leu Leu Ser Trp Val Arg Gln Thr Thr Arg Pro Tyr Ser Gln
        195                 200                 205

gtc aac gtc ctc aac ttc acc acc agc tgg aca gat gga ctc gcc ttt      672
Val Asn Val Leu Asn Phe Thr Thr Ser Trp Thr Asp Gly Leu Ala Phe
    210                 215                 220

aat gct gtc ctc cac cga cat aaa cct gat ctc ttc agc tgg gat aaa      720
Asn Ala Val Leu His Arg His Lys Pro Asp Leu Phe Ser Trp Asp Lys
225                 230                 235                 240

gtt gtc aaa atg tca cca att gag aga ctt gaa cat gcc ttc agc aag      768
Val Val Lys Met Ser Pro Ile Glu Arg Leu Glu His Ala Phe Ser Lys
                245                 250                 255

gct caa act tat ttg gga att gaa aag ctg tta gat cct gaa gat gtt      816
Ala Gln Thr Tyr Leu Gly Ile Glu Lys Leu Leu Asp Pro Glu Asp Val
            260                 265                 270

gcc gtt cag ctt cct gac aag aaa tcc ata att atg tat tta aca tct      864
Ala Val Gln Leu Pro Asp Lys Lys Ser Ile Ile Met Tyr Leu Thr Ser
        275                 280                 285

ttg ttt gag gtg cta cct cag caa gtc acc ata gac gcc atc cgt gag      912
Leu Phe Glu Val Leu Pro Gln Gln Val Thr Ile Asp Ala Ile Arg Glu
    290                 295                 300

gta gag aca ctc cca agg aaa tat aaa aaa gaa tgt gaa gaa gag gca      960
Val Glu Thr Leu Pro Arg Lys Tyr Lys Lys Glu Cys Glu Glu Glu Ala
305                 310                 315                 320

att aat ata cag agt aca gcg cct gag gag gag cat gag agt ccc cga     1008
Ile Asn Ile Gln Ser Thr Ala Pro Glu Glu Glu His Glu Ser Pro Arg
                325                 330                 335

gct gaa act ccc agc act gtc act gag gtt gac atg gat ctg gac agc     1056
Ala Glu Thr Pro Ser Thr Val Thr Glu Val Asp Met Asp Leu Asp Ser
            340                 345                 350

tat cag att gcg ttg gag gaa gtg ctg acc tgg ttg ctt tct gct gag     1104
Tyr Gln Ile Ala Leu Glu Glu Val Leu Thr Trp Leu Leu Ser Ala Glu
        355                 360                 365

gac act ttc cag gag cag gat gat att tct gat gat gtt gaa gaa gtc     1152
Asp Thr Phe Gln Glu Gln Asp Asp Ile Ser Asp Asp Val Glu Glu Val
    370                 375                 380

aaa gac cag ttt gca acc cat gaa gct ttt atg atg gaa ctg act gca     1200
Lys Asp Gln Phe Ala Thr His Glu Ala Phe Met Met Glu Leu Thr Ala
385                 390                 395                 400

cac cag agc agt gtg ggc agc gtc ctg cag gca ggc aac caa ctg ata     1248
His Gln Ser Ser Val Gly Ser Val Leu Gln Ala Gly Asn Gln Leu Ile
                405                 410                 415

aca caa gga act ctg tca gac gaa gaa gaa ttt gag att cag gaa cag     1296
Thr Gln Gly Thr Leu Ser Asp Glu Glu Glu Phe Glu Ile Gln Glu Gln
            420                 425                 430

atg acc ctg ctg aat gct aga tgg gag gct ctt agg gtg gag agt atg     1344
Met Thr Leu Leu Asn Ala Arg Trp Glu Ala Leu Arg Val Glu Ser Met
        435                 440                 445

gac aga cag tcc cgg ctg cac gat gtg ctg atg gaa ctg cag aag aag     1392
Asp Arg Gln Ser Arg Leu His Asp Val Leu Met Glu Leu Gln Lys Lys
    450                 455                 460

caa ctg cag cag ctc tcc gcc tgg tta aca ctc aca gag gag cgc att     1440
Gln Leu Gln Gln Leu Ser Ala Trp Leu Thr Leu Thr Glu Glu Arg Ile
465                 470                 475                 480

cag aag atg gaa act tgc ccc ctg gat gat gat gta aaa tct cta caa     1488
Gln Lys Met Glu Thr Cys Pro Leu Asp Asp Asp Val Lys Ser Leu Gln
                485                 490                 495

aag ctg cta gaa gaa cat aaa agt ttg caa agt gat ctt gag gct gaa     1536
Lys Leu Leu Glu Glu His Lys Ser Leu Gln Ser Asp Leu Glu Ala Glu
```

```
            500                 505                 510

cag gtg aaa gta aat tca cta act cac atg gtg gtc att gtt gat gaa      1584
Gln Val Lys Val Asn Ser Leu Thr His Met Val Val Ile Val Asp Glu
        515                 520                 525

aac agt ggt gag agt gct aca gct atc cta gaa gac cag tta cag aaa      1632
Asn Ser Gly Glu Ser Ala Thr Ala Ile Leu Glu Asp Gln Leu Gln Lys
    530                 535                 540

ctt ggt gag cgc tgg aca gca gta tgc cgt tgg act gaa gaa cgc tgg      1680
Leu Gly Glu Arg Trp Thr Ala Val Cys Arg Trp Thr Glu Glu Arg Trp
545                 550                 555                 560

aat agg tta caa gaa atc aat ata ttg tgg cag gaa tta ttg gaa gaa      1728
Asn Arg Leu Gln Glu Ile Asn Ile Leu Trp Gln Glu Leu Leu Glu Glu
                565                 570                 575

cag tgc ttg ttg aaa gct tgg tta acc gaa aaa gaa gag gct tta aat      1776
Gln Cys Leu Leu Lys Ala Trp Leu Thr Glu Lys Glu Glu Ala Leu Asn
            580                 585                 590

aaa gtc cag aca agc aac ttc aaa gac caa aag gaa cta agt gtc agt      1824
Lys Val Gln Thr Ser Asn Phe Lys Asp Gln Lys Glu Leu Ser Val Ser
        595                 600                 605

gtt cga cgt ctg gct att ttg aag gaa gac atg gaa atg aag cgt caa      1872
Val Arg Arg Leu Ala Ile Leu Lys Glu Asp Met Glu Met Lys Arg Gln
    610                 615                 620

aca ttg gat cag ctg agt gag att ggc cag gat gtg gga caa tta ctt      1920
Thr Leu Asp Gln Leu Ser Glu Ile Gly Gln Asp Val Gly Gln Leu Leu
625                 630                 635                 640

gat aat tcc aag gca tct aag aag atc aac agt gac tca gag gaa ctg      1968
Asp Asn Ser Lys Ala Ser Lys Lys Ile Asn Ser Asp Ser Glu Glu Leu
                645                 650                 655

act caa aga tgg gat tct ttg gtt cag aga cta gaa gat tcc tcc aac      2016
Thr Gln Arg Trp Asp Ser Leu Val Gln Arg Leu Glu Asp Ser Ser Asn
            660                 665                 670

cag gtg act cag gct gta gca aag ctg ggg atg tct cag att cct cag      2064
Gln Val Thr Gln Ala Val Ala Lys Leu Gly Met Ser Gln Ile Pro Gln
        675                 680                 685

aag gac ctt ttg gag act gtt cgt gta aga gaa caa gca att aca aaa      2112
Lys Asp Leu Leu Glu Thr Val Arg Val Arg Glu Gln Ala Ile Thr Lys
    690                 695                 700

aaa tct aag cag gaa ctg cct cct cct cct ccc cca aag aag aga cag      2160
Lys Ser Lys Gln Glu Leu Pro Pro Pro Pro Pro Pro Lys Lys Arg Gln
705                 710                 715                 720

atc cat gtg gat att gaa gct aag aaa aag ttt gat gct ata agt gca      2208
Ile His Val Asp Ile Glu Ala Lys Lys Lys Phe Asp Ala Ile Ser Ala
                725                 730                 735

gag ctg ttg aac tgg att ttg aaa tgg aaa act gcc att cag acc aca      2256
Glu Leu Leu Asn Trp Ile Leu Lys Trp Lys Thr Ala Ile Gln Thr Thr
            740                 745                 750

gag ata aaa gag tat atg aag atg caa gac act tcc gaa atg aaa aag      2304
Glu Ile Lys Glu Tyr Met Lys Met Gln Asp Thr Ser Glu Met Lys Lys
        755                 760                 765

aag ttg aag gca tta gaa aaa gaa cag aga gaa aga atc ccc aga gca      2352
Lys Leu Lys Ala Leu Glu Lys Glu Gln Arg Glu Arg Ile Pro Arg Ala
    770                 775                 780

gat gaa tta aac caa act gga caa atc ctt gtg gag caa atg gga aaa      2400
Asp Glu Leu Asn Gln Thr Gly Gln Ile Leu Val Glu Gln Met Gly Lys
785                 790                 795                 800

gaa ggc ctt cct act gaa gaa ata aaa aat gtt ctg gag aag gtt tca      2448
Glu Gly Leu Pro Thr Glu Glu Ile Lys Asn Val Leu Glu Lys Val Ser
                805                 810                 815

tca gaa tgg aag aat gta tct caa cat ttg gaa gat cta gaa aga aag      2496
Ser Glu Trp Lys Asn Val Ser Gln His Leu Glu Asp Leu Glu Arg Lys
```

```
        820                 825                 830

att cag cta cag gaa gat ata aat gct tat ttc aag cag ctt gat gag     2544
Ile Gln Leu Gln Glu Asp Ile Asn Ala Tyr Phe Lys Gln Leu Asp Glu
    835                 840                 845

ctt gaa aag gtc atc aag aca aag gag gag tgg gta aaa cac act tcc     2592
Leu Glu Lys Val Ile Lys Thr Lys Glu Glu Trp Val Lys His Thr Ser
    850                 855                 860

att tct gaa tct tcc cgg cag tcc ttg cca agc ttg aag gat tcc tgt     2640
Ile Ser Glu Ser Ser Arg Gln Ser Leu Pro Ser Leu Lys Asp Ser Cys
865                 870                 875                 880

cag cgg gaa ttg aca aat ctt ctt ggc ctt cac ccc aaa att gaa atg     2688
Gln Arg Glu Leu Thr Asn Leu Leu Gly Leu His Pro Lys Ile Glu Met
                885                 890                 895

gct cgt gca agc tgc tcg gcc ctg atg tct cag cct tct gcc cca gat     2736
Ala Arg Ala Ser Cys Ser Ala Leu Met Ser Gln Pro Ser Ala Pro Asp
            900                 905                 910

ttt gtc cag cgg ggc ttc gat agc ttt ctg ggc cgc tac caa gct gta     2784
Phe Val Gln Arg Gly Phe Asp Ser Phe Leu Gly Arg Tyr Gln Ala Val
        915                 920                 925

caa gag gct gta gag gat cgt caa caa cat cta gag aat gaa ctg aag     2832
Gln Glu Ala Val Glu Asp Arg Gln Gln His Leu Glu Asn Glu Leu Lys
    930                 935                 940

ggc caa cct gga cat gca tat ctg gaa aca ttg aaa aca ctg aaa gat     2880
Gly Gln Pro Gly His Ala Tyr Leu Glu Thr Leu Lys Thr Leu Lys Asp
945                 950                 955                 960

gtg cta aat gat tca gaa aat aag gcc cag gtg tct ctg aat gtc ctt     2928
Val Leu Asn Asp Ser Glu Asn Lys Ala Gln Val Ser Leu Asn Val Leu
                965                 970                 975

aat gat ctt gcc aag gtg gag aag gcc ctg caa gaa aaa aag acc ctt     2976
Asn Asp Leu Ala Lys Val Glu Lys Ala Leu Gln Glu Lys Lys Thr Leu
            980                 985                 990

gat gaa atc ctt gag aat cag aaa  cct gca tta cat aaa  ctt gca gaa   3024
Asp Glu Ile Leu Glu Asn Gln Lys  Pro Ala Leu His Lys  Leu Ala Glu
        995                 1000                1005

gaa aca  aag gct ctg gag aaa  aat gtt cat cct gat  gta gaa aaa     3069
Glu Thr  Lys Ala Leu Glu Lys  Asn Val His Pro Asp  Val Glu Lys
    1010                1015                1020

tta tat  aag caa gaa ttt gat  gat gtg caa gga aag  tgg aac aag     3114
Leu Tyr  Lys Gln Glu Phe Asp  Asp Val Gln Gly Lys  Trp Asn Lys
    1025                1030                1035

cta aag  gtc ttg gtt tcc aaa  gat cta cat ttg ctt  gag gaa att     3159
Leu Lys  Val Leu Val Ser Lys  Asp Leu His Leu Leu  Glu Glu Ile
    1040                1045                1050

gct ctc  aca ctc aga gct ttt  gag gcc gat tca aca  gtc att gag     3204
Ala Leu  Thr Leu Arg Ala Phe  Glu Ala Asp Ser Thr  Val Ile Glu
    1055                1060                1065

aag tgg  atg gat ggc gtg aaa  gac ttc tta atg aaa  cag cag gct     3249
Lys Trp  Met Asp Gly Val Lys  Asp Phe Leu Met Lys  Gln Gln Ala
    1070                1075                1080

gcc caa  gga gac gac gca ggt  cta cag agg cag tta  gac cag tgc     3294
Ala Gln  Gly Asp Asp Ala Gly  Leu Gln Arg Gln Leu  Asp Gln Cys
    1085                1090                1095

tct gca  ttt gtt aat gaa ata  gaa aca att gaa tca  tct ctg aaa     3339
Ser Ala  Phe Val Asn Glu Ile  Glu Thr Ile Glu Ser  Ser Leu Lys
    1100                1105                1110

aac atg  aag gaa ata gag act  aat ctt cga agt ggt  cca gtt gct     3384
Asn Met  Lys Glu Ile Glu Thr  Asn Leu Arg Ser Gly  Pro Val Ala
    1115                1120                1125

gga ata  aaa act tgg gtg cag  aca aga cta ggt gac  tac caa act     3429
Gly Ile  Lys Thr Trp Val Gln  Thr Arg Leu Gly Asp  Tyr Gln Thr
```

```
    1130                1135                1140

caa ctg  gag aaa ctt agc aag  gag atc gct act caa  aaa agt agg     3474
Gln Leu  Glu Lys Leu Ser Lys  Glu Ile Ala Thr Gln  Lys Ser Arg
    1145                1150                1155

ttg tct  gaa agt caa gaa aaa  gct gcg aac ctg aag  aaa gac ttg     3519
Leu Ser  Glu Ser Gln Glu Lys  Ala Ala Asn Leu Lys  Lys Asp Leu
    1160                1165                1170

gca gag  atg cag gaa tgg atg  acc cag gcc gag gaa  gaa tat ttg     3564
Ala Glu  Met Gln Glu Trp Met  Thr Gln Ala Glu Glu  Glu Tyr Leu
    1175                1180                1185

gag cgg  gat ttt gag tac aag  tca cca gaa gag ctt  gag agt gct     3609
Glu Arg  Asp Phe Glu Tyr Lys  Ser Pro Glu Glu Leu  Glu Ser Ala
    1190                1195                1200

gtg gaa  gag atg aag agg gca  aaa gag gat gtg ttg  cag aag gag     3654
Val Glu  Glu Met Lys Arg Ala  Lys Glu Asp Val Leu  Gln Lys Glu
    1205                1210                1215

gtg aga  gtg aag att ctc aag  gac aac atc aag tta  tta gct gcc     3699
Val Arg  Val Lys Ile Leu Lys  Asp Asn Ile Lys Leu  Leu Ala Ala
    1220                1225                1230

aag gtg  ccc tct ggt ggc cag  gag ttg acg tct gag  ctg aat gtt     3744
Lys Val  Pro Ser Gly Gly Gln  Glu Leu Thr Ser Glu  Leu Asn Val
    1235                1240                1245

gtg ctg  gag aat tac caa ctt  ctt tgt aat aga att  cga gga aag     3789
Val Leu  Glu Asn Tyr Gln Leu  Leu Cys Asn Arg Ile  Arg Gly Lys
    1250                1255                1260

tgc cac  acg cta gag gag gtc  tgg tct tgt tgg att  gaa ctg ctt     3834
Cys His  Thr Leu Glu Glu Val  Trp Ser Cys Trp Ile  Glu Leu Leu
    1265                1270                1275

cac tat  ttg gat ctt gaa act  acc tgg tta aac act  ttg gaa gag     3879
His Tyr  Leu Asp Leu Glu Thr  Thr Trp Leu Asn Thr  Leu Glu Glu
    1280                1285                1290

cgg atg  aag agc aca gag gtc  ctg cct gag aag acg  gat gct gtc     3924
Arg Met  Lys Ser Thr Glu Val  Leu Pro Glu Lys Thr  Asp Ala Val
    1295                1300                1305

aac gaa  gcc ctg gag tct ctg  gaa tct gtt ctg cgc  cac ccg gca     3969
Asn Glu  Ala Leu Glu Ser Leu  Glu Ser Val Leu Arg  His Pro Ala
    1310                1315                1320

gat aat  cgc acc cag att cga  gag ctt ggc cag act  ctg att gat     4014
Asp Asn  Arg Thr Gln Ile Arg  Glu Leu Gly Gln Thr  Leu Ile Asp
    1325                1330                1335

ggg ggg  atc ctg gat gat ata  atc agt gag aaa ctg  gag gct ttc     4059
Gly Gly  Ile Leu Asp Asp Ile  Ile Ser Glu Lys Leu  Glu Ala Phe
    1340                1345                1350

aac agc  cga tat gaa gat cta  agt cac ctg gca gag  agc aag cag     4104
Asn Ser  Arg Tyr Glu Asp Leu  Ser His Leu Ala Glu  Ser Lys Gln
    1355                1360                1365

att tct  ttg gaa aag caa ctc  cag gtg ctg cgg gaa  act gac cag     4149
Ile Ser  Leu Glu Lys Gln Leu  Gln Val Leu Arg Glu  Thr Asp Gln
    1370                1375                1380

atg ctt  caa gtc ttg caa gag  agc ttg ggg gag ctg  gac aaa cag     4194
Met Leu  Gln Val Leu Gln Glu  Ser Leu Gly Glu Leu  Asp Lys Gln
    1385                1390                1395

ctc acc  aca tac ctg act gac  agg ata gat gct ttc  caa gtt cca     4239
Leu Thr  Thr Tyr Leu Thr Asp  Arg Ile Asp Ala Phe  Gln Val Pro
    1400                1405                1410

cag gaa  gct cag aaa atc caa  gca gag atc tca gcc  cat gag cta     4284
Gln Glu  Ala Gln Lys Ile Gln  Ala Glu Ile Ser Ala  His Glu Leu
    1415                1420                1425

acc cta  gag gag ttg aga aga  aat atg cgt tct cag  ccc ctg acc     4329
Thr Leu  Glu Glu Leu Arg Arg  Asn Met Arg Ser Gln  Pro Leu Thr
```

```
    1430                1435                1440

tcc cca  gag agt agg act gcc  aga gga gga agt cag  atg gat gtg      4374
Ser Pro  Glu Ser Arg Thr Ala  Arg Gly Gly Ser Gln  Met Asp Val
    1445                1450                1455

cta cag  agg aaa ctc cga gag  gtg tcc aca aag ttc  cag ctt gcc      4419
Leu Gln  Arg Lys Leu Arg Glu  Val Ser Thr Lys Phe  Gln Leu Ala
    1460                1465                1470

cac aga  gat ttt gga cca tcc  tct cag cat ttt ctc  tct acg tca      4464
His Arg  Asp Phe Gly Pro Ser  Ser Gln His Phe Leu  Ser Thr Ser
    1475                1480                1485

gtc cag  ctg ccg tgg caa aga  tcc att tca cat aat  aaa gtg ccc      4509
Val Gln  Leu Pro Trp Gln Arg  Ser Ile Ser His Asn  Lys Val Pro
    1490                1495                1500

tat tac  atc aac cat caa aca  cag acc acc tgt tgg  gac cat cct      4554
Tyr Tyr  Ile Asn His Gln Thr  Gln Thr Thr Cys Trp  Asp His Pro
    1505                1510                1515

aaa atg  acc gaa ctc ttt caa  tcc ctt gct gac ctg  aat aat gta      4599
Lys Met  Thr Glu Leu Phe Gln  Ser Leu Ala Asp Leu  Asn Asn Val
    1520                1525                1530

cgt ttt  tct gcc tac cgt aca  gca atc aaa atc cga  aga cta caa      4644
Arg Phe  Ser Ala Tyr Arg Thr  Ala Ile Lys Ile Arg  Arg Leu Gln
    1535                1540                1545

aaa gca  cta tgt ttg gat ctc  tta gag ttg agt aca  aca aat gaa      4689
Lys Ala  Leu Cys Leu Asp Leu  Leu Glu Leu Ser Thr  Thr Asn Glu
    1550                1555                1560

att ttc  aaa cag cac aag ttg  aac caa aat gac cag  ctc ctc agt      4734
Ile Phe  Lys Gln His Lys Leu  Asn Gln Asn Asp Gln  Leu Leu Ser
    1565                1570                1575

gtt cca  gat gtc atc aac tgt  ctg aca aca act tat  gat gga ctt      4779
Val Pro  Asp Val Ile Asn Cys  Leu Thr Thr Thr Tyr  Asp Gly Leu
    1580                1585                1590

gag caa  atg cat aag gac ctg  gtc aac gtt cca ctc  tgt gtt gat      4824
Glu Gln  Met His Lys Asp Leu  Val Asn Val Pro Leu  Cys Val Asp
    1595                1600                1605

atg tgt  ctc aat tgg ttg ctc  aat gtc tat gac acg  ggt cga act      4869
Met Cys  Leu Asn Trp Leu Leu  Asn Val Tyr Asp Thr  Gly Arg Thr
    1610                1615                1620

gga aaa  att aga gtg cag agt  ctg aag att gga tta  atg tct ctc      4914
Gly Lys  Ile Arg Val Gln Ser  Leu Lys Ile Gly Leu  Met Ser Leu
    1625                1630                1635

tcc aaa  ggt ctc ttg gaa gaa  aaa tac aga tat ctc  ttt aag gaa      4959
Ser Lys  Gly Leu Leu Glu Glu  Lys Tyr Arg Tyr Leu  Phe Lys Glu
    1640                1645                1650

gtt gca  ggg cca aca gaa atg  tgt gac cag agg cag  ctg ggc ctg      5004
Val Ala  Gly Pro Thr Glu Met  Cys Asp Gln Arg Gln  Leu Gly Leu
    1655                1660                1665

tta ctt  cat gat gcc atc cag  atc ccc cgg cag cta  ggt gaa gta      5049
Leu Leu  His Asp Ala Ile Gln  Ile Pro Arg Gln Leu  Gly Glu Val
    1670                1675                1680

gca gct  ttt gga ggc agt aat  att gag cct agt gtt  cgc agc tgc      5094
Ala Ala  Phe Gly Gly Ser Asn  Ile Glu Pro Ser Val  Arg Ser Cys
    1685                1690                1695

ttc caa  cag aat aac aat aaa  cca gaa ata agt gtg  aaa gag ttt      5139
Phe Gln  Gln Asn Asn Asn Lys  Pro Glu Ile Ser Val  Lys Glu Phe
    1700                1705                1710

ata gat  tgg atg cat ttg gaa  cca cag tcc atg gtt  tgg ctc cca      5184
Ile Asp  Trp Met His Leu Glu  Pro Gln Ser Met Val  Trp Leu Pro
    1715                1720                1725

gtt tta  cat cga gtg gca gca  gcg gag act gca aaa  cat cag gcc      5229
Val Leu  His Arg Val Ala Ala  Ala Glu Thr Ala Lys  His Gln Ala
```

```
    1730                1735                1740

aaa tgc  aac atc tgt aaa gaa  tgt cca att gtc ggg  ttc agg tat      5274
Lys Cys  Asn Ile Cys Lys Glu  Cys Pro Ile Val Gly  Phe Arg Tyr
    1745                1750                1755

aga agc  ctt aag cat ttt aac  tat gat gtc tgc cag  agt tgt ttc      5319
Arg Ser  Leu Lys His Phe Asn  Tyr Asp Val Cys Gln  Ser Cys Phe
    1760                1765                1770

ttt tcg  ggt cga aca gca aaa  ggt cac aaa tta cat  tac cca atg      5364
Phe Ser  Gly Arg Thr Ala Lys  Gly His Lys Leu His  Tyr Pro Met
    1775                1780                1785

gtg gaa  tat tgt ata cct aca  aca tct ggg gaa gat  gta cga gac      5409
Val Glu  Tyr Cys Ile Pro Thr  Thr Ser Gly Glu Asp  Val Arg Asp
    1790                1795                1800

ttc aca  aag gta ctt aag aac  aag ttc agg tcg aag  aag tac ttt      5454
Phe Thr  Lys Val Leu Lys Asn  Lys Phe Arg Ser Lys  Lys Tyr Phe
    1805                1810                1815

gcc aaa  cac cct cga ctt ggt  tac ctg cct gtc cag  aca gtt ctt      5499
Ala Lys  His Pro Arg Leu Gly  Tyr Leu Pro Val Gln  Thr Val Leu
    1820                1825                1830

gaa ggt  gac aac tta gag act  cct atc aca ctc atc  agt atg tgg      5544
Glu Gly  Asp Asn Leu Glu Thr  Pro Ile Thr Leu Ile  Ser Met Trp
    1835                1840                1845

cca gag  cac tat gac ccc tca  caa tct cct caa ctg  ttt cat gat      5589
Pro Glu  His Tyr Asp Pro Ser  Gln Ser Pro Gln Leu  Phe His Asp
    1850                1855                1860

gac acc  cat tca aga ata gaa  caa tat gcc aca cga  ctg gcc cag      5634
Asp Thr  His Ser Arg Ile Glu  Gln Tyr Ala Thr Arg  Leu Ala Gln
    1865                1870                1875

atg gaa  agg act aat ggg tct  ttt ctc act gat agc  agc tcc acc      5679
Met Glu  Arg Thr Asn Gly Ser  Phe Leu Thr Asp Ser  Ser Ser Thr
    1880                1885                1890

aca gga  agt gtg gaa gac gag  cac gcc ctc atc cag  cag tat tgc      5724
Thr Gly  Ser Val Glu Asp Glu  His Ala Leu Ile Gln  Gln Tyr Cys
    1895                1900                1905

caa aca  ctc gga gga gag tcc  cca gtg agc cag ccg  cag agc cca      5769
Gln Thr  Leu Gly Gly Glu Ser  Pro Val Ser Gln Pro  Gln Ser Pro
    1910                1915                1920

gct cag  atc ctg aag tca gta  gag agg gaa gaa cgt  gga gaa ctg      5814
Ala Gln  Ile Leu Lys Ser Val  Glu Arg Glu Glu Arg  Gly Glu Leu
    1925                1930                1935

gag agg  atc att gct gac ctg  gag gaa gaa caa aga  aat cta cag      5859
Glu Arg  Ile Ile Ala Asp Leu  Glu Glu Glu Gln Arg  Asn Leu Gln
    1940                1945                1950

gtg gag  tat gag cag ctg aag  gac cag cac ctc cga  agg ggg ctc      5904
Val Glu  Tyr Glu Gln Leu Lys  Asp Gln His Leu Arg  Arg Gly Leu
    1955                1960                1965

cct gtc  ggt tca ccg cca gag  tcg att ata tct ccc  cat cac acg      5949
Pro Val  Gly Ser Pro Pro Glu  Ser Ile Ile Ser Pro  His His Thr
    1970                1975                1980

tct gag  gat tca gaa ctt ata  gca gaa gca aaa ctc  ctc agg cag      5994
Ser Glu  Asp Ser Glu Leu Ile  Ala Glu Ala Lys Leu  Leu Arg Gln
    1985                1990                1995

cac aaa  ggt cgg ctg gag gct  agg atg cag att tta  gaa gat cac      6039
His Lys  Gly Arg Leu Glu Ala  Arg Met Gln Ile Leu  Glu Asp His
    2000                2005                2010

aat aaa  cag ctg gag tct cag  ctc cac cgc ctc cga  cag ctg ctg      6084
Asn Lys  Gln Leu Glu Ser Gln  Leu His Arg Leu Arg  Gln Leu Leu
    2015                2020                2025

gag cag  cct gaa tct gat tcc  cga atc aat ggt gtt  tcc cca tgg      6129
Glu Gln  Pro Glu Ser Asp Ser  Arg Ile Asn Gly Val  Ser Pro Trp
```

```
    2030                2035                2040

gct tct  cct cag cat tct gca  ctg agc tac tcg ctt  gat cca gat      6174
Ala Ser  Pro Gln His Ser Ala  Leu Ser Tyr Ser Leu  Asp Pro Asp
    2045                2050                2055

gcc tcc  ggc cca cag ttc cac  cag gca gcg gga gag  gac ctg ctg      6219
Ala Ser  Gly Pro Gln Phe His  Gln Ala Ala Gly Glu  Asp Leu Leu
    2060                2065                2070

gcc cca  ccg cac gac acc agc  acg gat ctc acg gag  gtc atg gag      6264
Ala Pro  Pro His Asp Thr Ser  Thr Asp Leu Thr Glu  Val Met Glu
    2075                2080                2085

cag att  cac agc acg ttt cca  tct tgc tgc cca aat  gtt ccc agc      6309
Gln Ile  His Ser Thr Phe Pro  Ser Cys Cys Pro Asn  Val Pro Ser
    2090                2095                2100

agg cca  cag gca atg tga                                            6327
Arg Pro  Gln Ala Met
    2105


<210> SEQ ID NO 17
<211> LENGTH: 2108
<212> TYPE: PRT
<213> ORGANISM: Homo sapiens

<400> SEQUENCE: 17

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Glu His Glu Ala
        35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270
```

```
Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Ala
305                 310                 315                 320

Ile Asn Ile Gln Ser Thr Ala Pro Glu Glu Glu His Glu Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln Asp Asp Ile Ser Asp Asp Val Glu Glu Val
    370                 375                 380

Lys Asp Gln Phe Ala Thr His Glu Ala Phe Met Met Glu Leu Thr Ala
385                 390                 395                 400

His Gln Ser Ser Val Gly Ser Val Leu Gln Ala Gly Asn Gln Leu Ile
                405                 410                 415

Thr Gln Gly Thr Leu Ser Asp Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Asp Arg Gln Ser Arg Leu His Asp Val Leu Met Glu Leu Gln Lys Lys
    450                 455                 460

Gln Leu Gln Gln Leu Ser Ala Trp Leu Thr Leu Thr Glu Glu Arg Ile
465                 470                 475                 480

Gln Lys Met Glu Thr Cys Pro Leu Asp Asp Asp Val Lys Ser Leu Gln
                485                 490                 495

Lys Leu Leu Glu Glu His Lys Ser Leu Gln Ser Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Ile Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Asn Ile Leu Trp Gln Glu Leu Leu Glu Glu
                565                 570                 575

Gln Cys Leu Leu Lys Ala Trp Leu Thr Glu Lys Glu Glu Ala Leu Asn
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Asp Asn Ser Lys Ala Ser Lys Lys Ile Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val Arg Val Arg Glu Gln Ala Ile Thr Lys
```

```
    690                 695                 700

Lys Ser Lys Gln Glu Leu Pro Pro Pro Pro Pro Pro Lys Lys Arg Gln
705                 710                 715                 720

Ile His Val Asp Ile Glu Ala Lys Lys Lys Phe Asp Ala Ile Ser Ala
                725                 730                 735

Glu Leu Leu Asn Trp Ile Leu Lys Trp Lys Thr Ala Ile Gln Thr Thr
            740                 745                 750

Glu Ile Lys Glu Tyr Met Lys Met Gln Asp Thr Ser Glu Met Lys Lys
        755                 760                 765

Lys Leu Lys Ala Leu Glu Lys Glu Gln Arg Glu Arg Ile Pro Arg Ala
    770                 775                 780

Asp Glu Leu Asn Gln Thr Gly Gln Ile Leu Val Glu Gln Met Gly Lys
785                 790                 795                 800

Glu Gly Leu Pro Thr Glu Glu Ile Lys Asn Val Leu Glu Lys Val Ser
                805                 810                 815

Ser Glu Trp Lys Asn Val Ser Gln His Leu Glu Asp Leu Glu Arg Lys
            820                 825                 830

Ile Gln Leu Gln Glu Asp Ile Asn Ala Tyr Phe Lys Gln Leu Asp Glu
        835                 840                 845

Leu Glu Lys Val Ile Lys Thr Lys Glu Glu Trp Val Lys His Thr Ser
    850                 855                 860

Ile Ser Glu Ser Ser Arg Gln Ser Leu Pro Ser Leu Lys Asp Ser Cys
865                 870                 875                 880

Gln Arg Glu Leu Thr Asn Leu Leu Gly Leu His Pro Lys Ile Glu Met
                885                 890                 895

Ala Arg Ala Ser Cys Ser Ala Leu Met Ser Gln Pro Ser Ala Pro Asp
            900                 905                 910

Phe Val Gln Arg Gly Phe Asp Ser Phe Leu Gly Arg Tyr Gln Ala Val
        915                 920                 925

Gln Glu Ala Val Glu Asp Arg Gln Gln His Leu Glu Asn Glu Leu Lys
    930                 935                 940

Gly Gln Pro Gly His Ala Tyr Leu Glu Thr Leu Lys Thr Leu Lys Asp
945                 950                 955                 960

Val Leu Asn Asp Ser Glu Asn Lys Ala Gln Val Ser Leu Asn Val Leu
                965                 970                 975

Asn Asp Leu Ala Lys Val Glu Lys Ala Leu Gln Glu Lys Lys Thr Leu
            980                 985                 990

Asp Glu Ile Leu Glu Asn Gln Lys  Pro Ala Leu His Lys  Leu Ala Glu
        995                 1000                1005

Glu Thr  Lys Ala Leu Glu Lys  Asn Val His Pro Asp  Val Glu Lys
    1010                1015                1020

Leu Tyr  Lys Gln Glu Phe Asp  Asp Val Gln Gly Lys  Trp Asn Lys
    1025                1030                1035

Leu Lys  Val Leu Val Ser Lys  Asp Leu His Leu Leu  Glu Glu Ile
    1040                1045                1050

Ala Leu  Thr Leu Arg Ala Phe  Glu Ala Asp Ser Thr  Val Ile Glu
    1055                1060                1065

Lys Trp  Met Asp Gly Val Lys  Asp Phe Leu Met Lys  Gln Gln Ala
    1070                1075                1080

Ala Gln  Gly Asp Asp Ala Gly  Leu Gln Arg Gln Leu  Asp Gln Cys
    1085                1090                1095

Ser Ala  Phe Val Asn Glu Ile  Glu Thr Ile Glu Ser  Ser Leu Lys
    1100                1105                1110
```

```
Asn Met  Lys Glu Ile Glu Thr  Asn Leu Arg Ser Gly  Pro Val Ala
    1115                 1120                 1125

Gly Ile  Lys Thr Trp Val Gln  Thr Arg Leu Gly Asp  Tyr Gln Thr
    1130                 1135                 1140

Gln Leu  Glu Lys Leu Ser Lys  Glu Ile Ala Thr Gln  Lys Ser Arg
    1145                 1150                 1155

Leu Ser  Glu Ser Gln Glu Lys  Ala Ala Asn Leu Lys  Lys Asp Leu
    1160                 1165                 1170

Ala Glu  Met Gln Glu Trp Met  Thr Gln Ala Glu Glu  Glu Tyr Leu
    1175                 1180                 1185

Glu Arg  Asp Phe Glu Tyr Lys  Ser Pro Glu Glu Leu  Glu Ser Ala
    1190                 1195                 1200

Val Glu  Glu Met Lys Arg Ala  Lys Glu Asp Val Leu  Gln Lys Glu
    1205                 1210                 1215

Val Arg  Val Lys Ile Leu Lys  Asp Asn Ile Lys Leu  Leu Ala Ala
    1220                 1225                 1230

Lys Val  Pro Ser Gly Gly Gln  Glu Leu Thr Ser Glu  Leu Asn Val
    1235                 1240                 1245

Val Leu  Glu Asn Tyr Gln Leu  Leu Cys Asn Arg Ile  Arg Gly Lys
    1250                 1255                 1260

Cys His  Thr Leu Glu Glu Val  Trp Ser Cys Trp Ile  Glu Leu Leu
    1265                 1270                 1275

His Tyr  Leu Asp Leu Glu Thr  Thr Trp Leu Asn Thr  Leu Glu Glu
    1280                 1285                 1290

Arg Met  Lys Ser Thr Glu Val  Leu Pro Glu Lys Thr  Asp Ala Val
    1295                 1300                 1305

Asn Glu  Ala Leu Glu Ser Leu  Glu Ser Val Leu Arg  His Pro Ala
    1310                 1315                 1320

Asp Asn  Arg Thr Gln Ile Arg  Glu Leu Gly Gln Thr  Leu Ile Asp
    1325                 1330                 1335

Gly Gly  Ile Leu Asp Asp Ile  Ile Ser Glu Lys Leu  Glu Ala Phe
    1340                 1345                 1350

Asn Ser  Arg Tyr Glu Asp Leu  Ser His Leu Ala Glu  Ser Lys Gln
    1355                 1360                 1365

Ile Ser  Leu Glu Lys Gln Leu  Gln Val Leu Arg Glu  Thr Asp Gln
    1370                 1375                 1380

Met Leu  Gln Val Leu Gln Glu  Ser Leu Gly Glu Leu  Asp Lys Gln
    1385                 1390                 1395

Leu Thr  Thr Tyr Leu Thr Asp  Arg Ile Asp Ala Phe  Gln Val Pro
    1400                 1405                 1410

Gln Glu  Ala Gln Lys Ile Gln  Ala Glu Ile Ser Ala  His Glu Leu
    1415                 1420                 1425

Thr Leu  Glu Glu Leu Arg Arg  Asn Met Arg Ser Gln  Pro Leu Thr
    1430                 1435                 1440

Ser Pro  Glu Ser Arg Thr Ala  Arg Gly Gly Ser Gln  Met Asp Val
    1445                 1450                 1455

Leu Gln  Arg Lys Leu Arg Glu  Val Ser Thr Lys Phe  Gln Leu Ala
    1460                 1465                 1470

His Arg  Asp Phe Gly Pro Ser  Ser Gln His Phe Leu  Ser Thr Ser
    1475                 1480                 1485

Val Gln  Leu Pro Trp Gln Arg  Ser Ile Ser His Asn  Lys Val Pro
    1490                 1495                 1500

Tyr Tyr  Ile Asn His Gln Thr  Gln Thr Thr Cys Trp  Asp His Pro
    1505                 1510                 1515
```

```
Lys Met Thr Glu Leu Phe Gln Ser Leu Ala Asp Leu Asn Asn Val
    1520                1525                1530

Arg Phe Ser Ala Tyr Arg Thr Ala Ile Lys Ile Arg Arg Leu Gln
    1535                1540                1545

Lys Ala Leu Cys Leu Asp Leu Leu Glu Leu Ser Thr Thr Asn Glu
    1550                1555                1560

Ile Phe Lys Gln His Lys Leu Asn Gln Asn Asp Gln Leu Leu Ser
    1565                1570                1575

Val Pro Asp Val Ile Asn Cys Leu Thr Thr Thr Tyr Asp Gly Leu
    1580                1585                1590

Glu Gln Met His Lys Asp Leu Val Asn Val Pro Leu Cys Val Asp
    1595                1600                1605

Met Cys Leu Asn Trp Leu Leu Asn Val Tyr Asp Thr Gly Arg Thr
    1610                1615                1620

Gly Lys Ile Arg Val Gln Ser Leu Lys Ile Gly Leu Met Ser Leu
    1625                1630                1635

Ser Lys Gly Leu Leu Glu Glu Lys Tyr Arg Tyr Leu Phe Lys Glu
    1640                1645                1650

Val Ala Gly Pro Thr Glu Met Cys Asp Gln Arg Gln Leu Gly Leu
    1655                1660                1665

Leu Leu His Asp Ala Ile Gln Ile Pro Arg Gln Leu Gly Glu Val
    1670                1675                1680

Ala Ala Phe Gly Gly Ser Asn Ile Glu Pro Ser Val Arg Ser Cys
    1685                1690                1695

Phe Gln Gln Asn Asn Asn Lys Pro Glu Ile Ser Val Lys Glu Phe
    1700                1705                1710

Ile Asp Trp Met His Leu Glu Pro Gln Ser Met Val Trp Leu Pro
    1715                1720                1725

Val Leu His Arg Val Ala Ala Ala Glu Thr Ala Lys His Gln Ala
    1730                1735                1740

Lys Cys Asn Ile Cys Lys Glu Cys Pro Ile Val Gly Phe Arg Tyr
    1745                1750                1755

Arg Ser Leu Lys His Phe Asn Tyr Asp Val Cys Gln Ser Cys Phe
    1760                1765                1770

Phe Ser Gly Arg Thr Ala Lys Gly His Lys Leu His Tyr Pro Met
    1775                1780                1785

Val Glu Tyr Cys Ile Pro Thr Thr Ser Gly Glu Asp Val Arg Asp
    1790                1795                1800

Phe Thr Lys Val Leu Lys Asn Lys Phe Arg Ser Lys Lys Tyr Phe
    1805                1810                1815

Ala Lys His Pro Arg Leu Gly Tyr Leu Pro Val Gln Thr Val Leu
    1820                1825                1830

Glu Gly Asp Asn Leu Glu Thr Pro Ile Thr Leu Ile Ser Met Trp
    1835                1840                1845

Pro Glu His Tyr Asp Pro Ser Gln Ser Pro Gln Leu Phe His Asp
    1850                1855                1860

Asp Thr His Ser Arg Ile Glu Gln Tyr Ala Thr Arg Leu Ala Gln
    1865                1870                1875

Met Glu Arg Thr Asn Gly Ser Phe Leu Thr Asp Ser Ser Ser Thr
    1880                1885                1890

Thr Gly Ser Val Glu Asp Glu His Ala Leu Ile Gln Gln Tyr Cys
    1895                1900                1905

Gln Thr Leu Gly Gly Glu Ser Pro Val Ser Gln Pro Gln Ser Pro
```

```
    1910                1915                1920

Ala Gln  Ile Leu Lys Ser Val  Glu Arg Glu Glu Arg  Gly Glu Leu
    1925                1930                1935

Glu Arg  Ile Ile Ala Asp Leu  Glu Glu Glu Gln Arg  Asn Leu Gln
    1940                1945                1950

Val Glu  Tyr Glu Gln Leu Lys  Asp Gln His Leu Arg  Arg Gly Leu
    1955                1960                1965

Pro Val  Gly Ser Pro Pro Glu  Ser Ile Ile Ser Pro  His His Thr
    1970                1975                1980

Ser Glu  Asp Ser Glu Leu Ile  Ala Glu Ala Lys Leu  Leu Arg Gln
    1985                1990                1995

His Lys  Gly Arg Leu Glu Ala  Arg Met Gln Ile Leu  Glu Asp His
    2000                2005                2010

Asn Lys  Gln Leu Glu Ser Gln  Leu His Arg Leu Arg  Gln Leu Leu
    2015                2020                2025

Glu Gln  Pro Glu Ser Asp Ser  Arg Ile Asn Gly Val  Ser Pro Trp
    2030                2035                2040

Ala Ser  Pro Gln His Ser Ala  Leu Ser Tyr Ser Leu  Asp Pro Asp
    2045                2050                2055

Ala Ser  Gly Pro Gln Phe His  Gln Ala Ala Gly Glu  Asp Leu Leu
    2060                2065                2070

Ala Pro  Pro His Asp Thr Ser  Thr Asp Leu Thr Glu  Val Met Glu
    2075                2080                2085

Gln Ile  His Ser Thr Phe Pro  Ser Cys Cys Pro Asn  Val Pro Ser
    2090                2095                2100

Arg Pro  Gln Ala Met
    2105


<210> SEQ ID NO 18
<211> LENGTH: 4080
<212> TYPE: DNA
<213> ORGANISM: Mus musculus
<220> FEATURE:
<221> NAME/KEY: CDS
<222> LOCATION: (1)..(4080)
<220> FEATURE:
<221> NAME/KEY: misc_feature
<222> LOCATION: (1)..(117)
<223> OTHER INFORMATION: TAT and epitope tag coding sequence

<400> SEQUENCE: 18

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
Arg Gln Arg Arg Arg Gly Gly Ser Thr Met Ser Gly Tyr Pro Tyr Asp
            20                  25                  30

gtc cca gac tat gct ggc tcc atg gcc aag tat ggg gac ctt gaa gcc      144
Val Pro Asp Tyr Ala Gly Ser Met Ala Lys Tyr Gly Asp Leu Glu Ala
        35                  40                  45

agg cct gat gat ggg cag aac gaa ttc agt gac atc att aag tcc aga      192
Arg Pro Asp Asp Gly Gln Asn Glu Phe Ser Asp Ile Ile Lys Ser Arg
    50                  55                  60

tct gat gaa cac aat gat gta cag aag aaa acc ttt acc aaa tgg ata      240
Ser Asp Glu His Asn Asp Val Gln Lys Lys Thr Phe Thr Lys Trp Ile
65                  70                  75                  80

aac gct cga ttt tcc aag agt ggg aaa cca ccc atc agt gat atg ttc      288
Asn Ala Arg Phe Ser Lys Ser Gly Lys Pro Pro Ile Ser Asp Met Phe
                85                  90                  95
```

```
tca gac ctc aaa gat ggg aga aag ctc ttg gat ctt ctc gaa ggc ctc      336
Ser Asp Leu Lys Asp Gly Arg Lys Leu Leu Asp Leu Leu Glu Gly Leu
            100                 105                 110

aca gga aca tca ttg cca aag gaa cgt ggt tcc aca agg gtg cat gcc      384
Thr Gly Thr Ser Leu Pro Lys Glu Arg Gly Ser Thr Arg Val His Ala
        115                 120                 125

tta aac aat gtc aac cga gtg cta cag gtt tta cat cag aac aat gtg      432
Leu Asn Asn Val Asn Arg Val Leu Gln Val Leu His Gln Asn Asn Val
    130                 135                 140

gac ttg gtg aat att gga ggc acg gac att gtg gct gga aat ccc aag      480
Asp Leu Val Asn Ile Gly Gly Thr Asp Ile Val Ala Gly Asn Pro Lys
145                 150                 155                 160

ctg act tta ggg tta ctc tgg agc atc att ctg cac tgg cag gtg aag      528
Leu Thr Leu Gly Leu Leu Trp Ser Ile Ile Leu His Trp Gln Val Lys
                165                 170                 175

gat gtc atg aaa gat atc atg tca gac ctg cag cag aca aac agc gag      576
Asp Val Met Lys Asp Ile Met Ser Asp Leu Gln Gln Thr Asn Ser Glu
            180                 185                 190

aag atc ctg ctg agc tgg gtg cgg cag acc acc agg ccc tac agt caa      624
Lys Ile Leu Leu Ser Trp Val Arg Gln Thr Thr Arg Pro Tyr Ser Gln
        195                 200                 205

gtc aac gtc ctc aac ttc acc acc agc tgg acc gat gga ctc gcg ttc      672
Val Asn Val Leu Asn Phe Thr Thr Ser Trp Thr Asp Gly Leu Ala Phe
    210                 215                 220

aac gcc gtg ctc cac cgg cac aaa cca gat ctc ttc gac tgg gac gag      720
Asn Ala Val Leu His Arg His Lys Pro Asp Leu Phe Asp Trp Asp Glu
225                 230                 235                 240

atg gtc aaa atg tcc cca att gag aga ctt gac cat gct ttt gac aag      768
Met Val Lys Met Ser Pro Ile Glu Arg Leu Asp His Ala Phe Asp Lys
                245                 250                 255

gcc cac act tct ttg gga att gaa aag ctc cta agt cct gaa act gtt      816
Ala His Thr Ser Leu Gly Ile Glu Lys Leu Leu Ser Pro Glu Thr Val
            260                 265                 270

gct gtg cat ctc cct gac aag aaa tcc ata att atg tat tta acg tct      864
Ala Val His Leu Pro Asp Lys Lys Ser Ile Ile Met Tyr Leu Thr Ser
        275                 280                 285

ctg ttt gag gtg ctt cct cag caa gtc acg ata gat gcc atc cga gag      912
Leu Phe Glu Val Leu Pro Gln Gln Val Thr Ile Asp Ala Ile Arg Glu
    290                 295                 300

gtg gag act ctc cca agg aag tat aag aaa gaa tgt gaa gag gaa gaa      960
Val Glu Thr Leu Pro Arg Lys Tyr Lys Lys Glu Cys Glu Glu Glu Glu
305                 310                 315                 320

att cat atc cag agt gca gtg ctg gca gag gaa ggc cag agt ccc cga     1008
Ile His Ile Gln Ser Ala Val Leu Ala Glu Glu Gly Gln Ser Pro Arg
                325                 330                 335

gct gag acc cct agc acc gtc act gaa gtg gac atg gat ttg gac agc     1056
Ala Glu Thr Pro Ser Thr Val Thr Glu Val Asp Met Asp Leu Asp Ser
            340                 345                 350

tac cag ata gcg cta gag gaa gtg ctg acg tgg ctg ctg tcc gcg gag     1104
Tyr Gln Ile Ala Leu Glu Glu Val Leu Thr Trp Leu Leu Ser Ala Glu
        355                 360                 365

gac acg ttc cag gag caa cat gac att tct gat gat gtc gaa gaa gtc     1152
Asp Thr Phe Gln Glu Gln His Asp Ile Ser Asp Asp Val Glu Glu Val
    370                 375                 380

aaa gag cag ttt gct acc cat gaa act ttt atg atg gag ctg aca gca     1200
Lys Glu Gln Phe Ala Thr His Glu Thr Phe Met Met Glu Leu Thr Ala
385                 390                 395                 400

cac cag agc agc gtg ggg agc gtc ctg cag gct ggc aac cag ctg atg     1248
His Gln Ser Ser Val Gly Ser Val Leu Gln Ala Gly Asn Gln Leu Met
                405                 410                 415
```

```
aca caa ggg act ctg tcc aga gag gag gag ttt gag atc cag gaa cag      1296
Thr Gln Gly Thr Leu Ser Arg Glu Glu Glu Phe Glu Ile Gln Glu Gln
            420                 425                 430

atg acc ttg ctg aat gca agg tgg gag gcg ctc cgg gtg gag agc atg      1344
Met Thr Leu Leu Asn Ala Arg Trp Glu Ala Leu Arg Val Glu Ser Met
        435                 440                 445

gag agg cag tcc cgg ctg cac gac gct ctg atg gag ctg cag aag aaa      1392
Glu Arg Gln Ser Arg Leu His Asp Ala Leu Met Glu Leu Gln Lys Lys
    450                 455                 460

cag ctg cag cag ctc tca agc tgg ctg gcc ctc aca gaa gag cgc att      1440
Gln Leu Gln Gln Leu Ser Ser Trp Leu Ala Leu Thr Glu Glu Arg Ile
465                 470                 475                 480

cag aag atg gag agc ctc ccg ctg ggt gat gac ctg ccc tcc ctg cag      1488
Gln Lys Met Glu Ser Leu Pro Leu Gly Asp Asp Leu Pro Ser Leu Gln
                485                 490                 495

aag ctg ctt caa gaa cat aaa agt ttg caa aat gac ctt gaa gct gaa      1536
Lys Leu Leu Gln Glu His Lys Ser Leu Gln Asn Asp Leu Glu Ala Glu
            500                 505                 510

cag gtg aag gta aat tcc tta act cac atg gtg gtg att gtg gat gaa      1584
Gln Val Lys Val Asn Ser Leu Thr His Met Val Val Ile Val Asp Glu
        515                 520                 525

aac agt ggg gag agt gcc aca gct ctt ctg gaa gat cag tta cag aaa      1632
Asn Ser Gly Glu Ser Ala Thr Ala Leu Leu Glu Asp Gln Leu Gln Lys
    530                 535                 540

ctg ggt gag cgc tgg aca gct gta tgc cgc tgg act gaa gaa cgt tgg      1680
Leu Gly Glu Arg Trp Thr Ala Val Cys Arg Trp Thr Glu Glu Arg Trp
545                 550                 555                 560

aac agg ttg caa gaa atc agt att ctg tgg cag gaa tta ttg gaa gag      1728
Asn Arg Leu Gln Glu Ile Ser Ile Leu Trp Gln Glu Leu Leu Glu Glu
                565                 570                 575

cag tgt ctg ttg gag gct tgg ctc acc gaa aag gaa gag gct ttg gat      1776
Gln Cys Leu Leu Glu Ala Trp Leu Thr Glu Lys Glu Glu Ala Leu Asp
            580                 585                 590

aaa gtt caa acc agc aac ttt aaa gac cag aag gaa cta agt gtc agt      1824
Lys Val Gln Thr Ser Asn Phe Lys Asp Gln Lys Glu Leu Ser Val Ser
        595                 600                 605

gtc cgg cgt ctg gct ata ttg aag gaa gac atg gaa atg aag agg cag      1872
Val Arg Arg Leu Ala Ile Leu Lys Glu Asp Met Glu Met Lys Arg Gln
    610                 615                 620

act ctg gat caa ctg agt gag att ggc cag gat gtg ggc caa tta ctc      1920
Thr Leu Asp Gln Leu Ser Glu Ile Gly Gln Asp Val Gly Gln Leu Leu
625                 630                 635                 640

agt aat ccc aag gca tct aag aag atg aac agt gac tct gag gag cta      1968
Ser Asn Pro Lys Ala Ser Lys Lys Met Asn Ser Asp Ser Glu Glu Leu
                645                 650                 655

aca cag aga tgg gat tct ctg gtt cag aga ctc gaa gac tct tct aac      2016
Thr Gln Arg Trp Asp Ser Leu Val Gln Arg Leu Glu Asp Ser Ser Asn
            660                 665                 670

cag gtg act cag gcg gta gcg aag ctc ggc atg tcc cag att cca cag      2064
Gln Val Thr Gln Ala Val Ala Lys Leu Gly Met Ser Gln Ile Pro Gln
        675                 680                 685

aag gac cta ttg gag acc gtt cat gtg aga gaa caa ggg atg gtg aag      2112
Lys Asp Leu Leu Glu Thr Val His Val Arg Glu Gln Gly Met Val Lys
    690                 695                 700

aag ccc aag cag gaa ctg cct cct cct ccc cca cca aag aag aga cag      2160
Lys Pro Lys Gln Glu Leu Pro Pro Pro Pro Pro Pro Lys Lys Arg Gln
705                 710                 715                 720

att cac gtg gac gcc cac aga gat ttt ggg cca tct tct caa cac ttt      2208
Ile His Val Asp Ala His Arg Asp Phe Gly Pro Ser Ser Gln His Phe
                725                 730                 735
```

```
ctg tcc act tca gtc cag ctg ccg tgg cag aga tcc att tca cat aat     2256
Leu Ser Thr Ser Val Gln Leu Pro Trp Gln Arg Ser Ile Ser His Asn
            740                 745                 750

aaa gtg ccc tat tac atc aac cat caa aca cag aca acc tgt tgg gat     2304
Lys Val Pro Tyr Tyr Ile Asn His Gln Thr Gln Thr Thr Cys Trp Asp
        755                 760                 765

cat cct aaa atg act gag ctc ttc caa tcc ctt gct gat ctg aat aat     2352
His Pro Lys Met Thr Glu Leu Phe Gln Ser Leu Ala Asp Leu Asn Asn
    770                 775                 780

gta cgt ttc tct gcc tac cgc aca gca atc aaa att cga agg ctg caa     2400
Val Arg Phe Ser Ala Tyr Arg Thr Ala Ile Lys Ile Arg Arg Leu Gln
785                 790                 795                 800

aaa gca tta tgt ctg gat ctc tta gag ctg aat acg acg aat gaa gtt     2448
Lys Ala Leu Cys Leu Asp Leu Leu Glu Leu Asn Thr Thr Asn Glu Val
                805                 810                 815

ttc aag cag cac aaa ctg aac caa aat gat cag ctc ctg agt gtc cca     2496
Phe Lys Gln His Lys Leu Asn Gln Asn Asp Gln Leu Leu Ser Val Pro
            820                 825                 830

gac gtc atc aac tgt ctg acc acc act tac gat ggg ctt gag cag ctg     2544
Asp Val Ile Asn Cys Leu Thr Thr Thr Tyr Asp Gly Leu Glu Gln Leu
        835                 840                 845

cac aag gac ttg gtc aat gtt cca ctc tgc gtc gat atg tgt ctc aac     2592
His Lys Asp Leu Val Asn Val Pro Leu Cys Val Asp Met Cys Leu Asn
    850                 855                 860

tgg ctg ctc aac gta tac gac acg ggc cgg act gga aaa att cgg gta     2640
Trp Leu Leu Asn Val Tyr Asp Thr Gly Arg Thr Gly Lys Ile Arg Val
865                 870                 875                 880

cag agt ctg aag att gga ttg atg tct ctc tcc aaa ggc ctc tta gaa     2688
Gln Ser Leu Lys Ile Gly Leu Met Ser Leu Ser Lys Gly Leu Leu Glu
                885                 890                 895

gag aaa tac aga tgt ctc ttt aag gag gtg gca ggg cca act gag atg     2736
Glu Lys Tyr Arg Cys Leu Phe Lys Glu Val Ala Gly Pro Thr Glu Met
            900                 905                 910

tgt gac cag cgg cag ctt ggc ctg cta ctt cac gat gcc atc cag atc     2784
Cys Asp Gln Arg Gln Leu Gly Leu Leu Leu His Asp Ala Ile Gln Ile
        915                 920                 925

cct agg cag ctg ggg gaa gta gca gcc ttt ggg ggc agt aac att gag     2832
Pro Arg Gln Leu Gly Glu Val Ala Ala Phe Gly Gly Ser Asn Ile Glu
    930                 935                 940

ccc agt gtc cgc agc tgc ttc cag cag aat aac aac aag cca gaa atc     2880
Pro Ser Val Arg Ser Cys Phe Gln Gln Asn Asn Asn Lys Pro Glu Ile
945                 950                 955                 960

agt gtg aag gag ttt ata gac tgg atg cat ttg gaa ccc cag tcc atg     2928
Ser Val Lys Glu Phe Ile Asp Trp Met His Leu Glu Pro Gln Ser Met
                965                 970                 975

gtg tgg ttg ccg gtt ctg cat cgg gtc gca gct gct gag act gca aaa     2976
Val Trp Leu Pro Val Leu His Arg Val Ala Ala Ala Glu Thr Ala Lys
            980                 985                 990

cat cag gcc aaa tgc aac atc tgc  aaa gaa tgc ccg att  gtt ggg ttc     3024
His Gln Ala Lys Cys Asn Ile Cys  Lys Glu Cys Pro Ile  Val Gly Phe
        995                 1000                1005

aga tac  agg agc cta aag cat  ttt aat tat gat gtc  tgc cag agt     3069
Arg Tyr  Arg Ser Leu Lys His  Phe Asn Tyr Asp Val  Cys Gln Ser
    1010                1015                1020

tgc ttc  ttt tct gga aga aca  gca aag ggc cac aag  tta cat tac     3114
Cys Phe  Phe Ser Gly Arg Thr  Ala Lys Gly His Lys  Leu His Tyr
    1025                1030                1035

ccg atg  gta gaa tac tgc ata  ccg aca aca tct ggg  gaa gat gtg     3159
Pro Met  Val Glu Tyr Cys Ile  Pro Thr Thr Ser Gly  Glu Asp Val
    1040                1045                1050
```

```
aga gat  ttc act aag gtg ctg  aag aac aag ttc agg  tcc aag aaa      3204
Arg Asp  Phe Thr Lys Val Leu  Lys Asn Lys Phe Arg  Ser Lys Lys
    1055                 1060                 1065

tat ttt  gcc aaa cat cct cgg  ctt ggc tac ctg cct  gtc cag acc      3249
Tyr Phe  Ala Lys His Pro Arg  Leu Gly Tyr Leu Pro  Val Gln Thr
    1070                 1075                 1080

gtg ctg  gaa ggg gac aac tta  gaa act cct atc acg  ctc atc agt      3294
Val Leu  Glu Gly Asp Asn Leu  Glu Thr Pro Ile Thr  Leu Ile Ser
    1085                 1090                 1095

atg tgg  cca gag cac tat gac  ccc tcc cag tcc cct  cag ctg ttt      3339
Met Trp  Pro Glu His Tyr Asp  Pro Ser Gln Ser Pro  Gln Leu Phe
    1100                 1105                 1110

cat gat  gac acc cac tca aga  ata gag caa tac gct  aca cga ctg      3384
His Asp  Asp Thr His Ser Arg  Ile Glu Gln Tyr Ala  Thr Arg Leu
    1115                 1120                 1125

gcc cag  atg gaa agg aca aac  ggg tcc ttc cta act  gat agc agc      3429
Ala Gln  Met Glu Arg Thr Asn  Gly Ser Phe Leu Thr  Asp Ser Ser
    1130                 1135                 1140

tct aca  aca gga agc gtg gag  gat gag cat gcc ctc  atc cag cag      3474
Ser Thr  Thr Gly Ser Val Glu  Asp Glu His Ala Leu  Ile Gln Gln
    1145                 1150                 1155

tac tgc  cag acc ctg ggc ggg  gag tca cct gtg agt  cag ccg cag      3519
Tyr Cys  Gln Thr Leu Gly Gly  Glu Ser Pro Val Ser  Gln Pro Gln
    1160                 1165                 1170

agt cca  gct cag atc ctg aag  tcc gtg gag agg gaa  gag cgt ggg      3564
Ser Pro  Ala Gln Ile Leu Lys  Ser Val Glu Arg Glu  Glu Arg Gly
    1175                 1180                 1185

gaa ctg  gag cgg atc att gct  gac ttg gag gaa gag  caa aga aat      3609
Glu Leu  Glu Arg Ile Ile Ala  Asp Leu Glu Glu Glu  Gln Arg Asn
    1190                 1195                 1200

ctg cag  gtg gag tat gag cag  ctg aag gag cag cac  cta aga agg      3654
Leu Gln  Val Glu Tyr Glu Gln  Leu Lys Glu Gln His  Leu Arg Arg
    1205                 1210                 1215

ggt ctc  cct gtg ggc tcc cct  cca gac tcc atc gta  tct cct cac      3699
Gly Leu  Pro Val Gly Ser Pro  Pro Asp Ser Ile Val  Ser Pro His
    1220                 1225                 1230

cac aca  tct gag gac tca gaa  ctt ata gca gaa gct  aaa ctc ctg      3744
His Thr  Ser Glu Asp Ser Glu  Leu Ile Ala Glu Ala  Lys Leu Leu
    1235                 1240                 1245

cgg cag  cac aaa ggg cgg ctg  gag gcg agg atg caa  att ttg gaa      3789
Arg Gln  His Lys Gly Arg Leu  Glu Ala Arg Met Gln  Ile Leu Glu
    1250                 1255                 1260

gat cac  aat aaa cag ctg gag  tct cag ctg cac cgc  ctc aga cag      3834
Asp His  Asn Lys Gln Leu Glu  Ser Gln Leu His Arg  Leu Arg Gln
    1265                 1270                 1275

ctc ctg  gag cag cct gac tct  gac tcc cgc atc aat  ggt gtc tcc      3879
Leu Leu  Glu Gln Pro Asp Ser  Asp Ser Arg Ile Asn  Gly Val Ser
    1280                 1285                 1290

ccc tgg  gct tcc cca cag cat  tct gca ttg agc tac  tca ctt gac      3924
Pro Trp  Ala Ser Pro Gln His  Ser Ala Leu Ser Tyr  Ser Leu Asp
    1295                 1300                 1305

act gac  cca ggc cca cag ttc  cac cag gca gca tct  gag gac ctg      3969
Thr Asp  Pro Gly Pro Gln Phe  His Gln Ala Ala Ser  Glu Asp Leu
    1310                 1315                 1320

ctg gcc  cca cct cac gac act  agc acg gac ctc acg  gac gtg atg      4014
Leu Ala  Pro Pro His Asp Thr  Ser Thr Asp Leu Thr  Asp Val Met
    1325                 1330                 1335

gag cag  atc aac agc acg ttt  ccc tct tgc agc tca  aat gtc ccc      4059
Glu Gln  Ile Asn Ser Thr Phe  Pro Ser Cys Ser Ser  Asn Val Pro
    1340                 1345                 1350
```

```
agc agg  cca cag gca atg tga                                    4080
Ser Arg  Pro Gln Ala Met
    1355
```

<210> SEQ ID NO 19
<211> LENGTH: 1359
<212> TYPE: PRT
<213> ORGANISM: Mus musculus

<400> SEQUENCE: 19

```
Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305                 310                 315                 320

Ile His Ile Gln Ser Ala Val Leu Ala Glu Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365
```

```
Asp Thr Phe Gln Glu Gln His Asp Ile Ser Asp Asp Val Glu Glu Val
    370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val His Val Arg Glu Gln Gly Met Val Lys
    690                 695                 700

Lys Pro Lys Gln Glu Leu Pro Pro Pro Pro Pro Pro Lys Lys Arg Gln
705                 710                 715                 720

Ile His Val Asp Ala His Arg Asp Phe Gly Pro Ser Ser Gln His Phe
                725                 730                 735

Leu Ser Thr Ser Val Gln Leu Pro Trp Gln Arg Ser Ile Ser His Asn
            740                 745                 750

Lys Val Pro Tyr Tyr Ile Asn His Gln Thr Gln Thr Thr Cys Trp Asp
        755                 760                 765

His Pro Lys Met Thr Glu Leu Phe Gln Ser Leu Ala Asp Leu Asn Asn
    770                 775                 780

Val Arg Phe Ser Ala Tyr Arg Thr Ala Ile Lys Ile Arg Arg Leu Gln
```

```
785                 790                 795                 800

Lys Ala Leu Cys Leu Asp Leu Leu Glu Leu Asn Thr Thr Asn Glu Val
                805                 810                 815

Phe Lys Gln His Lys Leu Asn Gln Asn Asp Gln Leu Leu Ser Val Pro
            820                 825                 830

Asp Val Ile Asn Cys Leu Thr Thr Thr Tyr Asp Gly Leu Glu Gln Leu
        835                 840                 845

His Lys Asp Leu Val Asn Val Pro Leu Cys Val Asp Met Cys Leu Asn
    850                 855                 860

Trp Leu Leu Asn Val Tyr Asp Thr Gly Arg Thr Gly Lys Ile Arg Val
865                 870                 875                 880

Gln Ser Leu Lys Ile Gly Leu Met Ser Leu Ser Lys Gly Leu Leu Glu
                885                 890                 895

Glu Lys Tyr Arg Cys Leu Phe Lys Glu Val Ala Gly Pro Thr Glu Met
            900                 905                 910

Cys Asp Gln Arg Gln Leu Gly Leu Leu Leu His Asp Ala Ile Gln Ile
        915                 920                 925

Pro Arg Gln Leu Gly Glu Val Ala Ala Phe Gly Gly Ser Asn Ile Glu
    930                 935                 940

Pro Ser Val Arg Ser Cys Phe Gln Gln Asn Asn Asn Lys Pro Glu Ile
945                 950                 955                 960

Ser Val Lys Glu Phe Ile Asp Trp Met His Leu Glu Pro Gln Ser Met
                965                 970                 975

Val Trp Leu Pro Val Leu His Arg Val Ala Ala Ala Glu Thr Ala Lys
            980                 985                 990

His Gln Ala Lys Cys Asn Ile Cys  Lys Glu Cys Pro Ile  Val Gly Phe
        995                 1000                1005

Arg Tyr  Arg Ser Leu Lys His  Phe Asn Tyr Asp Val  Cys Gln Ser
    1010                1015                1020

Cys Phe  Phe Ser Gly Arg Thr  Ala Lys Gly His Lys  Leu His Tyr
    1025                1030                1035

Pro Met  Val Glu Tyr Cys Ile  Pro Thr Thr Ser Gly  Glu Asp Val
    1040                1045                1050

Arg Asp  Phe Thr Lys Val Leu  Lys Asn Lys Phe Arg  Ser Lys Lys
    1055                1060                1065

Tyr Phe  Ala Lys His Pro Arg  Leu Gly Tyr Leu Pro  Val Gln Thr
    1070                1075                1080

Val Leu  Glu Gly Asp Asn Leu  Glu Thr Pro Ile Thr  Leu Ile Ser
    1085                1090                1095

Met Trp  Pro Glu His Tyr Asp  Pro Ser Gln Ser Pro  Gln Leu Phe
    1100                1105                1110

His Asp  Asp Thr His Ser Arg  Ile Glu Gln Tyr Ala  Thr Arg Leu
    1115                1120                1125

Ala Gln  Met Glu Arg Thr Asn  Gly Ser Phe Leu Thr  Asp Ser Ser
    1130                1135                1140

Ser Thr  Thr Gly Ser Val Glu  Asp Glu His Ala Leu  Ile Gln Gln
    1145                1150                1155

Tyr Cys  Gln Thr Leu Gly Gly  Glu Ser Pro Val Ser  Gln Pro Gln
    1160                1165                1170

Ser Pro  Ala Gln Ile Leu Lys  Ser Val Glu Arg Glu  Glu Arg Gly
    1175                1180                1185

Glu Leu  Glu Arg Ile Ile Ala  Asp Leu Glu Glu Glu  Gln Arg Asn
    1190                1195                1200
```

```
Leu Gln  Val Glu Tyr Glu Gln  Leu Lys Glu Gln His  Leu Arg Arg
    1205                 1210                 1215

Gly Leu  Pro Val Gly Ser Pro  Pro Asp Ser Ile Val  Ser Pro His
    1220                 1225                 1230

His Thr  Ser Glu Asp Ser Glu  Leu Ile Ala Glu Ala  Lys Leu Leu
    1235                 1240                 1245

Arg Gln  His Lys Gly Arg Leu  Glu Ala Arg Met Gln  Ile Leu Glu
    1250                 1255                 1260

Asp His  Asn Lys Gln Leu Glu  Ser Gln Leu His Arg  Leu Arg Gln
    1265                 1270                 1275

Leu Leu  Glu Gln Pro Asp Ser  Asp Ser Arg Ile Asn  Gly Val Ser
    1280                 1285                 1290

Pro Trp  Ala Ser Pro Gln His  Ser Ala Leu Ser Tyr  Ser Leu Asp
    1295                 1300                 1305

Thr Asp  Pro Gly Pro Gln Phe  His Gln Ala Ala Ser  Glu Asp Leu
    1310                 1315                 1320

Leu Ala  Pro Pro His Asp Thr  Ser Thr Asp Leu Thr  Asp Val Met
    1325                 1330                 1335

Glu Gln  Ile Asn Ser Thr Phe  Pro Ser Cys Ser Ser  Asn Val Pro
    1340                 1345                 1350

Ser Arg  Pro Gln Ala Met
    1355


<210> SEQ ID NO 20
<211> LENGTH: 5067
<212> TYPE: DNA
<213> ORGANISM: Mus musculus
<220> FEATURE:
<221> NAME/KEY: CDS
<222> LOCATION: (1)..(5067)
<220> FEATURE:
<221> NAME/KEY: misc_feature
<222> LOCATION: (1)..(117)
<223> OTHER INFORMATION: TAT and epitope tag coding sequence

<400> SEQUENCE: 20

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
Arg Gln Arg Arg Arg Gly Gly Ser Thr Met Ser Gly Tyr Pro Tyr Asp
            20                  25                  30

gtc cca gac tat gct ggc tcc atg gcc aag tat ggg gac ctt gaa gcc      144
Val Pro Asp Tyr Ala Gly Ser Met Ala Lys Tyr Gly Asp Leu Glu Ala
        35                  40                  45

agg cct gat gat ggg cag aac gaa ttc agt gac atc att aag tcc aga      192
Arg Pro Asp Asp Gly Gln Asn Glu Phe Ser Asp Ile Ile Lys Ser Arg
    50                  55                  60

tct gat gaa cac aat gat gta cag aag aaa acc ttt acc aaa tgg ata      240
Ser Asp Glu His Asn Asp Val Gln Lys Lys Thr Phe Thr Lys Trp Ile
65                  70                  75                  80

aac gct cga ttt tcc aag agt ggg aaa cca ccc atc agt gat atg ttc      288
Asn Ala Arg Phe Ser Lys Ser Gly Lys Pro Pro Ile Ser Asp Met Phe
                85                  90                  95

tca gac ctc aaa gat ggg aga aag ctc ttg gat ctt ctc gaa ggc ctc      336
Ser Asp Leu Lys Asp Gly Arg Lys Leu Leu Asp Leu Leu Glu Gly Leu
            100                 105                 110

aca gga aca tca ttg cca aag gaa cgt ggt tcc aca agg gtg cat gcc      384
Thr Gly Thr Ser Leu Pro Lys Glu Arg Gly Ser Thr Arg Val His Ala
        115                 120                 125
```

-continued

```
tta aac aat gtc aac cga gtg cta cag gtt tta cat cag aac aat gtg      432
Leu Asn Asn Val Asn Arg Val Leu Gln Val Leu His Gln Asn Asn Val
    130                 135                 140

gac ttg gtg aat att gga ggc acg gac att gtg gct gga aat ccc aag      480
Asp Leu Val Asn Ile Gly Gly Thr Asp Ile Val Ala Gly Asn Pro Lys
145                 150                 155                 160

ctg act tta ggg tta ctc tgg agc atc att ctg cac tgg cag gtg aag      528
Leu Thr Leu Gly Leu Leu Trp Ser Ile Ile Leu His Trp Gln Val Lys
                165                 170                 175

gat gtc atg aaa gat atc atg tca gac ctg cag cag aca aac agc gag      576
Asp Val Met Lys Asp Ile Met Ser Asp Leu Gln Gln Thr Asn Ser Glu
            180                 185                 190

aag atc ctg ctg agc tgg gtg cgg cag acc acc agg ccc tac agt caa      624
Lys Ile Leu Leu Ser Trp Val Arg Gln Thr Thr Arg Pro Tyr Ser Gln
        195                 200                 205

gtc aac gtc ctc aac ttc acc acc agc tgg acc gat gga ctc gcg ttc      672
Val Asn Val Leu Asn Phe Thr Thr Ser Trp Thr Asp Gly Leu Ala Phe
    210                 215                 220

aac gcc gtg ctc cac cgg cac aaa cca gat ctc ttc gac tgg gac gag      720
Asn Ala Val Leu His Arg His Lys Pro Asp Leu Phe Asp Trp Asp Glu
225                 230                 235                 240

atg gtc aaa atg tcc cca att gag aga ctt gac cat gct ttt gac aag      768
Met Val Lys Met Ser Pro Ile Glu Arg Leu Asp His Ala Phe Asp Lys
                245                 250                 255

gcc cac act tct ttg gga att gaa aag ctc cta agt cct gaa act gtt      816
Ala His Thr Ser Leu Gly Ile Glu Lys Leu Leu Ser Pro Glu Thr Val
            260                 265                 270

gct gtg cat ctc cct gac aag aaa tcc ata att atg tat tta acg tct      864
Ala Val His Leu Pro Asp Lys Lys Ser Ile Ile Met Tyr Leu Thr Ser
        275                 280                 285

ctg ttt gag gtg ctt cct cag caa gtc acg ata gat gcc atc cga gag      912
Leu Phe Glu Val Leu Pro Gln Gln Val Thr Ile Asp Ala Ile Arg Glu
    290                 295                 300

gtg gag act ctc cca agg aag tat aag aaa gaa tgt gaa gag gaa gaa      960
Val Glu Thr Leu Pro Arg Lys Tyr Lys Lys Glu Cys Glu Glu Glu Glu
305                 310                 315                 320

att cat atc cag agt gca gtg ctg gca gag gaa ggc cag agt ccc cga     1008
Ile His Ile Gln Ser Ala Val Leu Ala Glu Glu Gly Gln Ser Pro Arg
                325                 330                 335

gct gag acc cct agc acc gtc act gaa gtg gac atg gat ttg gac agc     1056
Ala Glu Thr Pro Ser Thr Val Thr Glu Val Asp Met Asp Leu Asp Ser
            340                 345                 350

tac cag ata gcg cta gag gaa gtg ctg acg tgg ctg ctg tcc gcg gag     1104
Tyr Gln Ile Ala Leu Glu Glu Val Leu Thr Trp Leu Leu Ser Ala Glu
        355                 360                 365

gac acg ttc cag gag caa cat gac att tct gat gat gtc gaa gaa gtc     1152
Asp Thr Phe Gln Glu Gln His Asp Ile Ser Asp Asp Val Glu Glu Val
    370                 375                 380

aaa gag cag ttt gct acc cat gaa act ttt atg atg gag ctg aca gca     1200
Lys Glu Gln Phe Ala Thr His Glu Thr Phe Met Met Glu Leu Thr Ala
385                 390                 395                 400

cac cag agc agc gtg ggg agc gtc ctg cag gct ggc aac cag ctg atg     1248
His Gln Ser Ser Val Gly Ser Val Leu Gln Ala Gly Asn Gln Leu Met
                405                 410                 415

aca caa ggg act ctg tcc aga gag gag gag ttt gag atc cag gaa cag     1296
Thr Gln Gly Thr Leu Ser Arg Glu Glu Glu Phe Glu Ile Gln Glu Gln
            420                 425                 430

atg acc ttg ctg aat gca agg tgg gag gcg ctc cgg gtg gag agc atg     1344
Met Thr Leu Leu Asn Ala Arg Trp Glu Ala Leu Arg Val Glu Ser Met
        435                 440                 445
```

```
gag agg cag tcc cgg ctg cac gac gct ctg atg gag ctg cag aag aaa      1392
Glu Arg Gln Ser Arg Leu His Asp Ala Leu Met Glu Leu Gln Lys Lys
    450                 455                 460

cag ctg cag cag ctc tca agc tgg ctg gcc ctc aca gaa gag cgc att      1440
Gln Leu Gln Gln Leu Ser Ser Trp Leu Ala Leu Thr Glu Glu Arg Ile
465                 470                 475                 480

cag aag atg gag agc ctc ccg ctg ggt gat gac ctg ccc tcc ctg cag      1488
Gln Lys Met Glu Ser Leu Pro Leu Gly Asp Asp Leu Pro Ser Leu Gln
                485                 490                 495

aag ctg ctt caa gaa cat aaa agt ttg caa aat gac ctt gaa gct gaa      1536
Lys Leu Leu Gln Glu His Lys Ser Leu Gln Asn Asp Leu Glu Ala Glu
            500                 505                 510

cag gtg aag gta aat tcc tta act cac atg gtg gtg att gtg gat gaa      1584
Gln Val Lys Val Asn Ser Leu Thr His Met Val Val Ile Val Asp Glu
        515                 520                 525

aac agt ggg gag agt gcc aca gct ctt ctg gaa gat cag tta cag aaa      1632
Asn Ser Gly Glu Ser Ala Thr Ala Leu Leu Glu Asp Gln Leu Gln Lys
    530                 535                 540

ctg ggt gag cgc tgg aca gct gta tgc cgc tgg act gaa gaa cgt tgg      1680
Leu Gly Glu Arg Trp Thr Ala Val Cys Arg Trp Thr Glu Glu Arg Trp
545                 550                 555                 560

aac agg ttg caa gaa atc agt att ctg tgg cag gaa tta ttg gaa gag      1728
Asn Arg Leu Gln Glu Ile Ser Ile Leu Trp Gln Glu Leu Leu Glu Glu
                565                 570                 575

cag tgt ctg ttg gag gct tgg ctc acc gaa aag gaa gag gct ttg gat      1776
Gln Cys Leu Leu Glu Ala Trp Leu Thr Glu Lys Glu Glu Ala Leu Asp
            580                 585                 590

aaa gtt caa acc agc aac ttt aaa gac cag aag gaa cta agt gtc agt      1824
Lys Val Gln Thr Ser Asn Phe Lys Asp Gln Lys Glu Leu Ser Val Ser
        595                 600                 605

gtc cgg cgt ctg gct ata ttg aag gaa gac atg gaa atg aag agg cag      1872
Val Arg Arg Leu Ala Ile Leu Lys Glu Asp Met Glu Met Lys Arg Gln
    610                 615                 620

act ctg gat caa ctg agt gag att ggc cag gat gtg ggc caa tta ctc      1920
Thr Leu Asp Gln Leu Ser Glu Ile Gly Gln Asp Val Gly Gln Leu Leu
625                 630                 635                 640

agt aat ccc aag gca tct aag aag atg aac agt gac tct gag gag cta      1968
Ser Asn Pro Lys Ala Ser Lys Lys Met Asn Ser Asp Ser Glu Glu Leu
                645                 650                 655

aca cag aga tgg gat tct ctg gtt cag aga ctc gaa gac tct tct aac      2016
Thr Gln Arg Trp Asp Ser Leu Val Gln Arg Leu Glu Asp Ser Ser Asn
            660                 665                 670

cag gtg act cag gcg gta gcg aag ctc ggc atg tcc cag att cca cag      2064
Gln Val Thr Gln Ala Val Ala Lys Leu Gly Met Ser Gln Ile Pro Gln
        675                 680                 685

aag gac cta ttg gag acc gtt cat gtg aga gaa caa ggg atg gtg aag      2112
Lys Asp Leu Leu Glu Thr Val His Val Arg Glu Gln Gly Met Val Lys
    690                 695                 700

aag ccc aag cag gaa ctg cct cct cct ccc cca cca aag aag aga cag      2160
Lys Pro Lys Gln Glu Leu Pro Pro Pro Pro Pro Pro Lys Lys Arg Gln
705                 710                 715                 720

att cac gtg gac gtg gag gcc aag aaa aag ttt gat gct ata agt aca      2208
Ile His Val Asp Val Glu Ala Lys Lys Lys Phe Asp Ala Ile Ser Thr
                725                 730                 735

gag ctg ctg aac tgg att ttg aaa tca aag act gcc att cag aac aca      2256
Glu Leu Leu Asn Trp Ile Leu Lys Ser Lys Thr Ala Ile Gln Asn Thr
            740                 745                 750

gag atg aaa gaa tat aag aag tcg cag gag acc tca gga atg aaa aag      2304
Glu Met Lys Glu Tyr Lys Lys Ser Gln Glu Thr Ser Gly Met Lys Lys
        755                 760                 765
```

```
aaa ttg aag gga tta gag aaa gaa cag aag gaa aat ctg ccc cga ctg      2352
Lys Leu Lys Gly Leu Glu Lys Glu Gln Lys Glu Asn Leu Pro Arg Leu
    770                 775                 780

gac gaa ctg aat caa acc gga caa acc ctc cgg gag caa atg gga aaa      2400
Asp Glu Leu Asn Gln Thr Gly Gln Thr Leu Arg Glu Gln Met Gly Lys
785                 790                 795                 800

gaa ggc ctt cca ctg aaa gaa gta aac gat gtt ctg gaa agg gtt tcg      2448
Glu Gly Leu Pro Leu Lys Glu Val Asn Asp Val Leu Glu Arg Val Ser
                805                 810                 815

ttg gag tgg aag atg ata tct cag cag cta gaa gat ctg gga agg aag      2496
Leu Glu Trp Lys Met Ile Ser Gln Gln Leu Glu Asp Leu Gly Arg Lys
            820                 825                 830

atc cag ctg cag gaa gat ata aat gct tat ttt aag cag ctt gat gcc      2544
Ile Gln Leu Gln Glu Asp Ile Asn Ala Tyr Phe Lys Gln Leu Asp Ala
        835                 840                 845

att gag gag acc atc aag gag aag gaa gag tgg ctg agg ggc aca ccc      2592
Ile Glu Glu Thr Ile Lys Glu Lys Glu Glu Trp Leu Arg Gly Thr Pro
    850                 855                 860

att tct gaa tcg ccc cgg cag ccc ttg cca ggc tta aag gat tct tgc      2640
Ile Ser Glu Ser Pro Arg Gln Pro Leu Pro Gly Leu Lys Asp Ser Cys
865                 870                 875                 880

cag agg gaa ctg aca gat ctc ctt ggc ctt cac ccc aga att gag acg      2688
Gln Arg Glu Leu Thr Asp Leu Leu Gly Leu His Pro Arg Ile Glu Thr
                885                 890                 895

ctg tgt gca agc tgt tca gcc ctg aag tct cag ccc tgt gtc cca ggt      2736
Leu Cys Ala Ser Cys Ser Ala Leu Lys Ser Gln Pro Cys Val Pro Gly
            900                 905                 910

ttt gtc cag cag ggt ttt gac gac ctt cga cat cat tac cag gct gtt      2784
Phe Val Gln Gln Gly Phe Asp Asp Leu Arg His His Tyr Gln Ala Val
        915                 920                 925

gcg aag gct tta gag gaa tac caa caa caa cta gaa aat gag ctg aag      2832
Ala Lys Ala Leu Glu Glu Tyr Gln Gln Gln Leu Glu Asn Glu Leu Lys
    930                 935                 940

agc cag cct gga ccc gag tat ttg gac aca ctg aat acc ctg aaa aaa      2880
Ser Gln Pro Gly Pro Glu Tyr Leu Asp Thr Leu Asn Thr Leu Lys Lys
945                 950                 955                 960

atg cta agc gag tca gaa aag gcg gcc cag gcc tct ctg aat gcc ctg      2928
Met Leu Ser Glu Ser Glu Lys Ala Ala Gln Ala Ser Leu Asn Ala Leu
                965                 970                 975

aac gat ccc ata gcg gtg gag cag gcc ctg cag gag aaa aag gcc ctt      2976
Asn Asp Pro Ile Ala Val Glu Gln Ala Leu Gln Glu Lys Lys Ala Leu
            980                 985                 990

gat gaa acc ctt gag aat cag aaa  cat acg tta cat aag  ctt tca gaa    3024
Asp Glu Thr Leu Glu Asn Gln Lys  His Thr Leu His Lys  Leu Ser Glu
        995                 1000                1005

gaa acg  aag act ttg gag aaa  aat atg ctt cct gat  gtg ggg aaa      3069
Glu Thr  Lys Thr Leu Glu Lys  Asn Met Leu Pro Asp  Val Gly Lys
    1010                1015                1020

atg tat  aaa caa gaa ttt gat  gat gtc caa ggc aga  tgg aat aaa      3114
Met Tyr  Lys Gln Glu Phe Asp  Asp Val Gln Gly Arg  Trp Asn Lys
    1025                1030                1035

gta aag  acc aag gtt tcc aga  gac tta cac ttg ctc  gag gaa atc      3159
Val Lys  Thr Lys Val Ser Arg  Asp Leu His Leu Leu  Glu Glu Ile
    1040                1045                1050

gcc cac  aga gat ttt ggg cca  tct tct caa cac ttt  ctg tcc act      3204
Ala His  Arg Asp Phe Gly Pro  Ser Ser Gln His Phe  Leu Ser Thr
    1055                1060                1065

tca gtc  cag ctg ccg tgg cag  aga tcc att tca cat  aat aaa gtg      3249
Ser Val  Gln Leu Pro Trp Gln  Arg Ser Ile Ser His  Asn Lys Val
    1070                1075                1080
```

-continued

```
ccc tat  tac atc aac cat caa  aca cag aca acc tgt  tgg gat cat      3294
Pro Tyr  Tyr Ile Asn His Gln  Thr Gln Thr Thr Cys  Trp Asp His
    1085                 1090                 1095

cct aaa  atg act gag ctc ttc  caa tcc ctt gct gat  ctg aat aat      3339
Pro Lys  Met Thr Glu Leu Phe  Gln Ser Leu Ala Asp  Leu Asn Asn
    1100                 1105                 1110

gta cgt  ttc tct gcc tac cgc  aca gca atc aaa att  cga agg ctg      3384
Val Arg  Phe Ser Ala Tyr Arg  Thr Ala Ile Lys Ile  Arg Arg Leu
    1115                 1120                 1125

caa aaa  gca tta tgt ctg gat  ctc tta gag ctg aat  acg acg aat      3429
Gln Lys  Ala Leu Cys Leu Asp  Leu Leu Glu Leu Asn  Thr Thr Asn
    1130                 1135                 1140

gaa gtt  ttc aag cag cac aaa  ctg aac caa aat gat  cag ctc ctg      3474
Glu Val  Phe Lys Gln His Lys  Leu Asn Gln Asn Asp  Gln Leu Leu
    1145                 1150                 1155

agt gtc  cca gac gtc atc aac  tgt ctg acc acc act  tac gat ggg      3519
Ser Val  Pro Asp Val Ile Asn  Cys Leu Thr Thr Thr  Tyr Asp Gly
    1160                 1165                 1170

ctt gag  cag ctg cac aag gac  ttg gtc aat gtt cca  ctc tgc gtc      3564
Leu Glu  Gln Leu His Lys Asp  Leu Val Asn Val Pro  Leu Cys Val
    1175                 1180                 1185

gat atg  tgt ctc aac tgg ctg  ctc aac gta tac gac  acg ggc cgg      3609
Asp Met  Cys Leu Asn Trp Leu  Leu Asn Val Tyr Asp  Thr Gly Arg
    1190                 1195                 1200

act gga  aaa att cgg gta cag  agt ctg aag att gga  ttg atg tct      3654
Thr Gly  Lys Ile Arg Val Gln  Ser Leu Lys Ile Gly  Leu Met Ser
    1205                 1210                 1215

ctc tcc  aaa ggc ctc tta gaa  gag aaa tac aga tgt  ctc ttt aag      3699
Leu Ser  Lys Gly Leu Leu Glu  Glu Lys Tyr Arg Cys  Leu Phe Lys
    1220                 1225                 1230

gag gtg  gca ggg cca act gag  atg tgt gac cag cgg  cag ctt ggc      3744
Glu Val  Ala Gly Pro Thr Glu  Met Cys Asp Gln Arg  Gln Leu Gly
    1235                 1240                 1245

ctg cta  ctt cac gat gcc atc  cag atc cct agg cag  ctg ggg gaa      3789
Leu Leu  Leu His Asp Ala Ile  Gln Ile Pro Arg Gln  Leu Gly Glu
    1250                 1255                 1260

gta gca  gcc ttt ggg ggc agt  aac att gag ccc agt  gtc cgc agc      3834
Val Ala  Ala Phe Gly Gly Ser  Asn Ile Glu Pro Ser  Val Arg Ser
    1265                 1270                 1275

tgc ttc  cag cag aat aac aac  aag cca gaa atc agt  gtg aag gag      3879
Cys Phe  Gln Gln Asn Asn Asn  Lys Pro Glu Ile Ser  Val Lys Glu
    1280                 1285                 1290

ttt ata  gac tgg atg cat ttg  gaa ccc cag tcc atg  gtg tgg ttg      3924
Phe Ile  Asp Trp Met His Leu  Glu Pro Gln Ser Met  Val Trp Leu
    1295                 1300                 1305

ccg gtt  ctg cat cgg gtc gca  gct gct gag act gca  aaa cat cag      3969
Pro Val  Leu His Arg Val Ala  Ala Ala Glu Thr Ala  Lys His Gln
    1310                 1315                 1320

gcc aaa  tgc aac atc tgc aaa  gaa tgc ccg att gtt  ggg ttc aga      4014
Ala Lys  Cys Asn Ile Cys Lys  Glu Cys Pro Ile Val  Gly Phe Arg
    1325                 1330                 1335

tac agg  agc cta aag cat ttt  aat tat gat gtc tgc  cag agt tgc      4059
Tyr Arg  Ser Leu Lys His Phe  Asn Tyr Asp Val Cys  Gln Ser Cys
    1340                 1345                 1350

ttc ttt  tct gga aga aca gca  aag ggc cac aag tta  cat tac ccg      4104
Phe Phe  Ser Gly Arg Thr Ala  Lys Gly His Lys Leu  His Tyr Pro
    1355                 1360                 1365

atg gta  gaa tac tgc ata ccg  aca aca tct ggg gaa  gat gtg aga      4149
Met Val  Glu Tyr Cys Ile Pro  Thr Thr Ser Gly Glu  Asp Val Arg
    1370                 1375                 1380
```

```
gat ttc  act aag gtg ctg aag  aac aag ttc agg tcc  aag aaa tat      4194
Asp Phe  Thr Lys Val Leu Lys  Asn Lys Phe Arg Ser  Lys Lys Tyr
    1385                 1390                 1395

ttt gcc  aaa cat cct cgg ctt  ggc tac ctg cct gtc  cag acc gtg      4239
Phe Ala  Lys His Pro Arg Leu  Gly Tyr Leu Pro Val  Gln Thr Val
    1400                 1405                 1410

ctg gaa  ggg gac aac tta gaa  act cct atc acg ctc  atc agt atg      4284
Leu Glu  Gly Asp Asn Leu Glu  Thr Pro Ile Thr Leu  Ile Ser Met
    1415                 1420                 1425

tgg cca  gag cac tat gac ccc  tcc cag tcc cct cag  ctg ttt cat      4329
Trp Pro  Glu His Tyr Asp Pro  Ser Gln Ser Pro Gln  Leu Phe His
    1430                 1435                 1440

gat gac  acc cac tca aga ata  gag caa tac gct aca  cga ctg gcc      4374
Asp Asp  Thr His Ser Arg Ile  Glu Gln Tyr Ala Thr  Arg Leu Ala
    1445                 1450                 1455

cag atg  gaa agg aca aac ggg  tcc ttc cta act gat  agc agc tct      4419
Gln Met  Glu Arg Thr Asn Gly  Ser Phe Leu Thr Asp  Ser Ser Ser
    1460                 1465                 1470

aca aca  gga agc gtg gag gat  gag cat gcc ctc atc  cag cag tac      4464
Thr Thr  Gly Ser Val Glu Asp  Glu His Ala Leu Ile  Gln Gln Tyr
    1475                 1480                 1485

tgc cag  acc ctg ggc ggg gag  tca cct gtg agt cag  ccg cag agt      4509
Cys Gln  Thr Leu Gly Gly Glu  Ser Pro Val Ser Gln  Pro Gln Ser
    1490                 1495                 1500

cca gct  cag atc ctg aag tcc  gtg gag agg gaa gag  cgt ggg gaa      4554
Pro Ala  Gln Ile Leu Lys Ser  Val Glu Arg Glu Glu  Arg Gly Glu
    1505                 1510                 1515

ctg gag  cgg atc att gct gac  ttg gag gaa gag caa  aga aat ctg      4599
Leu Glu  Arg Ile Ile Ala Asp  Leu Glu Glu Glu Gln  Arg Asn Leu
    1520                 1525                 1530

cag gtg  gag tat gag cag ctg  aag gag cag cac cta  aga agg ggt      4644
Gln Val  Glu Tyr Glu Gln Leu  Lys Glu Gln His Leu  Arg Arg Gly
    1535                 1540                 1545

ctc cct  gtg ggc tcc cct cca  gac tcc atc gta tct  cct cac cac      4689
Leu Pro  Val Gly Ser Pro Pro  Asp Ser Ile Val Ser  Pro His His
    1550                 1555                 1560

aca tct  gag gac tca gaa ctt  ata gca gaa gct aaa  ctc ctg cgg      4734
Thr Ser  Glu Asp Ser Glu Leu  Ile Ala Glu Ala Lys  Leu Leu Arg
    1565                 1570                 1575

cag cac  aaa ggg cgg ctg gag  gcg agg atg caa att  ttg gaa gat      4779
Gln His  Lys Gly Arg Leu Glu  Ala Arg Met Gln Ile  Leu Glu Asp
    1580                 1585                 1590

cac aat  aaa cag ctg gag tct  cag ctg cac cgc ctc  aga cag ctc      4824
His Asn  Lys Gln Leu Glu Ser  Gln Leu His Arg Leu  Arg Gln Leu
    1595                 1600                 1605

ctg gag  cag cct gac tct gac  tcc cgc atc aat ggt  gtc tcc ccc      4869
Leu Glu  Gln Pro Asp Ser Asp  Ser Arg Ile Asn Gly  Val Ser Pro
    1610                 1615                 1620

tgg gct  tcc cca cag cat tct  gca ttg agc tac tca  ctt gac act      4914
Trp Ala  Ser Pro Gln His Ser  Ala Leu Ser Tyr Ser  Leu Asp Thr
    1625                 1630                 1635

gac cca  ggc cca cag ttc cac  cag gca gca tct gag  gac ctg ctg      4959
Asp Pro  Gly Pro Gln Phe His  Gln Ala Ala Ser Glu  Asp Leu Leu
    1640                 1645                 1650

gcc cca  cct cac gac act agc  acg gac ctc acg gac  gtg atg gag      5004
Ala Pro  Pro His Asp Thr Ser  Thr Asp Leu Thr Asp  Val Met Glu
    1655                 1660                 1665

cag atc  aac agc acg ttt ccc  tct tgc agc tca aat  gtc ccc agc      5049
Gln Ile  Asn Ser Thr Phe Pro  Ser Cys Ser Ser Asn  Val Pro Ser
    1670                 1675                 1680
```

```
agg cca  cag gca atg tga                                          5067
Arg Pro  Gln Ala Met
    1685


<210> SEQ ID NO 21
<211> LENGTH: 1688
<212> TYPE: PRT
<213> ORGANISM: Mus musculus

<400> SEQUENCE: 21

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305                 310                 315                 320

Ile His Ile Gln Ser Ala Val Leu Ala Glu Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365
```

```
Asp Thr Phe Gln Glu Gln His Asp Ile Ser Asp Asp Val Glu Glu Val
    370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val His Val Arg Glu Gln Gly Met Val Lys
    690                 695                 700

Lys Pro Lys Gln Glu Leu Pro Pro Pro Pro Pro Pro Lys Lys Arg Gln
705                 710                 715                 720

Ile His Val Asp Val Glu Ala Lys Lys Lys Phe Asp Ala Ile Ser Thr
                725                 730                 735

Glu Leu Leu Asn Trp Ile Leu Lys Ser Lys Thr Ala Ile Gln Asn Thr
            740                 745                 750

Glu Met Lys Glu Tyr Lys Lys Ser Gln Glu Thr Ser Gly Met Lys Lys
        755                 760                 765

Lys Leu Lys Gly Leu Glu Lys Glu Gln Lys Glu Asn Leu Pro Arg Leu
    770                 775                 780

Asp Glu Leu Asn Gln Thr Gly Gln Thr Leu Arg Glu Gln Met Gly Lys
```

```
785                 790                 795                 800

Glu Gly Leu Pro Leu Lys Glu Val Asn Asp Val Leu Glu Arg Val Ser
                805                 810                 815

Leu Glu Trp Lys Met Ile Ser Gln Gln Leu Glu Asp Leu Gly Arg Lys
            820                 825                 830

Ile Gln Leu Gln Glu Asp Ile Asn Ala Tyr Phe Lys Gln Leu Asp Ala
        835                 840                 845

Ile Glu Glu Thr Ile Lys Glu Lys Glu Glu Trp Leu Arg Gly Thr Pro
    850                 855                 860

Ile Ser Glu Ser Pro Arg Gln Pro Leu Pro Gly Leu Lys Asp Ser Cys
865                 870                 875                 880

Gln Arg Glu Leu Thr Asp Leu Leu Gly Leu His Pro Arg Ile Glu Thr
                885                 890                 895

Leu Cys Ala Ser Cys Ser Ala Leu Lys Ser Gln Pro Cys Val Pro Gly
            900                 905                 910

Phe Val Gln Gln Gly Phe Asp Asp Leu Arg His His Tyr Gln Ala Val
        915                 920                 925

Ala Lys Ala Leu Glu Glu Tyr Gln Gln Gln Leu Glu Asn Glu Leu Lys
    930                 935                 940

Ser Gln Pro Gly Pro Glu Tyr Leu Asp Thr Leu Asn Thr Leu Lys Lys
945                 950                 955                 960

Met Leu Ser Glu Ser Glu Lys Ala Ala Gln Ala Ser Leu Asn Ala Leu
                965                 970                 975

Asn Asp Pro Ile Ala Val Glu Gln Ala Leu Gln Glu Lys Lys Ala Leu
            980                 985                 990

Asp Glu Thr Leu Glu Asn Gln Lys  His Thr Leu His Lys  Leu Ser Glu
        995                 1000                1005

Glu Thr  Lys Thr Leu Glu Lys  Asn Met Leu Pro Asp  Val Gly Lys
    1010                 1015                 1020

Met Tyr  Lys Gln Glu Phe Asp  Asp Val Gln Gly Arg  Trp Asn Lys
    1025                 1030                 1035

Val Lys  Thr Lys Val Ser Arg  Asp Leu His Leu Leu  Glu Glu Ile
    1040                 1045                 1050

Ala His  Arg Asp Phe Gly Pro  Ser Ser Gln His Phe  Leu Ser Thr
    1055                 1060                 1065

Ser Val  Gln Leu Pro Trp Gln  Arg Ser Ile Ser His  Asn Lys Val
    1070                 1075                 1080

Pro Tyr  Tyr Ile Asn His Gln  Thr Gln Thr Thr Cys  Trp Asp His
    1085                 1090                 1095

Pro Lys  Met Thr Glu Leu Phe  Gln Ser Leu Ala Asp  Leu Asn Asn
    1100                 1105                 1110

Val Arg  Phe Ser Ala Tyr Arg  Thr Ala Ile Lys Ile  Arg Arg Leu
    1115                 1120                 1125

Gln Lys  Ala Leu Cys Leu Asp  Leu Leu Glu Leu Asn  Thr Thr Asn
    1130                 1135                 1140

Glu Val  Phe Lys Gln His Lys  Leu Asn Gln Asn Asp  Gln Leu Leu
    1145                 1150                 1155

Ser Val  Pro Asp Val Ile Asn  Cys Leu Thr Thr Thr  Tyr Asp Gly
    1160                 1165                 1170

Leu Glu  Gln Leu His Lys Asp  Leu Val Asn Val Pro  Leu Cys Val
    1175                 1180                 1185

Asp Met  Cys Leu Asn Trp Leu  Leu Asn Val Tyr Asp  Thr Gly Arg
    1190                 1195                 1200
```

```
Thr Gly  Lys Ile Arg Val Gln  Ser Leu Lys Ile Gly  Leu Met Ser
    1205                 1210                 1215

Leu Ser  Lys Gly Leu Leu Glu  Glu Lys Tyr Arg Cys  Leu Phe Lys
    1220                 1225                 1230

Glu Val  Ala Gly Pro Thr Glu  Met Cys Asp Gln Arg  Gln Leu Gly
    1235                 1240                 1245

Leu Leu  Leu His Asp Ala Ile  Gln Ile Pro Arg Gln  Leu Gly Glu
    1250                 1255                 1260

Val Ala  Ala Phe Gly Gly Ser  Asn Ile Glu Pro Ser  Val Arg Ser
    1265                 1270                 1275

Cys Phe  Gln Gln Asn Asn Asn  Lys Pro Glu Ile Ser  Val Lys Glu
    1280                 1285                 1290

Phe Ile  Asp Trp Met His Leu  Glu Pro Gln Ser Met  Val Trp Leu
    1295                 1300                 1305

Pro Val  Leu His Arg Val Ala  Ala Ala Glu Thr Ala  Lys His Gln
    1310                 1315                 1320

Ala Lys  Cys Asn Ile Cys Lys  Glu Cys Pro Ile Val  Gly Phe Arg
    1325                 1330                 1335

Tyr Arg  Ser Leu Lys His Phe  Asn Tyr Asp Val Cys  Gln Ser Cys
    1340                 1345                 1350

Phe Phe  Ser Gly Arg Thr Ala  Lys Gly His Lys Leu  His Tyr Pro
    1355                 1360                 1365

Met Val  Glu Tyr Cys Ile Pro  Thr Thr Ser Gly Glu  Asp Val Arg
    1370                 1375                 1380

Asp Phe  Thr Lys Val Leu Lys  Asn Lys Phe Arg Ser  Lys Lys Tyr
    1385                 1390                 1395

Phe Ala  Lys His Pro Arg Leu  Gly Tyr Leu Pro Val  Gln Thr Val
    1400                 1405                 1410

Leu Glu  Gly Asp Asn Leu Glu  Thr Pro Ile Thr Leu  Ile Ser Met
    1415                 1420                 1425

Trp Pro  Glu His Tyr Asp Pro  Ser Gln Ser Pro Gln  Leu Phe His
    1430                 1435                 1440

Asp Asp  Thr His Ser Arg Ile  Glu Gln Tyr Ala Thr  Arg Leu Ala
    1445                 1450                 1455

Gln Met  Glu Arg Thr Asn Gly  Ser Phe Leu Thr Asp  Ser Ser Ser
    1460                 1465                 1470

Thr Thr  Gly Ser Val Glu Asp  Glu His Ala Leu Ile  Gln Gln Tyr
    1475                 1480                 1485

Cys Gln  Thr Leu Gly Gly Glu  Ser Pro Val Ser Gln  Pro Gln Ser
    1490                 1495                 1500

Pro Ala  Gln Ile Leu Lys Ser  Val Glu Arg Glu Glu  Arg Gly Glu
    1505                 1510                 1515

Leu Glu  Arg Ile Ile Ala Asp  Leu Glu Glu Glu Gln  Arg Asn Leu
    1520                 1525                 1530

Gln Val  Glu Tyr Glu Gln Leu  Lys Glu Gln His Leu  Arg Arg Gly
    1535                 1540                 1545

Leu Pro  Val Gly Ser Pro Pro  Asp Ser Ile Val Ser  Pro His His
    1550                 1555                 1560

Thr Ser  Glu Asp Ser Glu Leu  Ile Ala Glu Ala Lys  Leu Leu Arg
    1565                 1570                 1575

Gln His  Lys Gly Arg Leu Glu  Ala Arg Met Gln Ile  Leu Glu Asp
    1580                 1585                 1590

His Asn  Lys Gln Leu Glu Ser  Gln Leu His Arg Leu  Arg Gln Leu
    1595                 1600                 1605
```

```
Leu Glu  Gln Pro Asp Ser Asp  Ser Arg Ile Asn Gly  Val Ser Pro
    1610                1615                1620

Trp Ala  Ser Pro Gln His Ser  Ala Leu Ser Tyr Ser  Leu Asp Thr
    1625                1630                1635

Asp Pro  Gly Pro Gln Phe His  Gln Ala Ala Ser Glu  Asp Leu Leu
    1640                1645                1650

Ala Pro  Pro His Asp Thr Ser  Thr Asp Leu Thr Asp  Val Met Glu
    1655                1660                1665

Gln Ile  Asn Ser Thr Phe Pro  Ser Cys Ser Ser Asn  Val Pro Ser
    1670                1675                1680

Arg Pro  Gln Ala Met
    1685


<210> SEQ ID NO 22
<211> LENGTH: 6027
<212> TYPE: DNA
<213> ORGANISM: Mus musculus
<220> FEATURE:
<221> NAME/KEY: CDS
<222> LOCATION: (1)..(6027)
<220> FEATURE:
<221> NAME/KEY: misc_feature
<222> LOCATION: (1)..(117)

<400> SEQUENCE: 22

atg gac tac aag gac gac gat gac aag ggc tac ggc cgc aag aaa cgc       48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac       96
Arg Gln Arg Arg Arg Gly Gly Ser Thr Met Ser Gly Tyr Pro Tyr Asp
            20                  25                  30

gtc cca gac tat gct ggc tcc atg gcc aag tat ggg gac ctt gaa gcc      144
Val Pro Asp Tyr Ala Gly Ser Met Ala Lys Tyr Gly Asp Leu Glu Ala
        35                  40                  45

agg cct gat gat ggg cag aac gaa ttc agt gac atc att aag tcc aga      192
Arg Pro Asp Asp Gly Gln Asn Glu Phe Ser Asp Ile Ile Lys Ser Arg
    50                  55                  60

tct gat gaa cac aat gat gta cag aag aaa acc ttt acc aaa tgg ata      240
Ser Asp Glu His Asn Asp Val Gln Lys Lys Thr Phe Thr Lys Trp Ile
65                  70                  75                  80

aac gct cga ttt tcc aag agt ggg aaa cca ccc atc agt gat atg ttc      288
Asn Ala Arg Phe Ser Lys Ser Gly Lys Pro Pro Ile Ser Asp Met Phe
                85                  90                  95

tca gac ctc aaa gat ggg aga aag ctc ttg gat ctt ctc gaa ggc ctc      336
Ser Asp Leu Lys Asp Gly Arg Lys Leu Leu Asp Leu Leu Glu Gly Leu
            100                 105                 110

aca gga aca tca ttg cca aag gaa cgt ggt tcc aca agg gtg cat gcc      384
Thr Gly Thr Ser Leu Pro Lys Glu Arg Gly Ser Thr Arg Val His Ala
        115                 120                 125

tta aac aat gtc aac cga gtg cta cag gtt tta cat cag aac aat gtg      432
Leu Asn Asn Val Asn Arg Val Leu Gln Val Leu His Gln Asn Asn Val
    130                 135                 140

gac ttg gtg aat att gga ggc acg gac att gtg gct gga aat ccc aag      480
Asp Leu Val Asn Ile Gly Gly Thr Asp Ile Val Ala Gly Asn Pro Lys
145                 150                 155                 160

ctg act tta ggg tta ctc tgg agc atc att ctg cac tgg cag gtg aag      528
Leu Thr Leu Gly Leu Leu Trp Ser Ile Ile Leu His Trp Gln Val Lys
                165                 170                 175

gat gtc atg aaa gat atc atg tca gac ctg cag cag aca aac agc gag      576
Asp Val Met Lys Asp Ile Met Ser Asp Leu Gln Gln Thr Asn Ser Glu
            180                 185                 190
```

```
aag atc ctg ctg agc tgg gtg cgg cag acc acc agg ccc tac agt caa      624
Lys Ile Leu Leu Ser Trp Val Arg Gln Thr Thr Arg Pro Tyr Ser Gln
        195                 200                 205

gtc aac gtc ctc aac ttc acc acc agc tgg acc gat gga ctc gcg ttc      672
Val Asn Val Leu Asn Phe Thr Thr Ser Trp Thr Asp Gly Leu Ala Phe
    210                 215                 220

aac gcc gtg ctc cac cgg cac aaa cca gat ctc ttc gac tgg gac gag      720
Asn Ala Val Leu His Arg His Lys Pro Asp Leu Phe Asp Trp Asp Glu
225                 230                 235                 240

atg gtc aaa atg tcc cca att gag aga ctt gac cat gct ttt gac aag      768
Met Val Lys Met Ser Pro Ile Glu Arg Leu Asp His Ala Phe Asp Lys
                245                 250                 255

gcc cac act tct ttg gga att gaa aag ctc cta agt cct gaa act gtt      816
Ala His Thr Ser Leu Gly Ile Glu Lys Leu Leu Ser Pro Glu Thr Val
            260                 265                 270

gct gtg cat ctc cct gac aag aaa tcc ata att atg tat tta acg tct      864
Ala Val His Leu Pro Asp Lys Lys Ser Ile Ile Met Tyr Leu Thr Ser
        275                 280                 285

ctg ttt gag gtg ctt cct cag caa gtc acg ata gat gcc atc cga gag      912
Leu Phe Glu Val Leu Pro Gln Gln Val Thr Ile Asp Ala Ile Arg Glu
    290                 295                 300

gtg gag act ctc cca agg aag tat aag aaa gaa tgt gaa gag gaa gaa      960
Val Glu Thr Leu Pro Arg Lys Tyr Lys Lys Glu Cys Glu Glu Glu Glu
305                 310                 315                 320

att cat atc cag agt gca gtg ctg gca gag gaa ggc cag agt ccc cga     1008
Ile His Ile Gln Ser Ala Val Leu Ala Glu Glu Gly Gln Ser Pro Arg
                325                 330                 335

gct gag acc cct agc acc gtc act gaa gtg gac atg gat ttg gac agc     1056
Ala Glu Thr Pro Ser Thr Val Thr Glu Val Asp Met Asp Leu Asp Ser
            340                 345                 350

tac cag ata gcg cta gag gaa gtg ctg acg tgg ctg ctg tcc gcg gag     1104
Tyr Gln Ile Ala Leu Glu Glu Val Leu Thr Trp Leu Leu Ser Ala Glu
        355                 360                 365

gac acg ttc cag gag caa cat gac att tct gat gat gtc gaa gaa gtc     1152
Asp Thr Phe Gln Glu Gln His Asp Ile Ser Asp Asp Val Glu Glu Val
    370                 375                 380

aaa gag cag ttt gct acc cat gaa act ttt atg atg gag ctg aca gca     1200
Lys Glu Gln Phe Ala Thr His Glu Thr Phe Met Met Glu Leu Thr Ala
385                 390                 395                 400

cac cag agc agc gtg ggg agc gtc ctg cag gct ggc aac cag ctg atg     1248
His Gln Ser Ser Val Gly Ser Val Leu Gln Ala Gly Asn Gln Leu Met
                405                 410                 415

aca caa ggg act ctg tcc aga gag gag gag ttt gag atc cag gaa cag     1296
Thr Gln Gly Thr Leu Ser Arg Glu Glu Glu Phe Glu Ile Gln Glu Gln
            420                 425                 430

atg acc ttg ctg aat gca agg tgg gag gcg ctc cgg gtg gag agc atg     1344
Met Thr Leu Leu Asn Ala Arg Trp Glu Ala Leu Arg Val Glu Ser Met
        435                 440                 445

gag agg cag tcc cgg ctg cac gac gct ctg atg gag ctg cag aag aaa     1392
Glu Arg Gln Ser Arg Leu His Asp Ala Leu Met Glu Leu Gln Lys Lys
    450                 455                 460

cag ctg cag cag ctc tca agc tgg ctg gcc ctc aca gaa gag cgc att     1440
Gln Leu Gln Gln Leu Ser Ser Trp Leu Ala Leu Thr Glu Glu Arg Ile
465                 470                 475                 480

cag aag atg gag agc ctc ccg ctg ggt gat gac ctg ccc tcc ctg cag     1488
Gln Lys Met Glu Ser Leu Pro Leu Gly Asp Asp Leu Pro Ser Leu Gln
                485                 490                 495

aag ctg ctt caa gaa cat aaa agt ttg caa aat gac ctt gaa gct gaa     1536
Lys Leu Leu Gln Glu His Lys Ser Leu Gln Asn Asp Leu Glu Ala Glu
            500                 505                 510
```

```
cag gtg aag gta aat tcc tta act cac atg gtg gtg att gtg gat gaa     1584
Gln Val Lys Val Asn Ser Leu Thr His Met Val Val Ile Val Asp Glu
        515                 520                 525

aac agt ggg gag agt gcc aca gct ctt ctg gaa gat cag tta cag aaa     1632
Asn Ser Gly Glu Ser Ala Thr Ala Leu Leu Glu Asp Gln Leu Gln Lys
    530                 535                 540

ctg ggt gag cgc tgg aca gct gta tgc cgc tgg act gaa gaa cgt tgg     1680
Leu Gly Glu Arg Trp Thr Ala Val Cys Arg Trp Thr Glu Glu Arg Trp
545                 550                 555                 560

aac agg ttg caa gaa atc agt att ctg tgg cag gaa tta ttg gaa gag     1728
Asn Arg Leu Gln Glu Ile Ser Ile Leu Trp Gln Glu Leu Leu Glu Glu
                565                 570                 575

cag tgt ctg ttg gag gct tgg ctc acc gaa aag gaa gag gct ttg gat     1776
Gln Cys Leu Leu Glu Ala Trp Leu Thr Glu Lys Glu Glu Ala Leu Asp
            580                 585                 590

aaa gtt caa acc agc aac ttt aaa gac cag aag gaa cta agt gtc agt     1824
Lys Val Gln Thr Ser Asn Phe Lys Asp Gln Lys Glu Leu Ser Val Ser
        595                 600                 605

gtc cgg cgt ctg gct ata ttg aag gaa gac atg gaa atg aag agg cag     1872
Val Arg Arg Leu Ala Ile Leu Lys Glu Asp Met Glu Met Lys Arg Gln
    610                 615                 620

act ctg gat caa ctg agt gag att ggc cag gat gtg ggc caa tta ctc     1920
Thr Leu Asp Gln Leu Ser Glu Ile Gly Gln Asp Val Gly Gln Leu Leu
625                 630                 635                 640

agt aat ccc aag gca tct aag aag atg aac agt gac tct gag gag cta     1968
Ser Asn Pro Lys Ala Ser Lys Lys Met Asn Ser Asp Ser Glu Glu Leu
                645                 650                 655

aca cag aga tgg gat tct ctg gtt cag aga ctc gaa gac tct tct aac     2016
Thr Gln Arg Trp Asp Ser Leu Val Gln Arg Leu Glu Asp Ser Ser Asn
            660                 665                 670

cag gtg act cag gcg gta gcg aag ctc ggc atg tcc cag att cca cag     2064
Gln Val Thr Gln Ala Val Ala Lys Leu Gly Met Ser Gln Ile Pro Gln
        675                 680                 685

aag gac cta ttg gag acc gtt cat gtg aga gaa caa ggg atg gtg aag     2112
Lys Asp Leu Leu Glu Thr Val His Val Arg Glu Gln Gly Met Val Lys
    690                 695                 700

aag ccc aag cag gaa ctg cct cct cct ccc cca cca aag aag aga cag     2160
Lys Pro Lys Gln Glu Leu Pro Pro Pro Pro Pro Pro Lys Lys Arg Gln
705                 710                 715                 720

att cac gtg gac gtg gag gcc aag aaa aag ttt gat gct ata agt aca     2208
Ile His Val Asp Val Glu Ala Lys Lys Lys Phe Asp Ala Ile Ser Thr
                725                 730                 735

gag ctg ctg aac tgg att ttg aaa tca aag act gcc att cag aac aca     2256
Glu Leu Leu Asn Trp Ile Leu Lys Ser Lys Thr Ala Ile Gln Asn Thr
            740                 745                 750

gag atg aaa gaa tat aag aag tcg cag gag acc tca gga atg aaa aag     2304
Glu Met Lys Glu Tyr Lys Lys Ser Gln Glu Thr Ser Gly Met Lys Lys
        755                 760                 765

aaa ttg aag gga tta gag aaa gaa cag aag gaa aat ctg ccc cga ctg     2352
Lys Leu Lys Gly Leu Glu Lys Glu Gln Lys Glu Asn Leu Pro Arg Leu
    770                 775                 780

gac gaa ctg aat caa acc gga caa acc ctc cgg gag caa atg gga aaa     2400
Asp Glu Leu Asn Gln Thr Gly Gln Thr Leu Arg Glu Gln Met Gly Lys
785                 790                 795                 800

gaa ggc ctt cca ctg aaa gaa gta aac gat gtt ctg gaa agg gtt tcg     2448
Glu Gly Leu Pro Leu Lys Glu Val Asn Asp Val Leu Glu Arg Val Ser
                805                 810                 815

ttg gag tgg aag atg ata tct cag cag cta gaa gat ctg gga agg aag     2496
Leu Glu Trp Lys Met Ile Ser Gln Gln Leu Glu Asp Leu Gly Arg Lys
            820                 825                 830
```

```
atc cag ctg cag gaa gat ata aat gct tat ttt aag cag ctt gat gcc     2544
Ile Gln Leu Gln Glu Asp Ile Asn Ala Tyr Phe Lys Gln Leu Asp Ala
        835                 840                 845

att gag gag acc atc aag gag aag gaa gag tgg ctg agg ggc aca ccc     2592
Ile Glu Glu Thr Ile Lys Glu Lys Glu Glu Trp Leu Arg Gly Thr Pro
    850                 855                 860

att tct gaa tcg ccc cgg cag ccc ttg cca ggc tta aag gat tct tgc     2640
Ile Ser Glu Ser Pro Arg Gln Pro Leu Pro Gly Leu Lys Asp Ser Cys
865                 870                 875                 880

cag agg gaa ctg aca gat ctc ctt ggc ctt cac ccc aga att gag acg     2688
Gln Arg Glu Leu Thr Asp Leu Leu Gly Leu His Pro Arg Ile Glu Thr
                885                 890                 895

ctg tgt gca agc tgt tca gcc ctg aag tct cag ccc tgt gtc cca ggt     2736
Leu Cys Ala Ser Cys Ser Ala Leu Lys Ser Gln Pro Cys Val Pro Gly
            900                 905                 910

ttt gtc cag cag ggt ttt gac gac ctt cga cat cat tac cag gct gtt     2784
Phe Val Gln Gln Gly Phe Asp Asp Leu Arg His His Tyr Gln Ala Val
        915                 920                 925

gcg aag gct tta gag gaa tac caa caa caa cta gaa aat gag ctg aag     2832
Ala Lys Ala Leu Glu Glu Tyr Gln Gln Gln Leu Glu Asn Glu Leu Lys
    930                 935                 940

agc cag cct gga ccc gag tat ttg gac aca ctg aat acc ctg aaa aaa     2880
Ser Gln Pro Gly Pro Glu Tyr Leu Asp Thr Leu Asn Thr Leu Lys Lys
945                 950                 955                 960

atg cta agc gag tca gaa aag gcg gcc cag gcc tct ctg aat gcc ctg     2928
Met Leu Ser Glu Ser Glu Lys Ala Ala Gln Ala Ser Leu Asn Ala Leu
                965                 970                 975

aac gat ccc ata gcg gtg gag cag gcc ctg cag gag aaa aag gcc ctt     2976
Asn Asp Pro Ile Ala Val Glu Gln Ala Leu Gln Glu Lys Lys Ala Leu
            980                 985                 990

gat gaa acc ctt gag aat cag aaa  cat acg tta cat aag  ctt tca gaa   3024
Asp Glu Thr Leu Glu Asn Gln Lys  His Thr Leu His Lys  Leu Ser Glu
        995                 1000                1005

gaa acg  aag act ttg gag aaa  aat atg ctt cct gat  gtg ggg aaa     3069
Glu Thr  Lys Thr Leu Glu Lys  Asn Met Leu Pro Asp  Val Gly Lys
    1010                1015                1020

atg tat  aaa caa gaa ttt gat  gat gtc caa ggc aga  tgg aat aaa     3114
Met Tyr  Lys Gln Glu Phe Asp  Asp Val Gln Gly Arg  Trp Asn Lys
    1025                1030                1035

gta aag  acc aag gtt tcc aga  gac tta cac ttg ctc  gag gaa atc     3159
Val Lys  Thr Lys Val Ser Arg  Asp Leu His Leu Leu  Glu Glu Ile
    1040                1045                1050

acc ccc  aga ctc cga gat ttt  gag gct gat tca gaa  gtc att gag     3204
Thr Pro  Arg Leu Arg Asp Phe  Glu Ala Asp Ser Glu  Val Ile Glu
    1055                1060                1065

aag tgg  gtg agt ggc atc aaa  gac ttc ctc atg aaa  gaa cag gct     3249
Lys Trp  Val Ser Gly Ile Lys  Asp Phe Leu Met Lys  Glu Gln Ala
    1070                1075                1080

gcc caa  gga gac gct gct gcg  cag agc cag ctt gac  caa tgt gct     3294
Ala Gln  Gly Asp Ala Ala Ala  Gln Ser Gln Leu Asp  Gln Cys Ala
    1085                1090                1095

acg ttt  gct aat gaa atc gaa  acc atc gag tca tct  ctg aag aac     3339
Thr Phe  Ala Asn Glu Ile Glu  Thr Ile Glu Ser Ser  Leu Lys Asn
    1100                1105                1110

atg agg  gaa gta gag act agc  ctt cag agg tgt cca  gtc act gga     3384
Met Arg  Glu Val Glu Thr Ser  Leu Gln Arg Cys Pro  Val Thr Gly
    1115                1120                1125

gtc aag  aca tgg gta cag gca  aga cta gtg gat tac  caa tcc caa     3429
Val Lys  Thr Trp Val Gln Ala  Arg Leu Val Asp Tyr  Gln Ser Gln
    1130                1135                1140
```

```
ctg gag  aaa ttc agc aaa gag  att gct att caa aaa  agc agg ctg      3474
Leu Glu  Lys Phe Ser Lys Glu  Ile Ala Ile Gln Lys  Ser Arg Leu
    1145                 1150                 1155

tta gat  agt caa gaa aaa gcc  ctg aac ttg aaa aag  gat ttg gct      3519
Leu Asp  Ser Gln Glu Lys Ala  Leu Asn Leu Lys Lys  Asp Leu Ala
    1160                 1165                 1170

gag atg  cag gag tgg atg gca  cag gct gaa gag gac  tac ctg gag      3564
Glu Met  Gln Glu Trp Met Ala  Gln Ala Glu Glu Asp  Tyr Leu Glu
    1175                 1180                 1185

agg gac  ttc gag tac aaa tct  cca gaa gaa ctc gag  agt gcg gtg      3609
Arg Asp  Phe Glu Tyr Lys Ser  Pro Glu Glu Leu Glu  Ser Ala Val
    1190                 1195                 1200

gag gaa  atg aag agg gca aaa  gag gat gtg ctg cag  aag gag gtg      3654
Glu Glu  Met Lys Arg Ala Lys  Glu Asp Val Leu Gln  Lys Glu Val
    1205                 1210                 1215

agg gtg  aaa att ctg aag gac  agc atc aag ctg gtg  gct gcc aag      3699
Arg Val  Lys Ile Leu Lys Asp  Ser Ile Lys Leu Val  Ala Ala Lys
    1220                 1225                 1230

gtg ccc  tct ggt ggc cag gag  ttg acg tcg gaa ttc  aac gag gtg      3744
Val Pro  Ser Gly Gly Gln Glu  Leu Thr Ser Glu Phe  Asn Glu Val
    1235                 1240                 1245

ctg gag  agc tac cag ctt ctg  tgc aat aga att cga  ggg aag tgc      3789
Leu Glu  Ser Tyr Gln Leu Leu  Cys Asn Arg Ile Arg  Gly Lys Cys
    1250                 1255                 1260

cac aca  ctg gag gag gtc tgg  tct tgc tgg gtg gag  ctg ctt cac      3834
His Thr  Leu Glu Glu Val Trp  Ser Cys Trp Val Glu  Leu Leu His
    1265                 1270                 1275

tat ctg  gac ctg gag acc acg  tgg ttg aac acc ttg  gag gag cgc      3879
Tyr Leu  Asp Leu Glu Thr Thr  Trp Leu Asn Thr Leu  Glu Glu Arg
    1280                 1285                 1290

gtg agg  agc acg gag gcc ctg  cct gag agg gca gaa  gct gtt cat      3924
Val Arg  Ser Thr Glu Ala Leu  Pro Glu Arg Ala Glu  Ala Val His
    1295                 1300                 1305

gaa gct  ctg gag tct ctt gag  tct gtt ttg cgc cat  cca gcg gat      3969
Glu Ala  Leu Glu Ser Leu Glu  Ser Val Leu Arg His  Pro Ala Asp
    1310                 1315                 1320

aat cgc  acc cag att cgg gaa  ctt ggg cag act ctg  att gat ggt      4014
Asn Arg  Thr Gln Ile Arg Glu  Leu Gly Gln Thr Leu  Ile Asp Gly
    1325                 1330                 1335

gga atc  ctg gat gac ata atc  agc gag aag ctg gag  gct ttt aac      4059
Gly Ile  Leu Asp Asp Ile Ile  Ser Glu Lys Leu Glu  Ala Phe Asn
    1340                 1345                 1350

agc cgc  tac gaa gag ctg agt  cac ttg gcg gag agc  aaa cag att      4104
Ser Arg  Tyr Glu Glu Leu Ser  His Leu Ala Glu Ser  Lys Gln Ile
    1355                 1360                 1365

tct ttg  gag aag caa gcc cac  aga gat ttt ggg cca  tct tct caa      4149
Ser Leu  Glu Lys Gln Ala His  Arg Asp Phe Gly Pro  Ser Ser Gln
    1370                 1375                 1380

cac ttt  ctg tcc act tca gtc  cag ctg ccg tgg cag  aga tcc att      4194
His Phe  Leu Ser Thr Ser Val  Gln Leu Pro Trp Gln  Arg Ser Ile
    1385                 1390                 1395

tca cat  aat aaa gtg ccc tat  tac atc aac cat caa  aca cag aca      4239
Ser His  Asn Lys Val Pro Tyr  Tyr Ile Asn His Gln  Thr Gln Thr
    1400                 1405                 1410

acc tgt  tgg gat cat cct aaa  atg act gag ctc ttc  caa tcc ctt      4284
Thr Cys  Trp Asp His Pro Lys  Met Thr Glu Leu Phe  Gln Ser Leu
    1415                 1420                 1425

gct gat  ctg aat aat gta cgt  ttc tct gcc tac cgc  aca gca atc      4329
Ala Asp  Leu Asn Asn Val Arg  Phe Ser Ala Tyr Arg  Thr Ala Ile
    1430                 1435                 1440
```

```
aaa att  cga agg ctg caa aaa  gca tta tgt ctg gat  ctc tta gag      4374
Lys Ile  Arg Arg Leu Gln Lys  Ala Leu Cys Leu Asp  Leu Leu Glu
    1445                 1450                 1455

ctg aat  acg acg aat gaa gtt  ttc aag cag cac aaa  ctg aac caa      4419
Leu Asn  Thr Thr Asn Glu Val  Phe Lys Gln His Lys  Leu Asn Gln
    1460                 1465                 1470

aat gat  cag ctc ctg agt gtc  cca gac gtc atc aac  tgt ctg acc      4464
Asn Asp  Gln Leu Leu Ser Val  Pro Asp Val Ile Asn  Cys Leu Thr
    1475                 1480                 1485

acc act  tac gat ggg ctt gag  cag ctg cac aag gac  ttg gtc aat      4509
Thr Thr  Tyr Asp Gly Leu Glu  Gln Leu His Lys Asp  Leu Val Asn
    1490                 1495                 1500

gtt cca  ctc tgc gtc gat atg  tgt ctc aac tgg ctg  ctc aac gta      4554
Val Pro  Leu Cys Val Asp Met  Cys Leu Asn Trp Leu  Leu Asn Val
    1505                 1510                 1515

tac gac  acg ggc cgg act gga  aaa att cgg gta cag  agt ctg aag      4599
Tyr Asp  Thr Gly Arg Thr Gly  Lys Ile Arg Val Gln  Ser Leu Lys
    1520                 1525                 1530

att gga  ttg atg tct ctc tcc  aaa ggc ctc tta gaa  gag aaa tac      4644
Ile Gly  Leu Met Ser Leu Ser  Lys Gly Leu Leu Glu  Glu Lys Tyr
    1535                 1540                 1545

aga tgt  ctc ttt aag gag gtg  gca ggg cca act gag  atg tgt gac      4689
Arg Cys  Leu Phe Lys Glu Val  Ala Gly Pro Thr Glu  Met Cys Asp
    1550                 1555                 1560

cag cgg  cag ctt ggc ctg cta  ctt cac gat gcc atc  cag atc cct      4734
Gln Arg  Gln Leu Gly Leu Leu  Leu His Asp Ala Ile  Gln Ile Pro
    1565                 1570                 1575

agg cag  ctg ggg gaa gta gca  gcc ttt ggg ggc agt  aac att gag      4779
Arg Gln  Leu Gly Glu Val Ala  Ala Phe Gly Gly Ser  Asn Ile Glu
    1580                 1585                 1590

ccc agt  gtc cgc agc tgc ttc  cag cag aat aac aac  aag cca gaa      4824
Pro Ser  Val Arg Ser Cys Phe  Gln Gln Asn Asn Asn  Lys Pro Glu
    1595                 1600                 1605

atc agt  gtg aag gag ttt ata  gac tgg atg cat ttg  gaa ccc cag      4869
Ile Ser  Val Lys Glu Phe Ile  Asp Trp Met His Leu  Glu Pro Gln
    1610                 1615                 1620

tcc atg  gtg tgg ttg ccg gtt  ctg cat cgg gtc gca  gct gct gag      4914
Ser Met  Val Trp Leu Pro Val  Leu His Arg Val Ala  Ala Ala Glu
    1625                 1630                 1635

act gca  aaa cat cag gcc aaa  tgc aac atc tgc aaa  gaa tgc ccg      4959
Thr Ala  Lys His Gln Ala Lys  Cys Asn Ile Cys Lys  Glu Cys Pro
    1640                 1645                 1650

att gtt  ggg ttc aga tac agg  agc cta aag cat ttt  aat tat gat      5004
Ile Val  Gly Phe Arg Tyr Arg  Ser Leu Lys His Phe  Asn Tyr Asp
    1655                 1660                 1665

gtc tgc  cag agt tgc ttc ttt  tct gga aga aca gca  aag ggc cac      5049
Val Cys  Gln Ser Cys Phe Phe  Ser Gly Arg Thr Ala  Lys Gly His
    1670                 1675                 1680

aag tta  cat tac ccg atg gta  gaa tac tgc ata ccg  aca aca tct      5094
Lys Leu  His Tyr Pro Met Val  Glu Tyr Cys Ile Pro  Thr Thr Ser
    1685                 1690                 1695

ggg gaa  gat gtg aga gat ttc  act aag gtg ctg aag  aac aag ttc      5139
Gly Glu  Asp Val Arg Asp Phe  Thr Lys Val Leu Lys  Asn Lys Phe
    1700                 1705                 1710

agg tcc  aag aaa tat ttt gcc  aaa cat cct cgg ctt  ggc tac ctg      5184
Arg Ser  Lys Lys Tyr Phe Ala  Lys His Pro Arg Leu  Gly Tyr Leu
    1715                 1720                 1725

cct gtc  cag acc gtg ctg gaa  ggg gac aac tta gaa  act cct atc      5229
Pro Val  Gln Thr Val Leu Glu  Gly Asp Asn Leu Glu  Thr Pro Ile
    1730                 1735                 1740
```

```
acg ctc  atc agt atg tgg cca  gag cac tat gac ccc  tcc cag tcc      5274
Thr Leu  Ile Ser Met Trp Pro  Glu His Tyr Asp Pro  Ser Gln Ser
    1745                 1750                 1755

cct cag  ctg ttt cat gat gac  acc cac tca aga ata  gag caa tac      5319
Pro Gln  Leu Phe His Asp Asp  Thr His Ser Arg Ile  Glu Gln Tyr
    1760                 1765                 1770

gct aca  cga ctg gcc cag atg  gaa agg aca aac ggg  tcc ttc cta      5364
Ala Thr  Arg Leu Ala Gln Met  Glu Arg Thr Asn Gly  Ser Phe Leu
    1775                 1780                 1785

act gat  agc agc tct aca aca  gga agc gtg gag gat  gag cat gcc      5409
Thr Asp  Ser Ser Ser Thr Thr  Gly Ser Val Glu Asp  Glu His Ala
    1790                 1795                 1800

ctc atc  cag cag tac tgc cag  acc ctg ggc ggg gag  tca cct gtg      5454
Leu Ile  Gln Gln Tyr Cys Gln  Thr Leu Gly Gly Glu  Ser Pro Val
    1805                 1810                 1815

agt cag  ccg cag agt cca gct  cag atc ctg aag tcc  gtg gag agg      5499
Ser Gln  Pro Gln Ser Pro Ala  Gln Ile Leu Lys Ser  Val Glu Arg
    1820                 1825                 1830

gaa gag  cgt ggg gaa ctg gag  cgg atc att gct gac  ttg gag gaa      5544
Glu Glu  Arg Gly Glu Leu Glu  Arg Ile Ile Ala Asp  Leu Glu Glu
    1835                 1840                 1845

gag caa  aga aat ctg cag gtg  gag tat gag cag ctg  aag gag cag      5589
Glu Gln  Arg Asn Leu Gln Val  Glu Tyr Glu Gln Leu  Lys Glu Gln
    1850                 1855                 1860

cac cta  aga agg ggt ctc cct  gtg ggc tcc cct cca  gac tcc atc      5634
His Leu  Arg Arg Gly Leu Pro  Val Gly Ser Pro Pro  Asp Ser Ile
    1865                 1870                 1875

gta tct  cct cac cac aca tct  gag gac tca gaa ctt  ata gca gaa      5679
Val Ser  Pro His His Thr Ser  Glu Asp Ser Glu Leu  Ile Ala Glu
    1880                 1885                 1890

gct aaa  ctc ctg cgg cag cac  aaa ggg cgg ctg gag  gcg agg atg      5724
Ala Lys  Leu Leu Arg Gln His  Lys Gly Arg Leu Glu  Ala Arg Met
    1895                 1900                 1905

caa att  ttg gaa gat cac aat  aaa cag ctg gag tct  cag ctg cac      5769
Gln Ile  Leu Glu Asp His Asn  Lys Gln Leu Glu Ser  Gln Leu His
    1910                 1915                 1920

cgc ctc  aga cag ctc ctg gag  cag cct gac tct gac  tcc cgc atc      5814
Arg Leu  Arg Gln Leu Leu Glu  Gln Pro Asp Ser Asp  Ser Arg Ile
    1925                 1930                 1935

aat ggt  gtc tcc ccc tgg gct  tcc cca cag cat tct  gca ttg agc      5859
Asn Gly  Val Ser Pro Trp Ala  Ser Pro Gln His Ser  Ala Leu Ser
    1940                 1945                 1950

tac tca  ctt gac act gac cca  ggc cca cag ttc cac  cag gca gca      5904
Tyr Ser  Leu Asp Thr Asp Pro  Gly Pro Gln Phe His  Gln Ala Ala
    1955                 1960                 1965

tct gag  gac ctg ctg gcc cca  cct cac gac act agc  acg gac ctc      5949
Ser Glu  Asp Leu Leu Ala Pro  Pro His Asp Thr Ser  Thr Asp Leu
    1970                 1975                 1980

acg gac  gtg atg gag cag atc  aac agc acg ttt ccc  tct tgc agc      5994
Thr Asp  Val Met Glu Gln Ile  Asn Ser Thr Phe Pro  Ser Cys Ser
    1985                 1990                 1995

tca aat  gtc ccc agc agg cca  cag gca atg tga                      6027
Ser Asn  Val Pro Ser Arg Pro  Gln Ala Met
    2000                 2005
```

<210> SEQ ID NO 23
<211> LENGTH: 2008
<212> TYPE: PRT
<213> ORGANISM: Mus musculus

<400> SEQUENCE: 23

```
Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305                 310                 315                 320

Ile His Ile Gln Ser Ala Val Leu Ala Glu Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln His Asp Ile Ser Asp Asp Val Glu Glu Val
    370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Glu Phe Glu Ile Gln Glu Gln
```

```
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val His Val Arg Glu Gln Gly Met Val Lys
    690                 695                 700

Lys Pro Lys Gln Glu Leu Pro Pro Pro Pro Pro Pro Lys Lys Arg Gln
705                 710                 715                 720

Ile His Val Asp Val Glu Ala Lys Lys Lys Phe Asp Ala Ile Ser Thr
                725                 730                 735

Glu Leu Leu Asn Trp Ile Leu Lys Ser Lys Thr Ala Ile Gln Asn Thr
            740                 745                 750

Glu Met Lys Glu Tyr Lys Lys Ser Gln Glu Thr Ser Gly Met Lys Lys
        755                 760                 765

Lys Leu Lys Gly Leu Glu Lys Glu Gln Lys Glu Asn Leu Pro Arg Leu
    770                 775                 780

Asp Glu Leu Asn Gln Thr Gly Gln Thr Leu Arg Glu Gln Met Gly Lys
785                 790                 795                 800

Glu Gly Leu Pro Leu Lys Glu Val Asn Asp Val Leu Glu Arg Val Ser
                805                 810                 815

Leu Glu Trp Lys Met Ile Ser Gln Gln Leu Glu Asp Leu Gly Arg Lys
            820                 825                 830

Ile Gln Leu Gln Glu Asp Ile Asn Ala Tyr Phe Lys Gln Leu Asp Ala
        835                 840                 845
```

```
Ile Glu Glu Thr Ile Lys Glu Lys Glu Glu Trp Leu Arg Gly Thr Pro
    850                 855                 860

Ile Ser Glu Ser Pro Arg Gln Pro Leu Pro Gly Leu Lys Asp Ser Cys
865                 870                 875                 880

Gln Arg Glu Leu Thr Asp Leu Leu Gly Leu His Pro Arg Ile Glu Thr
                885                 890                 895

Leu Cys Ala Ser Cys Ser Ala Leu Lys Ser Gln Pro Cys Val Pro Gly
            900                 905                 910

Phe Val Gln Gln Gly Phe Asp Asp Leu Arg His His Tyr Gln Ala Val
        915                 920                 925

Ala Lys Ala Leu Glu Glu Tyr Gln Gln Gln Leu Glu Asn Glu Leu Lys
    930                 935                 940

Ser Gln Pro Gly Pro Glu Tyr Leu Asp Thr Leu Asn Thr Leu Lys Lys
945                 950                 955                 960

Met Leu Ser Glu Ser Glu Lys Ala Ala Gln Ala Ser Leu Asn Ala Leu
                965                 970                 975

Asn Asp Pro Ile Ala Val Glu Gln Ala Leu Gln Glu Lys Lys Ala Leu
            980                 985                 990

Asp Glu Thr Leu Glu Asn Gln Lys  His Thr Leu His Lys  Leu Ser Glu
        995                 1000                1005

Glu Thr  Lys Thr Leu Glu Lys  Asn Met Leu Pro Asp  Val Gly Lys
    1010                1015                1020

Met Tyr  Lys Gln Glu Phe Asp  Asp Val Gln Gly Arg  Trp Asn Lys
    1025                1030                1035

Val Lys  Thr Lys Val Ser Arg  Asp Leu His Leu Leu  Glu Glu Ile
    1040                1045                1050

Thr Pro  Arg Leu Arg Asp Phe  Glu Ala Asp Ser Glu  Val Ile Glu
    1055                1060                1065

Lys Trp  Val Ser Gly Ile Lys  Asp Phe Leu Met Lys  Glu Gln Ala
    1070                1075                1080

Ala Gln  Gly Asp Ala Ala Ala  Gln Ser Gln Leu Asp  Gln Cys Ala
    1085                1090                1095

Thr Phe  Ala Asn Glu Ile Glu  Thr Ile Glu Ser Ser  Leu Lys Asn
    1100                1105                1110

Met Arg  Glu Val Glu Thr Ser  Leu Gln Arg Cys Pro  Val Thr Gly
    1115                1120                1125

Val Lys  Thr Trp Val Gln Ala  Arg Leu Val Asp Tyr  Gln Ser Gln
    1130                1135                1140

Leu Glu  Lys Phe Ser Lys Glu  Ile Ala Ile Gln Lys  Ser Arg Leu
    1145                1150                1155

Leu Asp  Ser Gln Glu Lys Ala  Leu Asn Leu Lys Lys  Asp Leu Ala
    1160                1165                1170

Glu Met  Gln Glu Trp Met Ala  Gln Ala Glu Glu Asp  Tyr Leu Glu
    1175                1180                1185

Arg Asp  Phe Glu Tyr Lys Ser  Pro Glu Glu Leu Glu  Ser Ala Val
    1190                1195                1200

Glu Glu  Met Lys Arg Ala Lys  Glu Asp Val Leu Gln  Lys Glu Val
    1205                1210                1215

Arg Val  Lys Ile Leu Lys Asp  Ser Ile Lys Leu Val  Ala Ala Lys
    1220                1225                1230

Val Pro  Ser Gly Gly Gln Glu  Leu Thr Ser Glu Phe  Asn Glu Val
    1235                1240                1245

Leu Glu  Ser Tyr Gln Leu Leu  Cys Asn Arg Ile Arg  Gly Lys Cys
    1250                1255                1260
```

```
His Thr  Leu Glu Glu Val Trp  Ser Cys Trp Val Glu  Leu Leu His
    1265                 1270                 1275

Tyr Leu  Asp Leu Glu Thr Thr  Trp Leu Asn Thr Leu  Glu Glu Arg
    1280                 1285                 1290

Val Arg  Ser Thr Glu Ala Leu  Pro Glu Arg Ala Glu  Ala Val His
    1295                 1300                 1305

Glu Ala  Leu Glu Ser Leu Glu  Ser Val Leu Arg His  Pro Ala Asp
    1310                 1315                 1320

Asn Arg  Thr Gln Ile Arg Glu  Leu Gly Gln Thr Leu  Ile Asp Gly
    1325                 1330                 1335

Gly Ile  Leu Asp Asp Ile Ile  Ser Glu Lys Leu Glu  Ala Phe Asn
    1340                 1345                 1350

Ser Arg  Tyr Glu Glu Leu Ser  His Leu Ala Glu Ser  Lys Gln Ile
    1355                 1360                 1365

Ser Leu  Glu Lys Gln Ala His  Arg Asp Phe Gly Pro  Ser Ser Gln
    1370                 1375                 1380

His Phe  Leu Ser Thr Ser Val  Gln Leu Pro Trp Gln  Arg Ser Ile
    1385                 1390                 1395

Ser His  Asn Lys Val Pro Tyr  Tyr Ile Asn His Gln  Thr Gln Thr
    1400                 1405                 1410

Thr Cys  Trp Asp His Pro Lys  Met Thr Glu Leu Phe  Gln Ser Leu
    1415                 1420                 1425

Ala Asp  Leu Asn Asn Val Arg  Phe Ser Ala Tyr Arg  Thr Ala Ile
    1430                 1435                 1440

Lys Ile  Arg Arg Leu Gln Lys  Ala Leu Cys Leu Asp  Leu Leu Glu
    1445                 1450                 1455

Leu Asn  Thr Thr Asn Glu Val  Phe Lys Gln His Lys  Leu Asn Gln
    1460                 1465                 1470

Asn Asp  Gln Leu Leu Ser Val  Pro Asp Val Ile Asn  Cys Leu Thr
    1475                 1480                 1485

Thr Thr  Tyr Asp Gly Leu Glu  Gln Leu His Lys Asp  Leu Val Asn
    1490                 1495                 1500

Val Pro  Leu Cys Val Asp Met  Cys Leu Asn Trp Leu  Leu Asn Val
    1505                 1510                 1515

Tyr Asp  Thr Gly Arg Thr Gly  Lys Ile Arg Val Gln  Ser Leu Lys
    1520                 1525                 1530

Ile Gly  Leu Met Ser Leu Ser  Lys Gly Leu Leu Glu  Glu Lys Tyr
    1535                 1540                 1545

Arg Cys  Leu Phe Lys Glu Val  Ala Gly Pro Thr Glu  Met Cys Asp
    1550                 1555                 1560

Gln Arg  Gln Leu Gly Leu Leu  Leu His Asp Ala Ile  Gln Ile Pro
    1565                 1570                 1575

Arg Gln  Leu Gly Glu Val Ala  Ala Phe Gly Gly Ser  Asn Ile Glu
    1580                 1585                 1590

Pro Ser  Val Arg Ser Cys Phe  Gln Gln Asn Asn Asn  Lys Pro Glu
    1595                 1600                 1605

Ile Ser  Val Lys Glu Phe Ile  Asp Trp Met His Leu  Glu Pro Gln
    1610                 1615                 1620

Ser Met  Val Trp Leu Pro Val  Leu His Arg Val Ala  Ala Ala Glu
    1625                 1630                 1635

Thr Ala  Lys His Gln Ala Lys  Cys Asn Ile Cys Lys  Glu Cys Pro
    1640                 1645                 1650

Ile Val  Gly Phe Arg Tyr Arg  Ser Leu Lys His Phe  Asn Tyr Asp
```

```
    1655                1660                1665

Val Cys  Gln Ser Cys Phe Phe  Ser Gly Arg Thr Ala  Lys Gly His
    1670                1675                1680

Lys Leu  His Tyr Pro Met Val  Glu Tyr Cys Ile Pro  Thr Thr Ser
    1685                1690                1695

Gly Glu  Asp Val Arg Asp Phe  Thr Lys Val Leu Lys  Asn Lys Phe
    1700                1705                1710

Arg Ser  Lys Lys Tyr Phe Ala  Lys His Pro Arg Leu  Gly Tyr Leu
    1715                1720                1725

Pro Val  Gln Thr Val Leu Glu  Gly Asp Asn Leu Glu  Thr Pro Ile
    1730                1735                1740

Thr Leu  Ile Ser Met Trp Pro  Glu His Tyr Asp Pro  Ser Gln Ser
    1745                1750                1755

Pro Gln  Leu Phe His Asp Asp  Thr His Ser Arg Ile  Glu Gln Tyr
    1760                1765                1770

Ala Thr  Arg Leu Ala Gln Met  Glu Arg Thr Asn Gly  Ser Phe Leu
    1775                1780                1785

Thr Asp  Ser Ser Ser Thr Thr  Gly Ser Val Glu Asp  Glu His Ala
    1790                1795                1800

Leu Ile  Gln Gln Tyr Cys Gln  Thr Leu Gly Gly Glu  Ser Pro Val
    1805                1810                1815

Ser Gln  Pro Gln Ser Pro Ala  Gln Ile Leu Lys Ser  Val Glu Arg
    1820                1825                1830

Glu Glu  Arg Gly Glu Leu Glu  Arg Ile Ile Ala Asp  Leu Glu Glu
    1835                1840                1845

Glu Gln  Arg Asn Leu Gln Val  Glu Tyr Glu Gln Leu  Lys Glu Gln
    1850                1855                1860

His Leu  Arg Arg Gly Leu Pro  Val Gly Ser Pro Pro  Asp Ser Ile
    1865                1870                1875

Val Ser  Pro His His Thr Ser  Glu Asp Ser Glu Leu  Ile Ala Glu
    1880                1885                1890

Ala Lys  Leu Leu Arg Gln His  Lys Gly Arg Leu Glu  Ala Arg Met
    1895                1900                1905

Gln Ile  Leu Glu Asp His Asn  Lys Gln Leu Glu Ser  Gln Leu His
    1910                1915                1920

Arg Leu  Arg Gln Leu Leu Glu  Gln Pro Asp Ser Asp  Ser Arg Ile
    1925                1930                1935

Asn Gly  Val Ser Pro Trp Ala  Ser Pro Gln His Ser  Ala Leu Ser
    1940                1945                1950

Tyr Ser  Leu Asp Thr Asp Pro  Gly Pro Gln Phe His  Gln Ala Ala
    1955                1960                1965

Ser Glu  Asp Leu Leu Ala Pro  Pro His Asp Thr Ser  Thr Asp Leu
    1970                1975                1980

Thr Asp  Val Met Glu Gln Ile  Asn Ser Thr Phe Pro  Ser Cys Ser
    1985                1990                1995

Ser Asn  Val Pro Ser Arg Pro  Gln Ala Met
    2000                2005
```

<210> SEQ ID NO 24
<211> LENGTH: 6321
<212> TYPE: DNA
<213> ORGANISM: Mus musculus
<220> FEATURE:
<221> NAME/KEY: CDS
<222> LOCATION: (1)..(6321)
<220> FEATURE:

```
<221> NAME/KEY: misc_feature
<222> LOCATION: (1)..(117)
<223> OTHER INFORMATION: TAT and epitope tag coding sequence

<400> SEQUENCE: 24

atg gac tac aag gac gac gat gac aag ggc tac ggc cgc aag aaa cgc      48
Met Asp Tyr Lys Asp Asp Asp Asp Lys Gly Tyr Gly Arg Lys Lys Arg
1               5                   10                  15

cgc cag cgc cgc cgc ggt gga tcc acc atg tcc ggc tat cca tat gac      96
Arg Gln Arg Arg Arg Gly Gly Ser Thr Met Ser Gly Tyr Pro Tyr Asp
            20                  25                  30

gtc cca gac tat gct ggc tcc atg gcc aag tat ggg gac ctt gaa gcc     144
Val Pro Asp Tyr Ala Gly Ser Met Ala Lys Tyr Gly Asp Leu Glu Ala
        35                  40                  45

agg cct gat gat ggg cag aac gaa ttc agt gac atc att aag tcc aga     192
Arg Pro Asp Asp Gly Gln Asn Glu Phe Ser Asp Ile Ile Lys Ser Arg
    50                  55                  60

tct gat gaa cac aat gat gta cag aag aaa acc ttt acc aaa tgg ata     240
Ser Asp Glu His Asn Asp Val Gln Lys Lys Thr Phe Thr Lys Trp Ile
65                  70                  75                  80

aac gct cga ttt tcc aag agt ggg aaa cca ccc atc agt gat atg ttc     288
Asn Ala Arg Phe Ser Lys Ser Gly Lys Pro Pro Ile Ser Asp Met Phe
                85                  90                  95

tca gac ctc aaa gat ggg aga aag ctc ttg gat ctt ctc gaa ggc ctc     336
Ser Asp Leu Lys Asp Gly Arg Lys Leu Leu Asp Leu Leu Glu Gly Leu
            100                 105                 110

aca gga aca tca ttg cca aag gaa cgt ggt tcc aca agg gtg cat gcc     384
Thr Gly Thr Ser Leu Pro Lys Glu Arg Gly Ser Thr Arg Val His Ala
        115                 120                 125

tta aac aat gtc aac cga gtg cta cag gtt tta cat cag aac aat gtg     432
Leu Asn Asn Val Asn Arg Val Leu Gln Val Leu His Gln Asn Asn Val
    130                 135                 140

gac ttg gtg aat att gga ggc acg gac att gtg gct gga aat ccc aag     480
Asp Leu Val Asn Ile Gly Gly Thr Asp Ile Val Ala Gly Asn Pro Lys
145                 150                 155                 160

ctg act tta ggg tta ctc tgg agc atc att ctg cac tgg cag gtg aag     528
Leu Thr Leu Gly Leu Leu Trp Ser Ile Ile Leu His Trp Gln Val Lys
                165                 170                 175

gat gtc atg aaa gat atc atg tca gac ctg cag cag aca aac agc gag     576
Asp Val Met Lys Asp Ile Met Ser Asp Leu Gln Gln Thr Asn Ser Glu
            180                 185                 190

aag atc ctg ctg agc tgg gtg cgg cag acc acc agg ccc tac agt caa     624
Lys Ile Leu Leu Ser Trp Val Arg Gln Thr Thr Arg Pro Tyr Ser Gln
        195                 200                 205

gtc aac gtc ctc aac ttc acc acc agc tgg acc gat gga ctc gcg ttc     672
Val Asn Val Leu Asn Phe Thr Thr Ser Trp Thr Asp Gly Leu Ala Phe
    210                 215                 220

aac gcc gtg ctc cac cgg cac aaa cca gat ctc ttc gac tgg gac gag     720
Asn Ala Val Leu His Arg His Lys Pro Asp Leu Phe Asp Trp Asp Glu
225                 230                 235                 240

atg gtc aaa atg tcc cca att gag aga ctt gac cat gct ttt gac aag     768
Met Val Lys Met Ser Pro Ile Glu Arg Leu Asp His Ala Phe Asp Lys
                245                 250                 255

gcc cac act tct ttg gga att gaa aag ctc cta agt cct gaa act gtt     816
Ala His Thr Ser Leu Gly Ile Glu Lys Leu Leu Ser Pro Glu Thr Val
            260                 265                 270

gct gtg cat ctc cct gac aag aaa tcc ata att atg tat tta acg tct     864
Ala Val His Leu Pro Asp Lys Lys Ser Ile Ile Met Tyr Leu Thr Ser
        275                 280                 285

ctg ttt gag gtg ctt cct cag caa gtc acg ata gat gcc atc cga gag     912
Leu Phe Glu Val Leu Pro Gln Gln Val Thr Ile Asp Ala Ile Arg Glu
```

```
    290                 295                 300

gtg gag act ctc cca agg aag tat aag aaa gaa tgt gaa gag gaa gaa      960
Val Glu Thr Leu Pro Arg Lys Tyr Lys Lys Glu Cys Glu Glu Glu Glu
305                 310                 315                 320

att cat atc cag agt gca gtg ctg gca gag gaa ggc cag agt ccc cga     1008
Ile His Ile Gln Ser Ala Val Leu Ala Glu Glu Gly Gln Ser Pro Arg
                325                 330                 335

gct gag acc cct agc acc gtc act gaa gtg gac atg gat ttg gac agc     1056
Ala Glu Thr Pro Ser Thr Val Thr Glu Val Asp Met Asp Leu Asp Ser
            340                 345                 350

tac cag ata gcg cta gag gaa gtg ctg acg tgg ctg ctg tcc gcg gag     1104
Tyr Gln Ile Ala Leu Glu Glu Val Leu Thr Trp Leu Leu Ser Ala Glu
        355                 360                 365

gac acg ttc cag gag caa cat gac att tct gat gat gtc gaa gaa gtc     1152
Asp Thr Phe Gln Glu Gln His Asp Ile Ser Asp Asp Val Glu Glu Val
    370                 375                 380

aaa gag cag ttt gct acc cat gaa act ttt atg atg gag ctg aca gca     1200
Lys Glu Gln Phe Ala Thr His Glu Thr Phe Met Met Glu Leu Thr Ala
385                 390                 395                 400

cac cag agc agc gtg ggg agc gtc ctg cag gct ggc aac cag ctg atg     1248
His Gln Ser Ser Val Gly Ser Val Leu Gln Ala Gly Asn Gln Leu Met
                405                 410                 415

aca caa ggg act ctg tcc aga gag gag gag ttt gag atc cag gaa cag     1296
Thr Gln Gly Thr Leu Ser Arg Glu Glu Glu Phe Glu Ile Gln Glu Gln
            420                 425                 430

atg acc ttg ctg aat gca agg tgg gag gcg ctc cgg gtg gag agc atg     1344
Met Thr Leu Leu Asn Ala Arg Trp Glu Ala Leu Arg Val Glu Ser Met
        435                 440                 445

gag agg cag tcc cgg ctg cac gac gct ctg atg gag ctg cag aag aaa     1392
Glu Arg Gln Ser Arg Leu His Asp Ala Leu Met Glu Leu Gln Lys Lys
    450                 455                 460

cag ctg cag cag ctc tca agc tgg ctg gcc ctc aca gaa gag cgc att     1440
Gln Leu Gln Gln Leu Ser Ser Trp Leu Ala Leu Thr Glu Glu Arg Ile
465                 470                 475                 480

cag aag atg gag agc ctc ccg ctg ggt gat gac ctg ccc tcc ctg cag     1488
Gln Lys Met Glu Ser Leu Pro Leu Gly Asp Asp Leu Pro Ser Leu Gln
                485                 490                 495

aag ctg ctt caa gaa cat aaa agt ttg caa aat gac ctt gaa gct gaa     1536
Lys Leu Leu Gln Glu His Lys Ser Leu Gln Asn Asp Leu Glu Ala Glu
            500                 505                 510

cag gtg aag gta aat tcc tta act cac atg gtg gtg att gtg gat gaa     1584
Gln Val Lys Val Asn Ser Leu Thr His Met Val Val Ile Val Asp Glu
        515                 520                 525

aac agt ggg gag agt gcc aca gct ctt ctg gaa gat cag tta cag aaa     1632
Asn Ser Gly Glu Ser Ala Thr Ala Leu Leu Glu Asp Gln Leu Gln Lys
    530                 535                 540

ctg ggt gag cgc tgg aca gct gta tgc cgc tgg act gaa gaa cgt tgg     1680
Leu Gly Glu Arg Trp Thr Ala Val Cys Arg Trp Thr Glu Glu Arg Trp
545                 550                 555                 560

aac agg ttg caa gaa atc agt att ctg tgg cag gaa tta ttg gaa gag     1728
Asn Arg Leu Gln Glu Ile Ser Ile Leu Trp Gln Glu Leu Leu Glu Glu
                565                 570                 575

cag tgt ctg ttg gag gct tgg ctc acc gaa aag gaa gag gct ttg gat     1776
Gln Cys Leu Leu Glu Ala Trp Leu Thr Glu Lys Glu Glu Ala Leu Asp
            580                 585                 590

aaa gtt caa acc agc aac ttt aaa gac cag aag gaa cta agt gtc agt     1824
Lys Val Gln Thr Ser Asn Phe Lys Asp Gln Lys Glu Leu Ser Val Ser
        595                 600                 605

gtc cgg cgt ctg gct ata ttg aag gaa gac atg gaa atg aag agg cag     1872
Val Arg Arg Leu Ala Ile Leu Lys Glu Asp Met Glu Met Lys Arg Gln
```

```
    610                 615                 620

act ctg gat caa ctg agt gag att ggc cag gat gtg ggc caa tta ctc      1920
Thr Leu Asp Gln Leu Ser Glu Ile Gly Gln Asp Val Gly Gln Leu Leu
625                 630                 635                 640

agt aat ccc aag gca tct aag aag atg aac agt gac tct gag gag cta      1968
Ser Asn Pro Lys Ala Ser Lys Lys Met Asn Ser Asp Ser Glu Glu Leu
                645                 650                 655

aca cag aga tgg gat tct ctg gtt cag aga ctc gaa gac tct tct aac      2016
Thr Gln Arg Trp Asp Ser Leu Val Gln Arg Leu Glu Asp Ser Ser Asn
            660                 665                 670

cag gtg act cag gcg gta gcg aag ctc ggc atg tcc cag att cca cag      2064
Gln Val Thr Gln Ala Val Ala Lys Leu Gly Met Ser Gln Ile Pro Gln
        675                 680                 685

aag gac cta ttg gag acc gtt cat gtg aga gaa caa ggg atg gtg aag      2112
Lys Asp Leu Leu Glu Thr Val His Val Arg Glu Gln Gly Met Val Lys
    690                 695                 700

aag ccc aag cag gaa ctg cct cct cct ccc cca cca aag aag aga cag      2160
Lys Pro Lys Gln Glu Leu Pro Pro Pro Pro Pro Pro Lys Lys Arg Gln
705                 710                 715                 720

att cac gtg gac gtg gag gcc aag aaa aag ttt gat gct ata agt aca      2208
Ile His Val Asp Val Glu Ala Lys Lys Lys Phe Asp Ala Ile Ser Thr
                725                 730                 735

gag ctg ctg aac tgg att ttg aaa tca aag act gcc att cag aac aca      2256
Glu Leu Leu Asn Trp Ile Leu Lys Ser Lys Thr Ala Ile Gln Asn Thr
            740                 745                 750

gag atg aaa gaa tat aag aag tcg cag gag acc tca gga atg aaa aag      2304
Glu Met Lys Glu Tyr Lys Lys Ser Gln Glu Thr Ser Gly Met Lys Lys
        755                 760                 765

aaa ttg aag gga tta gag aaa gaa cag aag gaa aat ctg ccc cga ctg      2352
Lys Leu Lys Gly Leu Glu Lys Glu Gln Lys Glu Asn Leu Pro Arg Leu
    770                 775                 780

gac gaa ctg aat caa acc gga caa acc ctc cgg gag caa atg gga aaa      2400
Asp Glu Leu Asn Gln Thr Gly Gln Thr Leu Arg Glu Gln Met Gly Lys
785                 790                 795                 800

gaa ggc ctt cca ctg aaa gaa gta aac gat gtt ctg gaa agg gtt tcg      2448
Glu Gly Leu Pro Leu Lys Glu Val Asn Asp Val Leu Glu Arg Val Ser
                805                 810                 815

ttg gag tgg aag atg ata tct cag cag cta gaa gat ctg gga agg aag      2496
Leu Glu Trp Lys Met Ile Ser Gln Gln Leu Glu Asp Leu Gly Arg Lys
            820                 825                 830

atc cag ctg cag gaa gat ata aat gct tat ttt aag cag ctt gat gcc      2544
Ile Gln Leu Gln Glu Asp Ile Asn Ala Tyr Phe Lys Gln Leu Asp Ala
        835                 840                 845

att gag gag acc atc aag gag aag gaa gag tgg ctg agg ggc aca ccc      2592
Ile Glu Glu Thr Ile Lys Glu Lys Glu Glu Trp Leu Arg Gly Thr Pro
    850                 855                 860

att tct gaa tcg ccc cgg cag ccc ttg cca ggc tta aag gat tct tgc      2640
Ile Ser Glu Ser Pro Arg Gln Pro Leu Pro Gly Leu Lys Asp Ser Cys
865                 870                 875                 880

cag agg gaa ctg aca gat ctc ctt ggc ctt cac ccc aga att gag acg      2688
Gln Arg Glu Leu Thr Asp Leu Leu Gly Leu His Pro Arg Ile Glu Thr
                885                 890                 895

ctg tgt gca agc tgt tca gcc ctg aag tct cag ccc tgt gtc cca ggt      2736
Leu Cys Ala Ser Cys Ser Ala Leu Lys Ser Gln Pro Cys Val Pro Gly
            900                 905                 910

ttt gtc cag cag ggt ttt gac gac ctt cga cat cat tac cag gct gtt      2784
Phe Val Gln Gln Gly Phe Asp Asp Leu Arg His His Tyr Gln Ala Val
        915                 920                 925

gcg aag gct tta gag gaa tac caa caa caa cta gaa aat gag ctg aag      2832
Ala Lys Ala Leu Glu Glu Tyr Gln Gln Gln Leu Glu Asn Glu Leu Lys
```

```
    930                 935                 940

agc cag cct gga ccc gag tat ttg gac aca ctg aat acc ctg aaa aaa     2880
Ser Gln Pro Gly Pro Glu Tyr Leu Asp Thr Leu Asn Thr Leu Lys Lys
945                 950                 955                 960

atg cta agc gag tca gaa aag gcg gcc cag gcc tct ctg aat gcc ctg     2928
Met Leu Ser Glu Ser Glu Lys Ala Ala Gln Ala Ser Leu Asn Ala Leu
                965                 970                 975

aac gat ccc ata gcg gtg gag cag gcc ctg cag gag aaa aag gcc ctt     2976
Asn Asp Pro Ile Ala Val Glu Gln Ala Leu Gln Glu Lys Lys Ala Leu
            980                 985                 990

gat gaa acc ctt gag aat cag aaa  cat acg tta cat aag  ctt tca gaa   3024
Asp Glu Thr Leu Glu Asn Gln Lys  His Thr Leu His Lys  Leu Ser Glu
        995                 1000                1005

gaa acg  aag act ttg gag aaa  aat atg ctt cct gat  gtg ggg aaa      3069
Glu Thr  Lys Thr Leu Glu Lys  Asn Met Leu Pro Asp  Val Gly Lys
    1010                1015                1020

atg tat  aaa caa gaa ttt gat  gat gtc caa ggc aga  tgg aat aaa      3114
Met Tyr  Lys Gln Glu Phe Asp  Asp Val Gln Gly Arg  Trp Asn Lys
    1025                1030                1035

gta aag  acc aag gtt tcc aga  gac tta cac ttg ctc  gag gaa atc      3159
Val Lys  Thr Lys Val Ser Arg  Asp Leu His Leu Leu  Glu Glu Ile
    1040                1045                1050

acc ccc  aga ctc cga gat ttt  gag gct gat tca gaa  gtc att gag      3204
Thr Pro  Arg Leu Arg Asp Phe  Glu Ala Asp Ser Glu  Val Ile Glu
    1055                1060                1065

aag tgg  gtg agt ggc atc aaa  gac ttc ctc atg aaa  gaa cag gct      3249
Lys Trp  Val Ser Gly Ile Lys  Asp Phe Leu Met Lys  Glu Gln Ala
    1070                1075                1080

gcc caa  gga gac gct gct gcg  cag agc cag ctt gac  caa tgt gct      3294
Ala Gln  Gly Asp Ala Ala Ala  Gln Ser Gln Leu Asp  Gln Cys Ala
    1085                1090                1095

acg ttt  gct aat gaa atc gaa  acc atc gag tca tct  ctg aag aac      3339
Thr Phe  Ala Asn Glu Ile Glu  Thr Ile Glu Ser Ser  Leu Lys Asn
    1100                1105                1110

atg agg  gaa gta gag act agc  ctt cag agg tgt cca  gtc act gga      3384
Met Arg  Glu Val Glu Thr Ser  Leu Gln Arg Cys Pro  Val Thr Gly
    1115                1120                1125

gtc aag  aca tgg gta cag gca  aga cta gtg gat tac  caa tcc caa      3429
Val Lys  Thr Trp Val Gln Ala  Arg Leu Val Asp Tyr  Gln Ser Gln
    1130                1135                1140

ctg gag  aaa ttc agc aaa gag  att gct att caa aaa  agc agg ctg      3474
Leu Glu  Lys Phe Ser Lys Glu  Ile Ala Ile Gln Lys  Ser Arg Leu
    1145                1150                1155

tta gat  agt caa gaa aaa gcc  ctg aac ttg aaa aag  gat ttg gct      3519
Leu Asp  Ser Gln Glu Lys Ala  Leu Asn Leu Lys Lys  Asp Leu Ala
    1160                1165                1170

gag atg  cag gag tgg atg gca  cag gct gaa gag gac  tac ctg gag      3564
Glu Met  Gln Glu Trp Met Ala  Gln Ala Glu Glu Asp  Tyr Leu Glu
    1175                1180                1185

agg gac  ttc gag tac aaa tct  cca gaa gaa ctc gag  agt gcg gtg      3609
Arg Asp  Phe Glu Tyr Lys Ser  Pro Glu Glu Leu Glu  Ser Ala Val
    1190                1195                1200

gag gaa  atg aag agg gca aaa  gag gat gtg ctg cag  aag gag gtg      3654
Glu Glu  Met Lys Arg Ala Lys  Glu Asp Val Leu Gln  Lys Glu Val
    1205                1210                1215

agg gtg  aaa att ctg aag gac  agc atc aag ctg gtg  gct gcc aag      3699
Arg Val  Lys Ile Leu Lys Asp  Ser Ile Lys Leu Val  Ala Ala Lys
    1220                1225                1230

gtg ccc  tct ggt ggc cag gag  ttg acg tcg gaa ttc  aac gag gtg      3744
Val Pro  Ser Gly Gly Gln Glu  Leu Thr Ser Glu Phe  Asn Glu Val
```

```
    1235                1240                1245

ctg gag  agc tac cag ctt ctg  tgc aat aga att cga  ggg aag tgc      3789
Leu Glu  Ser Tyr Gln Leu Leu  Cys Asn Arg Ile Arg  Gly Lys Cys
    1250                1255                1260

cac aca  ctg gag gag gtc tgg  tct tgc tgg gtg gag  ctg ctt cac      3834
His Thr  Leu Glu Glu Val Trp  Ser Cys Trp Val Glu  Leu Leu His
    1265                1270                1275

tat ctg  gac ctg gag acc acg  tgg ttg aac acc ttg  gag gag cgc      3879
Tyr Leu  Asp Leu Glu Thr Thr  Trp Leu Asn Thr Leu  Glu Glu Arg
    1280                1285                1290

gtg agg  agc acg gag gcc ctg  cct gag agg gca gaa  gct gtt cat      3924
Val Arg  Ser Thr Glu Ala Leu  Pro Glu Arg Ala Glu  Ala Val His
    1295                1300                1305

gaa gct  ctg gag tct ctt gag  tct gtt ttg cgc cat  cca gcg gat      3969
Glu Ala  Leu Glu Ser Leu Glu  Ser Val Leu Arg His  Pro Ala Asp
    1310                1315                1320

aat cgc  acc cag att cgg gaa  ctt ggg cag act ctg  att gat ggt      4014
Asn Arg  Thr Gln Ile Arg Glu  Leu Gly Gln Thr Leu  Ile Asp Gly
    1325                1330                1335

gga atc  ctg gat gac ata atc  agc gag aag ctg gag  gct ttt aac      4059
Gly Ile  Leu Asp Asp Ile Ile  Ser Glu Lys Leu Glu  Ala Phe Asn
    1340                1345                1350

agc cgc  tac gaa gag ctg agt  cac ttg gcg gag agc  aaa cag att      4104
Ser Arg  Tyr Glu Glu Leu Ser  His Leu Ala Glu Ser  Lys Gln Ile
    1355                1360                1365

tct ttg  gag aag caa ctc cag  gtc ctc cgc gaa act  gac cac atg      4149
Ser Leu  Glu Lys Gln Leu Gln  Val Leu Arg Glu Thr  Asp His Met
    1370                1375                1380

ctt cag  gtg ctg aag gag agc  ctg ggg gag ctg gac  aaa cag ctt      4194
Leu Gln  Val Leu Lys Glu Ser  Leu Gly Glu Leu Asp  Lys Gln Leu
    1385                1390                1395

acc aca  tac ctg acg gac agg  atc gat gcc ttc caa  ctg cca cag      4239
Thr Thr  Tyr Leu Thr Asp Arg  Ile Asp Ala Phe Gln  Leu Pro Gln
    1400                1405                1410

gaa gct  cag aag atc caa gcc  gaa atc tca gcc cat  gag ctc acc      4284
Glu Ala  Gln Lys Ile Gln Ala  Glu Ile Ser Ala His  Glu Leu Thr
    1415                1420                1425

ctg gag  gag ctg agg aag aat  gtg cgc tcc cag ccc  ccg acg tcc      4329
Leu Glu  Glu Leu Arg Lys Asn  Val Arg Ser Gln Pro  Pro Thr Ser
    1430                1435                1440

cct gag  ggc agg gcc acc aga  gga gga agt cag atg  gac atg cta      4374
Pro Glu  Gly Arg Ala Thr Arg  Gly Gly Ser Gln Met  Asp Met Leu
    1445                1450                1455

cag agg  aaa ctt cga gag gtc  tcc acc aaa ttc cag  ctt gcc cac      4419
Gln Arg  Lys Leu Arg Glu Val  Ser Thr Lys Phe Gln  Leu Ala His
    1460                1465                1470

aga gat  ttt ggg cca tct tct  caa cac ttt ctg tcc  act tca gtc      4464
Arg Asp  Phe Gly Pro Ser Ser  Gln His Phe Leu Ser  Thr Ser Val
    1475                1480                1485

cag ctg  ccg tgg cag aga tcc  att tca cat aat aaa  gtg ccc tat      4509
Gln Leu  Pro Trp Gln Arg Ser  Ile Ser His Asn Lys  Val Pro Tyr
    1490                1495                1500

tac atc  aac cat caa aca cag  aca acc tgt tgg gat  cat cct aaa      4554
Tyr Ile  Asn His Gln Thr Gln  Thr Thr Cys Trp Asp  His Pro Lys
    1505                1510                1515

atg act  gag ctc ttc caa tcc  ctt gct gat ctg aat  aat gta cgt      4599
Met Thr  Glu Leu Phe Gln Ser  Leu Ala Asp Leu Asn  Asn Val Arg
    1520                1525                1530

ttc tct  gcc tac cgc aca gca  atc aaa att cga agg  ctg caa aaa      4644
Phe Ser  Ala Tyr Arg Thr Ala  Ile Lys Ile Arg Arg  Leu Gln Lys
```

```
    1535                1540                1545

gca tta  tgt ctg gat ctc tta  gag ctg aat acg acg  aat gaa gtt      4689
Ala Leu  Cys Leu Asp Leu Leu  Glu Leu Asn Thr Thr  Asn Glu Val
    1550                1555                1560

ttc aag  cag cac aaa ctg aac  caa aat gat cag ctc  ctg agt gtc      4734
Phe Lys  Gln His Lys Leu Asn  Gln Asn Asp Gln Leu  Leu Ser Val
    1565                1570                1575

cca gac  gtc atc aac tgt ctg  acc acc act tac gat  ggg ctt gag      4779
Pro Asp  Val Ile Asn Cys Leu  Thr Thr Thr Tyr Asp  Gly Leu Glu
    1580                1585                1590

cag ctg  cac aag gac ttg gtc  aat gtt cca ctc tgc  gtc gat atg      4824
Gln Leu  His Lys Asp Leu Val  Asn Val Pro Leu Cys  Val Asp Met
    1595                1600                1605

tgt ctc  aac tgg ctg ctc aac  gta tac gac acg ggc  cgg act gga      4869
Cys Leu  Asn Trp Leu Leu Asn  Val Tyr Asp Thr Gly  Arg Thr Gly
    1610                1615                1620

aaa att  cgg gta cag agt ctg  aag att gga ttg atg  tct ctc tcc      4914
Lys Ile  Arg Val Gln Ser Leu  Lys Ile Gly Leu Met  Ser Leu Ser
    1625                1630                1635

aaa ggc  ctc tta gaa gag aaa  tac aga tgt ctc ttt  aag gag gtg      4959
Lys Gly  Leu Leu Glu Glu Lys  Tyr Arg Cys Leu Phe  Lys Glu Val
    1640                1645                1650

gca ggg  cca act gag atg tgt  gac cag cgg cag ctt  ggc ctg cta      5004
Ala Gly  Pro Thr Glu Met Cys  Asp Gln Arg Gln Leu  Gly Leu Leu
    1655                1660                1665

ctt cac  gat gcc atc cag atc  cct agg cag ctg ggg  gaa gta gca      5049
Leu His  Asp Ala Ile Gln Ile  Pro Arg Gln Leu Gly  Glu Val Ala
    1670                1675                1680

gcc ttt  ggg ggc agt aac att  gag ccc agt gtc cgc  agc tgc ttc      5094
Ala Phe  Gly Gly Ser Asn Ile  Glu Pro Ser Val Arg  Ser Cys Phe
    1685                1690                1695

cag cag  aat aac aac aag cca  gaa atc agt gtg aag  gag ttt ata      5139
Gln Gln  Asn Asn Asn Lys Pro  Glu Ile Ser Val Lys  Glu Phe Ile
    1700                1705                1710

gac tgg  atg cat ttg gaa ccc  cag tcc atg gtg tgg  ttg ccg gtt      5184
Asp Trp  Met His Leu Glu Pro  Gln Ser Met Val Trp  Leu Pro Val
    1715                1720                1725

ctg cat  cgg gtc gca gct gct  gag act gca aaa cat  cag gcc aaa      5229
Leu His  Arg Val Ala Ala Ala  Glu Thr Ala Lys His  Gln Ala Lys
    1730                1735                1740

tgc aac  atc tgc aaa gaa tgc  ccg att gtt ggg ttc  aga tac agg      5274
Cys Asn  Ile Cys Lys Glu Cys  Pro Ile Val Gly Phe  Arg Tyr Arg
    1745                1750                1755

agc cta  aag cat ttt aat tat  gat gtc tgc cag agt  tgc ttc ttt      5319
Ser Leu  Lys His Phe Asn Tyr  Asp Val Cys Gln Ser  Cys Phe Phe
    1760                1765                1770

tct gga  aga aca gca aag ggc  cac aag tta cat tac  ccg atg gta      5364
Ser Gly  Arg Thr Ala Lys Gly  His Lys Leu His Tyr  Pro Met Val
    1775                1780                1785

gaa tac  tgc ata ccg aca aca  tct ggg gaa gat gtg  aga gat ttc      5409
Glu Tyr  Cys Ile Pro Thr Thr  Ser Gly Glu Asp Val  Arg Asp Phe
    1790                1795                1800

act aag  gtg ctg aag aac aag  ttc agg tcc aag aaa  tat ttt gcc      5454
Thr Lys  Val Leu Lys Asn Lys  Phe Arg Ser Lys Lys  Tyr Phe Ala
    1805                1810                1815

aaa cat  cct cgg ctt ggc tac  ctg cct gtc cag acc  gtg ctg gaa      5499
Lys His  Pro Arg Leu Gly Tyr  Leu Pro Val Gln Thr  Val Leu Glu
    1820                1825                1830

ggg gac  aac tta gaa act cct  atc acg ctc atc agt  atg tgg cca      5544
Gly Asp  Asn Leu Glu Thr Pro  Ile Thr Leu Ile Ser  Met Trp Pro
```

```
    1835                1840                1845

gag cac  tat gac ccc tcc cag  tcc cct cag ctg ttt  cat gat gac      5589
Glu His  Tyr Asp Pro Ser Gln  Ser Pro Gln Leu Phe  His Asp Asp
    1850                1855                1860

acc cac  tca aga ata gag caa  tac gct aca cga ctg  gcc cag atg      5634
Thr His  Ser Arg Ile Glu Gln  Tyr Ala Thr Arg Leu  Ala Gln Met
    1865                1870                1875

gaa agg  aca aac ggg tcc ttc  cta act gat agc agc  tct aca aca      5679
Glu Arg  Thr Asn Gly Ser Phe  Leu Thr Asp Ser Ser  Ser Thr Thr
    1880                1885                1890

gga agc  gtg gag gat gag cat  gcc ctc atc cag cag  tac tgc cag      5724
Gly Ser  Val Glu Asp Glu His  Ala Leu Ile Gln Gln  Tyr Cys Gln
    1895                1900                1905

acc ctg  ggc ggg gag tca cct  gtg agt cag ccg cag  agt cca gct      5769
Thr Leu  Gly Gly Glu Ser Pro  Val Ser Gln Pro Gln  Ser Pro Ala
    1910                1915                1920

cag atc  ctg aag tcc gtg gag  agg gaa gag cgt ggg  gaa ctg gag      5814
Gln Ile  Leu Lys Ser Val Glu  Arg Glu Glu Arg Gly  Glu Leu Glu
    1925                1930                1935

cgg atc  att gct gac ttg gag  gaa gag caa aga aat  ctg cag gtg      5859
Arg Ile  Ile Ala Asp Leu Glu  Glu Glu Gln Arg Asn  Leu Gln Val
    1940                1945                1950

gag tat  gag cag ctg aag gag  cag cac cta aga agg  ggt ctc cct      5904
Glu Tyr  Glu Gln Leu Lys Glu  Gln His Leu Arg Arg  Gly Leu Pro
    1955                1960                1965

gtg ggc  tcc cct cca gac tcc  atc gta tct cct cac  cac aca tct      5949
Val Gly  Ser Pro Pro Asp Ser  Ile Val Ser Pro His  His Thr Ser
    1970                1975                1980

gag gac  tca gaa ctt ata gca  gaa gct aaa ctc ctg  cgg cag cac      5994
Glu Asp  Ser Glu Leu Ile Ala  Glu Ala Lys Leu Leu  Arg Gln His
    1985                1990                1995

aaa ggg  cgg ctg gag gcg agg  atg caa att ttg gaa  gat cac aat      6039
Lys Gly  Arg Leu Glu Ala Arg  Met Gln Ile Leu Glu  Asp His Asn
    2000                2005                2010

aaa cag  ctg gag tct cag ctg  cac cgc ctc aga cag  ctc ctg gag      6084
Lys Gln  Leu Glu Ser Gln Leu  His Arg Leu Arg Gln  Leu Leu Glu
    2015                2020                2025

cag cct  gac tct gac tcc cgc  atc aat ggt gtc tcc  ccc tgg gct      6129
Gln Pro  Asp Ser Asp Ser Arg  Ile Asn Gly Val Ser  Pro Trp Ala
    2030                2035                2040

tcc cca  cag cat tct gca ttg  agc tac tca ctt gac  act gac cca      6174
Ser Pro  Gln His Ser Ala Leu  Ser Tyr Ser Leu Asp  Thr Asp Pro
    2045                2050                2055

ggc cca  cag ttc cac cag gca  gca tct gag gac ctg  ctg gcc cca      6219
Gly Pro  Gln Phe His Gln Ala  Ala Ser Glu Asp Leu  Leu Ala Pro
    2060                2065                2070

cct cac  gac act agc acg gac  ctc acg gac gtg atg  gag cag atc      6264
Pro His  Asp Thr Ser Thr Asp  Leu Thr Asp Val Met  Glu Gln Ile
    2075                2080                2085

aac agc  acg ttt ccc tct tgc  agc tca aat gtc ccc  agc agg cca      6309
Asn Ser  Thr Phe Pro Ser Cys  Ser Ser Asn Val Pro  Ser Arg Pro
    2090                2095                2100

cag gca  atg tga                                                    6321
Gln Ala  Met
    2105
```

<210> SEQ ID NO 25
<211> LENGTH: 2106
<212> TYPE: PRT
<213> ORGANISM: Mus musculus

<400> SEQUENCE: 25

```
Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305                 310                 315                 320

Ile His Ile Gln Ser Ala Val Leu Ala Glu Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln His Asp Ile Ser Asp Asp Val Glu Glu Val
    370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415
```

```
Thr Gln Gly Thr Leu Ser Arg Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val His Val Arg Glu Gln Gly Met Val Lys
    690                 695                 700

Lys Pro Lys Gln Glu Leu Pro Pro Pro Pro Pro Pro Lys Lys Arg Gln
705                 710                 715                 720

Ile His Val Asp Val Glu Ala Lys Lys Lys Phe Asp Ala Ile Ser Thr
                725                 730                 735

Glu Leu Leu Asn Trp Ile Leu Lys Ser Lys Thr Ala Ile Gln Asn Thr
            740                 745                 750

Glu Met Lys Glu Tyr Lys Lys Ser Gln Glu Thr Ser Gly Met Lys Lys
        755                 760                 765

Lys Leu Lys Gly Leu Glu Lys Glu Gln Lys Glu Asn Leu Pro Arg Leu
    770                 775                 780

Asp Glu Leu Asn Gln Thr Gly Gln Thr Leu Arg Glu Gln Met Gly Lys
785                 790                 795                 800

Glu Gly Leu Pro Leu Lys Glu Val Asn Asp Val Leu Glu Arg Val Ser
                805                 810                 815

Leu Glu Trp Lys Met Ile Ser Gln Gln Leu Glu Asp Leu Gly Arg Lys
            820                 825                 830

Ile Gln Leu Gln Glu Asp Ile Asn Ala Tyr Phe Lys Gln Leu Asp Ala
        835                 840                 845
```

```
Ile Glu Glu Thr Ile Lys Glu Lys Glu Glu Trp Leu Arg Gly Thr Pro
    850                 855                 860

Ile Ser Glu Ser Pro Arg Gln Pro Leu Pro Gly Leu Lys Asp Ser Cys
865                 870                 875                 880

Gln Arg Glu Leu Thr Asp Leu Leu Gly Leu His Pro Arg Ile Glu Thr
                885                 890                 895

Leu Cys Ala Ser Cys Ser Ala Leu Lys Ser Gln Pro Cys Val Pro Gly
            900                 905                 910

Phe Val Gln Gln Gly Phe Asp Asp Leu Arg His His Tyr Gln Ala Val
        915                 920                 925

Ala Lys Ala Leu Glu Glu Tyr Gln Gln Gln Leu Glu Asn Glu Leu Lys
    930                 935                 940

Ser Gln Pro Gly Pro Glu Tyr Leu Asp Thr Leu Asn Thr Leu Lys Lys
945                 950                 955                 960

Met Leu Ser Glu Ser Glu Lys Ala Ala Gln Ala Ser Leu Asn Ala Leu
                965                 970                 975

Asn Asp Pro Ile Ala Val Glu Gln Ala Leu Gln Glu Lys Lys Ala Leu
            980                 985                 990

Asp Glu Thr Leu Glu Asn Gln Lys  His Thr Leu His Lys  Leu Ser Glu
        995                 1000                1005

Glu Thr  Lys Thr Leu Glu Lys  Asn Met Leu Pro Asp  Val Gly Lys
    1010                1015                1020

Met Tyr  Lys Gln Glu Phe Asp  Asp Val Gln Gly Arg  Trp Asn Lys
    1025                1030                1035

Val Lys  Thr Lys Val Ser Arg  Asp Leu His Leu Leu  Glu Glu Ile
    1040                1045                1050

Thr Pro  Arg Leu Arg Asp Phe  Glu Ala Asp Ser Glu  Val Ile Glu
    1055                1060                1065

Lys Trp  Val Ser Gly Ile Lys  Asp Phe Leu Met Lys  Glu Gln Ala
    1070                1075                1080

Ala Gln  Gly Asp Ala Ala Ala  Gln Ser Gln Leu Asp  Gln Cys Ala
    1085                1090                1095

Thr Phe  Ala Asn Glu Ile Glu  Thr Ile Glu Ser Ser  Leu Lys Asn
    1100                1105                1110

Met Arg  Glu Val Glu Thr Ser  Leu Gln Arg Cys Pro  Val Thr Gly
    1115                1120                1125

Val Lys  Thr Trp Val Gln Ala  Arg Leu Val Asp Tyr  Gln Ser Gln
    1130                1135                1140

Leu Glu  Lys Phe Ser Lys Glu  Ile Ala Ile Gln Lys  Ser Arg Leu
    1145                1150                1155

Leu Asp  Ser Gln Glu Lys Ala  Leu Asn Leu Lys Lys  Asp Leu Ala
    1160                1165                1170

Glu Met  Gln Glu Trp Met Ala  Gln Ala Glu Glu Asp  Tyr Leu Glu
    1175                1180                1185

Arg Asp  Phe Glu Tyr Lys Ser  Pro Glu Glu Leu Glu  Ser Ala Val
    1190                1195                1200

Glu Glu  Met Lys Arg Ala Lys  Glu Asp Val Leu Gln  Lys Glu Val
    1205                1210                1215

Arg Val  Lys Ile Leu Lys Asp  Ser Ile Lys Leu Val  Ala Ala Lys
    1220                1225                1230

Val Pro  Ser Gly Gly Gln Glu  Leu Thr Ser Glu Phe  Asn Glu Val
    1235                1240                1245

Leu Glu  Ser Tyr Gln Leu Leu  Cys Asn Arg Ile Arg  Gly Lys Cys
```

```
    1250                1255                1260

His Thr  Leu Glu Glu Val Trp  Ser Cys Trp Val Glu  Leu Leu His
    1265                1270                1275

Tyr Leu  Asp Leu Glu Thr Thr  Trp Leu Asn Thr Leu  Glu Glu Arg
    1280                1285                1290

Val Arg  Ser Thr Glu Ala Leu  Pro Glu Arg Ala Glu  Ala Val His
    1295                1300                1305

Glu Ala  Leu Glu Ser Leu Glu  Ser Val Leu Arg His  Pro Ala Asp
    1310                1315                1320

Asn Arg  Thr Gln Ile Arg Glu  Leu Gly Gln Thr Leu  Ile Asp Gly
    1325                1330                1335

Gly Ile  Leu Asp Asp Ile Ile  Ser Glu Lys Leu Glu  Ala Phe Asn
    1340                1345                1350

Ser Arg  Tyr Glu Glu Leu Ser  His Leu Ala Glu Ser  Lys Gln Ile
    1355                1360                1365

Ser Leu  Glu Lys Gln Leu Gln  Val Leu Arg Glu Thr  Asp His Met
    1370                1375                1380

Leu Gln  Val Leu Lys Glu Ser  Leu Gly Glu Leu Asp  Lys Gln Leu
    1385                1390                1395

Thr Thr  Tyr Leu Thr Asp Arg  Ile Asp Ala Phe Gln  Leu Pro Gln
    1400                1405                1410

Glu Ala  Gln Lys Ile Gln Ala  Glu Ile Ser Ala His  Glu Leu Thr
    1415                1420                1425

Leu Glu  Glu Leu Arg Lys Asn  Val Arg Ser Gln Pro  Pro Thr Ser
    1430                1435                1440

Pro Glu  Gly Arg Ala Thr Arg  Gly Gly Ser Gln Met  Asp Met Leu
    1445                1450                1455

Gln Arg  Lys Leu Arg Glu Val  Ser Thr Lys Phe Gln  Leu Ala His
    1460                1465                1470

Arg Asp  Phe Gly Pro Ser Ser  Gln His Phe Leu Ser  Thr Ser Val
    1475                1480                1485

Gln Leu  Pro Trp Gln Arg Ser  Ile Ser His Asn Lys  Val Pro Tyr
    1490                1495                1500

Tyr Ile  Asn His Gln Thr Gln  Thr Thr Cys Trp Asp  His Pro Lys
    1505                1510                1515

Met Thr  Glu Leu Phe Gln Ser  Leu Ala Asp Leu Asn  Asn Val Arg
    1520                1525                1530

Phe Ser  Ala Tyr Arg Thr Ala  Ile Lys Ile Arg Arg  Leu Gln Lys
    1535                1540                1545

Ala Leu  Cys Leu Asp Leu Leu  Glu Leu Asn Thr Thr  Asn Glu Val
    1550                1555                1560

Phe Lys  Gln His Lys Leu Asn  Gln Asn Asp Gln Leu  Leu Ser Val
    1565                1570                1575

Pro Asp  Val Ile Asn Cys Leu  Thr Thr Thr Tyr Asp  Gly Leu Glu
    1580                1585                1590

Gln Leu  His Lys Asp Leu Val  Asn Val Pro Leu Cys  Val Asp Met
    1595                1600                1605

Cys Leu  Asn Trp Leu Leu Asn  Val Tyr Asp Thr Gly  Arg Thr Gly
    1610                1615                1620

Lys Ile  Arg Val Gln Ser Leu  Lys Ile Gly Leu Met  Ser Leu Ser
    1625                1630                1635

Lys Gly  Leu Leu Glu Glu Lys  Tyr Arg Cys Leu Phe  Lys Glu Val
    1640                1645                1650
```

```
Ala Gly  Pro Thr Glu Met Cys  Asp Gln Arg Gln Leu  Gly Leu Leu
    1655                 1660                 1665

Leu His  Asp Ala Ile Gln Ile  Pro Arg Gln Leu Gly  Glu Val Ala
    1670                 1675                 1680

Ala Phe  Gly Gly Ser Asn Ile  Glu Pro Ser Val Arg  Ser Cys Phe
    1685                 1690                 1695

Gln Gln  Asn Asn Asn Lys Pro  Glu Ile Ser Val Lys  Glu Phe Ile
    1700                 1705                 1710

Asp Trp  Met His Leu Glu Pro  Gln Ser Met Val Trp  Leu Pro Val
    1715                 1720                 1725

Leu His  Arg Val Ala Ala Ala  Glu Thr Ala Lys His  Gln Ala Lys
    1730                 1735                 1740

Cys Asn  Ile Cys Lys Glu Cys  Pro Ile Val Gly Phe  Arg Tyr Arg
    1745                 1750                 1755

Ser Leu  Lys His Phe Asn Tyr  Asp Val Cys Gln Ser  Cys Phe Phe
    1760                 1765                 1770

Ser Gly  Arg Thr Ala Lys Gly  His Lys Leu His Tyr  Pro Met Val
    1775                 1780                 1785

Glu Tyr  Cys Ile Pro Thr Thr  Ser Gly Glu Asp Val  Arg Asp Phe
    1790                 1795                 1800

Thr Lys  Val Leu Lys Asn Lys  Phe Arg Ser Lys Lys  Tyr Phe Ala
    1805                 1810                 1815

Lys His  Pro Arg Leu Gly Tyr  Leu Pro Val Gln Thr  Val Leu Glu
    1820                 1825                 1830

Gly Asp  Asn Leu Glu Thr Pro  Ile Thr Leu Ile Ser  Met Trp Pro
    1835                 1840                 1845

Glu His  Tyr Asp Pro Ser Gln  Ser Pro Gln Leu Phe  His Asp Asp
    1850                 1855                 1860

Thr His  Ser Arg Ile Glu Gln  Tyr Ala Thr Arg Leu  Ala Gln Met
    1865                 1870                 1875

Glu Arg  Thr Asn Gly Ser Phe  Leu Thr Asp Ser Ser  Ser Thr Thr
    1880                 1885                 1890

Gly Ser  Val Glu Asp Glu His  Ala Leu Ile Gln Gln  Tyr Cys Gln
    1895                 1900                 1905

Thr Leu  Gly Gly Glu Ser Pro  Val Ser Gln Pro Gln  Ser Pro Ala
    1910                 1915                 1920

Gln Ile  Leu Lys Ser Val Glu  Arg Glu Glu Arg Gly  Glu Leu Glu
    1925                 1930                 1935

Arg Ile  Ile Ala Asp Leu Glu  Glu Glu Gln Arg Asn  Leu Gln Val
    1940                 1945                 1950

Glu Tyr  Glu Gln Leu Lys Glu  Gln His Leu Arg Arg  Gly Leu Pro
    1955                 1960                 1965

Val Gly  Ser Pro Pro Asp Ser  Ile Val Ser Pro His  His Thr Ser
    1970                 1975                 1980

Glu Asp  Ser Glu Leu Ile Ala  Glu Ala Lys Leu Leu  Arg Gln His
    1985                 1990                 1995

Lys Gly  Arg Leu Glu Ala Arg  Met Gln Ile Leu Glu  Asp His Asn
    2000                 2005                 2010

Lys Gln  Leu Glu Ser Gln Leu  His Arg Leu Arg Gln  Leu Leu Glu
    2015                 2020                 2025

Gln Pro  Asp Ser Asp Ser Arg  Ile Asn Gly Val Ser  Pro Trp Ala
    2030                 2035                 2040

Ser Pro  Gln His Ser Ala Leu  Ser Tyr Ser Leu Asp  Thr Asp Pro
    2045                 2050                 2055
```

```
Gly Pro  Gln Phe His Gln Ala  Ala Ser Glu Asp Leu  Leu Ala Pro
    2060                 2065                 2070

Pro His  Asp Thr Ser Thr Asp  Leu Thr Asp Val Met  Glu Gln Ile
    2075                 2080                 2085

Asn Ser  Thr Phe Pro Ser Cys  Ser Ser Asn Val Pro  Ser Arg Pro
    2090                 2095                 2100

Gln Ala  Met
    2105


<210> SEQ ID NO 26
<211> LENGTH: 59
<212> TYPE: DNA
<213> ORGANISM: Artificial Sequence
<220> FEATURE:
<223> OTHER INFORMATION: PCR primer

<400> SEQUENCE: 26

gcggccgcac accatggact acaaggacga cgatgacaag ggctacggcc gcaagaaac      59


<210> SEQ ID NO 27
<211> LENGTH: 32
<212> TYPE: DNA
<213> ORGANISM: Artificial Sequence
<220> FEATURE:
<223> OTHER INFORMATION: PCR primer

<400> SEQUENCE: 27

ggagatgcac agcaacagtt tcaggactta gg                                   32


<210> SEQ ID NO 28
<211> LENGTH: 4
<212> TYPE: PRT
<213> ORGANISM: Artificial
<220> FEATURE:
<223> OTHER INFORMATION: Artificial polypeptide/FLAG fragment

<400> SEQUENCE: 28

Asp Tyr Lys Asp
1
```